United States Patent
Toda et al.

(10) Patent No.: US 9,051,255 B2
(45) Date of Patent: *Jun. 9, 2015

(54) PIPERAZINYL CYCLOHEXANE COMPOUNDS AS GPR38 AGONISTS

(71) Applicant: Daiichi Sankyo Company, Limited, Chuo-ku, Tokyo (JP)

(72) Inventors: Narihiro Toda, Kanagawa (JP); Rieko Takano, Tokyo (JP); Takeshi Shida, Tokyo (JP); Takahiro Katagiri, Tokyo (JP); Mitsuhiro Iwamoto, Chiba (JP); Shinji Ashida, Chiba (JP); Mami Yamazaki, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/142,479

(22) Filed: Dec. 27, 2013

(65) Prior Publication Data

US 2014/0221391 A1 Aug. 7, 2014

Related U.S. Application Data

(63) Continuation of application No. 13/850,981, filed on Mar. 26, 2013, now Pat. No. 8,710,060, which is a continuation of application No. PCT/JP2011/071830, filed on Sep. 26, 2011.

(30) Foreign Application Priority Data

Sep. 27, 2010 (JP) ................................. 2010-215403

(51) Int. Cl.
| | |
|---|---|
| *A61K 31/495* | (2006.01) |
| *A61K 31/496* | (2006.01) |
| *C07D 241/04* | (2006.01) |
| *C07D 401/12* | (2006.01) |
| *C07D 413/12* | (2006.01) |
| *C07C 59/255* | (2006.01) |
| *C07D 213/64* | (2006.01) |
| *C07D 295/135* | (2006.01) |
| *C07D 403/12* | (2006.01) |
| *C07D 213/643* | (2006.01) |
| *C07D 295/155* | (2006.01) |

(52) U.S. Cl.
CPC ............ *C07C 59/255* (2013.01); *C07D 213/64* (2013.01); *C07D 241/04* (2013.01); *C07D 295/135* (2013.01); *C07D 401/12* (2013.01); *C07D 403/12* (2013.01); *C07D 413/12* (2013.01); *C07D 213/643* (2013.01); *C07D 295/155* (2013.01)

(58) Field of Classification Search
None
See application file for complete search history.

(56) References Cited

U.S. PATENT DOCUMENTS

| | | | |
|---|---|---|---|
| 8,710,060 B2 * | 4/2014 | Toda et al. ............... | 514/252.12 |
| 2005/0080116 A1 | 4/2005 | Li | |
| 2008/0027065 A1 | 1/2008 | Mitchell | |
| 2009/0131453 A1 | 5/2009 | Seal | |
| 2009/0192160 A1 | 7/2009 | Mitchell | |
| 2010/0256364 A1 | 10/2010 | Mitchell | |

FOREIGN PATENT DOCUMENTS

WO 01/85694 A2 11/2001

OTHER PUBLICATIONS

Hackh's Chemical Dictionary,5th edition, (McGraw-Hill Book Co.), pp. 5 and 30 (1987).*
Sudo et al. Neurogastroenterology & Motility. vol. 19, pp. 318-326 (2007).*

(Continued)

*Primary Examiner* — Emily Bernhardt
(74) *Attorney, Agent, or Firm* — Christensen O'Connor Johnson Kindness PLLC

(57) ABSTRACT

To find a therapeutic and/or prophylactic agent for gastrointestinal disorders and so on, the agent having excellent activity and high safety. A compound represented by the following general formula (I) or a pharmacologically acceptable salt thereof. In the formula, A represents an optionally substituted phenylene group; B represents an optionally substituted 4- to 10-membered heterocyclic group, an optionally substituted C6-C10 aryl group, or an optionally substituted C3-C10 cycloalkyl group; $R^1$ represents a hydrogen atom or a C1-C3 alkyl group; $R^2$ represents a hydrogen atom or a C1-C3 alkyl group; $R^3$ represents a C1-C6 alkyl group, a C3-C10 cycloalkyl group, a C1-C3 alkoxy C1-C3 alkyl group, or a C1-C3 hydroxyalkyl group; $R^4$ represents a hydrogen atom, a C1-C6 alkyl group, or a halogen atom; n represents an integer of 1 to 4; and X represents methylene, —O—, —NH—, —N(C1-C3 alkyl)-, —C(=O)—, —S—, —S(O)—, —S(O$_2$)—, or a single bond.

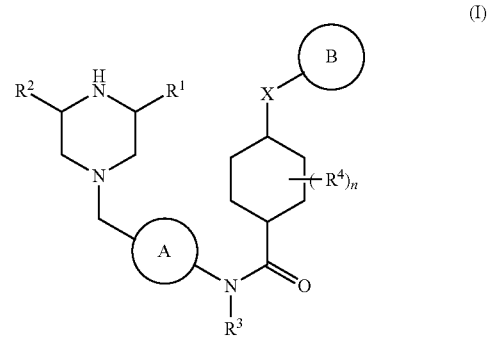

18 Claims, No Drawings

(56) References Cited

OTHER PUBLICATIONS

Office Action mailed May 20, 2014, issued in Columbian Application No. 13-101.069, filed Sep. 26, 2011, and Comments regarding Office Action from Columbian Associate Clarke, Modet & Co., dated Jun. 20, 2014, 11 pages.

International Search Report mailed Oct. 25, 2011, issued in corresponding International Application No. PCT/JP2011/071830, filed Sep. 26, 2011, 3 pages.

International Preliminary Report on Patentability and Written Opinion mailed Apr. 16, 2013, issued in corresponding International Application No. PCT/JP2011/071830, filed Sep. 26, 2011, 6 pages.

Takanashi, H., and O. Cynshi, "Motilides: A Long and Winding Road: Lessons From Mitemcinal (GM-611) on Diabetic Gastroparesis," Regulatory Peptides 155(1-3):Jun. 18-23, 2009.

Takanashi, H., et al., "In Vitro Pharmacological Characterization of Mitemcinal (GM-611), the First Acid-Resistant Non-Peptide Motilin Receptor Agonist, in Smooth Muscle of Rabbit Small Intestine," Pharmacology 79(3):137-148, Apr. 2007.

\* cited by examiner

PIPERAZINYL CYCLOHEXANE COMPOUNDS AS GPR38 AGONISTS

TECHNICAL FIELD

The present invention relates to a novel cyclohexane derivative compound having pharmacological activity, a method for manufacturing the same, a pharmaceutical composition containing the same, and use thereof for treating various disorders.

Further, since the compound or a pharmacologically acceptable salt thereof according to the invention has agonistic activity for G protein-coupled receptor (GPR) 38, the compound or a pharmacologically acceptable salt thereof for use as a therapeutic or prophylactic agent for a condition or a disorder mediated by GPR38 is provided. In particular, the invention provides the compound or a pharmacologically acceptable salt thereof for use as a therapeutic and/or prophylactic agent for gastrointestinal disorders associated with hypomotility, for example, gastroesophageal reflux disease (GERD) (particularly nonerosive reflux disease (NERD)), functional dyspepsia (FD), functional bowel disorders such as irritable bowel syndrome (particularly irritable bowel syndrome with constipation (IBS-C)), diabetic gastroparesis, constipation (particularly functional constipation), opioid-induced bowel dysfunction, paralytic ileus, postoperative gastrointestinal paralysis (particularly postoperative intestinal obstruction), gastrointestinal symptoms associated with scleroderma, etc. (preferably, a therapeutic and/or prophylactic agent for functional bowel disorders such as IBS-C, diabetic gastroparesis, and constipation), and further as a pharmaceutical aid for use in pretreatment for barium enema X-ray examination by oral intestinal lavage.

Further, the invention relates to a prophylactic or therapeutic agent for the above-described diseases containing the compound of the invention as an active ingredient, a composition for preventing or treating the above-described diseases containing the compound as an active ingredient, use of the compound for producing a pharmaceutical product for preventing or treating the above-described diseases, and a method for preventing or treating the above-described diseases, comprising administering a pharmacologically effective amount of the compound to a mammal (preferably a human).

BACKGROUND ART

GPR38 is a seven transmembrane G protein-coupled receptor having high affinity for the peptide motilin, and a GPR38 agonist is considered to mimic the activity of motilin.

A method for measuring a GPR38 agonistic activity, a low molecular weight compound having GPR38 agonistic activity, and the usefulness of the compound in the treatment of gastrointestinal disorders are generally known and described in Patent Documents 1 to 3, etc.

Further, a method for evaluating gastrointestinal disorders in rabbits by a test using a Magnus apparatus is also generally known and described in Non-patent Document 1, etc.

PRIOR ART DOCUMENTS

Patent Documents

Patent Document 1: WO 2008/729 (corresponding U.S. Publication Nos. 2008/27065 and 2009/192160)
Patent Document 2: WO 2007/144400 (corresponding U.S. Publication No. 2009/131453)
Patent Document 3: WO 2009/68552 (corresponding U.S. Publication No. 2010/0256364)

Non-Patent Document

Non-Patent Document 1: Pharmacology, 79(3), pp. 137-148, 2007

SUMMARY OF THE INVENTION

Problems to be Solved by the Invention

The present inventors have made intensive studies, and as a result, have found that a compound represented by the below-described formula (I) unexpectedly has excellent GPR38 agonistic activity based on its specific chemical structure, and further has excellent physical properties as a pharmaceutical preparation such as stability, and therefore can be used in a pharmaceutical product which is safe and useful as a prophylactic or therapeutic agent for pathological conditions or diseases associated with gastrointestinal disorders, etc. Thus, the invention has been completed based on these findings.

That is, the invention is useful as a prophylactic or therapeutic agent for diseases such as gastrointestinal disorders associated with hypomotility, for example, GERD, FD, functional bowel disorders such as irritable bowel syndrome, diabetic gastroparesis, constipation, opioid-induced bowel dysfunction, paralytic ileus, postoperative gastrointestinal paralysis, gastrointestinal symptoms associated with scleroderma, etc., and further as a pharmaceutical aid for use in pretreatment for barium enema X-ray examination by oral intestinal lavage.

Means for Solving the Problems

The invention is directed to:

(1) a compound represented by the following general formula (I) or a pharmacologically acceptable salt thereof:

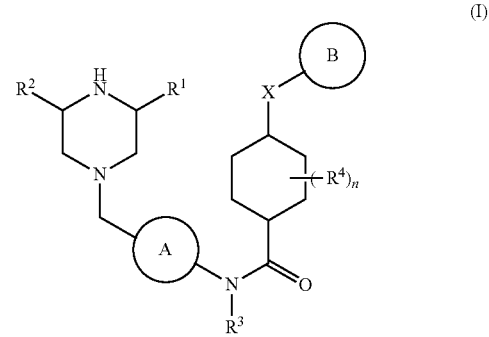

[wherein A represents a phenylene group (the phenylene group may be optionally substituted with 1 to 3 groups selected from a C1-C3 alkyl group, a C1-C3 alkoxy group, and a halogen atom); B represents a 4- to 10-membered heterocyclic group containing 1 to 4 heteroatoms which may be the same or different and are selected from nitrogen, oxygen, and sulfur (the heterocyclic group may be optionally substituted with 1 to 5 groups selected from substituent group α), a C6-C10 aryl group (the aryl group may be optionally substituted with 1 to 5 groups selected from substituent group α), or a C3-C10 cycloalkyl group (the cycloalkyl group may be optionally substituted with 1 to 5 groups selected from substituent group α); R¹ represents a hydrogen atom or a C1-C3 alkyl group; R² represents a hydrogen atom or a C1-C3 alkyl group; R³ represents a C1-C6 alkyl group, a C3-C10 cycloalkyl group, a C1-C3 alkoxy C1-C3 alkyl group, or a C1-C3 hydroxyalkyl group; R⁴ represents a hydrogen atom, a C1-C6 alkyl group, or a halogen atom; n represents an integer of 1 to 4; X represents methylene, —O—, —NH—, —N(C1-C3 alkyl)-, —C(=O)—, —S—, —S(O)—, —S(O₂)— or a single bond; and substituent group α consists of a halogen atom, a C1-C6 alkyl group {the alkyl group may be optionally substituted with 1 to 3 groups selected from a C1-C6 aliphatic acyl group, a carboxyl group, a C1-C6 alkoxycarbonyl group, an aminocarbonyl group (the aminocarbonyl group may be optionally substituted with 1 or 2 groups selected from a C1-C6 alkyl group, a C1-C6 haloalkyl group, and a C1-C6 alkoxy C1-C6 alkyl group), a carbamido group which may be optionally substituted with one or three C1-C6 alkyl groups, a C1-C6 aliphatic acylamino group which may be optionally substituted with a C1-C6 alkoxy group, a C1-C6 aliphatic acyl C1-C6 alkylamino group, an amidoxy group which may be optionally substituted with one or two C1-C6 alkyl groups, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C3-C10 cycloalkyl group (the cycloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group may be optionally substituted with 1 to 3 groups selected from a hydroxy group, a C1-C6 alkoxy group, a C1-C6 hydroxyalkyl group, an aminocarbonyl group which may be optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a C6-C10 aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a cyano group, a nitro group, a C1-C6 alkylsulfonyl group, a C1-C6 dialkylaminosulfonyl group, and a C6-C10 aryl group];

(2) the compound or pharmacologically acceptable salt thereof according to the above (1), wherein A is a phenylene group which may be optionally substituted with one to three C1-C3 alkyl groups;

(3) the compound or pharmacologically acceptable salt thereof according to the above (1) or (2), wherein B is a 4- to 10-membered heterocyclic group containing 1 to 4 heteroatoms which may be the same or different and are selected from nitrogen, oxygen, and sulfur (the heterocyclic group may be optionally substituted with 1 to 5 groups selected from substituent group α) or a C6-C10 aryl group (the aryl group may be optionally substituted with 1 to 5 groups selected from substituent group α);

(4) the compound or pharmacologically acceptable salt thereof according to the above (1) or (2), wherein B is a pyridyl group which may be optionally substituted with 1 to 5 groups selected from substituent group α or a phenyl group which may be optionally substituted with 1 to 5 groups selected from substituent group α;

(5) the compound or pharmacologically acceptable salt thereof according to any one of the above (1) to (4), wherein R¹ is a C1-C3 alkyl group;

(6) the compound or pharmacologically acceptable salt thereof according to any one of the above (1) to (5), wherein R² is a hydrogen atom.

(7) the compound or pharmacologically acceptable salt thereof according to any one of the above (1) to (6), wherein R³ is a C1-C3 alkyl group; (8) the compound or pharmacologically acceptable salt thereof according to any one of the above (1) to (7), wherein R⁴ is a hydrogen atom.

(9) the compound or pharmacologically acceptable salt thereof according to any one of the above (1) to (8), wherein X is —O— or —NH—;

(10) a compound represented by the following general formula (IA) or a pharmacologically acceptable salt thereof:

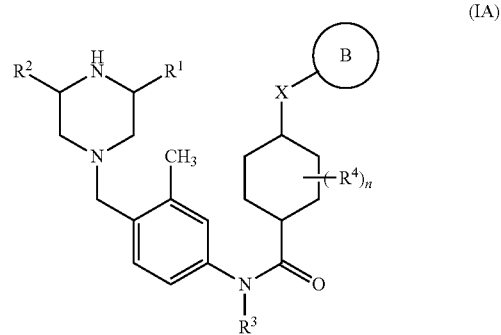

(IA)

[wherein B represents a 4- to 10-membered heterocyclic group containing 1 to 4 heteroatoms which may be the same or different and are selected from nitrogen, oxygen, and sulfur (the heterocyclic group may be optionally substituted with 1 to 5 groups selected from substituent group α), a C6-C10 aryl group (the aryl group may be optionally substituted with 1 to 5 groups selected from substituent group α), or a C3-C10 cycloalkyl group (the cycloalkyl group may be optionally substituted with 1 to 5 groups selected from substituent group α); R¹ represents a hydrogen atom or a C1-C3 alkyl group; R² represents a hydrogen atom or a C1-C3 alkyl group; R³ represents a C1-C6 alkyl group, a C3-C10 cycloalkyl group, a C1-C3 alkoxy C1-C3 alkyl group, or a C1-C3 hydroxyalkyl group; R⁴ represents a hydrogen atom, a C1-C6 alkyl group, or a halogen atom; n represents an integer of 1 to 4; X represents methylene, —O—, —NH—, —N(C1-C3 alkyl), —C(═O)—, —S—, —S(O)—, —S(O₂)— or a single bond; and substituent group α consists of a halogen atom, a C1-C6 alkyl group {the alkyl group may be optionally substituted with 1 to 3 groups selected from a C1-C6 aliphatic acyl group, a carboxyl group, a C1-C6 alkoxycarbonyl group, an aminocarbonyl group (the aminocarbonyl group may be optionally substituted with 1 or 2 groups selected from a C1-C6 alkyl group, a C1-C6 haloalkyl group, and a C1-C6 alkoxy C1-C6 alkyl group), a carbamido group which may be optionally substituted with one or three C1-C6 alkyl groups, a C1-C6 aliphatic acylamino group which may be optionally substituted with a C1-C6 alkoxy group, a C1-C6 aliphatic acyl C1-C6 alkylamino group, an amidoxy group which may be optionally substituted with one or two C1-C6 alkyl groups, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C3-C10 cycloalkyl group (the cycloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group being optionally substituted with 1 to 3 groups selected from a hydroxy group, a C1-C6 alkoxy group, a C1-C6 hydroxyalkyl group, an aminocarbonyl group which may be optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a C6-C10 aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a cyano group, a nitro group, a C1-C6 alkylsulfonyl group, a C1-C6 dialkylaminosulfonyl group, and a C6-C10 aryl group];

(11) a compound represented by the following general formula (IB) or a pharmacologically acceptable salt thereof:

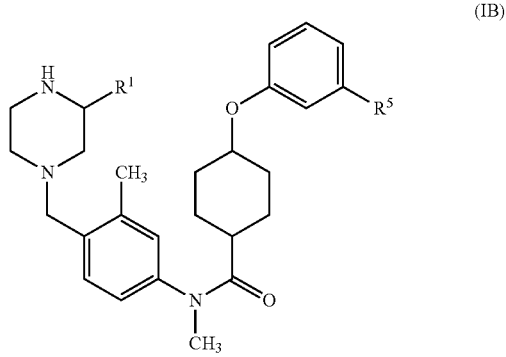

(IB)

[wherein R¹ represents a hydrogen atom or a C1-C3 alkyl group; R⁵ represents a group selected from substituent group α; and substituent group α consists of a halogen atom, a C1-C6 alkyl group {the alkyl group may be optionally substituted with 1 to 3 groups selected from a C1-C6 aliphatic acyl group, a carboxyl group, a C1-C6 alkoxycarbonyl group, an aminocarbonyl group (the aminocarbonyl group may be optionally substituted with 1 or 2 groups selected from a C1-C6 alkyl group, a C1-C6 haloalkyl group, and a C1-C6 alkoxy C1-C6 alkyl group), a carbamido group which may be optionally substituted with one or three C1-C6 alkyl groups, a C1-C6 aliphatic acylamino group which may be optionally substituted with a C1-C6 alkoxy group, a C1-C6 aliphatic acyl C1-C6 alkylamino group, an amidoxy group which may be optionally substituted with one or two C1-C6 alkyl groups, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C3-C10 cycloalkyl group (the cycloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group may be optionally substituted with 1 to 3 groups selected from a hydroxy group, a C1-C6 alkoxy group, a C1-C6 hydroxyalkyl group, an aminocarbonyl group which may be optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a C6-C10 aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a cyano group, a nitro group, a C1-C6 alkylsulfonyl group, a C1-C6 dialkylaminosulfonyl group, and a C6-C10 aryl group].

(12) the compound or pharmacologically acceptable salt thereof according to the above (10) or (11), wherein $R^1$ is a methyl group;

(13) the compound or pharmacologically acceptable salt thereof according to the above (11) or (12), wherein $R^5$ is a C1-C6 alkyl group {the alkyl group may be optionally substituted with 1 to 3 groups selected from a C1-C6 aliphatic acyl group, a carboxyl group, a C1-C6 alkoxycarbonyl group, an aminocarbonyl group (the aminocarbonyl group may be optionally substituted with 1 or 2 groups selected from a C1-C6 alkyl group, a C1-C6 haloalkyl group, and a C1-C6 alkoxy C1-C6 alkyl group), a carbamido group which may be optionally substituted with one or three C1-C6 alkyl groups, a C1-C6 aliphatic acylamino group which may be optionally substituted with a C1-C6 alkoxy group, a C1-C6 aliphatic acyl C1-C6 alkylamino group, an amidoxy group which may be optionally substituted with one or two C1-C6 alkyl groups, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C1-C6 hydroxyalkyl group (the hydroxyalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), or a C1-C6 alkoxy C1-C6 alkyl group (the alkoxyalkyl group may be optionally substituted with 1 to groups selected from a hydroxy group, a C1-C6 alkoxy group, a C1-C6 hydroxyalkyl group, an aminocarbonyl group which may be optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur);

(14) a compound represented by the following general formula (I) or a pharmacologically acceptable salt thereof:

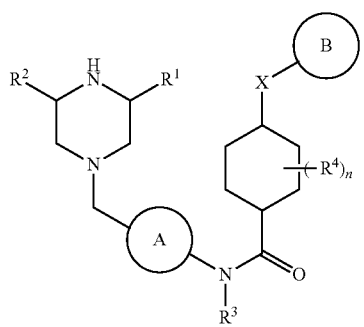

(I)

[wherein A represents a phenylene group (the phenylene group may be optionally substituted with 1 to 3 groups selected from a C1-C3 alkyl group, a C1-C3 alkoxy group, and a halogen atom); B represents a 4- to 10-membered heterocyclic group containing 1 to 4 heteroatoms which may be the same or different and are selected from nitrogen, oxygen, and sulfur (the heterocyclic group may be optionally substituted with 1 to 5 groups selected from substituent group α), a C6-C10 aryl group (the aryl group may be optionally substituted with 1 to 5 groups selected from substituent group α), or a C3-C10 cycloalkyl group (the cycloalkyl group may be optionally substituted with 1 to 5 groups selected from substituent group α); $R^1$ represents a hydrogen atom or a C1-C3 alkyl group; $R^2$ represents a hydrogen atom or a C1-C3 alkyl group; $R^3$ represents a C1-C6 alkyl group, a C3-C10 cycloalkyl group, a C1-C3 alkoxy C1-C3 alkyl group, or a C1-C3 hydroxyalkyl group; $R^4$ represents a hydrogen atom, a C1-C6 alkyl group, or a halogen atom; n represents an integer of 1 to 4; X represents methylene, —O—, —NH—, —N(C1-C3 alkyl)-, —C(=O)—, —S—, —S(O)—, —S(O$_2$)— or a single bond; and substituent group α consists of a halogen atom, a C1-C6 alkyl group (the alkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C3-C10 cycloalkyl group (the cycloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a C6-C10 aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a cyano group, a nitro group, a C1-C6 alkylsulfonyl group, a C1-C6 dialkylaminosulfonyl group, and a C6-C10 aryl group];

(15) trans-4-(4-fluorophenoxy)-N-methyl-N-(4-{[(3S)-3-methylpiperazin-1-yl]methyl}phenyl)cyclohexanecarboxamide, trans-4-(4-fluorophenoxy)-N-methyl-N-(3-methyl-4-{[(3S)-3-methylpiperazin-1-yl]methyl}phenyl) cyclohexanecarboxamide, trans-4-[(5-fluoropyridin-2-yl)

oxy]-N-methyl-N-(3-methyl-4-{[(3S)-3-methylpiperazin-1-yl]methyl}phenyl)cyclohexanecarboxamide, trans-4-[3-(hydroxymethyl)phenoxy]-N-methyl-N-(3-methyl-4-{[(3S)-3-methylpiperazin-1-yl]methyl}phenyl)cyclohexanecarboxamide, trans-4-[3-(2-hydroxyethyl)phenoxy]-N-methyl-N-(3-methyl-4-{[(3S)-3-methylpiperazin-1-yl]methyl}phenyl)cyclohexanecarboxamide, ethyl [3-({trans-4-[methyl(3-methyl-4-{[(3S)-3-methylpiperazin-1-yl]methyl}phenyl)carbamoyl]cyclohexyl}oxy)phenyl]acetate, [3-({trans-4-[methyl(3-methyl-4-{[(3S)-3-methylpiperazin-1-yl]methyl}phenyl)carbamoyl]cyclohexyl}oxy)phenyl]acetic acid, isopropyl[3-({trans-4-[methyl(3-methyl-4-{[(3S)-3-methylpiperazin-1-yl]methyl}phenyl)carbamoyl]cyclohexyl}oxy)phenyl]acetate, or a pharmacologically acceptable salt thereof.

(16) trans-4-{3-[(2-hydroxy-2-methylpropoxy)methyl]phenoxy}-N-methyl-N-(3-methyl-4-{[(3S)-3-methylpiperazin-1-yl]methyl}phenyl)cyclohexanecarboxamide, trans-4-({3-[(2-hydroxy-2-methylpropoxy)methyl]phenyl}amino)-N-methyl-N-(3-methyl-4-{[(3S)-3-methylpiperazin-1-yl]methyl}phenyl)cyclohexanecarboxamide, 3-({trans-4-[methyl(3-methyl-4-{[(3S)-3-methylpiperazin-1-yl]methyl}phenyl)carbamoyl]cyclohexyl}oxy)benzylmethylcarbamate, 2-[3-({trans-4-[methyl(3-methyl-4-{[(3S)-3-methylpiperazin-1-yl]methyl}phenyl)carbamoyl]cyclohexyl}oxy)phenyl]ethylcarbamate, 2-[3-({trans-4-[methyl(3-methyl-4-{[(3S)-3-methylpiperazin-1-yl]methyl}phenyl)carbamoyl]cyclohexyl}amino)phenyl]ethyl methylcarbamate, 2-[3-({trans-4-[methyl(3-methyl-4-{[(3S)-3-methylpiperazin-1-yl]methyl}phenyl)carbamoyl]cyclohexyl}amino)phenyl]ethyl dimethylcarbamate, trans-4-{3-[2-(isopropylamino)-2-oxoethyl]phenoxy}-N-methyl-N-(3-methyl-4-{[(3S)-3-methylpiperazin-1-yl]methyl}phenyl)cyclohexanecarboxamide, trans-4-[(2-cyanopyridin-4-yl)oxy]-N-methyl-N-(3-methyl-4-{[(3S)-3-methylpiperazin-1-yl]methyl}phenyl)cyclohexanecarboxamide, or a pharmacologically acceptable salt thereof;

(17) trans-4-[3-(hydroxymethyl)phenoxy]-N-methyl-N-(3-methyl-4-{[(3S)-3-methylpiperazin-1-yl]methyl}phenyl)cyclohexanecarboxamide or a pharmacologically acceptable salt thereof;

(17-1) trans-4-[3-(hydroxymethyl)phenoxy]-N-methyl-N-(3-methyl-4-{[(3S)-3-methylpiperazin-1-yl]methyl}phenyl)cyclohexanecarboxamide;

(18) trans-4-[(2-cyanopyridin-4-yl)oxy]-N-methyl-N-(3-methyl-4-{[(3S)-3-methylpiperazin-1-yl]methyl}phenyl)cyclohexanecarboxamide or a pharmacologically acceptable salt thereof;

(18-1) trans-4-[(2-cyanopyridin-4-yl)oxy]-N-methyl-N-(3-methyl-4-{[(3S)-3-methylpiperazin-1-yl]methyl}phenyl)cyclohexanecarboxamide;

(19) trans-4-{3-[2-(isopropylamino)-2-oxoethyl]phenoxy}-N-methyl-N-(3-methyl-4-{[(3S)-3-methylpiperazin-1-yl]methyl}phenyl)cyclohexanecarboxamide or a pharmacologically acceptable salt thereof;

(19-1) trans-4-{3-[2-(isopropylamino)-2-oxoethyl]phenoxy}-N-methyl-N-(3-methyl-4-{[(3S)-3-methylpiperazin-1-yl]methyl}phenyl)cyclohexanecarboxamide;

(20) trans-4-{3-[(2-hydroxy-2-methylpropoxy)methyl]phenoxy}-N-methyl-N-(3-methyl-4-{[(3S)-3-methylpiperazin-1-yl]methyl}phenyl)cyclohexanecarboxamide or a pharmacologically acceptable salt thereof;

(20-1) trans-4-{3-[(2-hydroxy-2-methylpropoxy)methyl]phenoxy}-N-methyl-N-(3-methyl-4-{[(3S)-3-methylpiperazin-1-yl]methyl}phenyl)cyclohexanecarboxamide;

(21) trans-4-({3-[(2-hydroxy-2-methylpropoxy)methyl]phenyl}amino)-N-methyl-N-(3-methyl-4-{[(3S)-3-methylpiperazin-1-yl]methyl}phenyl)cyclohexanecarboxamide or a pharmacologically acceptable salt thereof;

(21-1) trans-4-({3-[(2-hydroxy-2-methylpropoxy)methyl]phenyl}amino)-N-methyl-N-(3-methyl-4-{[(3S)-3-methylpiperazin-1-yl]methyl}phenyl)cyclohexanecarboxamide;

(22) 3-({trans-4-[methyl(3-methyl-4-{[(3S)-3-methylpiperazin-1-yl]methyl}phenyl)carbamoyl]cyclohexyl}oxy)benzylmethylcarbamate or a pharmacologically acceptable salt thereof;

(22-1) 3-({trans-4-[methyl(3-methyl-4-{[(3S)-3-methylpiperazin-1-yl]methyl}phenyl)carbamoyl]cyclohexyl}oxy)benzylmethylcarbamate;

(23) 2-[3-({trans-4-[methyl(3-methyl-4-{[(3S)-3-methylpiperazin-1-yl]methyl}phenyl)carbamoyl]cyclohexyl}oxy)phenyl]ethylcarbamate or a pharmacologically acceptable salt thereof;

(23-1) 2-[3-({trans-4-[methyl(3-methyl-4-{[(3S)-3-methylpiperazin-1-yl]methyl}phenyl)carbamoyl]cyclohexyl}oxy)phenyl]ethylcarbamate;

(24) 2-[3-({trans-4-[methyl(3-methyl-4-{[(3S)-3-methylpiperazin-1-yl]methyl}phenyl)carbamoyl]cyclohexyl}amino)phenyl]ethyl methylcarbamate or a pharmacologically acceptable salt thereof;

(24-1) 2-[3-({trans-4-[methyl(3-methyl-4-{[(3S)-3-methylpiperazin-1-yl]methyl}phenyl)carbamoyl]cyclohexyl}amino)phenyl]ethyl methylcarbamate;

(25) 2-[3-({trans-4-[methyl(3-methyl-4-{[(3S)-3-methylpiperazin-1-yl]methyl}phenyl)carbamoyl]cyclohexyl}amino)phenyl]ethyl dimethylcarbamate or a pharmacologically acceptable salt thereof;

(25-1) 2-[3-({trans-4-[methyl(3-methyl-4-{[(3S)-3-methylpiperazin-1-yl]methyl}phenyl)carbamoyl]cyclohexyl}amino)phenyl]ethyl dimethylcarbamate;

(26) a medicament comprising the compound or pharmacologically acceptable salt thereof according to any one of the above (1) to (25) as an active ingredient;

(27) the medicament according to the above (26), for use in preventing or treating a disease associated with GPR38;

(28) a therapeutic or prophylactic agent for a gastrointestinal disorder associated with hypomotility, comprising the compound or pharmacologically acceptable salt thereof according to any one of the above (1) to (25) as an active ingredient;

(28-1) preferably, a therapeutic agent for a gastrointestinal disorder associated with hypomotility;

(29) a therapeutic or prophylactic agent for irritable bowel syndrome with constipation, diabetic gastroparesis, or constipation, comprising the compound or pharmacologically acceptable salt thereof according to any one of the above (1) to (25) as an active ingredient;

(29-1) preferably, a therapeutic or prophylactic agent for irritable bowel syndrome with constipation, more preferably, a therapeutic agent for irritable bowel syndrome with constipation;

(30) a therapeutic or prophylactic agent for gastroesophageal reflux disease, functional dyspepsia, irritable bowel syndrome, diabetic gastroparesis, constipation, opioid-induced bowel dysfunction, paralytic ileus, or postoperative gastrointestinal paralysis, comprising the compound or pharmacologically acceptable salt thereof according to any one of the above (1) to (25) as an active ingredient;

(31) use of the compound or pharmacologically acceptable salt thereof according to any one of the above (1) to (25) for the manufacturee of a prophylactic or therapeutic agent for a gastrointestinal disorder associated with hypomotility;

(31-1) preferably, use of the compound or pharmacologically acceptable salt thereof according to any one of the above (1) to (25) for producing a therapeutic or prophylactic agent for irritable bowel syndrome with constipation, diabetic gastroparesis, or constipation;

(31-2) more preferably, use of the compound or pharmacologically acceptable salt thereof according to any one of the above (1) to (25) for producing a therapeutic agent for irritable bowel syndrome with constipation, diabetic gastroparesis, or constipation;

(32) a method for preventing or treating a gastrointestinal disorder associated with hypomotility, comprising administering an effective amount of the medicament according to the above (26);

(32-1) preferably, a method for preventing or treating irritable bowel syndrome with constipation, diabetic gastroparesis, or constipation, comprising administering an effective amount of the medicament according to the above (26); and (32-2) more preferably, a method for preventing irritable bowel syndrome with constipation, diabetic gastroparesis, or constipation.

In the invention, the "C1-C3 alkyl group" refers to a straight or branched chain alkyl group having 1 to 3 carbon atoms, and can be, for example, a methyl, ethyl, or n-propyl group. In the case of $R^1$, $R^2$, the substituent on the phenylene group represented by A, and —N(C1-C3 alkyl)-, the C1-C3 alkyl group is preferably a methyl group.

In the invention, the "C1-C6 alkyl group" refers to a straight or branched chain alkyl group having 1 to 6 carbon atoms, and can be, for example, a group described above as an example of the "C1-C3 alkyl group" or an n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl group. In the case of $R^3$ and $R^4$, the C1-C6 alkyl group is preferably a methyl group. In the case of substituent group α, the substituent on the aminocarbonyl group substitutable on the C1-C6 alkyl group in substituent group α, the substituent on the amidoxy group substitutable on the C1-C6 alkyl group in substituent group α, the substituent on the carbamido group substitutable on the C1-C6 alkyl group in substituent group α, and the substituent on the aminocarbonyl group substitutable on the C1-C6 alkoxy C1-C6 alkyl group in substituent group α, the C1-C6 alkyl group is preferably an alkyl group having 1 to 3 carbon atoms, and most preferably a methyl group.

In the invention, the "C3-C10 cycloalkyl group" refers to a 3- to 10-membered saturated cyclic hydrocarbon group which may be fused with another ring, and can be, for example, a cyclopropyl, cyclobutyl, cyclopentyl, cyclohexyl, cycloheptyl, norbornyl, adamantyl, 2,3-dihydroindenyl, 1,2,3,4-tetrahydronaphthalenyl, or 6,7,8,9-tetrahydro-5H-benzo[7]annulenyl group. In the case of M, the C3-C10 cycloalkyl group is preferably a 3- to 7-membered saturated cyclic hydrocarbon group or a C3-C7 cycloalkyl group fused with a phenyl group, and more preferably a cyclohexyl, 2,3-dihydroindenyl, 1,2,3,4-tetrahydronaphthalenyl, or 6,7,8,9-tetrahydro-5H-benzo[7]annulenyl group. In the case of $R^3$, B, and substituent group α, the C3-C10 cycloalkyl group is preferably a 3- to 7-membered saturated cyclic hydrocarbon group, and more preferably a cyclopropyl, cyclobutyl, cyclopentyl, or cyclohexyl group.

In the invention, the "C1-C6 haloalkyl group" refers to a group in which the above-described "C1-C6 alkyl group" is substituted with a halogen atom(s), and can be, for example, a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 2,2-dibromoethyl, 4-fluorobutyl, 6-iodohexyl, or 2,2-dibromoethyl group. In the case of $R^1$, the C1-C6 haloalkyl group is preferably a trifluoromethyl or difluoroethyl group, and in the case of substituent group α, the C1-C6 haloalkyl group is preferably a trifluoromethyl or difluoromethyl group.

In the invention, the "C1-C6 aminoalkyl group" refers to a group in which the above-described "C1-C6 alkyl group" is substituted with an amino group, and can be, for example, an aminomethyl, aminoethyl, aminopropyl, or aminobutyl group. In the case of substituent group α, the C1-C6 aminoalkyl group is preferably aminomethyl.

In the invention, the "C1-C3 hydroxyalkyl group" refers to a group in which the above-described "C1-C3 alkyl group" is substituted with a hydroxy group, and can be, for example, a hydroxymethyl, hydroxyethyl, 1-hydroxyethyl, or hydroxypropyl group. In the case of $R^3$, the C1-C3 hydroxyalkyl group is preferably a hydroxymethyl group or a 1-hydroxyethyl group.

In the invention, the "C1-C6 hydroxyalkyl group" refers to a group in which the above-described "C1-C6 alkyl group" is substituted with a hydroxy group, and can be, for example, a group described above as an example of the "C1-C3 hydroxyalkyl group" or a hydroxybutyl, hydroxypentyl, or hydroxyhexyl group. In the case of substituent group α and the substituent on the C1-C6 alkoxy C1-C6 alkyl group in substituent group α, the C1-C6 hydroxyalkyl group is preferably a hydroxymethyl group or a 1-hydroxyethyl group.

In the invention, the "C1-C3 alkoxy group" refers to a group in which the above-described "C1-C3 alkyl group" is bonded to an oxygen atom, and can be, for example, a straight or branched chain alkoxy group having 1 to 3 carbon atoms such as methoxy, ethoxy, n-propoxy, or isopropoxy. In the case of the substituent on the phenylene represented by A, the C1-C3 alkoxy group is preferably a methoxy or ethoxy group.

In the invention, the "C1-C6 alkoxy group" refers to a group in which the above-described "C1-C6 alkyl group" is bonded to an oxygen atom, and can be, for example, a group described above as an example of the "C1-C3 alkoxy group" or a straight or branched chain alkoxy group having 1 to 6 carbon atoms such as n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, or 2,3-dimethylbutoxy. In the case of substituent group α, the substituent on the C1-C6 aliphatic acylamino group to be substituted for the C1-C6 alkyl group in substituent group α, the substituent on the C1-C6 alkoxy C1-C6 alkyl group in substituent group α, the C1-C6 alkoxy group is preferably a methoxy or ethoxy group.

In the invention, the "C1-C6 haloalkoxy group" refers to a group in which the above-described "C1-C6 haloalkyl group" is bonded to an oxygen atom, and can be, for example, a trifluoromethoxy, trichloromethoxy, difluoromethoxy, dichloromethoxy, dibromomethoxy, fluoromethoxy, 2,2,2-trichloroethoxy, 2,2,2-trifluoroethoxy, 2-bromoethoxy, 2-chloroethoxy, 2-fluoroethoxy, or 2,2-dibromoethoxy group. In the case of substituent group α, the C1-C6 haloalkoxy group is preferably a trifluoromethoxy or difluoromethoxy group.

In the invention, the "C1-C3 alkoxy C1-C3 alkyl group" refers to a group in which the above-described "C1-C3 alkoxy group" is bonded to the above-described "C1-C3 alkyl group", and can be, for example, a methoxymethyl, methoxyethyl, ethoxymethyl, ethoxyethyl, n-propoxymethyl, n-propoxyethyl, or isopropoxymethyl group. In the case of $R^3$, the C1-C3 alkoxy C1-C3 alkyl group is preferably a methoxyethyl group.

In the invention, the "C1-C6 alkoxy C1-C6 alkyl group" refers to a group in which the above-described "C1-C6 alkoxy group" is bonded to the above-described "C1-C6 alkyl group", and can be, for example, a group described above as an example of the "C1-C3 alkoxy C1-C3 alkyl group" or an n-butoxymethyl, isobutoxymethyl, s-butoxymethyl, tert-butoxymethyl, n-pentoxymethyl, isopentoxymethyl, 2-methylbutoxymethyl, neopentoxymethyl, n-hexyloxymethyl, 4-methylpentoxymethyl, 3-methylpentoxymethyl, 2-methylpentoxymethyl, 3,3-dimethylbutoxymethyl, 2,2-dimethylbutoxymethyl, or 1,1-dimethylbutoxymethyl group. In the case of substituent group α, the C1-C6 alkoxy C1-C6 alkyl group is preferably a methoxymethyl group.

In the invention, the "C1-C6 hydroxyalkoxy group" refers to a group in which a hydroxy group is bonded to the above-described "C1-C6 alkoxy group", and can be, for example, a hydroxymethoxy or hydroxyethoxy group. In the case of substituent group α, the C1-C6 hydroxyalkoxy group is preferably a hydroxymethoxy group.

In the invention, the "C1-C6 alkylthio group" refers to a group in which the above-described "C1-C6 alkyl group" is bonded to a sulfur atom, and can be, for example, a methylthio, ethylthio, or t-butylthio group. In the case of substituent group α, the C1-C6 alkylthio group is preferably a methylthio group.

In the invention, the "C6-C10 aryl group" refers to an aromatic hydrocarbon group having 6 to 10 carbon atoms, and can be, for example, a phenyl, indenyl, naphthyl, or biphenyl group. In the case of B and substituent group α, the C6-C10 aryl group is preferably a phenyl group.

In the invention, the "C6-C10 aryloxy group" refers to a group in which the above-described "C6-C10 aryl group" is bonded to an oxygen atom, and can be, for example, a phenyloxy, indenyloxy, or naphthyloxy group. In the case of substituent group α, the C6-C10 aryloxy group is preferably a phenyloxy group.

In the invention, the "4- to 10-membered heterocyclic group containing 1 to 4 heteroatoms which may be the same or different and are selected from nitrogen, oxygen, and sulfur" refers to a 4- to 10-membered heterocyclic group containing 1 to 4 atoms selected from a sulfur atom, an oxygen atom, and a nitrogen atom, and can be, for example, an aromatic heterocyclic group such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, or tetrazolyl; or a partially or completely reduced group corresponding to any of these aromatic heterocyclic groups such as morpholinyl, thiomorpholinyl, pyrrolidinyl, pyrrolinyl, imidazolidinyl, imidazolinyl, pyrazolidinyl, piperidinyl, piperazinyl, or tetrahydropyranyl. Incidentally, the above-described "4- to 10-membered heterocyclic group" may be fused with another cyclic group, and can be, for example, a benzofuranyl, chromenyl, indolidinyl, isoindolyl, indolyl, indazolyl, purinyl, quinolidinyl, isoquinolyl, quinolyl, phthalazinyl, naphthylidinyl, quinoxalinyl, quinazolinyl, isoindolinyl, 2,3-dihydro-1-benzofuranyl, 3,4-dihydro-1H-isochromenyl, 1,2,3,4-tetrahydroquinolinyl, or 1,2,3,4-tetrahydroisoquinolinyl group. In the case of B, the 4- to 10-membered heterocyclic group is preferably a 4- to 10-membered heterocyclic group which contains at least one nitrogen atom and may contain an oxygen atom or a sulfur atom, and can be, for example, an aromatic heterocyclic group such as pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl, or pyrazinyl; or a partially or completely reduced group corresponding to any of these aromatic heterocyclic groups such as morpholinyl, thiomorpholinyl, pyrrolidinyl, pyrrolinyl, imidazolidinyl, imidazolinyl, pyrazolidinyl, pyrazolinyl, piperidinyl, piperazinyl, or tetrahydropyranyl, more preferably a pyridyl, pyrimidyl, pyrazolyl, pyrrolidinyl, piperidinyl, piperazinyl, morpholinyl, or tetrahydropyranyl group, and further more preferably, an aromatic heterocyclic group. In the case of substituent group α, the substituent on the C1-C6 alkyl group in substituent group α, the substituent on the C3-C10 cycloalkyl group in substituent group α, the substituent on the C1-C6 haloalkyl group in substituent group α, the substituent on the C1-C6 hydroxyalkyl group in substituent group α, and the substituent on the C1-C6 alkoxy C1-C6 alkyl group in substituent group α, the 4- to 10-membered heterocyclic group is preferably an aromatic heterocyclic group.

In the invention, the "4- to 10-membered heterocyclic carbonyl group containing 1 to 4 heteroatoms which may be the same or different and are selected from nitrogen, oxygen, and sulfur" refers to a group in which the above-described "4- to 10-membered heterocyclic group containing 1 to 4 heteroatoms which may be the same or different and are selected from nitrogen, oxygen, and sulfur" is bonded to a carbonyl group, and in the case of the substituent on the C1-C6 alkyl group substitutable on the C1-C6 alkyl group in substituent group α, the 4- to 10-membered heterocyclic carbonyl group is preferably a 4- to 10-membered heterocyclic carbonyl group which contains at least one nitrogen atom and may contain an oxygen atom or a sulfur atom, and can be, for example, an aromatic heterocyclic carbonyl group such as pyrrolecarbonyl, azepinecarbonyl, pyrazolecarbonyl, imidazolecarbonyl, oxazolecarbonyl, isoxazolecarbonyl, thiazolecarbonyl, isothiazolecarbonyl, 1,2,3-oxadiazolecarbonyl, triazolecarbonyl, tetrazolecarbonyl, thiadiazolecarbonyl, pyridinecarbonyl, pyridazinecarbonyl, pyrimidinecarbonyl, or pyrazinecarbonyl; a partially or completely reduced heterocyclic carbonyl group corresponding to any of these aromatic heterocyclic carbonyl groups such as morpholinecarbonyl, thiomorpholinecarbonyl, pyrrolidinecarbonyl, pyrrolinecarbonyl, imidazolidinecarbonyl, imidazolinecarbonyl, pyrazolinecarbonyl, piperidinecarbonyl, piperazinecarbonyl, or tetrahydropyranecarbonyl; or a group having an oxo group on the ring such as a 2-oxopyrrolidinecarbonyl or 2-oxo-1,3-oxazolidinecarbonyl group, and more preferably a pyrrolidinecarbonyl group.

In the invention, the "C1-C6 alkoxycarbonyl group" refers to a group in which the above-described "C1-C6 alkoxy group" is bonded to a carbonyl group, and can be, for example, a straight or branched chain alkoxycarbonyl group having 1 to 6 carbon atoms such as methoxycarbonyl, ethoxycarbonyl, n-propoxycarbonyl, isopropoxycarbonyl, n-butoxycarbonyl, isobutoxycarbonyl, s-butoxycarbonyl, tert-butoxycarbonyl, n-pentoxycarbonyl, isopentoxycarbonyl, 2-methylbutoxycarbonyl, neopentoxycarbonyl, n-hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, or 2,3-dimethylbutoxycarbonyl. In the case of substituent group α, the substituent on the C1-C6 alkyl group in substituent group α, the substituent on the C3-C10 cycloalkyl group in substituent group α, the substituent on the C1-C6 haloalkyl group in substituent group α, the substituent on the C1-C6 hydroxyalkyl group in substituent group α, and the substituent on the C1-C6 alkoxy C1-C6 alkyl group in substituent group α, the C1-C6 alkoxycarbonyl group is preferably methoxycarbonyl, ethoxycarbonyl, or isopropoxycarbonyl.

In the invention, the "C1-C6 aliphatic acyl group" refers to a group in which an aliphatic hydrocarbon group having 1 to 6 carbon atoms is bonded to a carbonyl group, and can be, for example, an alkylcarbonyl group such as a formyl, acetyl, propionyl, butylyl, isobutylyl, pentanoyl, pivaloyl, valeryl, or isovaleryl group; a haloalkylcarbonyl group such as chloroacetyl, dichloroacetyl, trichloroacetyl, or trifluoroacetyl; a lower alkoxyalkylcarbonyl group such as methoxyacetyl; an unsaturated alkylcarbonyl group such as (E)-2-methyl-2-butenoyl; or the like. In the case of substituent group α and the substituent on the C1-C6 alkyl group in substituent group α, the C1-C6 aliphatic acyl group is preferably a formyl group, an acetyl group, or a trifluoroacetyl group.

In the invention, the "C1-C6 alkylamino group" refers to a group in which the above-described "C1-C6 alkyl group" is bonded to an amino group, and can be, for example, a methylamino, ethylamino, n-propylamino, isopropylamino, n-butylamino, isobutylamino, s-butylamino, tert-butylamino, n-pentylamino, isopentylamino, 2-methylbutylamino, neopentylamino, 1-ethylpropylamino, n-hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino, or 2-ethylbutylamino group. In the case of substituent group α, the C1-C6 alkylamino group is preferably a methylamino group, an ethylamino group, or an isopropylamino group.

In the invention, the "C3-C10 cycloalkylamino group" refers to a group in which the above-described "C3-C10 cycloalkyl" is bonded to an amino group, and can be, for example, a cyclopropylamino, cyclobutylamino, cyclopentylamino, cyclohexylamino, cycloheptylamino, norbornylamino, or adamantylamino group. In the case of substituent group α, the C3-C10 cycloalkylamino group is preferably a 3- to 7-membered saturated cyclic hydrocarbon amino group.

In the invention, the "C1-C6 dialkylamino group" refers to a group in which an amino group is substituted with two of the above-described "C1-C6 alkyl groups" which may be the same or different, and can be, for example, an N,N-dimethylamino, N,N-diethylamino, N,N-di-n-propylamino, N,N-diisopropylamino, N,N-di-n-butylamino, N,N-diisobutylamino, N,N-di-s-butylamino, N,N-di-tert-butylamino, N,N-di-n-pentylamino, N,N-diisopentylamino, N,N-di-2-methylbutylamino, N,N-dineopentylamino, N,N-di-1-ethylpropylamino, N,N-di-n-hexylamino, N,N-diisohexylamino, N,N-di-4-methylpentylamino, N,N-di-3-methylpentylamino, N,N-di-2-methylpentylamino, N,N-di-1-methylpentylamino, N,N-ethylmethylamino, or N,N-isopropylmethylamino group. In the case of substituent group α, the C1-C6 dialkylamino group is preferably a dimethylamino or diethylamino group.

In the invention, the "C1-C6 alkoxyamino group" refers to a group in which the above-described "C1-C6 alkoxy group" is bonded to an amino group, and can be, for example, a straight or branched chain alkoxyamino group having 1 to 6 carbon atoms such as methoxyamino, ethoxyamino, n-propoxyamino, isopropoxyamino, n-butoxyamino, isobutoxyamino, s-butoxyamino, tert-butoxyamino, n-pentoxyamino, isopentoxyamino, 2-methylbutoxyamino, neopentoxyamino, n-hexyloxyamino, 4-methylpentoxyamino, 3-methylpentoxyamino, 2-methylpentoxyamino, 3,3-dimethylbutoxyamino, 2,2-dimethylbutoxyamino, 1,1-dimethylbutoxyamino, 1,2-dimethylbutoxyamino, 1,3-dimethylbutoxyamino, or 2,3-dimethylbutoxyamino. In the case of substituent group α, the C1-C6 alkoxyamino group is preferably a methoxyamino group, an ethoxyamino group, or an n-propoxyamino group.

In the invention, the "C1-C6 aliphatic acylamino group" refers to a group in which the above-described "C1-C6 aliphatic acyl group" is bonded to an amino group, and can be, for example, an alkylcarbonylamino group such as a formylamino, acetylamino, propionylamino, isopropanoylamino, butanoylamino, isobutanoylamino, pentanoylamino, pivaloylamino, valerylamino, or isovalerylamino group; a haloalkylcarbonylamino group such as chloroacetylamino, dichloroacetylamino, trichloroacetylamino, or trifluoroacetylamino; a lower alkoxyalkylcarbonylamino group such as methoxyacetylamino; an unsaturated alkylcarbonylamino group such as (E)-2-methyl-2-butenoylamino; or the like. In the case of substituent group α and the substituent on the C1-C6 alkyl group in substituent group α, the C1-C6 aliphatic acylamino group is preferably an isopropanoylamino group.

In the invention, the "C1-C6 aliphatic acyl C1-C6 alkylamino group" refers to a group in which the above-described "C1-C6 aliphatic acyl group" is bonded to the amino group of the above-described "C1-C6 alkylamino group", and can be, for example, an alkylcarbonylalkylamino group such as a formylmethylamino, acetylmethylamino, propionylmethylamino, isopropanoylmethylamino, butanoylmethylamino, or isobutanoylmethylamino group; a haloalkylcarbonylalkylamino group such as chloroacetylmethylamino, dichloroacetylmethylamino, trichloroacetylmethylamino, or trifluoroacetylmethylamino; a lower alkoxyalkylcarbonylalkylamino group such as methoxyacetylmethylamino; or the like. In the case of the substituent on the C1-C6 alkyl group in substituent group α, the C1-C6 aliphatic acyl C1-C6 alkylamino group is preferably an isopropanoylmethylamino group.

In the invention, the "C1-C6 alkoxycarbonylamino group" refers to a group in which the above-described "C1-C6 alkoxy group" is bonded to a carbonylamino group, and can be, for example, a straight or branched chain alkoxycarbonylamino group having 1 to 6 carbon atoms such as methoxycarbonylamino, ethoxycarbonylamino, n-propoxycarbonylamino, isopropoxycarbonylamino, n-butoxycarbonylamino, isobutoxycarbonylamino, s-butoxycarbonylamino, tert-butoxycarbonylamino, n-pent oxycarbonylamino, isopentoxycarbonylamino, 2-methylbutoxycarbonylamino, neopentoxycarbonylamino, n-hexyloxycarbonylamino, 4-methylpentoxycarbonylamino, 3-methylpentoxycarbonylamino, 2-methylpentoxycarbonylamino, 3,3-dimethylbutoxycarbonylamino, 2,2-dimethylbutoxycarbonylamino, 1,1-dimethylbutoxycarbonylamino, 1,2-dimethylbutoxycarbonylamino, 1,3-dimethylbutoxycarbonylamino, or 2,3-dimethylbutoxycarbonylamino. In the case of substituent group α and the substituent on the C1-C6 alkyl group in substituent group α, the C1-C6 alkoxycarbonylamino group is preferably a methoxycarbonylamino group, an ethoxycarbonylamino group, or an n-propoxycarbonylamino group.

In the invention, the "C1-C6 alkylsulfonyl group" refers to a group in which the above-described "C1-C6 alkyl group" is bonded to a sulfonyl group, and can be, for example, a methanesulfonyl, ethanesulfonyl, n-propanesulfonyl, isopropanesulfonyl, n-butanesulfonyl, isobutanesulfonyl, s-butanesulfonyl, tert-butanesulfonyl, n-pentanesulfonyl, isopentanesulfonyl, 2-methylbutanesulfonyl, neopentanesulfonyl, n-hexanesulfonyl, 4-methylpentanesulfonyl, 3-methylpentanesulfonyl, 2-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl, or 2,3-dimethylbutanesulfonyl group. In the case of substituent group α and the substituent on the C1-C6 alkyl group in substituent group α, the C1-C6 alkylsulfonyl group is preferably a straight or branched chain alkanesulfonyl group having 1 to 4-carbon atoms, and most preferably a methanesulfonyl group.

In the invention, the "C1-C6 dialkylaminosulfonyl group" refers to a group in which the above-described "C1-C6 dialkylamino group" is bonded to a sulfonyl group, and can be, for example, an N,N-dimethylaminosulfonyl, N,N-diethylaminosulfonyl, N,N-di-n-propylaminosulfonyl, N,N-diisopropylaminosulfonyl, N,N-di-n-butylaminosulfonyl, N,N-diisobutylaminosulfonyl, N,N-di-s-butylaminosulfonyl, N,N-di-tert-butylaminosulfonyl, N,N-di-n-pentylaminosulfonyl, N,N-diisopentylaminosulfonyl, N,N-di-2-methylbutylaminosulfonyl, N,N-dineopentylaminosulfonyl, N,N-di-1-ethylpropylaminosulfonyl, N,N-di-n-hexylaminosulfonyl, N,N-diisohexylaminosulfonyl, N,N-di-4-methylpentylaminosulfonyl, N,N-di-3-methylpentylaminosulfonyl, N,N-di-2-methylpentylaminosulfonyl, N,N-di-1-methylpentylaminosulfonyl, N,N-ethylmethylaminosulfonyl, or N,N-isopropylmethylaminosulfonyl group. In the case of substituent group α, the C1-C6 dialkylaminosulfonyl group is preferably a dimethylaminosulfonyl or diethylaminosulfonyl group.

In the invention, the "halogen atom" is a fluorine atom, a chlorine atom, a bromine atom, or an iodine atom. In the case of $R^4$, the substituent on the phenylene group represented by A, and substituent group α, the halogen atom is preferably a chlorine atom or a fluorine atom, and more preferably a fluorine atom.

In the invention, the "pharmacologically acceptable salt" refers to a salt which can be formed by reacting with an acid in the case where the compound of the invention has a basic group such as an amino group, or by reacting with a base in the case where the compound of the invention has an acidic group such as a carboxyl group.

The salt derived from a basic group can be preferably a hydrohalide salt such as a hydrofluoride, a hydrochloride, a hydrobromide, or a hydroiodide; an inorganic acid salt such as a nitrate, a perchlorate, a sulfate, or a phosphate; a lower alkanesulfonate such as a methanesulfonate, a trifluoromethanesulfonate, or an ethanesulfonate; an arylsulfonate such as a benzenesulfonate or a p-toluenesulfonate; an organic acid salt such as an acetate, a malate, a fumarate, a succinate, a citrate, an ascorbate, a tartrate, an oxalate, or a maleate; or an amino acid salt such as a glycine salt, a lysine salt, an arginine salt, an ornithine salt, a glutamic acid salt, or an aspartic acid salt. The salt is preferably a hydrohalide salt or an inorganic acid salt.

On the other hand, the salt derived from an acidic group can be preferably a metal salt such as an alkali metal salt (such as a sodium salt, a potassium salt, or a lithium salt), an alkaline earth metal salt (such as a calcium salt or a magnesium salt), an aluminum salt, or an iron salt; an amine salt such as an inorganic amine salt (such as an ammonium salt) or an organic amine salt (such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenethylamine salt, a piperazine salt, a tetramethylammonium salt, or a tris(hydroxymethyl)aminomethane salt); or an amino acid salt such as a glycine salt, a lysine salt, an arginine salt, an ornithine salt, a glutamic acid salt, or an aspartic acid salt.

Incidentally, the cyclohexane derivative compound having the above-described general formula (I) may have various isomers. As for the above-described general formula (I), these isomers and racemic and non-racemic mixtures of these isomers are all represented by a single formula. Therefore, the invention includes all of these isomers and mixtures of these isomers in various proportions. Further, the invention also includes compounds labeled with any of various radioisotopes [tritium ($^3$H), iodine-125 ($^{125}$I), carbon-14 ($^{14}$C), and the like] or non-radioisotopes [deuterium ($^2$H) and the like].

Further, in the case where the cyclohexane derivative compounds having the above-described general formula (I) and salts thereof form solvates (for example, hydrates), the invention also includes all of these solvates.

Further, the invention also includes all of the compounds that are metabolized in the body and converted to cyclohexane derivative compounds having the above-described general formula (I) or salts thereof.

In the invention, the general formula (I) is preferably the following general formula (IA).

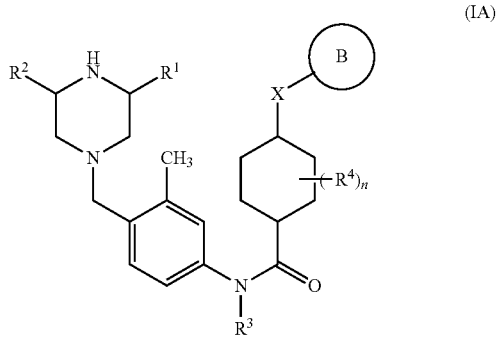

(IA)

In this formula, B, X, $R^1$, $R^2$, $R^3$, $R^4$, and n have the same definitions as described above. The general formula (I) is more preferably the following general formula (IB).

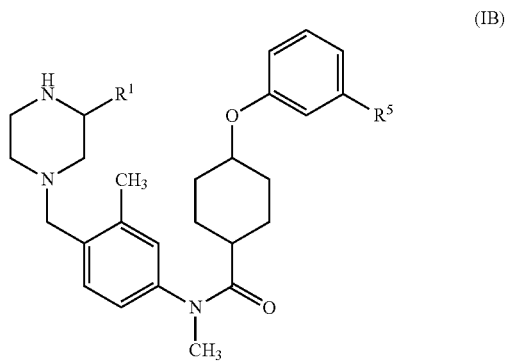

(IB)

In this formula, $R^1$ and $R^5$ have the same definitions as described above.

The general formula (IA) is preferably the following general formula (Ia).

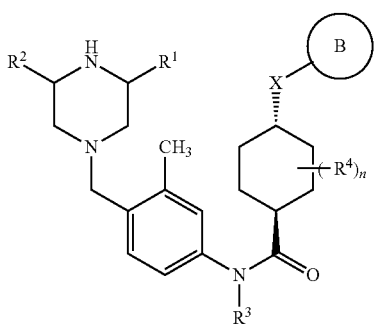

(Ia)

In the formula, B, X, $R^1$, $R^2$, $R^3$, $R^4$, and n have the same definitions as described above. The general formula (IA) is more preferably the following general formula (Ib).

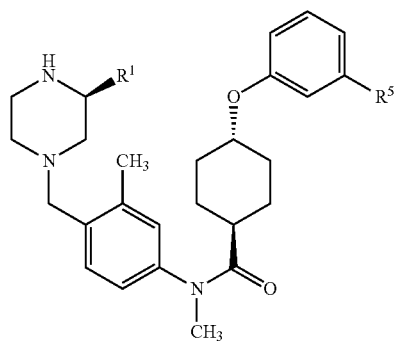

(Ib)

In this formula, $R^1$ and $R^5$ have the same definitions as described above.

A is preferably a phenylene group or a phenylene group substituted with one to three C1-C3 alkyl groups, and more preferably a phenylene group optionally substituted with one C1-C3 alkyl group.

B is preferably a 4- to 10-membered heterocyclic group containing 1 to 4 heteroatoms which may be the same or different and are selected from nitrogen, oxygen, and sulfur (the heterocyclic group may be optionally substituted with 1 to 5 groups selected from substituent group α) or a C6-C10 aryl group (the aryl group may be optionally substituted with 1 to 5 groups selected from substituent group α), and more preferably a phenyl group which may be optionally substituted with 1 to 5 groups selected from substituent group α or a pyridyl group which may be optionally substituted with 1 to 5 groups selected from substituent group α.

$R^1$ is preferably a C1-C3 alkyl group and more preferably a methyl group.

$R^2$ is preferably a hydrogen atom.

$R^3$ is preferably a C1-C6 alkyl group, and more preferably a methyl group.

$R^4$ is preferably a hydrogen atom.

n is preferably 1 or 2.

X is preferably —N— or —O—, and more preferably —O—.

In the case where the C6-C10 aryl group represented by B is substituted, substituent group α is preferably a halogen atom, a C1-C6 alkyl group {the alkyl group may be optionally substituted with 1 to 3 groups selected from a C1-C6 aliphatic acyl group, a carboxyl group, a C1-C6 alkoxycarbonyl group, an aminocarbonyl group (the aminocarbonyl group may be optionally substituted with 1 or 2 groups selected from a C1-C6 alkyl group, a C1-C6 haloalkyl group, and a C1-C6 alkoxy C1-C6 alkyl group), a carbamido group which may be optionally substituted with one or three C1-C6 alkyl groups, a C1-C6 aliphatic acylamino group which may be optionally substituted with a C1-C6 alkoxy group, a C1-C6 aliphatic acyl C1-C6 alkylamino group an amidoxy group which may be optionally substituted with one or two C1-C6 alkyl groups, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C1-C6 hydroxyalkyl group, or a C1-C6 alkoxy C1-C6 alkyl group (the alkoxyalkyl group may be optionally substituted with 1 to 3 groups selected from a hydroxy group, a C1-C6 alkoxy group, a C1-C6 hydroxyalkyl group, a C1-C6 alkyl aminocarbonyl group, a carboxyl group, a C1-C6 alkoxycarbonyl group, and a 4- to 10-membered heterocyclic group containing 1 to 4 heteroatoms which may be the same or different and are selected from nitrogen, oxygen, and sulfur), and more preferably a C1-C6 alkyl group {the alkyl group may be optionally substituted with 1 to 3 groups selected from an aminocarbonyl group (the aminocarbonyl group may be optionally substituted with one or two C1-C6 alkyl groups) and an amidoxy group which may be optionally substituted with one or two C1-C6 alkyl groups} or a C1-C6 hydroxyalkyl group.

In the case where the C3-C10 cycloalkyl group represented by B is substituted, substituent group α is preferably a halogen atom, a C1-C6 alkyl group (the alkyl group being optionally substituted with 1 to 3 groups selected from a carboxyl group and a C1-C6 alkoxycarbonyl group) or a C1-C6 hydroxyalkyl group.

In the case where the 4- to 10-membered heterocyclic group containing 1 to 4 heteroatoms which may be the same or different and are selected from nitrogen, oxygen, and sulfur represented by B is substituted, substituent group α is preferably a halogen atom, a C1-C6 alkyl group (the alkyl group may be optionally substituted with 1 to 3 groups selected from a carboxyl group and a C1-C6 alkoxycarbonyl group), a C1-C6 hydroxyalkyl group, or a cyano group, and more preferably a cyano group.

$L^1$ is preferably a butoxycarbonyl group.

$L^2$ is preferably a t-butyl group.

$L^3$ is preferably a halogen atom.

A compound having the following general formula (I) of the invention can be produced by, for example, using a known compound as a starting material according to the processes described below.

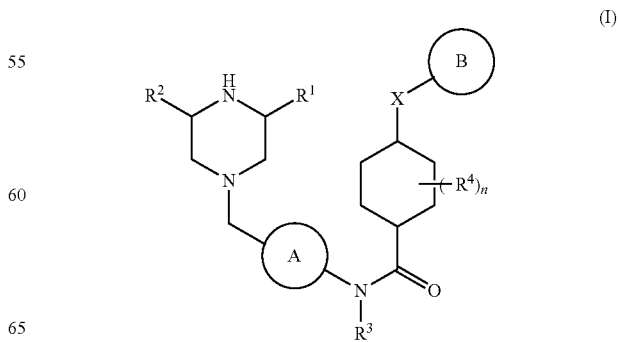

(I)

In the above-described formula and the following description, A, B, X, n, $R^1$, $R^2$, $R^3$, and $R^4$ have the same definitions as described above.

Process A: Process for Producing Intermediate

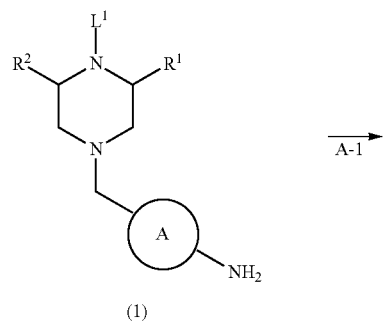

(1)

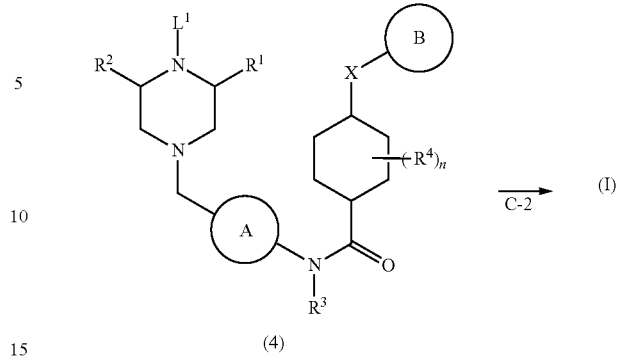

Process B: Process for Producing Intermediate

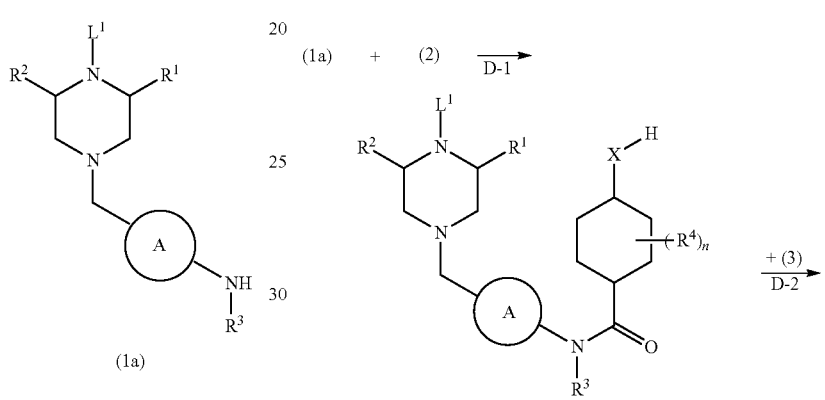

Process D (1a) + (2) $\xrightarrow{\text{D-1}}$

(4) $\xrightarrow{\text{C-2}}$ (I)

Process E (1) + (2c) $\xrightarrow{\text{E-1}}$

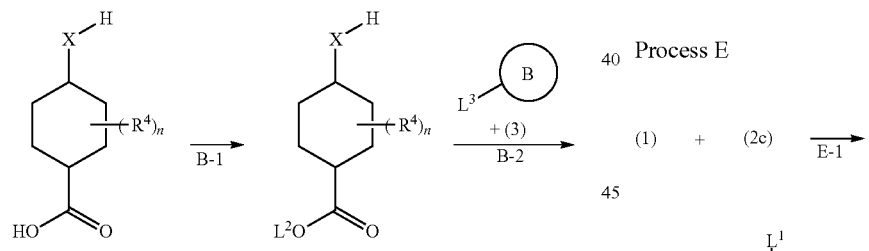

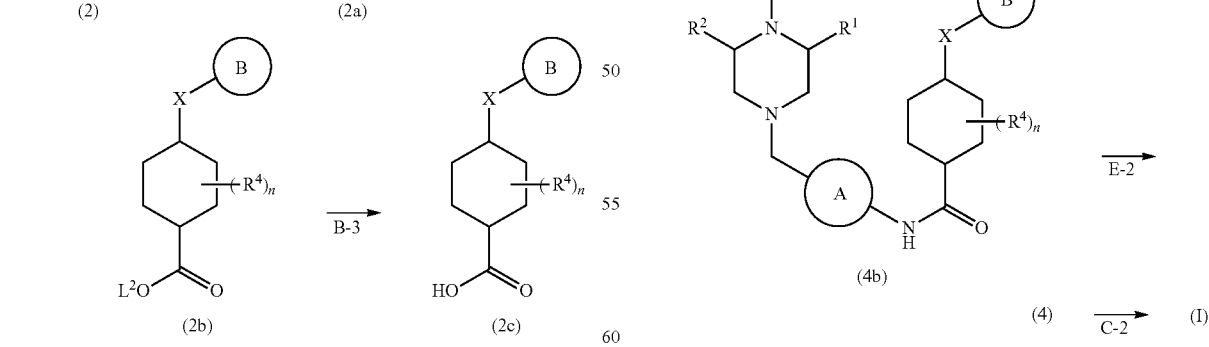

(4) $\xrightarrow{\text{C-2}}$ (I)

Process C (1a) + (2c) $\xrightarrow{\text{C-1}}$

Process F (1) + (2) $\xrightarrow{\text{F-1}}$

-continued

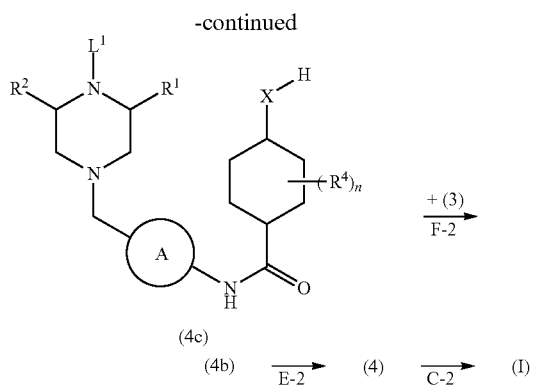

In the above-described processes and the following description, $L^1$ represents a protecting group of amine, $L^2$ represents a C1-C6 alkyl group, and $L^3$ represents a halogen atom or a hydroxy group.

In the above-described processes and the following description, the protecting group of amine in the definition of $L^1$ is not particularly limited as long as it is a group to be used in the field of organic synthetic chemistry, however, preferred is a butoxycarbonyl group.

A process for producing Compound (I) of the invention can be selected from the above-described Process C to Process F according to the desired compound.

Hereinafter, the respective processes will be described.
(Process A)
(Process A-1)

This process is a process for producing Compound (1a) by alkylating the amino group of Compound (1) in the presence of a metal boride using an aldehyde, a ketone, or a ketone equivalent.

As the solvent, a mixed solvent of an organic solvent and an acid, which does not inhibit the reaction and dissolves the starting material to some extent, is used. Examples of the organic solvent include ethers such as diethyl ether, diisopropyl ether, tetrahydrofuran, dioxane, dimethoxyethane, and diethylene glycol dimethyl ether; and halogenated hydrocarbons such as dichloromethane, chloroform, carbon tetrachloride, dichloroethane, chlorobenzene, and dichlorobenzene, and preferred is tetrahydrofuran. Examples of the acid include organic acids such as acetic acid, formic acid, oxalic acid, methanesulfonic acid, p-toluenesulfonic acid, camphorsulfonic acid, trifluoroacetic acid, and trifluoromethanesulfonic acid, and preferred is acetic acid.

As the aldehyde, ketone, or ketone equivalent, 2-methoxypropene or the like is preferably used.

As the reagent, an alkali metal boride such as sodium triacetoxy borohydride is used.

The reaction temperature is from 0° C. to 100° C., preferably from 10° C. to 50° C., and more preferably room temperature.

The reaction time is from 0.5 hour to 12 hours, and preferably from 0.5 hour to 3 hours.
(Process B)
(Process B-1)

This process is a process for producing Compound (2a) by esterifying the carboxyl group of Compound (2).

Examples of the reagent include N,N-dimethylformamide di-tert-butyl acetal and N,N'-diisopropyl-O-tert-butylisourea, and preferred is N,N-dimethylformamide di-tert-butyl acetal.

The solvent is not particularly limited as long as it does not inhibit the reaction. However, examples thereof include aromatic hydrocarbons such as benzene, toluene, and xylene, and preferred is toluene.

The reaction temperature is from 50° C. to 120° C.

The reaction time is from 0.5 hour to 24 hours.
(Process B-2)

This process is a process for producing Compound (2b) by adding Compound (3) to Compound (2a) in the presence of a base.

The solvent is not particularly limited as long as it does not inhibit the reaction and dissolves the starting material to some extent. However, examples thereof include amides such as formamide, dimethylformamide, dimethylacetamide, N-methyl-2-pyrrolidone, and hexamethylphosphorotriamide, and preferred is dimethylformamide.

Examples of the base include alkali metal hydrides such as lithium hydride, sodium hydride, and potassium hydride, and preferred is sodium hydride.

The reaction temperature is from 0° C. to 150° C.

The reaction time is from 1 hour to 24 hours.
(Process B-3)

This process is a process for producing Compound (2c) by hydrolyzing the ester of Compound (2b).

The hydrolysis of the ester can be carried out by a method well known in the field of organic synthetic chemistry, but is preferably a hydrolysis reaction carried out in the presence of an acid.

The solvent is not particularly limited as long as it does not inhibit the reaction. However, examples thereof include halogenated hydrocarbons such as dichloromethane, chloroform, carbon tetrachloride, dichloroethane, chlorobenzene, and dichlorobenzene, and preferred is dichloromethane.

Examples of the acid include organic acids such as methanesulfonic acid, p-toluenesulfonic acid, camphorsulfonic acid, trifluoroacetic acid, and trifluoromethanesulfonic acid, and preferred is trifluoroacetic acid.

The reaction temperature is from 0° C. to 50° C., and preferably room temperature.

The reaction time is from 0.5 hour to 6 hours.
(Process C)
(Process C-1)

This process is a process for producing Compound (4) by converting Compound (2c) into an acid halide, and then, condensing the resulting acid halide with Compound (1a) in the presence of a base.

The conversion into an acid halide can be carried out according to a method well known in the field of organic synthetic chemistry, but is preferably conversion into an acid chloride using thionyl chloride, oxalyl chloride, or the like. The conversion into an acid halide may be carried out in a solvent, and preferably, a halogenated hydrocarbon such as dichloromethane, chloroform, carbon tetrachloride, dichloroethane, chlorobenzene, or dichlorobenzene is used as the solvent.

The solvent to be used in the condensation is not particularly limited as long as it does not inhibit the reaction. However, examples thereof include halogenated hydrocarbons such as dichloromethane, chloroform, carbon tetrachloride, dichloroethane, chlorobenzene, and dichlorobenzene; and aromatic hydrocarbons such as benzene, toluene, and xylene, and preferred is an aromatic hydrocarbon.

As the base, preferred is an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), or 1,8-diazabicyclo[5.4.0]undec-7-ene (DBU), and more preferred is triethylamine.

The reaction temperature is from 0° C. to 80° C., and preferably from 0° C. to room temperature.

The reaction time is from 0.5 hour to 3 hours, and preferably from 1 hour to 2 hours.

(Process C-2)

This process is a process for producing Compound (I) by deprotecting the protecting group $L^1$ of piperazine of Compound (4).

The deprotection can be carried out according to a method well known in the field of organic synthetic chemistry, but is preferably a hydrolysis reaction carried out in the presence of an acid.

The solvent is not particularly limited as long as it does not inhibit the reaction. However, preferred is, for example, a halogenated hydrocarbon such as dichloromethane, chloroform, carbon tetrachloride, dichloroethane, chlorobenzene, or dichlorobenzene.

Examples of the acid include organic acids such as methanesulfonic acid, p-toluenesulfonic acid, camphorsulfonic acid, trifluoroacetic acid, and trifluoromethanesulfonic acid, and preferred is trifluoroacetic acid.

The reaction temperature is from 0° C. to 50° C., and preferably room temperature.

The reaction time is from 0.5 hour to 6 hours, and preferably from 1 hour to 2 hours.

(Process D)

(Process D-1)

This process is a process for producing Compound (4a) by condensing Compound (1a) and Compound 2c.

The condensation can be carried out according to a method well known in the field of organic synthetic chemistry, but is preferably a reaction carried out in the presence of a dehydration-condensing agent.

The solvent is not particularly limited as long as it does not inhibit the reaction and dissolves the starting material to some extent. However, examples thereof include amides such as formamide, dimethylformamide, dimethylacetamide, N-methyl-2-pyrrolidone, and hexamethylphosphorotriamide; and alcohols such as methanol, ethanol, n-propanol, isopropanol, n-butanol, isobutanol, t-butanol, isoamyl alcohol, diethylene glycol, glycerin, octanol, cyclohexanol, and methyl cellosolve, and preferred is dimethylformamide or ethanol.

Examples of the dehydration-condensing agent include N,N'-dicyclohexylcarbodiimide, 1-ethyl-3-(3-dimethylaminopropyl)carbodiimide hydrochloride, diphenylphosphoryl azide, and 4-(4,6-dimethoxy-1,3,5-triazin-2-yl)-4-methylmorpholium chloride hydrate, and preferred is 4-(4,6-dimethoxy-1,3,5-triazin-2-yl)-4-methylmorpholium chloride hydrate.

The reaction temperature is from 0° C. to 50° C., and preferably room temperature.

The reaction time is from 0.5 hour to 6 hours, and preferably from 1 hour to 2 hours.

(Process D-2)

This process is a process for producing Compound (4) by adding Compound (3) to Compound (4a), and according to the compound, a reaction such as a Mitsunobu reaction or a nucleophilic aromatic substitution reaction can be selected.

The reagent to be used in the Mitsunobu reaction is not particularly limited as long as it is a reagent which can be generally used in a Mitsunobu reaction, however, preferred is a combination of an azo compound such as a di(lower alkyl)azodicarboxylate (such as diethyl azodicarboxylate or diisopropyl azodicarboxylate) or a heteroaryl azodicarbonyl (such as 1,1'-(azodicarbonyl)dipiperidine) with a phosphine such as a triarylphosphine (such as triphenylphosphine) or a tri(lower alkyl)phosphine (such as tri-n-butyl phosphine) or a phosphorane reagent such as (cyanomethylene)trimethylphosphorane or (cyanomethylene)tributylphosphorane, more preferred is a phosphorane reagent such as (cyanomethylene)trimethylphosphorane or (cyanomethylene)tributylphosphorane, and most preferred is (cyanomethylene)tributylphosphorane.

The solvent to be used is not particularly limited as long as it does not inhibit the reaction and dissolves the starting material to some extent, however, preferred examples thereof include aromatic hydrocarbons such as benzene, toluene, and xylene; halogenated hydrocarbons such as methylene chloride, chloroform, carbon tetrachloride, dichloroethane, chlorobenzene, and dichlorobenzene; esters such as ethyl formate, ethyl acetate, propyl acetate, butyl acetate, and diethyl carbonate; ethers such as diethyl ether, diisopropyl ether, tetrahydrofuran, dioxane, dimethoxyethane, and diethylene glycol dimethyl ether; nitriles such as acetonitrile and isobutyronitrile; amides such as formamide, N,N-dimethylformamide, N,N-dimethylacetamide, N-methyl-2-pyrrolidone, N-methylpyrrolidinone, and hexamethylphosphorotriamide; and sulfoxides such as dimethylsulfoxide and sulfolane, and preferred are aromatic hydrocarbons and ethers.

The reaction temperature is from 20° C. to 120° C., and preferably from 50° C. to 100° C.

The reaction time varies depending on the reaction temperature, starting material compound, reaction reagent, or the type of solvent to be used, but is generally from 30 minutes to 12 hours, and preferably from 1 hour to 2 hours.

The nucleophilic aromatic substitution reaction can be carried out according to a method well known in the field of organic synthetic chemistry, but is preferably a reaction carried out in the presence of a base.

The solvent is not particularly limited as long as it does not inhibit the reaction and dissolves the starting material to some extent, however, examples thereof include amides such as formamide, dimethylformamide, dimethylacetamide, N-methyl-2-pyrrolidone, and hexamethylphosphorotriamide, and preferred is dimethylformamide.

Examples of the base include alkali metal hydrides such as lithium hydride, sodium hydride, and potassium hydride, and preferred is sodium hydride.

The reaction temperature is from 0° C. to 150° C., and preferably from 50° C. to 150° C.

The reaction time is from 1 hour to 24 hours, and preferably from 1 hour to 2 hours.

(Process E)

(Process E-1)

This process is a process for producing Compound (4b) by condensing Compound (1) and Compound (2c).

The condensation can be carried out according to a method well known in the field of organic synthetic chemistry, but is preferably a reaction carried out in the presence of a dehydration-condensing agent.

The solvent is not particularly limited as long as it does not inhibit the reaction and dissolves the starting material to some extent. However, examples thereof include amides such as formamide, dimethylformamide, dimethylacetamide, N-methyl-2-pyrrolidone, and hexamethylphosphorotriamide; and alcohols such as methanol, ethanol, n-propanol, isopropanol, n-butanol, isobutanol, t-butanol, isoamyl alcohol, diethylene glycol, glycerin, octanol, cyclohexanol, and methyl cellosolve, and preferred is dimethylformamide or ethanol.

Examples of the dehydration-condensing agent include N,N'-dicyclohexylcarbodiimide, 1-ethyl-3-(3-dimethylaminopropyl)carbodiimide hydrochloride, diphenylphosphoryl azide, and 4-(4,6-dimethoxy-1,3,5-triazin-2-yl)-4-methylmorpholium chloride hydrate, and preferred is 4-(4,6-dimethoxy-1,3,5-triazin-2-yl)-4-methylmorpholium chloride hydrate.

The reaction temperature is from 0° C. to 50° C., and preferably room temperature.

The reaction time is from 0.5 hour to 24 hours, and preferably from 6 hours to 12 hours.

(Process E-2)

This process is a process for producing Compound 4 by alkylating Compound (4b) in the presence of a base using an alkylating agent.

The solvent to be used is not particularly limited as long as it does not inhibit the reaction and dissolves the starting material to some extent, however, examples thereof include amides such as formamide, dimethylformamide, dimethylacetamide, N-methyl-2-pyrrolidone, and hexamethylphosphorotriamide, and preferred is dimethylformamide.

Examples of the base include alkali metal hydrides such as lithium hydride, sodium hydride, and potassium hydride, and preferred is sodium hydride.

As the alkylating agent, preferred is an alkyl halide, and more preferred is an alkyl iodide.

The reaction temperature is from 0° C. to 100° C., and preferably from room temperature to 60° C.

The reaction time is from 0.5 hour to 24 hours, and preferably from 6 hours to 12 hours.

(Process F)
(Process F-1)

This process is a process for producing Compound (4c) by condensing Compound (1) and Compound (2).

The condensation can be carried out according to a method well known in the field of organic synthetic chemistry, but is preferably a reaction carried out in the presence of a dehydration-condensing agent.

The solvent is not particularly limited as long as it does not inhibit the reaction and dissolves the starting material to some extent. However, examples thereof include amides such as formamide, dimethylformamide, dimethylacetamide, N-methyl-2-pyrrolidone, and hexamethylphosphorotriamide; and alcohols such as methanol, ethanol, n-propanol, isopropanol, n-butanol, isobutanol, t-butanol, isoamyl alcohol, diethylene glycol, glycerin, octanol, cyclohexanol, and methyl cellosolve, and preferred is dimethylformamide or ethanol.

Examples of the dehydration-condensing agent include N,N'-dicyclohexylcarbodiimide, 1-ethyl-3-(3-dimethylaminopropyl)carbodiimide hydrochloride, diphenylphosphoryl azide, and 4-(4,6-dimethoxy-1,3,5-triazin-2-yl)-4-methylmorpholium chloride hydrate, and preferred is 4-(4,6-dimethoxy-1,3,5-triazin-2-yl)-4-methylmorpholium chloride hydrate.

The reaction temperature is from 0° C. to 50° C., and preferably room temperature.

The reaction time is from 0.5 hour to 24 hours, and preferably from 6 hours to 12 hours.

(Process F-2)

This process is a process for producing Compound (4b) by adding Compound (3) to Compound (4c), and according to the compound, a reaction such as a Mitsunobu reaction or a nucleophilic aromatic substitution reaction can be selected.

The reagent to be used in the Mitsunobu reaction is not particularly limited as long as it is a reagent which can be generally used in a Mitsunobu reaction, however, preferred is a combination of an azo compound such as a di(lower alkyl) azodicarboxylate (such as diethyl azodicarboxylate or diisopropyl azodicarboxylate) or a heteroaryl azodicarbonyl (such as 1,1'-(azodicarbonyl)dipiperidine) with a phosphine such as a triarylphosphine (such as triphenylphosphine) or a tri(lower alkyl)phosphine (such as tri-n-butyl phosphine) or a phosphorane reagent such as (cyanomethylene)trimethylphosphorane or (cyanomethylene)tributylphosphorane, more preferred is a phosphorane reagent such as (cyanomethylene) trimethylphosphorane or (cyanomethylene) tributylphosphorane, and most preferred is (cyanomethylene) tributylphosphorane.

The solvent to be used is not particularly limited as long as it does not inhibit the reaction and dissolves the starting material to some extent, however, preferred examples thereof include aromatic hydrocarbons such as benzene, toluene, and xylene; halogenated hydrocarbons such as methylene chloride, chloroform, carbon tetrachloride, dichloroethane, chlorobenzene, and dichlorobenzene; esters such as ethyl formate, ethyl acetate, propyl acetate, butyl acetate, and diethyl carbonate; ethers such as diethyl ether, diisopropyl ether, tetrahydrofuran, dioxane, dimethoxyethane, and diethylene glycol dimethyl ether; nitriles such as acetonitrile and isobutyronitrile; amides such as formamide, N,N-dimethylformamide, N,N-dimethylacetamide, N-methyl-2-pyrrolidone, N-methylpyrrolidinone, and hexamethylphosphorotriamide; and sulfoxides such as dimethylsulfoxide and sulfolane, and preferred are aromatic hydrocarbons and ethers.

The reaction temperature is from 20° C. to 120° C., and preferably from 50° C. to 100° C.

The reaction time varies depending on the reaction temperature, starting material compound, reaction reagent, or the type of solvent to be used, but is generally from minutes to 12 hours, and preferably from 1 hour to 2 hours.

The nucleophilic aromatic substitution reaction can be carried out according to a method well known in the field of organic synthetic chemistry, but is preferably a reaction carried out in the presence of a base.

The solvent to be used is not particularly limited as long as it does not inhibit the reaction and dissolves the starting material to some extent, however, examples thereof include amides such as formamide, dimethylformamide, dimethylacetamide, N-methyl-2-pyrrolidone, and hexamethylphosphorotriamide, and preferred is dimethylformamide.

Examples of the base include alkali metal hydrides such as lithium hydride, sodium hydride, and potassium hydride, and preferred is sodium hydride.

The reaction temperature is from 0° C. to 150° C., and preferably from 50° C. to 150° C.

The reaction time is from 1 hour to 24 hours, and preferably from 1 hour to 2 hours.

After completion of the reactions of the above-described respective processes, the target compound is collected from the reaction mixture according to a common procedure. For example, the reaction mixture is appropriately neutralized, or in the case where insoluble matter is contained therein, the insoluble matter is removed by filtration, and then, water and an organic solvent immiscible with water such as ethyl acetate are added to the filtrate, and the organic layer is washed with water or the like. Then, the organic layer containing the target compound is separated and dried over anhydrous magnesium sulfate or the like, and then, the solvent is distilled off, whereby the target compound can be obtained.

If necessary, the obtained target compound can be separated and purified by a common procedure such as recrystallization or reprecipitation, or by appropriately combining a method commonly and usually used for the separation and purification of an organic compound, for example, a method using a synthetic adsorbent such as adsorption column chromatography or partition column chromatography, a method using ion exchange chromatography, or normal and reverse phase column chromatography using silica gel or alkylated silica gel and performing elution with an appropriate eluent.

Further, if necessary, the separation and purification of optically active compounds can also be performed using a chiral column.

The cyclohexane derivative compound having the above-described general formula (I) or a pharmacologically acceptable salt thereof of the invention is administered in various forms. The administration route is not particularly limited and is determined according to the dosage form of various preparations, the age and gender of the patient, other conditions, the severity of the disease, and the like. For example, in the case of a tablet, a pill, a powder, a granule, a syrup, a liquid, a suspension, an emulsion, a granule, or a capsule, the compound is orally administered. Further, in the case of an injection, the compound is intravenously administered singly or in admixture with a common fluid replacement solution containing glucose, an amino acid, or the like, and further if necessary, the compound is intramuscularly, intradermally, subcutaneously, or intraperitoneally administered singly. In the case of a suppository, the compound is intrarectally administered. The administration route is preferably oral administration.

These various preparations can be formulated according to common procedures using known pharmaceutical auxiliaries which can be commonly used in the known field of pharmaceutical preparations such as an excipient, a binder, a disintegrant, a lubricant, a solubilizer, a corrigent, or a coating agent, as well as a base component.

When the compound is formed into a tablet, a wide variety of substances conventionally known as carriers in this field can be used, and examples thereof include excipients such as lactose, sucrose, sodium chloride, glucose, urea, starch, calcium carbonate, kaolin, crystalline cellulose, and silicic acid; binders such as water, ethanol, propanol, simple syrup, glucose syrup, a starch solution, a gelatin solution, carboxymethyl cellulose, shellac, methyl cellulose, potassium phosphate, and polyvinylpyrrolidone; disintegrants such as dried starch, sodium alginate, agar powder, laminaran powder, sodium hydrogen carbonate, calcium carbonate, a polyoxyethylene sorbitan fatty acid ester, sodium lauryl sulfate, monoglyceride stearate, starch, and lactose; disintegration inhibitors such as sucrose, stearin, cacao butter, and a hydrogenated oil; absorption enhancers such as a quaternary ammonium base and sodium lauryl sulfate; humectants such as glycerin and starch; adsorbents such as starch, lactose, kaolin, bentonite, and colloidal silicic acid; and lubricants such as purified talc, a stearate salt, boric acid powder, and polyethylene glycol. Further, if necessary, the tablet can be formed into a tablet coated with a usual coating composition such as a sugar-coated tablet, a gelatin-coated tablet, an enteric-coated tablet, a film-coated tablet, a double-layer tablet, or a multi-layer tablet.

When the compound is formed into a pill, a wide variety of substances conventionally known as carriers in this field can be used, and examples thereof include excipients such as glucose, lactose, starch, cacao butter, a hydrogenated vegetable oil, kaolin, and talc; binders such as arabic gum powder, tragacanth powder, gelatin, and ethanol; and disintegrants such as laminaran and agar.

When the compound is formed into a suppository, a wide variety of substances conventionally known as carriers in this field can be used, and examples thereof include polyethylene glycol, cacao butter, higher alcohols, higher alcohol esters, gelatin, and semi-synthetic glycerides.

When the compound is formulated as an injection, a liquid or a suspension is sterilized and is preferably isotonic to blood. When the compound is formulated as a liquid, an emulsion, or a suspension, any substance commonly used as a diluent in this field can be used, and examples thereof include water, ethyl alcohol, propylene glycol, ethoxylated isostearyl alcohol, polyoxylated isostearyl alcohol, and polyoxyethylene sorbitan fatty acid esters. In this case, sodium chloride, glucose, or glycerin may be added to the pharmaceutical preparation in an amount sufficient to prepare an isotonic solution. Further, a common solubilizing agent, a buffer, a soothing agent, or the like may also be added to the preparation.

Further, if necessary, a coloring agent, a preservative, a perfume, a flavor, a sweetener, or the like, or another pharmaceutical product may be added to the preparation.

The amount of the active ingredient compound to be contained in the above-described pharmaceutical preparation is not particularly limited and is suitably selected from a wide range of amount, however, it is preferred to set the amount in a range generally from 1 to 70% by weight, preferably from 1 to 30% by weight of the total composition.

The dose of the active ingredient compound varies depending on the symptoms, age, body weight, administration method, dosage form, and the like, however, the compound can be administered to an adult at a daily dose of generally 0.001 mg/kg (preferably 0.01 mg/kg, more preferably 0.1 mg/kg) as the lower limit and 200 mg/kg (preferably 20 mg/kg, more preferably 10 mg/kg) as the upper limit once or several times.

The compound of the invention can be used in combination with any of various therapeutic or prophylactic agents for the above-described diseases in which the invention is considered to be effective. For example, the compound of the invention can be used in combination with one or more compounds having activity of decreasing gastric acid secretion, one or more compounds having activity of relieving gastroesophageal reflux, and particularly in the case where the compound of the invention is used for reducing erosive or nonerosive esophagitis, one or more compounds having activity of reducing irritation to the esophagus and stomach or inflammation therein, a compound having analgesic activity, one or more compounds having activity of promoting the intestinal secretion of intestinal fluid thereby to alleviate the symptoms of irritable bowel syndrome with constipation and constipation, one or more compounds having antidepressive-anxiolytic activity, and/or one or more compounds having mixed activity for motility and pain. In the case where the compound is used in combination with another compound, these compounds can be administered simultaneously, or separately and continuously or at a desired time interval. The preparations to be co-administered may be formulated as a combination preparation or separate preparations.

Further, the compound of the invention has excellent GPR38 agonistic activity, high safety, and low toxicity, and therefore is useful as a pharmaceutical product. In particular, by reducing the half-life of the compound, the compound acts locally on gastrointestinal tissues before being metabolized in the liver and causes less systemic exposure so that the compound has higher safety and lower toxicity, and therefore is extremely useful as a pharmaceutical product.

Advantage of the Invention

The cyclohexane derivative compound and a pharmacologically acceptable salt thereof which are each the compound of the invention have excellent GPR38 agonistic activity and an excellent improving effect on gastrointestinal disorders, and so on, and therefore are useful as a prophylactic or therapeutic agent for diseases such as gastrointestinal disorders associated with hypomotility, for example, GERD, FD, functional bowel disorders such as irritable bowel syndrome, diabetic gastroparesis, constipation, opioid-induced bowel dysfunction, paralytic ileus, postoperative gastrointestinal paralysis, gastrointestinal symptoms associated with scleroderma, etc., and further as a pharmaceutical aid for use in a pretreatment for barium enema X-ray examination by oral intestinal lavage.

MODE FOR CARRYING OUT THE INVENTION

Subsequently, the invention will be described in more detail with reference to Examples and the like, however, the invention is not limited thereto.

EXAMPLES

Example 1

Trans-4-(4-fluorophenoxy)-N-methyl-N-(4-{[(3S)-3-methylpiperazin-1-yl]methyl}phenyl)cyclohexanecarboxamide

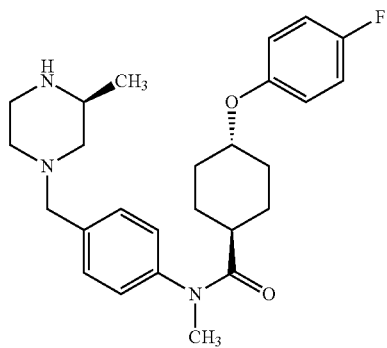 [SMILES: C[C@H]1CN(Cc2ccc(N(C)C(=O)[C@H]3CC[C@H](Oc4ccc(F)cc4)CC3)cc2)CCN1]

(1A)
Trans-4-(4-fluorophenoxy)cyclohexanecarboxylic acid

Methyl trans-4-(4-fluorophenoxy)cyclohexanecarboxylate (501 mg, 1.98 mmol), which is a known compound, was dissolved in tetrahydrofuran (10 mL) and ethanol (10 mL), and a 1 N aqueous solution of sodium hydroxide (6.0 mL) was added thereto at room temperature, and then, the resulting mixture was stirred at 60° C. for 2 hours.

To the reaction solution, 2 N hydrochloric acid was added and the organic matter was extracted with ethyl acetate. The organic layer was dried over anhydrous sodium sulfate and filtered. Then, the solvent was distilled off under reduced pressure, whereby the target compound was obtained as a white solid (478 mg, 100%).

$^1$H NMR (CDCl$_3$, 400 MHz): δ1.40-1.67 (4H, m), 2.05-2.21 (4H, m), 2.41 (1H, m), 4.10 (1H, m), 6.80-6.87 (2H, m), 6.92-6.98 (2H, m).

(1B) Tert-butyl (2S)-4-[4-({[trans-4-(4-fluorophenoxy)cyclohexyl]carbonyl}amino)benzyl]-2-methylpiperazine-1-carboxylate Tert-butyl (2S)-4-[(4-aminophenyl)methyl]-2-methylpiperazine-1-carboxylate (709 mg, 2.32 mmol), which is a known compound, was dissolved in dimethylformamide (10 mL), and trans-4-(4-fluorophenoxy)cyclohexanecarboxylic acid (553 mg, 2.32 mmol) produced in (1A) and 4-(4,6-dimethoxy-1,3,5-triazin-2-yl)-4-methylmorpholium chloride hydrate (1.09 g, about 3.5 mmol) were added thereto at room temperature, and then, the resulting mixture was stirred overnight at room temperature.

To the reaction solution, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the target compound was obtained as a colorless oil (1.15 g, yield: 94%).

$^1$H NMR (CDCl$_3$, 400 MHz): δ1.21 (3H, d, J=6.7 Hz), 1.39-1.51 (2H, m), 1.46 (9H, s), 1.66-1.80 (2H, m), 1.91-2.13 (4H, m), 2.19-2.34 (3H, m), 2.56 (1H, d, J=11.0 Hz), 2.73 (1H, d, J=11.0 Hz), 3.08 (1H, td, J=3.0, 12.7 Hz), 3.34 (1H, d, J=8.6 Hz), 3.48 (1H, d, J=13.1 Hz), 3.79 (1H, m), 4.08-4.22 (2H, m), 6.80-6.88 (2H, m), 6.92-6.99 (2H, m), 7.26 (2H, d, J=8.6 Hz), 7.49 (2H, d, J=8.6 Hz), 7.68 (1H, m).

(1C) Tert-butyl (2S)-4-{4-[{[trans-4-(4-fluorophenoxy)cyclohexyl]carbonyl}(methyl)amino]benzyl}-2-methylpiperazine-1-carboxylate Tert-butyl (2S)-4-[4-({[trans-4-(4-fluorophenoxy)cyclohexyl]carbonyl}amino)benzyl]-2-methylpiperazine-1-carboxylate (1.15 g, 2.18 mmol) produced in (1B) was dissolved in dimethylformamide (30 mL), and sodium hydride (60%, 279 mg, 6.98 mmol) was added thereto at room temperature. After the resulting mixture was stirred under a nitrogen atmosphere at room temperature for 10 minutes, methyl iodide (727 μL, 11.7 mmol) was added thereto at room temperature, and then, the resulting mixture was stirred under a nitrogen atmosphere at 60° C. for 1.5 hours.

To the reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the target compound was obtained as a light yellow oil (1.06 g, yield: 90%).

$^1$H NMR (CDCl$_3$, 400 MHz): δ1.05-1.19 (2H, m), 1.26 (3H, d, J=6.7 Hz), 1.47 (9H, s), 1.60-1.83 (4H, m), 1.99-2.14 (3H, m), 2.14-2.28 (2H, m), 2.61 (1H, d, J=11.3 Hz), 2.77 (1H, d, J=11.0 Hz), 3.13 (1H, td, J=3.1, 12.7 Hz), 3.25 (3H, s), 3.45 (1H, d, J=13.7 Hz), 3.56 (1H, d, J=13.7 Hz), 3.83 (1H, d, J=12.9 Hz), 4.06 (1H, m), 4.22 (1H, brs), 6.74-6.81 (2H, m), 6.88-6.96 (2H, m), 7.13 (2H, d, J=8.2 Hz), 7.40 (2H, d, J=8.2 Hz).

(1D) Trans-4-(4-fluorophenoxy)-N-methyl-N-(4-{[(3S)-3-methylpiperazin-1-yl]methyl}phenyl)cyclohexanecarboxamide Tert-butyl (2S)-4-{4-[{[trans-4-(4-fluorophenoxy)cyclohexyl]carbonyl}(methyl)amino]benzyl}-2-methylpiperazine-1-carboxylate (237 mg, 0.439 mmol) produced in (1C)

was dissolved in dichloromethane (4 mL), and trifluoroacetic acid (1 mL) was added thereto at room temperature, and then, the resulting mixture was stirred at room temperature for 1 hour.

To the residue obtained by distilling off the solvent in the reaction solution under reduced pressure, a saturated aqueous solution of sodium hydrogen carbonate was added, and the organic matter was extracted three times with ethyl acetate. The organic layer was dried over anhydrous sodium sulfate and filtered. Then, the solvent was distilled off under reduced pressure, whereby a crude product was obtained. The obtained crude product was purified by NH silica gel column chromatography {a silica gel in which aminopropylsilane was chemically bonded to a silanol group on the surface of silica (hexane:ethyl acetate=50:50 to 20:80 (v/v))}, whereby the target compound was obtained as a colorless oil (83.0 mg, yield: 43%).

1H NMR (CDCl3, 400 MHz): δ1.04 (3H, d, J=6.7 Hz), 1.04-1.12 (2H, m), 1.48-1.84 (6H, m), 1.99-2.14 (3H, m), 2.24 (1H, m), 2.71-2.81 (2H, m), 2.83-3.02 (3H, m), 3.24 (3H, s), 3.52 (2H, s), 4.06 (1H, m), 6.72-6.81 (2H, m), 6.88-6.97 (2H, m), 7.13 (2H, d, J=8.2 Hz), 7.39 (2H, d, J=8.2 Hz).

MS (ESI) m/z: 440 (M+H)+.

Example 2

Trans-4-(4-fluorophenoxy)-N-methyl-N-(3-methyl-4-{[(3S)-3-methylpiperazin-1-yl]methyl}phenyl)cyclohexanecarboxamide

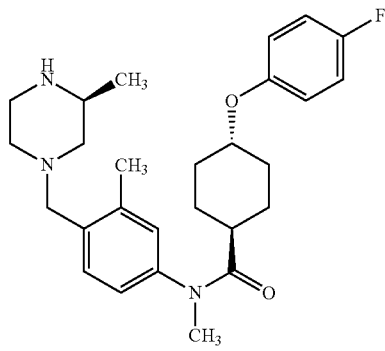 [SMILES: Cc1cc(N(C)C(=O)[C@H]2CC[C@H](Oc3ccc(F)cc3)CC2)ccc1CN1CCN[C@@H](C)C1]

(2A) Tert-butyl (2S)-4-(4-{[(cis-4-hydroxycyclohexyl)carbonyl](methyl)amino}-2-methylbenzyl)-2-methylpiperazine-1-carboxylate Tert-butyl (2S)-2-methyl-4-[2-methyl-4-(methylamino)benzyl]piperazine-1-carboxylate (3.04 g, 9.13 mmol), which is a known compound, was dissolved in dimethylformamide (30 mL), and cis-4-hydroxycyclohexanecarboxylic acid (5.27 g, 36.6 mmol) and 4-(4,6-dimethoxy-1,3,5-triazin-2-yl)-4-methylmorpholium chloride hydrate (11.5 g, about 37 mmol) were added thereto at room temperature, and then, the resulting mixture was stirred overnight at room temperature.

To the reaction solution, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (ethyl acetate:methanol=100:0 to 80:20 (v/v)), whereby the target compound was obtained as a white solid (4.05 g, yield: 97%).

1H NMR (CDCl3, 400 MHz): δ1.22 (3H, d, J=6.7 Hz), 1.23-1.35 (2H, m), 1.40-1.50 (2H, m), 1.46 (9H, s), 1.72-1.82 (2H, m), 1.86-2.07 (3H, m), 2.16-2.31 (2H, m), 2.38 (3H, s), 2.59 (1H, d, J=11.3 Hz), 2.73 (1H, d, J=11.7 Hz), 3.08 (1H, td, J=3.2, 12.6 Hz), 3.23 (3H, s), 3.42 (2H, s), 3.81 (1H, d, J=13.3 Hz), 3.89 (1H, brs), 4.21 (1H, brs), 6.92-6.98 (2H, m), 7.29 (1H, d, J=7.8 Hz).

(2B) Tert-butyl 2S)-4-{4-[{[trans-4-(4-fluorophenoxy)cyclohexyl]carbonyl}(methyl)amino]-2-methylbenzyl}-2-methylpiperazine-1-carboxylate Tert-butyl (2S)-4-(4-{[(cis-4-hydroxycyclohexyl)carbonyl](methyl)amino}-2-methylbenzyl)-2-methylpiperazine-1-carboxylate (221 mg, 0.482 mmol) produced in (2A) was dissolved in toluene (10 mL), and 4-fluorophenol (97.2 mg, 0.867 mmol) and cyanomethylenetributylphosphorane (232 µL, 0.866 mmol) were added thereto at room temperature, and then, the resulting mixture was stirred for 2 hours while heating to reflux. The residue obtained by distilling off the solvent in the reaction solution under reduced pressure was dissolved in tetrahydrofuran (8 mL) and water (2 mL), and N-methylmorpholine-N-oxide (169 mg, 1.44 mmol) and an aqueous solution of osmium tetroxide (10%, 147 µL, 0.0241 mmol) were added thereto, and then, the resulting mixture was stirred overnight at room temperature.

To the reaction solution, a saturated aqueous solution of sodium sulfite was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the target compound was obtained as a light yellow oil (80.0 mg, yield: 30%).

1H NMR (CDCl3, 400 MHz): δ1.04-1.20 (2H, m), 1.23 (3H, d, J=6.7 Hz), 1.47 (9H, s), 1.61-1.84 (4H, m), 1.98-2.14 (3H, m), 2.17-2.30 (2H, m), 2.39 (3H, s), 2.60 (1H, d, J=11.0 Hz), 2.73 (1H, d, J=11.0 Hz), 3.08 (1H, td, J=3.0, 12.7 Hz), 3.23 (3H, s), 3.43 (2H, s), 3.82 (1H, d, J=12.9 Hz), 4.07 (1H, m), 4.23 (1H, brs), 6.74-6.81 (2H, m), 6.89-6.99 (4H, m), 7.31 (1H, d, J=7.8 Hz).

(2C) Trans-4-(4-fluorophenoxy)-N-methyl-N-(3-methyl-4-{[(3S)-3-methylpiperazin-1-yl]methyl}phenyl)cyclohexanecarboxamide Tert-butyl 2S)-4-{4-[{[trans-4-(4-fluorophenoxy)cyclohexyl]carbonyl}(methyl)amino]-2-methylbenzyl}-2-methylpiperazine-1-carboxylate (271 mg, 0.490 mmol) produced in (2B) was dissolved in dichloromethane (4 mL), and trifluoroacetic acid (1 mL) was added thereto at room temperature, and then, the resulting mixture was stirred at room temperature for 1.5 hours.

To the residue obtained by distilling off the solvent in the reaction solution under reduced pressure, a saturated aqueous solution of sodium hydrogen carbonate was added, and the organic matter was extracted with ethyl acetate. The organic layer was dried over anhydrous sodium sulfate and filtered, whereby the target compound was obtained as a colorless oil (133 mg, yield: 60%).

1H NMR (CDCl3, 400 MHz): δ1.10 (3H, d, J=6.3 Hz), 1.13-1.21 (2H, m), 1.62-1.90 (6H, m), 2.03-2.30 (4H, m), 2.37 (3H, s), 2.73-2.82 (2H, m), 2.89-3.07 (3H, m), 3.23 (3H, s), 3.47 (2H, s), 4.07 (1H, m), 6.74-6.82 (2H, m), 6.88-7.00 (4H, m), 7.32 (1H, d, J=7.4 Hz).

MS (ESI) m/z: 454 (M+H)+.

Example 3

Trans-N-(3-chloro-4-{[(3S)-3-methylpiperazin-1-yl]methyl}phenyl)-4-(4-fluorophenoxy)-N-methylcyclohexanecarboxamide

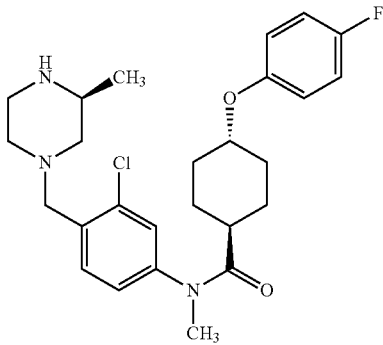 [SMILES: C[C@H]1CN(Cc2ccc(N(C)C(=O)[C@H]3CC[C@H](Oc4ccc(F)cc4)CC3)cc2Cl)CCN1]

(3A) Tert-butyl (2S)-4-[2-chloro-4-({[trans-4-(4-fluorophenoxy)cyclohexyl]carbonyl}amino)benzyl]-2-methylpiperazine-1-carboxylate Tert-butyl (2S)-4-[(4-amino-2-chlorophenyl)methyl]-2-methylpiperazine-1-carboxylate (309 mg, 0.912 mmol), which is a known compound, was dissolved in dimethylformamide (5 mL), and trans-4-(4-fluorophenoxy)cyclohexanecarboxylic acid (217 mg, 0.912 mmol) produced in (1A) and 4-(4,6-dimethoxy-1,3,5-triazin-2-yl)-4-methylmorpholium chloride hydrate (515 mg, about 1.6 mmol) were added thereto at room temperature, and then, the resulting mixture was stirred overnight at room temperature.

To the reaction solution, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the target compound was obtained as a light yellow oil (336 mg, yield: 66%).

$^1$H NMR (CDCl$_3$, 400 MHz): δ1.23 (3H, d, J=6.7 Hz), 1.46 (9H, s), 1.43-1.55 (2H, m), 1.66-1.80 (2H, m), 2.01-2.12 (3H, m), 2.18-2.32 (4H, m), 2.59 (1H, d, J=11.0 Hz), 2.73 (1H, d, J=11.3 Hz), 3.08 (1H, td, J=3.4, 12.7 Hz), 3.52 (2H, s), 3.80 (1H, d, J=12.1 Hz), 4.07-4.24 (2H, m), 6.81-6.88 (2H, m), 6.92-7.01 (2H, m), 7.28 (1H, brs), 7.34 (1H, dd, J=2.2, 8.4 Hz), 7.42 (1H, d, J=8.2 Hz), 7.67 (1H, d, J=2.0 Hz).

(3B) Tert-butyl (2S)-4-{2-chloro-4-[{[trans-4-(4-fluorophenoxy)cyclohexyl]carbonyl}(methyl)amino]benzyl}-2-methylpiperazine-1-carboxylate Tert-butyl (2S)-4-[2-chloro-4-({[trans-4-(4-fluorophenoxy)cyclohexyl]carbonyl}amino)benzyl]-2-methylpiperazine-1-carboxylate (336 mg, 0.602 mmol) produced in (3A) was dissolved in dimethylformamide (10 mL), and sodium hydride (60%, 72.3 mg, 1.81 mmol) was added thereto at room temperature. After the resulting mixture was stirred under a nitrogen atmosphere at room temperature for 10 minutes, methyl iodide (113 μL, 1.81 mmol) was added thereto at room temperature, and then, the resulting mixture was stirred under a nitrogen atmosphere at 50° C. for 1 hour. Further, methyl iodide (113 μL, 1.81 mmol) was added thereto, and the resulting mixture was stirred at 50° C. for 30 minutes, and then, sodium hydride (60%, 72.3 mg, 1.81 mmol) was added thereto, and the resulting mixture was stirred at 50° C. for 1 hour.

To reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 60:40 (v/v)), whereby the target compound was obtained as a light yellow oil (296 mg, yield: 86%).

$^1$H NMR (CDCl$_3$, 400 MHz): δ1.08-1.24 (2H, m), 1.29 (3H, d, J=6.7 Hz), 1.47 (9H, s), 1.61-1.84 (4H, m), 2.06-2.28 (4H, m), 2.32 (1H, dd, J=3.7, 11.1 Hz), 2.64 (1H, d, J=11.3 Hz), 2.79 (1H, d, J=11.0 Hz), 3.14 (1H, td, J=3.2, 12.7 Hz), 3.24 (3H, s), 3.59 (2H, s), 3.85 (1H, d, J=12.5 Hz), 4.08 (1H, m), 4.25 (1H, brs), 6.74-6.83 (2H, m), 6.89-6.97 (2H, m), 7.09 (1H, dd, J=2.0, 8.2 Hz), 7.21 (1H, d, J=2.0 Hz), 7.60 (1H, d, J=7.8 Hz).

(3C) Trans-N-(3-chloro-4-{[(3S)-3-methylpiperazin-1-yl]methyl}phenyl)-4-(4-fluorophenoxy)-N-methyl-cyclohexanecarboxamide Tert-butyl (2S)-4-{2-chloro-4-[{[trans-4-(4-fluorophenoxy)cyclohexyl]carbonyl}(methyl)amino]benzyl}-2-methylpiperazine-1-carboxylate (296 mg, 0.517 mmol) produced in (3B) was dissolved in dichloromethane (4 mL), and trifluoroacetic acid (1 mL) was added thereto at room temperature, and then, the resulting mixture was stirred at room temperature for 1 hour.

To the residue obtained by distilling off the solvent in the reaction solution under reduced pressure, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby the target compound was obtained as a light yellow oil (230 mg, yield: 94%).

$^1$H NMR (CDCl$_3$, 400 MHz): δ1.15-1.25 (2H, m), 1.19 (3H, d, J=6.7 Hz), 1.62-1.85 (4H, m), 2.05-2.17 (3H, m), 2.23 (1H, m), 2.39 (1H, m), 2.79-2.90 (2H, m), 2.98-3.18 (3H, m), 3.23 (3H, s), 3.66 (2H, s), 4.08 (1H, m), 6.74-6.82 (2H, m), 6.88-6.98 (2H, m), 7.09 (1H, dd, J=2.4, 8.2 Hz), 7.22 (1H, d, J=2.4 Hz), 7.53 (1H, d, J=8.2 Hz).

MS (ESI) m/z: 474 (M+H)$^+$.

Example 4

Trans-4-[(5-fluoropyridin-2-yl)oxy]-N-methyl-N-(3-methyl-4-{[(3S)-3-methylpiperazin-1-yl]methyl}phenyl)cyclohexanecarboxamide and hydrochloride thereof

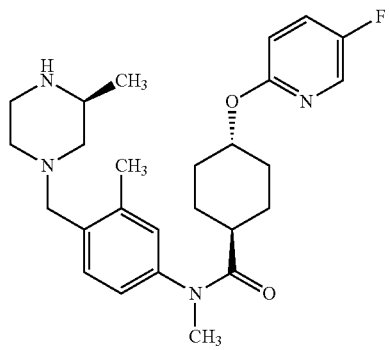 [SMILES: Cc1cc(N(C)C(=O)[C@H]2CC[C@H](Oc3ccc(F)cn3)CC2)ccc1CN1CCN[C@@H](C)C1]

(4A) Tert-butyl (2S)-4-(4-{[(trans-4-hydroxycyclohexyl)carbonyl](methyl)amino}-2-methylbenzyl)-2-methylpiperazine-1-carboxylate Tert-butyl (2S)-4-[(4-amino-2-methylphenyl)methyl]-2-methylpiperazine-1-carboxylate (2.99 g, 8.98 mmol), which is a known compound, was dissolved in ethanol (50 mL), and trans-4-hydroxycyclohexanecarboxylic acid (5.18 g, 35.9 mmol) and 4-(4,6-dimethoxy-1,3,5-triazin-2-yl)-4-methylmorpholium chloride hydrate (11.3 g, about 36 mmol) were added thereto at room temperature, and then, the resulting mixture was stirred overnight at room temperature. Further, trans-4-hydroxycyclohexanecarboxylic acid (2.59 g, 18.0 mmol) and 4-(4,6-dimethoxy-1,3,5-triazin-2-yl)-4-methylmorpholium chloride hydrate (5.65 g, about 18 mmol) were added thereto at room temperature, and then, the resulting mixture was stirred overnight at room temperature.

To the reaction solution, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (ethyl acetate:methanol=100:0 to 80:20 (v/v)), whereby the target compound was obtained as a white solid (3.92 g, yield: 95%).

$^1$H NMR (CDCl$_3$, 400 MHz): δ0.90-1.05 (2H, m), 1.23 (3H, d, J=6.7 Hz), 1.21-1.35 (2H, m), 1.46 (9H, s), 1.54-1.75 (2H, m), 1.86-1.96 (2H, m), 2.01 (1H, m), 2.10-2.28 (2H, m), 2.39 (3H, s), 2.60 (1H, d, J=11.3 Hz), 2.73 (1H, d, J=11.0 Hz), 3.08 (1H, td, J=3.0, 12.7 Hz), 3.21 (3H, s), 3.43 (2H, s), 3.57 (1H, m), 3.81 (1H, d, J=12.9 Hz), 4.21 (1H, brs), 6.91-6.97 (2H, m), 7.31 (1H, d, J=8.2 Hz).

(4B) Tert-butyl (2S)-4-{4-[({trans-4-[(5-fluoropyridin-2-yl)oxy]cyclohexyl}carbonyl)(methyl)amino]-2-methylbenzyl}-2-methylpiperazine-1-carboxylate Tert-butyl (2S)-4-(4-{[(trans-4-hydroxycyclohexyl)carbonyl](methyl)amino}-2-methylbenzyl)-2-methylpiperazine-1-carboxylate (796 mg, 1.73 mmol) produced in (4A) was dissolved in dimethylformamide (10 mL), and sodium hydride (60%, 346 mg, 8.65 mmol) was added thereto at room temperature. After the resulting mixture was stirred under a nitrogen atmosphere at room temperature for 10 minutes, 2,5-difluoropyridine (283 μL, 3.11 mmol) was added thereto at room temperature, and then, the resulting mixture was stirred under a nitrogen atmosphere at 60° C. for 2 hours, and then stirred under a nitrogen atmosphere at 100° C. for 1.5 hours.

To the reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the target compound was obtained as a colorless oil (592 mg, yield: 62%).

$^1$H NMR (CDCl$_3$, 400 MHz): δ1.04-1.19 (2H, m), 1.23 (3H, d, J=6.7 Hz), 1.47 (9H, s), 1.70-1.83 (4H, m), 2.03 (1H, td, J=3.2, 11.6 Hz), 2.08-2.17 (2H, m), 2.17-2.30 (2H, m), 2.39 (3H, s), 2.60 (1H, d, J=11.3 Hz), 2.74 (1H, d, J=11.0 Hz), 3.08 (1H, td, J=3.0, 12.7 Hz), 3.24 (3H, s), 3.43 (2H, s), 3.82 (1H, d, J=12.9 Hz), 4.22 (1H, brs), 4.87 (1H, m), 6.56 (1H, dd, J=3.5, 9.4 Hz), 6.92-7.00 (2H, m), 7.22-7.35 (2H, m), 7.94 (1H, d, J=3.1 Hz).

(4C) Trans-4-[(5-fluoropyridin-2-yl)oxy]-N-methyl-N-(3-methyl-4-{[(3S)-3-methylpiperazin-1-yl]methyl}phenyl)cyclohexanecarboxamide Tert-butyl (2S)-4-{4-[({trans-4-[(5-fluoropyridin-2-yl)oxy]cyclohexyl}carbonyl)(methyl)amino]-2-methylbenzyl}-2-methylpiperazine-1-carboxylate (592 mg, 1.07 mmol) produced in (4B) was dissolved in dichloromethane (8 mL), and trifluoroacetic acid (2 mL) was added thereto at room temperature, and then, the resulting mixture was stirred at room temperature for 2 hours.

To the residue obtained by distilling off the solvent in the reaction solution under reduced pressure, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby the target compound was obtained as a white solid (462 mg, yield: 95%).

$^1$H NMR (CDCl$_3$, 400 MHz): δ1.05-1.22 (2H, m), 1.30 (3H, d, J=6.7 Hz), 1.69-1.83 (4H, m), 2.08-2.17 (2H, m), 2.19-2.32 (2H, m), 2.38 (3H, s), 2.48 (1H, m), 2.82-2.91 (2H, m), 3.08 (1H, m), 3.20-3.32 (2H, m), 3.23 (3H, s), 3.55 (2H, s), 4.87 (1H, m), 6.55 (1H, dd, J=3.5, 9.0 Hz), 6.96-7.03 (2H, m), 7.23-7.33 (2H, m), 7.94 (1H, d, J=3.1 Hz).

MS (ESI) m/z: 455 (M+H)$^+$.

(4D) Trans-4-[(5-fluoropyridin-2-yl)oxy]-N-methyl-N-(3-methyl-4-{[(3S)-3-methylpiperazin-1-yl]methyl}phenyl)cyclohexanecarboxamide hydrochloride Trans-4-[(5-fluoropyridin-2-yl)oxy]-N-methyl-N-(3-methyl-4-{[(3S)-3-methylpiperazin-1-yl]methyl}phenyl)cyclohexanecarboxamide (520 mg, 1.14 mmol) produced in (4C) was dissolved in dioxane (2 mL) and water (2 mL), and 2 N hydrochloric acid (570 μL, 1.14 mmol) was added thereto at room temperature, and then, the resulting mixture was frozen at −78° C. The frozen mixture was lyophilized using a lyophilizer, whereby the target compound was obtained as a white solid (556 mg, yield: 100%).

MS (ESI) m/z: 455 (M+H)$^+$.

Example 5

Trans-4-[3-(hydroxymethyl)phenoxy]-N-methyl-N-(3-methyl-4-{[(3S)-3-methylpiperazin-1-yl]methyl}phenyl)cyclohexanecarboxamide

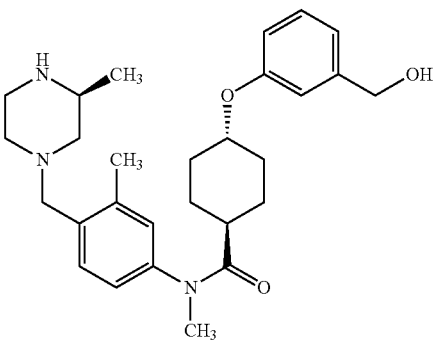 [SMILES: Cc1cc(N(C)C(=O)[C@H]2CC[C@H](Oc3cccc(CO)c3)CC2)ccc1CN1CCN[C@@H](C)C1]

(5A) Tert-butyl (2S)-4-{4-[({trans-4-[3-(methoxycarbonyl)phenoxy]cyclohexyl}carbonyl)(methyl)amino]-2-methylbenzyl}-2-methylpiperazine-1-carboxylate Tert-butyl (2S)-4-(4-{[(cis-4-hydroxycyclohexyl)carbonyl](methyl)amino}-2-methylbenzyl)-2-methylpiperazine-1-carboxylate (525 mg, 1.14 mmol) produced in (2A) was dissolved in toluene (20 mL), and methyl 3-hydroxybenzoate (313 mg, 2.05 mmol) and cyanomethylenetributylphosphorane (550 µL, 2.05 mmol) were added thereto at room temperature, and then, the resulting mixture was stirred for 2.5 hours while heating to reflux.

The residue obtained by distilling off the solvent in the reaction solution under reduced pressure was purified by silica gel column chromatography (hexane:ethyl acetate=80:20 to 50:50 (v/v)), whereby the target compound was obtained as a light yellow oil (172 mg, yield: 25%).

$^1$H NMR (CDCl$_3$, 400 MHz): δ1.09-1.25 (2H, m), 1.23 (3H, d, J=6.7 Hz), 1.47 (9H, s), 1.66-1.84 (4H, m), 2.04 (1H, m), 2.08-2.16 (2H, m), 2.17-2.31 (2H, m), 2.39 (3H, s), 2.60 (1H, d, J=11.3 Hz), 2.74 (1H, m), 3.09 (1H, m), 3.24 (3H, s), 3.43 (2H, s), 3.82 (1H, d, J=13.3 Hz), 3.90 (3H, s), 4.18-4.28 (2H, m), 6.92-6.99 (2H, m), 7.02 (1H, dd, J=2.2, 8.4 Hz), 7.27-7.35 (2H, m), 7.49 (1H, m), 7.59 (1H, d, J=7.8 Hz).

(5B) Tert-butyl (2S)-4-{4-[({trans-4-[3-(hydroxymethyl)phenoxy]cyclohexyl}carbonyl)(methyl)amino]-2-methylbenzyl}-2-methylpiperazine-1-carboxylate Tert-butyl (2S)-4-{4-[({trans-4-[3-(methoxycarbonyl)phenoxy]cyclohexyl}carbonyl)(methyl)amino]-2-methylbenzyl}-2-methylpiperazine-1-carboxylate (431 mg, 0.727 mmol) produced in (5A) was dissolved in tetrahydrofuran (20 mL), and lithium aluminum hydride (82.8 mg, 2.18 mmol) was added thereto at 0° C., and then, the resulting mixture was stirred at 0° C. for 30 minutes.

To the reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 0:100 (v/v)), whereby the target compound was obtained as a colorless oil (165 mg, yield: 40%).

$^1$H NMR (CDCl$_3$, 400 MHz): δ1.05-1.23 (2H, m), 1.23 (3H, d, J=6.7 Hz), 1.46 (9H, s), 1.60-1.84 (4H, m), 1.96-2.16 (3H, m), 2.16-2.30 (2H, m), 2.39 (3H, s), 2.60 (1H, d, J=11.0 Hz), 2.73 (1H, d, J=9.8 Hz), 3.08 (1H, m), 3.23 (3H, s), 3.43 (2H, s), 3.81 (1H, d, J=14.1 Hz), 4.10-4.26 (2H, m), 4.64 (2H, s), 6.75 (1H, dd, J=1.8, 8.0 Hz), 6.83-7.01 (4H, m), 7.22 (1H, t, J=7.8 Hz), 7.31 (1H, d, J=7.8 Hz).

(5C) Trans-4-[3-(hydroxymethyl)phenoxy]-N-methyl-N-(3-methyl-4-{[(3S)-3-methylpiperazin-1-yl]methyl}phenyl)cyclohexanecarboxamide Tert-butyl (2S)-4-{4-[({trans-4-[3-(hydroxymethyl)phenoxy]cyclohexyl}carbonyl)(methyl)amino]-2-methylbenzyl}-2-methylpiperazine-1-carboxylate (718 mg, 1.27 mmol) produced in (5B) was dissolved in dichloromethane (8 mL), and trifluoroacetic acid (2 mL) was added thereto at room temperature, and then, the resulting mixture was stirred at room temperature for 1 hour.

The residue obtained by distilling off the solvent in the reaction solution under reduced pressure was purified by NH silica gel column chromatography (ethyl acetate:methanol=100:00 to 90:10 (v/v)), whereby the target compound was obtained as a colorless oil (533 mg, yield: 90%).

$^1$H NMR (CDCl$_3$, 400 MHz): δ1.04 (3H, d, J=6.3 Hz), 1.08-1.22 (2H, m), 1.63-1.90 (5H, m), 2.00-2.15 (3H, m), 2.26 (1H, m), 2.37 (3H, s), 2.69-2.79 (2H, m), 2.81-3.00 (3H, m), 3.23 (3H, s), 3.45 (2H, s), 4.18 (1H, m), 4.64 (2H, s), 6.76 (1H, dd, J=2.2, 8.0 Hz), 6.84-6.99 (4H, m), 7.23 (1H, t, J=8.0 Hz), 7.33 (1H, d, J=8.2 Hz).

MS (ESI) m/z: 466 (M+H)$^+$.

(5D) Trans-4-[3-(hydroxymethyl)phenoxy]-N-methyl-N-(3-methyl-4-{[(3S)-3-methylpiperazin-1-yl]methyl}phenyl)cyclohexanecarboxamide hydrochloride Trans-4-[3-(hydroxymethyl)phenoxy]-N-methyl-N-(3-methyl-4-{[(3S)-3-methylpiperazin-1-yl]methyl}phenyl)cyclohexanecarboxamide (532 mg, 1.14 mmol) produced in (5C) was dissolved in a mixed solvent of dioxane (4 mL) and water (2 mL), and 2 N hydrochloric acid (570 µL, 1.14 mmol) was added thereto at room temperature, and then, the resulting mixture was frozen at −78° C. The frozen mixture was lyophilized using a lyophilizer, whereby the target compound was obtained as a white solid (477 mg, yield: 84%).

MS (ESI) m/z: 466 (M+H)$^+$.

Example 6

Methyl [3-({trans-4-[methyl(3-methyl-4-{[(3S)-3-methylpiperazin-1-yl]methyl}phenyl)carbamoyl]cyclohexyl}oxy)phenyl]acetate

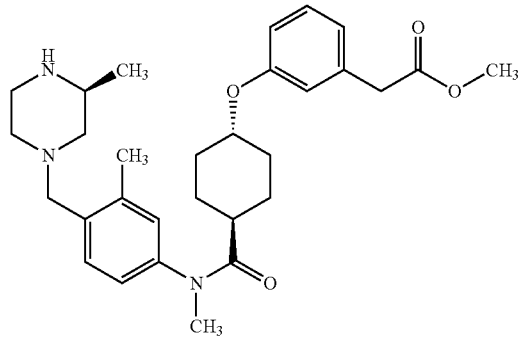 [SMILES: COC(=O)Cc1cccc(O[C@H]2CC[C@H](C(=O)N(C)c3ccc(CN4CCN[C@@H](C)C4)c(C)c3)CC2)c1]

(6A) Tert-butyl (2S)-4-{4-[({trans-4-[3-(2-methoxy-2-oxyethyl)phenoxy]cyclohexyl}carbonyl)(methyl)amino]-2-methylbenzyl}-2-methylpiperazine-1-carboxylate Tert-butyl (2S)-4-(4-{[(cis-4-hydroxycyclohexyl)carbonyl](methyl)amino}-2-methylbenzyl)-2-methylpiperazine-1-carboxylate (430 mg, 0.937 mmol) produced in (2A) was dissolved in toluene (20 mL), and methyl 3-hydroxyphenylacetate (311 mg, 1.87 mmol) and cyanomethylenetributylphosphorane (502 µL, 1.87 mmol) were added thereto at room temperature, and then, the resulting mixture was stirred for 2 hours while heating to reflux.

The residue obtained by distilling off the solvent in the reaction solution under reduced pressure was purified by silica gel column chromatography (hexane:ethyl acetate=80: 20 to 40:60 (v/v)), whereby the target compound was obtained as a light yellow oil (255 mg, yield: 45%).

$^1$H NMR (CDCl$_3$, 400 MHz): δ1.07-1.23 (2H, m), 1.23 (3H, d, J=6.7 Hz), 1.47 (9H, s), 1.66-1.82 (4H, m), 2.04 (1H, m), 2.07-2.15 (2H, m), 2.18-2.29 (2H, m), 2.39 (3H, s), 2.60 (1H, d, J=11.0 Hz), 2.74 (1H, d, J=10.6 Hz), 3.08 (1H, m), 3.23 (3H, s), 3.43 (2H, s), 3.56 (2H, s), 3.68 (3H, s), 3.82 (1H, d, J=11.7 Hz), 4.11-4.27 (2H, m), 6.71-6.78 (2H, m), 6.82 (1H, d, J=7.4 Hz), 6.91-7.00 (2H, m), 7.19 (1H, t, J=7.8 Hz), 7.32 (1H, d, J=7.8 Hz).

(6B) Methyl [3-({trans-4-[methyl(3-methyl-4-{[(3S)-3-methylpiperazin-1-yl]methyl}phenyl)carbamoyl]cyclohexyl}oxy)phenyl]acetate Tert-butyl (2S)-4-{4-[({trans-4-[3-(2-methoxy-2-oxyethyl)phenoxy]cyclohexyl}carbonyl)(methyl)amino]-2-methylbenzyl}-2-methylpiperazine-1-carboxylate (45.2 mg, 0.0745 mmol) produced in (6A) was dissolved in dichloromethane (4 mL), and trifluoroacetic acid (1 mL) was added thereto at room temperature, and then, the resulting mixture was stirred at room temperature for 1 hour.

The residue obtained by distilling off the solvent in the reaction solution under reduced pressure was purified by NH silica gel column chromatography (hexane:ethyl acetate=50: 50 to 0:100 (v/v)), whereby the target compound was obtained as a colorless oil (30.8 mg, yield: 82%).

$^1$H NMR (CDCl$_3$, 400 MHz): δ1.05 (3H, d, J=6.3 Hz), 1.08-1.22 (2H, m), 1.63-1.91 (6H, m), 2.03-2.16 (3H, m), 2.26 (1H, m), 2.37 (3H, s), 2.70-2.80 (2H, m), 2.83-3.02 (3H, m), 3.23 (3H, s), 3.45 (2H, s), 3.56 (2H, s), 3.68 (3H, s), 4.17 (1H, m), 6.71-6.78 (2H, m), 6.82 (1H, d, J=7.8 Hz), 6.92-6.99 (2H, m), 7.19 (1H, t, J=7.6 Hz), 7.33 (1H, d, J=7.8 Hz).

MS (ESI) m/z: 508 (M+H)$^+$.

Example 7

Trans-4-[3-(2-hydroxyethyl)phenoxy]-N-methyl-N-(3-methyl-4-{[(3S)-3-methylpiperazin-1-yl]methyl}phenyl)cyclohexanecarboxamide

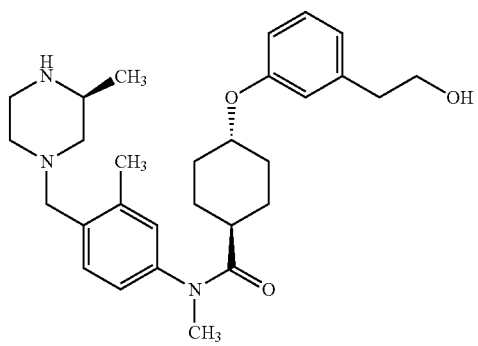 [SMILES: Cc1cc(N(C)C(=O)[C@H]2CC[C@H](Oc3cccc(CCO)c3)CC2)ccc1CN1CCN[C@@H](C)C1]

(7A) Tert-butyl (2S)-4-{4-[({trans-4-[3-(2-hydroxyethyl)phenoxy]cyclohexyl}carbonyl)(methyl)amino]-2-methylbenzyl}-2-methylpiperazine-1-carboxylate Tert-butyl (2S)-4-{4-[({trans-4-[3-(2-methoxy-2-oxyethyl)phenoxy]cyclohexyl}carbonyl)(methyl)amino]-2-methylbenzyl}-2-methylpiperazine-1-carboxylate (71.1 mg, 0.117 mmol) produced in (6A) was dissolved in tetrahydrofuran (3 mL), and lithium aluminum hydride (13.4 mg, 0.351 mmol) was added thereto at 0° C., and then, the resulting mixture was stirred at 0° C. for 20 minutes.

To the reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 0:100 (v/v)), whereby the target compound was obtained as a colorless oil (61.0 mg, yield: 90%).

$^1$H NMR (CDCl$_3$, 400 MHz): δ1.08-1.22 (2H, m), 1.23 (3H, d, J=7.0 Hz), 1.47 (9H, s), 1.64-1.83 (4H, m), 2.03 (1H, m), 2.07-2.15 (2H, m), 2.16-2.28 (2H, m), 2.39 (3H, s), 2.60 (1H, d, J=11.0 Hz), 2.74 (1H, d, J=11.7 Hz), 2.81 (2H, t, J=6.5 Hz), 3.08 (1H, m), 3.24 (3H, s), 3.43 (2H, s), 3.78-3.89 (3H, m), 4.11-4.28 (2H, m), 6.68-6.74 (2H, m), 6.78 (1H, d, J=7.4 Hz), 6.92-6.99 (2H, m), 7.19 (1H, m), 7.32 (1H, d, J=7.8 Hz).

(7B) Trans-4-[3-(2-hydroxyethyl)phenoxy]-N-methyl-N-(3-methyl-4-{[(3S)-3-methylpiperazin-1-yl]methyl}phenyl)cyclohexanecarboxamide Tert-butyl (2S)-4-{4-[({trans-4-[3-(2-hydroxyethyl)phenoxy]cyclohexyl}carbonyl)(methyl)amino]-2-methylbenzyl}-2-methylpiperazine-1-carboxylate (61.0 mg, 0.105 mmol) produced in (7A) was dissolved in dichloromethane (4 mL), and trifluoroacetic acid (1 mL) was added thereto at room temperature, and then, the resulting mixture was stirred at room temperature for 1 hour.

The residue obtained by distilling off the solvent in the reaction solution under reduced pressure was purified by NH silica gel column chromatography (ethyl acetate:methanol=100:0 to 90:10 (v/v)), whereby the target compound was obtained as a colorless oil (45.3 mg, yield: 90%).

$^1$H NMR (CDCl$_3$, 400 MHz): δ1.04 (3H, d, J=6.3 Hz), 1.09-1.22 (2H, m), 1.63-1.83 (7H, m), 2.01-2.15 (3H, m), 2.26 (1H, m), 2.37 (3H, s), 2.70-2.78 (2H, m), 2.81 (2H, t, J=6.5 Hz), 2.83-3.00 (3H, m), 3.23 (3H, s), 3.45 (2H, s), 3.83 (2H, t, J=6.5 Hz), 4.17 (1H, m), 6.67-6.74 (2H, m), 6.78 (1H, d, J=7.4 Hz), 6.92-6.98 (2H, m), 7.18 (1H, m), 7.33 (1H, d, J=8.2 Hz).

MS (ESI) m/z: 480 (M+H)$^+$.

Example 8

Trans-4-(4-fluorophenoxy)-N-methyl-N-(4-{[(3S)-3-ethylpiperazin-1-yl]methyl}phenyl)cyclohexanecarboxamide

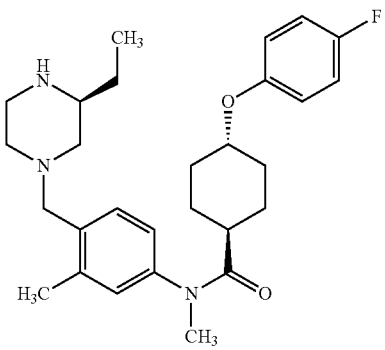 [SMILES: CC[C@H]1CN(Cc2ccc(N(C)C(=O)[C@H]3CC[C@H](Oc4ccc(F)cc4)CC3)cc2C)CCN1]

(8A) Trans-N-(4-bromo-3-methylphenyl)-4-(4-fluorophenoxy)-N-methylcyclohexanecarboxamide Tert-butyl (2S)-4-[(4-aminophenyl)methyl]-2-methylpiperazine-1-carboxylate (744 mg, 3.99 mmol), which is a known compound, was dissolved in dimethylformamide (20 mL), and trans-4-(4-fluorophenoxy)cyclohexanecarboxylic acid (1.05 g, 4.41 mmol) produced in (1A) and 4-(4,6-dimethoxy-1,3,5-triazin-2-yl)-4-methylmorpholium chloride hydrate (1.38 g, about 4.4 mmol) were added thereto at room temperature, and then, the resulting mixture was stirred overnight at room temperature.

To the reaction solution, water was added, and the organic matter was extracted with dichloromethane. The organic layer was dried over anhydrous sodium sulfate and filtered. Then, the solvent was distilled off under reduced pressure, and the obtained solid was washed with hexane. The resulting solid was dissolved in dimethylformamide (20 mL), and sodium hydride (60%, 182 mg, 4.55 mmol) was added thereto at 0° C. After the resulting mixture was stirred under a nitrogen atmosphere at 0° C. for 10 minutes, methyl iodide (355 μL, 5.72 mmol) was added thereto at 0° C., and the resulting mixture was stirred under a nitrogen atmosphere at room temperature for 3 hours. To the reaction solution, a saturated aqueous solution of ammonium chloride was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by silica gel column chromatography (hexane:ethyl acetate=100:0 to 60:40 (v/v)), whereby the target compound was obtained as a light yellow solid (1.31 g, yield: 78%).

$^1$H-NMR (CDCl$_3$, 400 MHz): δ 1.23-1.10 (2H, m), 1.81-1.62 (4H, m), 2.09 (2H, d, J=10.6 Hz), 2.29-2.16 (1H, m), 2.43 (3H, s), 3.21 (3H, s), 4.11-4.02 (1H, m), 6.81-6.75 (2H, m), 6.95-6.86 (3H, m), 7.06 (1H, d, J=2.7 Hz), 7.58 (1H, d, J=8.6 Hz).

(8B) Trans-4-(4-fluorophenoxy)-N-methyl-N-(3-methyl-4-vinylphenyl)cyclohexanecarboxamide Trans-N-(4-bromo-3-methylphenyl)-4-(4-fluorophenoxy)-N-methylcyclohexanecarboxamide (709 mg, 1.82 mmol) produced in (8A), palladium acetate (20.0 mg, 0.0891 mmol), 2-cyclohexylphosphino-2',6'-dimethoxybiphenyl (74.0 mg, 0.180 mmol), and potassium carbonate (745 mg, 5.39 mmol) were dissolved in dioxane (4 mL) and water (2 mL), and pinacol vinylboronate (416 mg, 2.70 mmol) was added thereto at room temperature, and then, the resulting mixture was stirred under a nitrogen atmosphere at 100° C. for 3 hours. To the reaction solution, water was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a light yellow oil (548 mg, yield: 82%).

$^1$H-NMR (CDCl$_3$, 400 MHz): δ1.23-1.10 (2H, m), 1.84-1.62 (4H, m), 2.09 (2H, d, J=9.4 Hz), 2.32-2.22 (1H, m), 2.38 (3H, s), 3.23 (3H, s), 4.12-4.02 (1H, m), 5.38 (1H, d, J=11.3 Hz), 5.69 (1H, d, J=17.2 Hz), 6.81-6.74 (2H, m), 7.01-6.88 (5H, m), 7.51 (1H, d, J=7.8 Hz).

(8C) Trans-4-(4-fluorophenoxy)-N-(4-formyl-3-methylphenyl)-N-methylcyclohexanecarboxamide Trans-4-(4-fluorophenoxy)-N-methyl-N-(3-methyl-4-vinylphenyl)cyclohexanecarboxamide (548 mg, 1.49 mmol) produced in (8B) and N-methylmorpholine-N-oxide (228 mg, 1.95 mmol) were dissolved in tetrahydrofuran (1.5 mL), acetone (1.5 mL), and water (1.5 mL), and a solution of osmium tetroxide in tert-butanol (0.15 ml, 0.0120 mmol) was added thereto at 0° C. After the resulting mixture was stirred at room temperature for 3 hours, sodium periodate (640 mg, 2.99 mmol) was added thereto at 0° C., and then, the resulting mixture was stirred at 0° C. for 3 hours.

To the reaction solution, a saturated aqueous solution of sodium sulfite was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a light yellow oil (394 mg, yield: 72%).

$^1$H-NMR (CDCl$_3$, 400 MHz): δ1.25–1.11 (2H, m), 1.85–1.64 (4H, m), 2.16–2.07 (2H, m), 2.34–2.22 (1H, m), 2.71 (3H, s), 3.28 (3H, s), 4.12–4.03 (1H, m), 6.81–6.75 (2H, m), 7.10 (1H, s), 6.96–6.89 (2H, m), 7.19 (1H, dd, J=8.2, 1.6 Hz), 7.88 (1H, d, J=8.2 Hz), 10.29 (1H, s).

(8D) Tert-butyl (2S)-4-{4-[{[trans-4-(4-fluorophenoxy)cyclohexyl]carbonyl}(methyl)amino]-2-methylbenzyl}-2-ethylpiperazine-1-carboxylate Trans-4-(4-fluorophenoxy)-N-(4-formyl-3-methylphenyl)-N-methylcyclohexanecarboxamide (55.0 mg, 0.149 mmol) produced in (8C) and tert-butyl (2S)-2-ethylpiperazine-1-carboxylate (39.0 mg, 0.182 mmol) were dissolved in dichloromethane (3 mL), and acetic acid (45.0 mg, 0.749 mmol) was added thereto at room temperature, and then, sodium triacetoxy borohydride (48 mg, 0.226 mmol) was added thereto at 0° C. Then, the resulting mixture was stirred under a nitrogen atmosphere at room temperature for 2 hours.

To the reaction solution, a saturated aqueous solution of sodium hydrogen carbonate was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a colorless oil (70.0 mg, yield: 83%).

$^1$H-NMR (CDCl$_3$, 400 MHz): δ0.78 (3H, t, J=7.6 Hz), 1.19-1.05 (2H, m), 1.46 (9H, s), 1.82–1.58 (6H, m), 2.16–2.02 (4H, m), 2.28–2.18 (1H, m), 2.38 (3H, s), 2.77–2.64 (2H, m), 3.08–2.96 (1H, m), 3.23 (3H, s), 3.48–3.35 (2H, m), 4.13–3.82 (3H, m), 6.80–6.74 (2H, m), 6.98–6.88 (4H, m), 7.29 (1H, d, J=7.4 Hz).

(8E) Trans-4-(4-fluorophenoxy)-N-methyl-N-(3-methyl-4-{[(3S)-3-ethylpiperazin-1-yl]methyl}phenyl)cyclohexanecarboxamide Tert-butyl (2S)-4-{4-[{[trans-4-(4-fluorophenoxy)cyclohexyl]carbonyl}(methyl)amino]-2-methylbenzyl}-2-ethylpiperazine-1-carboxylate (70.0 mg, 0.123 mmol) produced in (8D) was dissolved in dichloromethane (1 mL), and trifluoroacetic acid (0.5 mL) was added thereto at room temperature, and then, the resulting mixture was stirred at room temperature for 1 hour.

To the residue obtained by distilling off the solvent in the reaction solution under reduced pressure, a 1 N aqueous solution of sodium hydroxide was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:80:20 (v/v/v)), whereby the target compound was obtained as a colorless oil (50.0 mg, yield: 88%).

$^1$H-NMR (CDCl$_3$, 400 MHz): δ0.92 (3H, t, J=7.4 Hz), 1.20–1.07 (2H, m), 1.45–1.35 (2H, m), 1.84–1.61 (5H, m), 2.15–2.05 (3H, m), 2.29–2.19 (1H, m), 2.37 (3H, s), 2.71–2.63 (1H, m), 2.83–2.71 (2H, m), 2.90 (1H, td, J=11.5, 2.9 Hz), 3.04–2.97 (1H, m), 3.23 (3H, s), 3.46 (2H, s), 4.09–4.02 (1H, m), 6.80–6.74 (2H, m), 6.97–6.89 (4H, m), 7.33 (1H, d, J=7.82 Hz).

Example 9

Trans-4-(4-fluorophenoxy)-N-methyl-N-[3-methyl-4-(piperazin-1-ylmethyl)phenyl]cyclohexanecarboxamide

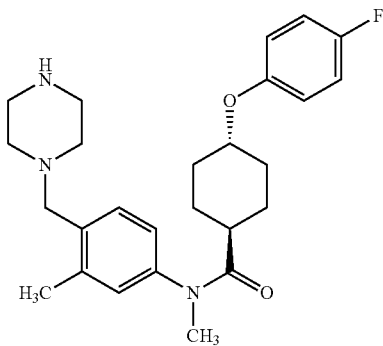 [SMILES: Cc1cc(N(C)C(=O)[C@H]2CC[C@H](Oc3ccc(F)cc3)CC2)ccc1CN1CCNCC1]

(9A) Tert-butyl 4-{4-[{[trans-4-(4-fluorophenoxy)cyclohexyl]carbonyl}(methyl)amino]-2-methylbenzyl}piperazine-1-carboxylate Trans-4-(4-fluorophenoxy)-N-(4-formyl-3-methylphenyl)-N-methylcyclohexanecarboxamide (55.0 mg, 0.149 mmol) produced in (8C) and tert-butyl piperazine-1-carboxylate (33.0 mg, 0.177 mmol) were dissolved in dichloromethane (3 mL), and acetic acid (45.0 mg, 0.749 mmol) was added thereto at room temperature, and then, sodium triacetoxy borohydride (48 mg, 0.226 mmol) was added thereto at 0° C. Then, the resulting mixture was stirred under a nitrogen atmosphere at room temperature for 2 hours. To the reaction solution, a saturated aqueous solution of sodium hydrogen carbonate was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a colorless oil (47.0 mg, yield: 58%).

$^1$H-NMR (CDCl$_3$, 400 MHz): δ1.21–1.08 (2H, m), 1.47 (9H, s), 1.83–1.63 (4H, m), 2.15–2.00 (2H, m), 2.30–2.19 (1H, m), 2.46–2.35 (7H, m), 3.23 (3H, s), 3.51–3.40 (6H, m), 4.12–4.02 (1H, m), 6.81–6.74 (2H, m), 7.00–6.87 (4H, m), 7.31 (1H, d, J=7.4 Hz).

(9B) Trans-4-(4-fluorophenoxy)-N-methyl-N-[3-methyl-4-(piperazin-1-ylmethyl)phenyl]cyclohexanecarboxamide Tert-butyl 4-{4-[{[trans-4-(4-fluorophenoxy)cyclohexyl]carbonyl}(methyl)amino]-2-methylbenzyl}piperazine-1-carboxylate (47.0 mg, 0.0870 mmol) produced in (9A) was dissolved in dichloromethane (1 mL), and trifluoroacetic acid (0.5 mL) was added thereto at room temperature, and then, the resulting mixture was stirred at room temperature for 1 hour.

To the residue obtained by distilling off the solvent in the reaction solution under reduced pressure, a 1 N aqueous solution of sodium hydroxide was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:80:20 (v/v/v)), whereby the target compound was obtained as a colorless oil (35.0 mg, yield: 91%).

$^1$H-NMR (CDCl$_3$, 400 MHz): δ1.20–1.08 (2H, m), 1.82–1.61 (4H, m), 2.13–2.05 (2H, m), 2.30–2.20 (1H, m), 2.38 (3H, s), 2.45 (4H, s), 2.91 (4H, t, J=4.9 Hz), 3.22 (3H, s), 3.46 (2H, s), 4.09–4.01 (1H, m), 6.80–6.74 (2H, m), 6.97–6.89 (4H, m), 7.33 (1H, d, J=7.8 Hz).

Example 10

4-[(4-Chlorophenyl)sulfonyl]-N-methyl-N-(3-methyl-4-{[(3S)-3-methylpiperazin-1-yl]methyl}phenyl)cyclohexanecarboxamide

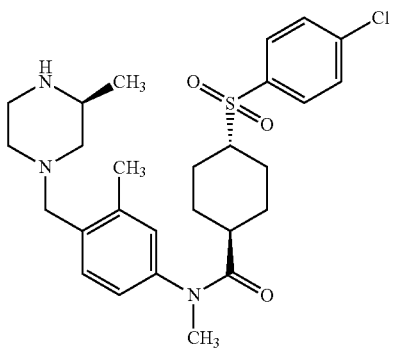 [SMILES: Cc1cc(N(C)C(=O)[C@H]2CC[C@H](S(=O)(=O)c3ccc(Cl)cc3)CC2)ccc1CN1CCN[C@@H](C)C1]

(10A) Methyl trans-4-[(4-chlorophenyl)sulfanyl]cyclohexanecarboxylate

To a solution of methyl cis-4-hydroxycyclohexanecarboxylate (500 mg, 3.16 mmol) in toluene (30 mL), 4-chlorobenzenethiol (457 mg, 3.16 mmol) and cyanomethylenetributylphosphorane (915 mg, 3.16 mmol) were added, and the resulting mixture was stirred at 100° C. for 2 hours. Then, the residue obtained by distilling off the solvent in the reaction solution under reduced pressure was purified by silica gel column chromatography (hexane:ethyl acetate=95:5 to 85:15 (v/v)), whereby the title compound was obtained as an oil (206 mg, yield: 26%).

$^1$H-NMR (CDCl$_3$, 400 MHz) δppm: 7.33 (2H, dd, J=6.1, 2.0 Hz), 7.26 (2H, dd, J=6.3, 3.2 Hz), 3.66 (3H, s), 2.97 (1H, s), 2.29 (1H, s), 2.05 (4H, m), 1.52 (2H, m), 1.35 (2H, m).

(10B) Methyl trans-4-[(4-chlorophenyl)sulfonyl]cyclohexanecarboxylate

To a solution of methyl trans-4-[(4-chlorophenyl)sulfanyl]cyclohexanecarboxylate (206 mg, 0.82 mmol) produced in (10A) in dichloromethane (8 mL), at 0° C., m-chloroperoxybenzoic benzoic acid (390 mg, 1.80 mmol) was added, and the resulting mixture was stirred at the same temperature for 1 hour. Then, to the reaction solution, a saturated aqueous solution of sodium hydrogen carbonate was added, and extraction was performed once with ethyl acetate. The obtained organic layer was washed with water and a 10% aqueous solution of sodium chloride and then dried over anhydrous sodium sulfate. The solvent was distilled off under reduced pressure, and the obtained residue was purified by silica gel column chromatography (hexane:ethyl acetate=90:10 to 80:20 (v/v)), whereby the title compound was obtained as an oil (229 mg, yield: 99%).

$^1$H-NMR (CDCl$_3$, 400 MHz) δppm: 7.80 (2H, d, J=1.2 Hz), 7.55 (2H, d, J=7.3 Hz), 3.66 (3H, s), 2.89 (1H, m), 2.25 (1H, m), 2.14 (4H, m), 1.46 (4H, m).

(10C) Trans-4-[(4-chlorophenyl)sulfonyl]cyclohexanecarboxylic acid

To a solution of methyl trans-4-[(4-chlorophenyl)sulfonyl]cyclohexanecarboxylate (209 mg, 0.81 mol) synthesized in (10B) in methanol (10 ml), 2 N sodium hydroxide (0.5 ml, 1 mmol) was added at room temperature, and the resulting mixture was stirred at the same temperature for 1 hour. Then, to the reaction solution, 2 N hydrochloric acid (0.5 ml, 1 mmol) was added, and extraction was performed once with ethyl acetate. The obtained organic layer was washed with water and a saturated aqueous solution of sodium chloride and then dried over anhydrous sodium sulfate. The solvent was distilled off under reduced pressure, and the obtained residue was purified by silica gel column chromatography (hexane:ethyl acetate=10:90 to 0:100 (v/v)), whereby the title compound was obtained as an oil (180 mg, yield: 73%).

$^1$H-NMR (CDCl$_3$, 400 MHz) δppm: 7.75 (2H, d, J=9.2 Hz), 7.52 (2H, d, J=9.2 Hz), 7.33 (1H, d, J=7.1 Hz), 6.90 (2H, m), 4.24 (1H, brs), 3.83 (1H, d, J=13.5 Hz), 3.44 (3H, m), 3.20 (3H, s), 3.10 (1H, m), 2.87 (1H, m), 2.76 (1H, m), 2.63 (1H, m), 2.38 (3H, s), 2.24 (2H, m), 2.05 (1H, m), 1.97 (2H, m), 1.81 (2H, m), 1.55 (9H, s), 1.28 (9H, m).

(10D) Tert-butyl (2S)-4-{4-[({4-[(4-chlorophenyl)sulfonyl]cyclohexyl}carbonyl)(methyl)amino]-2-methylbenzyl}-2-methylpiperazine-1-carboxylate To a solution of tert-butyl (2S)-4-[(4-amino-2-methylphenyl)methyl]-2-methylpiperazine-1-carboxylate (90.6 mg, 0.30 mmol), which is a known compound, and trans-4-[(4-chlorophenyl)sulfonyl]cyclohexanecarboxylic acid (100 mg, 0.30 mmol) synthesized in (10C) in N,N-dimethylformamide (8 mL), 4-(4,6-dimethoxy-1,3,5-triazin-2-yl)-4-methylmorpholium chloride hydrate (106 mg, 0.36 mmol) was added at room temperature, and then, the resulting mixture was stirred at the same temperature for 20 hours. Then, to the reaction solution, water was added, and extraction was performed once with ethyl acetate. The obtained organic layer was washed with water and a saturated aqueous solution of sodium chloride and then dried over anhydrous sodium sulfate. The solvent was distilled off under reduced pressure, and the obtained residue was purified by silica gel column chromatography (hexane:ethyl acetate=80:20 to 50:50 (v/v)), whereby the title compound was obtained as an oil (80.2 mg, yield: 45%).

$^1$H-NMR (CDCl$_3$, 400 MHz) δppm: 7.75 (2H, d, J=9.1 Hz), 7.52 (2H, d, J=9.0 Hz), 7.33 (1H, d, J=7.1 Hz), 6.90 (2H, m), 4.24 (1H, brs), 3.83 (1H, d, J=13.0 Hz), 3.44 (3H, m), 3.20 (3H, s), 3.10 (1H, m), 2.87 (1H, m), 2.76 (1H, m), 2.63 (1H, m), 2.38 (3H, s), 2.24 (2H, m), 2.05 (1H, m), 1.97 (2H, m), 1.81 (2H, m), 1.55 (9H, s), 1.28 (9H, m).

(10E) 4-[(4-Chlorophenyl)sulfonyl]-N-methyl-N-(3-methyl-4-{[(3S)-3-methylpiperazin-1-yl]methyl}phenyl)cyclohexanecarboxamide To a solution of tert-butyl (2S)-4-{4-[({4-[(4-chlorophenyl)sulfonyl]cyclohexyl}carbonyl)(methyl)amino]-2-methylbenzyl}-2-methylpiperazine-1-carboxylate (80.2 mg, 0.13 mmol) synthesized in (10D) in dichloromethane (1 mL), trifluoroacetic acid (10 mL) was added at room temperature, and the resulting mixture was stirred at room temperature for 30 minutes. The solvent was distilled off under reduced pressure, and the obtained residue was purified by NH silica gel column chromatography (ethyl acetate:methanol=100:0 to 90:10 (v/v)), whereby the title compound was obtained as an oil (50.1 mg, yield: 100%).

$^1$H-NMR (CDCl$_3$, 400 MHz) δppm: 7.75 (2H, d, J=9.0 Hz), 7.52 (2H, d, J=9.0 Hz), 7.34 (1H, d, J=9.0 Hz), 6.91 (2H, m), 3.46 (3H, s), 3.19 (3H, s), 2.98 (4H, m), 2.76 (2H, m), 2.37 (3H, s), 2.20 (3H, m), 2.07 (1H, m), 1.96 (2H, m), 1.78 (3H, m), 1.54 (2H, m), 1.26 (2H, m), 1.05 (3H, d, J=6.3 Hz).

Example 11

4-[(4-Fluorophenyl)amino]-N-methyl-N-(4-{[(3S)-3-methylpiperazin-1-yl]methyl}phenyl)cyclohexanecarboxamide

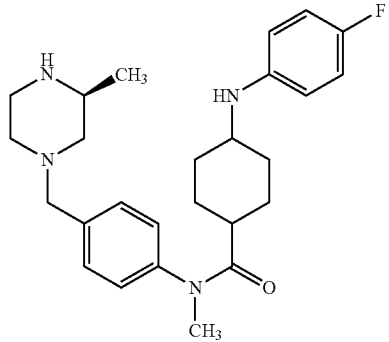 [SMILES: C[C@H]1CN(Cc2ccc(N(C)C(=O)C3CCC(Nc4ccc(F)cc4)CC3)cc2)CCN1]

(11A) Tert-butyl (2S)-2-methyl-4-(4-{methyl[(4-oxocyclohexyl)carbonyl]amino}benzyl)piperazine-1-carboxylate 4-Oxocyclohexanecarboxylic acid (90 mg, 0.633 mmol) was dissolved in dichloromethane (5 mL), and oxalyl chloride (265 μL, 3.16 mmol) and a catalytic amount of dimethylformamide were added thereto at 0° C., and then, the resulting mixture was stirred under a nitrogen atmosphere at room temperature for 30 minutes. The residue obtained by distilling off the solvent in the reaction solution under reduced pressure was dissolved in dichloromethane (15 mL), and tert-butyl (2S)-2-methyl-4-[2-methyl-4-(methylamino)benzyl]piperazine-1-carboxylate (100 mg, 0.313 mmol), which is a known compound, and triethylamine (130 μL, 0.939 mmol) were added thereto at 0° C., and then, the resulting mixture was stirred under a nitrogen atmosphere at room temperature for 1 hour. To the reaction solution, water was added at room temperature, and the organic matter was extracted with dichloromethane. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a white solid substance (44.5 mg, yield: 32%).

$^1$H NMR (CDCl$_3$, 400 MHz): δ1.26 (3H, d, J=7.3 Hz), 1.46 (9H, s), 1.94-2.08 (m, 5H), 2.18 (2H, d, J=11.2 Hz), 2.44 (2H, d, J=12.7 Hz), 2.60-2.66 (3H, m), 2.77 (1H, d, J=10.7 Hz), 3.14 (1H, d, J=12.7 Hz), 3.27 (3H, s), 3.47 (1H, d, J=13.6 Hz), 3.57 (1H, d, J=13.6 Hz), 3.83 (1H, d, J=13.2 Hz), 4.22 (1H, s), 7.18 (2H, d, J=8.0 Hz), 7.43 (2H, d, J=8.0 Hz).

(11B) Tert-butyl (2S)-4-{4-[({4-[(4-fluorophenyl)amino]cyclohexyl}carbonyl)(methyl)amino]benzyl}-2-methylpiperazine-1-carboxylate Tert-butyl (2S)-2-methyl-4-(4-{methyl[(4-oxocyclohexyl)carbonyl]amino}benzyl)piperazine-1-carboxylate (44 mg, 0.10 mmol) produced in (11A), 4-fluoroaniline (0.010 ml, 0.10 mmol), and acetic acid (0.029 ml, 0.50 mmol) were dissolved in tetrahydrofuran (5.0 mL), and sodium triacetoxyborohydride (42 mg, 0.20 mmol) was added thereto, and then, the resulting mixture was stirred at 80° C. for 2 hours.

After the temperature of the reaction solution was returned to room temperature, water was added thereto, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 50:50 (v/v)), whereby the target compound was obtained as a yellow oil (28.8 mg, yield: 53%).

$^1$H NMR (CDCl$_3$, 400 MHz): δ1.25 (3H, d, J=7.3 Hz), 1.31-1.37 (2H, m), 1.46 (9H, s), 1.78-1.85 (5H, m), 2.04-2.09 (1H, m), 2.18 (1H, d, J=11.2 Hz), 2.30 (1H, m), 2.59 (1H, d, J=11.2 Hz), 2.77 (1H, d, J=10.8 Hz), 3.10-3.15 (2H, m), 3.24 (3H, s), 3.45 (2H, d, J=13.7 Hz), 3.55 (1H, d, J=13.7 Hz), 3.83 (1H, d, J=13.2 Hz), 4.22 (1H, s), 6.51 (2H, dd, J=4.4, 9.3 Hz), 6.86 (2H, dd, J=8.8, 8.8 Hz), 7.13 (2H, d, J=8.0 Hz), 7.39 (2H, d, J=8.0 Hz).

(11C) 4-[(4-Fluorophenyl)amino]-N-methyl-N-(4-{[(3S)-3-methylpiperazin-1-yl]methyl}phenyl)cyclohexanecarboxamide Tert-butyl (2S)-4-{4-[({4-[(4-fluorophenyl)amino]cyclohexyl}carbonyl)(methyl)amino]benzyl}-2-methylpiperazine-1-carboxylate (28.8 mg, 0.053 mmol) produced in (11B) was dissolved in dichloromethane (2 mL), and trifluoroacetic acid (2 mL) was added thereto at room temperature, and then, the resulting mixture was stirred under a nitrogen atmosphere at room temperature for 1 hour. After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:80:20 (v/v/v)), whereby the target compound was obtained as a white solid (18.0 mg, yield: 77%).

$^1$H NMR (CDCl$_3$, 400 MHz): δ1.06 (3H, d, J=6.3 Hz), 1.32-1.39 (2H, m), 1.48 (2H, d, J=11.3 Hz), 1.74-1.88 (6H, m), 2.31 (1H, m), 2.77 (2H, d, J=10.9 Hz), 2.95-2.99 (3H, m), 3.24 (3H, s), 3.47 (1H, m), 3.53 (2H, s), 6.51 (2H, dd, J=4.3, 9.0 Hz), 6.86 (2H, dd, J=8.6, 8.6 Hz), 7.12 (2H, d, J=8.3 Hz), 7.37 (2H, d, J=8.3 Hz).

Example 12

Trans-N-ethyl-4-[(5-fluoropyridin-2-yl)oxy]-N-[3-methyl-4-(piperazin-1-ylmethyl)phenyl]cyclohexanecarboxamide

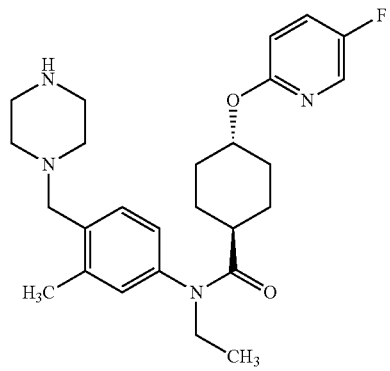 [SMILES: CCN(c1ccc(CN2CCNCC2)c(C)c1)C(=O)[C@H]1CC[C@H](Oc2ccc(F)cn2)CC1]

(12A) Tert-butyl 4-(4-{[(trans-4-hydroxycyclohexyl)carbonyl]amino}-2-methylbenzyl)piperazine-1-carboxylate Tert-butyl 4-(4-amino-2-methylbenzyl)piperazine-1-carboxylate (1.00 g, 3.27 mmol), 4-hydroxycyclohexanecarboxylic acid (1.42 g, 9.85 mmol), and 4-(4,6-dimethoxy-1,3,5-triazin-2-yl)-4-methylmorpholium chloride hydrate (2.74 g, about 9.9 mmol) were dissolved in dimethylformamide (35 mL), and the resulting mixture was stirred at room temperature for 12 hours.

To the reaction solution, water was added at room temperature, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a white solid (1.04 g, yield: 74%).

$^1$H NMR (CDCl$_3$, 400 MHz): δ1.34 (2H, m), 1.45 (9H, s), 1.67 (2H, m), 2.01 (2H, d, J=12.2 Hz), 2.11 (2H, d, J=12.2 Hz), 2.14-2.19 (1H, m), 2.34 (3H, s), 2.35 (4H, m), 3.38 (4H, m), 3.40 (2H, s), 3.64-3.69 (1H, m), 7.08 (1H, s), 7.17 (1H, d, J=8.3 Hz), 7.26 (1H, d, J=8.3 Hz), 7.35 (1H, s).

(12B) Tert-butyl 4-{4-[({trans-4-[(5-fluoropyridin-2-yl)oxy]cyclohexyl}carbonyl)amino]-2-methylbenzyl}piperazine-1-carboxylate Tert-butyl 4-(4-{[(trans-4-hydroxycyclohexyl)carbonyl]amino}-2-methylbenzyl)piperazine-1-carboxylate (950 mg, 2.20 mmol) produced in (12A) was dissolved in dimethylformamide (30 mL), and sodium hydride (63%, 100 mg, 2.64 mmol) was added thereto. After the resulting mixture was stirred at room temperature for 30 minutes, 2,5-difluoropyridine (320 mg, 2.78 mmol) was added thereto, and the resulting mixture was stirred under a nitrogen atmosphere at 100° C. for 3 hours. To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 0:100 (v/v)), whereby the target compound was obtained as a colorless oil (514 mg, yield: 44%).

$^1$H NMR (CDCl$_3$, 400 MHz): δ1.42-1.51 (2H, m), 1.46 (9H, s), 1.80 (2H, m), 2.04-2.08 (2H, m), 2.24-2.31 (3H, m), 2.33 (3H, s), 2.35 (4H, m), 3.38 (4H, m), 3.40 (2H, s), 4.92-4.97 (1H, m), 6.65 (1H, dd, J=3.6, 9.0 Hz), 7.17 (1H, d, J=8.3 Hz), 7.29-7.34 (2H, m), 7.39 (1H, s), 7.46 (1H, s), 7.97 (1H, d, J=3.6 Hz).

(12C) Tert-butyl 4-{4-[ethyl({trans-4-[(5-fluoropyridin-2-yl)oxy]cyclohexyl}carbonyl)amino]-2-methylbenzyl}piperazine-1-carboxylate Tert-butyl 4-{4-[({trans-4-[(5-fluoropyridin-2-yl)oxy]cyclohexyl}carbonyl)amino]-2-methylbenzyl}piperazine-1-carboxylate (48 mg, 0.0911 mmol) produced in (12B) was dissolved in dimethylformamide (10 mL), and sodium hydride (63%, 10 mg, 0.182 mmol) was added thereto. After the resulting mixture was stirred under a nitrogen atmosphere at room temperature for 30 minutes, ethyl iodide (15 μL, 0.182 mmol) was added thereto at room temperature, and the resulting mixture was stirred under a nitrogen atmosphere at 100° C. for 30 minutes. To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 75:25 (v/v)), whereby the target compound was obtained as a colorless oil (50 mg, yield: 100%).

$^1$H NMR (CDCl$_3$, 400 MHz): δ1.09 (3H, t, J=7.1 Hz), 1.13 (1H, m), 1.28 (1H, m), 1.47 (9H, s), 1.73-1.77 (4H, m), 2.08-2.16 (3H, m), 2.38 (3H, s), 2.42 (4H, m), 3.44 (4H, m), 3.48 (2H, s), 3.71 (2H, q, J=7.1 Hz), 4.83-4.90 (1H, m), 6.56 (1H, dd, J=3.5, 9.0 Hz), 6.93 (1H, d, J=8.2 Hz), 6.94 (1H, s), 7.24-7.28 (1H, m), 7.32 (1H, d, J=7.5 Hz), 7.94 (1H, d, J=3.5 Hz).

(12D) Trans-N-ethyl-4-[(5-fluoropyridin-2-yl)oxy]-N-[3-methyl-4-(piperazin-1-ylmethyl)phenyl]cyclohexanecarboxamide Tert-butyl 4-{4-[ethyl({trans-4-[(5-fluoropyridin-2-yl)oxy]cyclohexyl}carbonyl)amino]-2-methylbenzyl}piperazine-1-carboxylate (50 mg, 0.0901 mmol) produced in (12C) was dissolved in dichloromethane (2 mL), and trifluoroacetic acid (1 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless amorphous substance (40 mg, yield: 98%).

$^1$H NMR (CDCl$_3$, 400 MHz): δ1.09 (3H, t, J=7.0 Hz), 1.13 (1H, m), 1.72-1.76 (5H, m), 2.09-2.12 (3H, m), 2.37 (3H, s), 2.68 (4H, m), 3.12 (4H, m), 3.54 (2H, s), 3.71 (2H, q, J=7.0 Hz), 4.82-4.89 (1H, m), 6.56 (1H, dd, J=3.5, 9.0 Hz), 6.91-6.95 (2H, m), 7.22-7.34 (2H, m), 7.94 (1H, d, J=3.1 Hz).

Example 13

Trans-4-[(5-fluoropyridin-2-yl)oxy]-N-[3-methyl-4-(piperazin-1-ylmethyl)phenyl]-N-propylcyclohexanecarboxamide

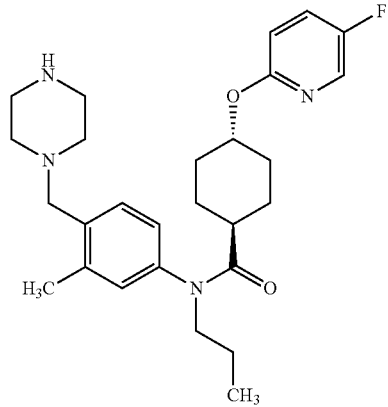 [SMILES: CCCN(c1ccc(CN2CCNCC2)c(C)c1)C(=O)[C@H]1CC[C@H](Oc2ccc(F)cn2)CC1]

(13A) Tert-butyl 4-{4-[({trans-4-[(5-fluoropyridin-2-yl)oxy]cyclohexyl}carbonyl)(propyl)amino]-2-methylbenzyl}piperazine-1-carboxylate Tert-butyl 4-{4-[({trans-4-[(5-fluoropyridin-2-yl)oxy]cyclohexyl}carbonyl)amino]-2-methylbenzyl}piperazine-1-carboxylate (100 mg, 0.190 mmol) produced in (12B) was dissolved in dimethylformamide (10 mL), and sodium hydride (63%, 15 mg, 0.379 mmol) was added thereto. After the resulting mixture was stirred under a nitrogen atmosphere at room temperature for 30 minutes, 1-iodopropane (37 μL, 0.379 mmol) was added thereto at room temperature, and the resulting mixture was stirred under a nitrogen atmosphere at 100° C. for 2 hours. To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 70:30 (v/v)), whereby the target compound was obtained as a colorless oil (100 mg, yield: 93%).

MS (ESI) m/z: 569 (M+H)+.

(13B) Trans-4-[(5-fluoropyridin-2-yl)oxy]-N-[3-methyl-4-(piperazin-1-ylmethyl)phenyl]-N-propylcyclohexanecarboxamide Tert-butyl 4-{4-[({trans-4-[(5-fluoropyridin-2-yl)oxy]cyclohexyl}carbonyl)(propyl)amino]-2-methylbenzyl}piperazine-1-carboxylate (100 mg, 0.176 mmol) produced in (13A) was dissolved in dichloromethane (5 mL), and trifluoroacetic acid (2 mL) was added thereto at room temperature, and then, the resulting mixture was stirred under a nitrogen atmosphere at room temperature for 2 hours. After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless amorphous substance (58 mg, yield: 70%).

1H NMR (CDCl3, 400 MHz): δ0.87 (3H, t, J=7.4 Hz), 1.09-1.16 (2H, m), 1.46-1.55 (2H, m), 1.73-1.77 (4H, m), 2.09-2.17 (3H, m), 2.37 (3H, s), 2.45 (4H, m), 2.90 (4H, m), 3.46 (2H, s), 3.61 (2H, t, J=7.4 Hz), 4.82-4.90 (1H, m), 6.55 (1H, dd, J=3.5, 9.0), 6.92 (1H, d, J=7.0 Hz), 6.93 (1H, s), 7.24-7.28 (1H, m), 7.33 (1H, d, J=8.6 Hz), 7.94 (1H, d, J=3.1 Hz).

Example 14

Trans-4-[(5-fluoropyridin-2-yl)oxy]-N-(2-methoxyethyl)-N-[3-methyl-4-(piperazin-1-ylmethyl)phenyl]cyclohexanecarboxamide

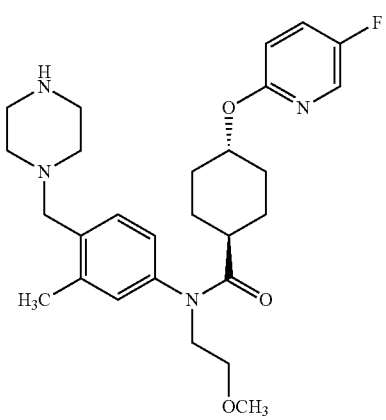 [SMILES: COCCN(c1ccc(CN2CCNCC2)c(C)c1)C(=O)[C@H]1CC[C@H](Oc2ccc(F)cn2)CC1]

(14A) Tert-butyl 4-{4-[({trans-4-[(5-fluoropyridin-2-yl)oxy]cyclohexyl}carbonyl)(2-methoxyethyl)amino]-2-methylbenzyl}piperazine-1-carboxylate Tert-butyl 4-{4-[({trans-4-[(5-fluoropyridin-2-yl)oxy]cyclohexyl}carbonyl)amino]-2-methylbenzyl}piperazine-1-carboxylate (78 mg, 0.148 mmol) produced in (12B) was dissolved in dimethylformamide (10 mL), and sodium hydride (63%, 12 mg, 0.296 mmol) was added thereto. After the resulting mixture was stirred under a nitrogen atmosphere at room temperature for 30 minutes, 2-bromoethylmethyl ether (28 μL, 0.296 mmol) was added thereto at room temperature, and the resulting mixture was stirred under a nitrogen atmosphere at 60° C. for 2 hours. To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. This crude product was purified by silica gel column chromatography (hexane:ethyl acetate=100:0 to 50:50 (v/v)), whereby the target compound was obtained as a colorless oil (60 mg, yield: 69%).

1H NMR (CDCl3, 400 MHz): δ1.06-1.16 (2H, m), 1.47 (9H, s), 1.75-1.77 (4H, m), 2.10-2.21 (3H, m), 2.37 (3H, s), 2.41 (4H, m), 3.31 (3H, s), 3.44 (4H, m), 3.47 (2H, s), 3.51 (2H, t, J=5.9 Hz), 3.61 (2H, t, J=5.9 Hz), 4.84-4.89 (1H, m), 6.56 (1H, dd, J=3.5, 9.0 Hz), 6.97 (1H, d, J=7.5 Hz), 6.99 (1H, s), 7.18-7.25 (1H, m), 7.30 (1H, d, J=7.5 Hz), 7.94 (1H, d, J=3.1 Hz).

(14B) Trans-4-[(5-fluoropyridin-2-yl)oxy]-N-(2-methoxyethyl)-N-[3-methyl-4-(piperazin-1-ylmethyl)phenyl]cyclohexanecarboxamide Tert-butyl 4-{4-[({trans-4-[(5-fluoropyridin-2-yl)oxy]cyclohexyl}carbonyl)(2-methoxyethyl)amino]-2-methylbenzyl}piperazine-1-carboxylate (60 mg, 0.103 mmol) produced in (14A) was dissolved in dichloromethane (5 mL), and trifluoroacetic acid (2 mL) was added thereto at room temperature, and then, the resulting mixture was stirred under a nitrogen atmosphere at room temperature for 2 hours.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless amorphous substance (41 mg, yield: 82%).

1H NMR (CDCl3, 400 MHz): δ1.07-1.17 (2H, m), 1.71-1.77 (4H, m), 2.08-2.12 (2H, m), 2.16-2.23 (1H, m), 2.37 (3H, s), 2.45 (4H, m), 2.90 (4H, m), 3.31 (3H, s), 3.45 (2H, s), 3.50 (2H, t, J=5.9 Hz), 3.84 (2H, t, J=5.9 Hz), 4.82-4.90 (1H, m), 6.56 (1H, dd, J=3.5, 9.0 Hz), 6.97 (1H, d, J=7.4 Hz), 6.98 (1H, s), 7.24-7.29 (1H, m), 7.32 (1H, d, J=7.4 Hz), 7.94 (1H, d, J=3.1 Hz).

Example 15

Trans-4-[(5-fluoropyridin-2-yl)oxy]-N-isopropyl-N-[3-methyl-4-(piperazin-1-ylmethyl)phenyl]cyclohexanecarboxamide

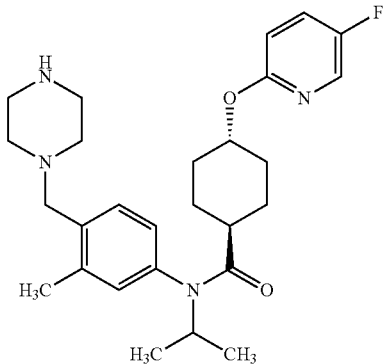 [SMILES: Cc1cc(N(C(=O)[C@H]2CC[C@H](Oc3ccc(F)cn3)CC2)C(C)C)ccc1CN1CCNCC1]

(15A) Tert-butyl 4-[4-(isopropylamino)-2-methylbenzyl]piperazine-1-carboxylate

Tert-butyl 4-(4-amino-2-methylbenzyl)piperazine-1-carboxylate (150 g, 0.491 mmol), 2-methoxypropene (0.070 mL, 0.735 mmol), acetic acid (0.042 mL, 0.735 mmol), and sodium triacetoxy borohydride (155 mg, 0.735 mmol) were dissolved in 1,2-dichloroethane (35 mL), and the resulting mixture was stirred at room temperature for 12 hours.

To the reaction solution, a saturated aqueous solution of sodium hydrogen carbonate was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate=100:0 to 85:15 (v/v)), whereby the target compound was obtained as a colorless amorphous substance (187 mg, yield: 100%).

$^1$H NMR (CDCl$_3$, 400 MHz): δ1.20 (6H, d, J=6.7 Hz), 1.45 (9H, s), 2.28 (3H, s), 2.35 (4H, m), 3.34 (2H, s), 3.38 (4H, m), 3.57-3.64 (1H, m), 6.37 (1H, dd, J=2.4, 8.2 Hz), 6.41 (1H, d, J=2.4 Hz), 6.98 (1H, d, J=8.2 Hz).

(15B) Tert-butyl trans-4-[(5-fluoropyridin-2-yl)oxy]cyclohexanecarboxylate

Trans-4-hydroxycyclohexanecarboxylic acid (1.51 g, 0.0104 mol) and N,N-dimethylformamide di-tert-butyl acetal (4.99 mL, 0.0208 mmol) were dissolved in toluene (50 mL), and the resulting mixture was stirred under a nitrogen atmosphere at 80° C. for 6 hours. To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby tert-butyl trans-4-cyclohexanecarboxylate was obtained as a colorless oil (0.960 g, yield: 46%).

The obtained tert-butyl trans-4-cyclohexanecarboxylate (760 mg, 3.79 mmol) was dissolved in dimethylformamide (50 mL), and sodium hydride (63%, 290 mg, 7.58 mmol) was added thereto, and then, the resulting mixture was stirred at room temperature for 30 minutes. To the reaction solution, 2,5-difluoropyridine (440 mg, 3.79 mmol) was added, and the resulting mixture was stirred at 100° C. for 2 hours. Then, to the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 95:5 (v/v)), whereby the target compound was obtained as a colorless oil (511 mg, yield: 45%).

$^1$H NMR (CDCl$_3$, 400 MHz): δ1.44 (9H, s), 1.60 (2H, m), 1.64-1.75 (1H, m), 1.87-1.99 (1H, m), 2.03 (2H, dd, J=2.5, 12.7 Hz), 2.16-2.26 (3H, m), 4.87-4.93 (1H, m), 6.64 (1H, dd, J=3.9, 9.3 Hz), 7.29-7.33 (1H, m), 7.96 (1H, d, J=3.9 Hz).

(15C) Tert-butyl 4-{4-[({trans-4-[(5-fluoropyridin-2-yl)oxy]cyclohexyl}carbonyl)(isopropyl)amino]-2-methylbenzyl}piperazine-1-carboxylate Tert-butyl trans-4-[(5-fluoropyridin-2-yl)oxy]cyclohexanecarboxylate (511 mg, 1.73 mmol) produced in (15B) was dissolved in dichloromethane (5 mL), and trifluoroacetic acid (2 mL) was added thereto at 0° C., and then, the resulting mixture was stirred under a nitrogen atmosphere for 2 hours. After toluene (10 mL) was added to the reaction solution, the solvent was distilled off under reduced pressure, followed by drying, whereby trans-4-[(5-fluoropyridin-2-yl)oxy]cyclohexanecarboxylic acid was obtained as a colorless oil (310 mg, yield: 74%). The obtained trans-4-[(5-fluoropyridin-2-yl)oxy]cyclohexanecarboxylic acid (310 mg, 0.892 mmol) was dissolved in dichloromethane (5 mL), and oxalyl chloride (235 μL, 2.68 mmol) and a catalytic amount of dimethylformamide were added thereto at 0° C., and then, the resulting mixture was stirred under a nitrogen atmosphere at room temperature for 30 minutes. The residue obtained by distilling off the solvent in the reaction solution under reduced pressure was dissolved in dichloromethane (15 mL), and tert-butyl 4-[4-(isopropylamino)-2-methylbenzyl]piperazine-1-carboxylate (113 mg, 0.325 mmol) produced in (5A) and triethylamine (125 μL, 0.892 mmol) were added thereto at 0° C., and then, the resulting mixture was stirred under a nitrogen atmosphere at room temperature for 1 hour.

To the reaction solution, water was added at room temperature, and the organic matter was extracted with dichloromethane. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 50:50 (v/v)), whereby the target compound was obtained as a colorless oil (130 mg, yield: 69%).

$^1$H NMR (CDCl$_3$, 400 MHz): δ1.03 (6H, d, J=5.9 Hz), 1.08 (1H, m), 1.20-1.24 (1H, m), 1.47 (9H, s), 1.73 (3H, m), 1.92-2.01 (3H, m), 2.07-2.10 (1H, m), 2.37 (3H, s), 2.43 (4H, m), 3.45 (4H, m), 3.50 (2H, d, J=10.6 Hz), 4.82-4.89 (1H, m), 4.94-5.01 (1H, m), 6.55 (1H, dd, J=3.5, 9.0 Hz), 6.88 (2H, m), 7.23-7.28 (1H, m), 7.32 (1H, d, J=8.6 Hz), 7.94 (1H, d, J=3.2 Hz).

(15D) Trans-4-[(5-fluoropyridin-2-yl)oxy]-N-(isopropyl)-N-[3-methyl-4-(piperazin-1-ylmethyl)phenyl]cyclohexanecarboxamide Tert-butyl 4-{4-[({trans-4-[(5-fluoropyridin-2-yl)oxy]cyclohexyl}carbonyl)(isopropyl)amino]-2-methylbenzyl}piperazine-1-carboxylate (130 mg, 0.229 mmol) produced in (15C) was dissolved in dichloromethane (5 mL), and trifluoroacetic acid (2 mL) was added thereto at 0° C., and then, the resulting mixture was stirred under a nitrogen atmosphere for 2 hours. After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless oil (101 mg, yield: 93%).

$^1$H NMR (CDCl$_3$, 400 MHz): δ1.03 (6H, d, J=4.7 Hz), 1.09 (1H, m), 1.20-1.22 (1H, m), 1.45 (1H, d, J=10.2 Hz), 1.73 (3H, m), 1.93-2.02 (2H, m), 2.07-2.10 (1H, m), 2.38 (3H, s), 2.45 (4H, m), 2.91 (4H, m), 3.48 (2H, d, J=8.6 Hz), 4.82-4.89 (1H, m), 4.94-5.01 (1H, m), 6.55 (1H, dd, J=3.9, 9.4 Hz), 6.88 (2H, m), 7.23-7.31 (1H, m), 7.33 (1H, d, J=8.6 Hz), 7.94 (1H, d, J=3.2 Hz).

Example 16

Ethyl [3-({trans-4-[methyl(3-methyl-4-{[(3S)-3-methylpiperazin-1-yl]methyl}phenyl)carbamoyl]cyclohexyl}oxy)phenyl]acetate and hydrochloride thereof

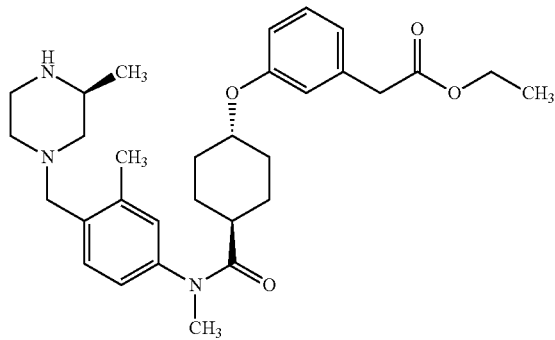

(16A) Tert-butyl (2S)-4-{4-[({trans-4-[3-(2-ethoxy-2-oxyethyl)phenoxy]cyclohexyl}carbonyl)(methyl)amino]-2-methylbenzyl}-2-methylpiperazine-1-carboxylate Tert-butyl (2S)-4-(4-{[(cis-4-hydroxycyclohexyl)carbonyl](methyl)amino}-2-methylbenzyl)-2-methylpiperazine-1-carboxylate (4.48 g, 9.76 mmol) produced in (2A) was dissolved in toluene (50 mL), and ethyl 3-hydroxyphenylacetate (1.76 g, 9.76 mmol) and cyanomethylenetributylphosphorane (3.92 mL, 14.6 mmol) were added thereto at room temperature, and then, the resulting mixture was stirred for 1.5 hours while heating to reflux.

The residue obtained by distilling off the solvent in the reaction solution under reduced pressure was purified by silica gel column chromatography (hexane:ethyl acetate=80:20 to 50:50 (v/v)), whereby the target compound was obtained as a colorless oil (2.13 g, yield: 35%).

$^1$H NMR (CDCl$_3$, 400 MHz): δ1.06-1.23 (2H, m), 1.23 (3H, d, J=7.0 Hz), 1.25 (3H, 7, J=7.0 Hz), 1.47 (9H, s), 1.63-1.84 (4H, m), 2.04 (1H, m), 2.07-2.15 (2H, m), 2.17-2.29 (2H, m), 2.39 (3H, s), 2.60 (1H, d, J=11.0 Hz), 2.74 (1H, d, J=11.7 Hz), 3.09 (1H, m), 3.24 (3H, s), 3.43 (2H, s), 3.54 (2H, s), 3.82 (1H, d, J=13.3 Hz), 4.14 (2H, q, J=7.0 Hz), 4.11-4.27 (2H, m), 6.70-6.79 (2H, m), 6.82 (1H, d, J=7.8 Hz), 6.92-6.99 (2H, m), 7.18 (1H, t, J=7.8 Hz), 7.32 (1H, d, J=8.2 Hz).

(16B) Ethyl [3-({trans-4-[methyl(3-methyl-4-{[(3S)-3-methylpiperazin-1-yl]methyl}phenyl)carbamoyl]cyclohexyl}oxy)phenyl]acetate Tert-butyl (2S)-4-{4-[({trans-4-[3-(2-ethoxy-2-oxyethyl)phenoxy]cyclohexyl}carbonyl)(methyl)amino]-2-methylbenzyl}-2-methylpiperazine-1-carboxylate (1.06 g, 1.71 mmol) produced in (16A) was dissolved in dichloromethane (8 mL), and trifluoroacetic acid (2 mL) was added thereto at room temperature, and then, the resulting mixture was stirred at room temperature for 1 hour.

The residue obtained by distilling off the solvent in the reaction solution under reduced pressure was purified by NH silica gel column chromatography (hexane:ethyl acetate=80:20 to 0:100 (v/v)), whereby the target compound was obtained as a colorless oil (696 mg, yield: 78%).

$^1$H NMR (CDCl$_3$, 400 MHz): δ1.04 (3H, d, J=6.3 Hz), 1.08-1.21 (2H, m), 1.25 (3H, t, J=7.2 Hz), 1.54-1.84 (6H, m), 2.01-2.17 (3H, m), 2.26 (1H, m), 2.38 (3H, s), 2.70-2.81 (2H, m), 2.82-3.02 (3H, m), 3.23 (3H, s), 3.45 (2H, s), 3.54 (2H, s), 4.09-4.22 (3H, m), 6.70-6.79 (2H, m), 6.82 (1H, d, J=7.8 Hz), 6.92-6.99 (2H, m), 7.18 (1H, t, J=8.0 Hz), 7.33 (1H, d, J=8.2 Hz).

MS (ESI) m/z: 522 (M+H)$^+$.

(16C) Ethyl [3-({trans-4-[methyl(3-methyl-4-{[(3S)-3-methylpiperazin-1-yl]methyl}phenyl)carbamoyl]cyclohexyl}oxy)phenyl]acetate hydrochloride Ethyl [3-({trans-4-[methyl(3-methyl-4-{[(3S)-3-methylpiperazin-1-yl]methyl}phenyl)carbamoyl]cyclohexyl}oxy)phenyl]acetate (631 mg, 1.21 mmol) produced in (16B) was dissolved in dioxane (4 mL) and water (1 mL), and 2 N hydrochloric acid (605 μL, 1.21 mmol) was added thereto at room temperature, and then, the resulting mixture was frozen at −78° C. The frozen mixture was lyophilized using a lyophilizer, whereby the target compound was obtained as a white solid (623 mg, yield: 92%).

MS (ESI) m/z: 522 (M+H)$^+$.

Example 17

[3-({Trans-4-[methyl(3-methyl-4-{[(3S)-3-methylpiperazin-1-yl]methyl}phenyl)carbamoyl]cyclohexyl}oxy)phenyl]acetic acid and hydrochloride thereof

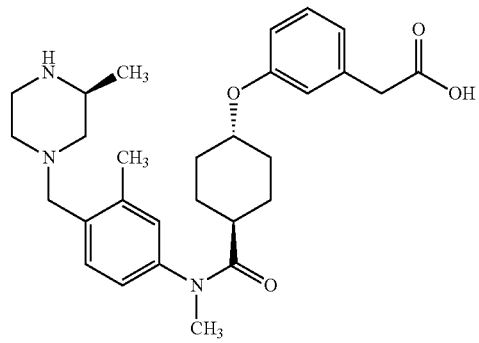 [SMILES: Cc1cc(N(C)C(=O)[C@H]2CC[C@H](Oc3cccc(CC(=O)O)c3)CC2)ccc1CN1CCN[C@@H](C)C1]

(17A) [3-({Trans-4-[methyl(3-methyl-4-{[(3S)-3-methylpiperazin-1-yl]methyl}phenyl)carbamoyl]cyclohexyl}oxy)phenyl]acetic acid Tert-butyl (2S)-4-{4-[({trans-4-[3-(2-ethoxy-2-oxyethyl)phenoxy]cyclohexyl}carbonyl)(methyl)amino]-2-methylbenzyl}-2-methylpiperazine-1-carboxylate (1.06 g, 1.71 mmol) produced in (16A) was dissolved in ethanol (20 mL), and a 2 N aqueous solution of sodium hydroxide (4.3 mL, 8.6 mmol) was added thereto at room temperature, and then, the resulting mixture was stirred at 60° C. for 1.5 hours. Then, to the solution obtained by distilling off ⅘ of the reaction solution under reduced pressure, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. The obtained crude product was dissolved in a solution (40 mL) of 4 N hydrochloric acid in dioxane, and the resulting mixture was stirred overnight at room temperature.

The residue obtained by distilling off the solvent in the reaction solution under reduced pressure was purified by ODS silica gel column chromatography (water:methanol=100:0 to 0:100 (v/v)), whereby the target compound was obtained as a white amorphous substance (790 mg, yield: 94%).

$^1$H NMR (CD$_3$OD, 400 MHz): δ0.99-1.12 (2H, m), 1.31 (3H, d, J=6.7 Hz), 1.59-1.73 (2H, m), 1.73-1.83 (2H, m), 2.04-2.15 (2H, m), 2.22-2.35 (2H, m), 2.44 (3H, s), 2.49 (1H, m), 3.02 (2H, d, J=12.3 Hz), 3.17 (1H, m), 3.21 (3H, s), 3.32-3.44 (2H, m), 3.53 (2H, s), 3.69 (2H, s), 4.19 (1H, m), 6.71-6.86 (3H, m), 7.08-7.22 (3H, m), 7.42 (1H, d, J=8.2 Hz).

MS (ESI) m/z: 494 (M+H)$^+$.

(17B) [3-({Trans-4-[methyl(3-methyl-4-{[(3S)-3-methylpiperazin-1-yl]methyl}phenyl)carbamoyl]cyclohexyl}oxy)phenyl]acetic acid hydrochloride

[3-({Trans-4-[methyl(3-methyl-4-{[(3S)-3-methylpiperazin-1-yl]methyl}phenyl)carbamoyl]cyclohexyl}oxy)phenyl]acetic acid (680 mg, 1.38 mmol) produced in (17A) was dissolved in dioxane (3 mL) and water (3 mL), and 2 N hydrochloric acid (689 μL, 1.38 mmol) was added thereto at room temperature, and then, the resulting mixture was frozen at −78° C. The frozen mixture was lyophilized using a lyophilizer, whereby the target compound was obtained as a white solid (728 mg, yield: 100%).

MS (ESI) m/z: 494 (M+H)$^+$.

Example 18

Isopropyl[3-({trans-4-[methyl(3-methyl-4-{[(3S)-3-methylpiperazin-1-yl]methyl}phenyl)carbamoyl]cyclohexyl}oxy)phenyl]acetate

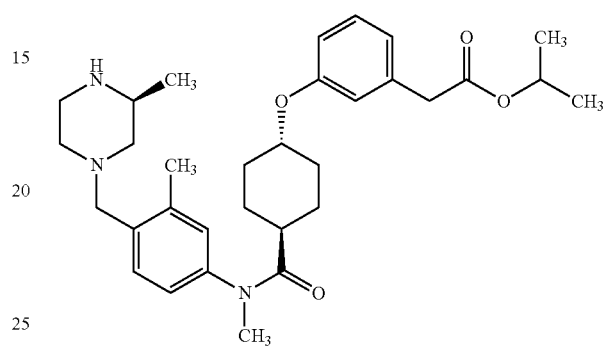

(18A) Isopropyl[3-({trans-4-[methyl(3-methyl-4-{[(3S)-3-methylpiperazin-1-yl]methyl}phenyl)carbamoyl]cyclohexyl}oxy)phenyl]acetate Tert-butyl (2S)-4-{4-[({trans-4-[3-(2-ethoxy-2-oxyethyl)phenoxy]cyclohexyl}carbonyl)(methyl)amino]-2-methylbenzyl}-2-methylpiperazine-1-carboxylate (150 mg, 0.242 mmol) produced in (16A) was dissolved in ethanol (5 mL), and a 2 N aqueous solution of sodium hydroxide (1.2 mL, 2.4 mmol) was added thereto at room temperature, and then, the resulting mixture was stirred at 60° C. for 1.5 hours.

To the reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. The obtained crude product was dissolved in isopropanol (4 mL), and 2 N hydrochloric acid (1 mL) was added thereto at room temperature, and then, the resulting mixture was stirred for 3 hours while heating to reflux.

The residue obtained by distilling off the solvent in the reaction solution under reduced pressure was purified by NH silica gel column chromatography (methanol:dichloromethane=0:100 to 5:95 (v/v)), whereby the target compound was obtained as a colorless oil (57.0 mg, yield: 44%).

$^1$H NMR (CDCl$_3$, 400 MHz): δ1.04 (3H, d, J=6.7 Hz), 1.08-1.21 (2H, m), 1.22 (6H, d, J=6.3 Hz), 1.56-1.83 (6H, m), 2.02-2.15 (3H, m), 2.26 (1H, m), 2.37 (3H, s), 2.71-2.79 (2H, m), 2.82-3.01 (3H, m), 3.23 (3H, s), 3.45 (2H, s), 3.51 (2H, s), 4.17 (1H, m), 5.00 (1H, m), 6.69-6.79 (2H, m), 6.82 (1H, d, J=7.8 Hz), 6.92-6.98 (2H, m), 7.18 (1H, t, J=7.8 Hz), 7.33 (1H, d, J=8.6 Hz).

MS (ESI) m/z: 536 (M+H)$^+$.

Example 19

Trans-4-(4-chlorophenoxy)-N-methyl-N-[3-methyl-4-(piperazin-1-ylmethyl)phenyl]cyclohexanecarboxamide $^1$H NMR (CDCl$_3$, 400 MHz): δ1.10-1.20 (2H, m), 1.64-1.77 (3H, m), 2.08 (2H, d, J=9.4 Hz), 2.23-2.29 (2H, m), 2.38

(3H, s), 2.45 (4H, m), 2.91 (4H, m), 3.23 (3H, s), 3.46 (2H, s), 4.10-4.14 (1H, m), 6.76 (2H, d, J=9.0 Hz), 6.94 (1H, d, J=7.9 Hz), 6.95 (1H, s), 7.18 (2H, d, J=9.0 Hz), 7.33 (1H, d, J=7.9 Hz).

Example 20

Trans-4-(4-cyanophenoxy)-N-methyl-N-[3-methyl-4-(piperazin-1-ylmethyl)phenyl]cyclohexanecarboxamide $^1$H NMR (CDCl$_3$, 400 MHz): δ1.16-1.24 (2H, m), 1.68-1.90 (4H, m), 2.10 (2H, d, J=10.2 Hz), 2.25-2.33 (1H, s), 2.38 (3H, s), 2.45 (4H, m), 2.90 (4H, m), 3.23 (3H, s), 3.46 (2H, s), 4.22-4.27 (1H, m), 6.86 (2H, d, J=8.7 Hz), 6.94 (1H, d, J=8.3 Hz), 6.95 (1H, s), 7.34 (1H, d, J=7.3 Hz), 7.53 (1H, d, J=8.7 Hz).

Example 21

2-Methyl-2-[3-({trans-4-[methyl(3-methyl-4-{[(3S)-3-methylpiperazin-1-yl]methyl}phenyl)carbamoyl]cyclohexyl}oxy)phenyl]proprionic acid $^1$H NMR (CDCl$_3$, 400 MHz): δ7.28-7.25 (2H, m), 7.21 (1H, s), 7.07-7.04 (1H, m), 6.94 (1H, d, J=8 Hz), 6.77 (1H, s), 6.74-6.72 (1H, m), 4.20-4.13 (1H, m), 3.79-3.75 (2H, m), 3.67-3.61 (2H, m), 3.49 (2H, s), 3.25 (3H, s), 2.45-2.42 (4H, m), 2.16-2.04 (4H, m), 1.61-1.58 (7H, m), 1.54 (6H, s), 1.25 (3H, s).

Example 22

Trans-4-[(2-cyanopyridin-4-yl)oxy]-N-methyl-N-(3-methyl-4-{[(3S)-3-methylpiperazin-1-yl]methyl}phenyl)cyclohexanecarboxamide

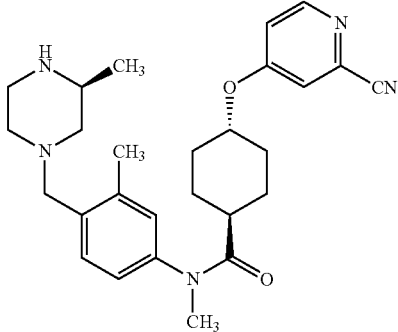 [SMILES: Cc1cc(N(C)C(=O)[C@H]2CC[C@H](Oc3ccnc(C#N)c3)CC2)ccc1CN1CCN[C@@H](C)C1]

(22A) Tert-butyl (2S)-4-{4-[({trans-4-[(2-cyanopyridin-4-yl)oxy]cyclohexyl}carbonyl)(methyl)amino]-2-methylbenzyl}-2-methylpiperazine-1-carboxylate Tert-butyl (2S)-4-(4-{[(trans-4-hydroxycyclohexyl)carbonyl](methyl)amino}-2-methylbenzyl)-2-methylpiperazine-1-carboxylate (100 mg, 0.21 mmol) produced in (4A) was dissolved in N,N-dimethylformamide (1.5 mL), and sodium hydride (63%, 16 mg, 0.42 mmol) was added thereto at 0° C., and then, the resulting mixture was stirred for 20 minutes. Then, 2-cyano-4-nitropyridine (97 mg, 0.65 mmol) was added thereto, and the resulting mixture was stirred for 1.5 hours.

After the reaction solution was cooled to 0° C., a saturated aqueous solution of ammonium chloride was added thereto, and the organic matter was extracted with ethyl acetate. The organic layer was washed with a 10% aqueous solution of sodium chloride and then dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the target compound was obtained as a light yellow oil (100 mg, yield: 82%).

$^1$H NMR (CDCl$_3$, 400 MHz): δ1.28–1.20 (5H, m), 1.47 (9H, s), 1.86–1.72 (4H, m), 2.14–2.00 (3H, m), 2.30–2.20 (2H, m), 2.40 (3H, s), 2.63–2.58 (1H, m), 2.76–2.71 (1H, m), 3.13–3.04 (1H, m), 3.25 (3H, s), 3.44 (2H, s), 3.86–3.79 (1H, m), 4.34–4.19 (2H, m), 6.91 (1H, dd, J=5.8 Hz, 2.5 Hz), 6.99–6.95 (2H, m), 7.12 (1H, d, J=2.5 Hz), 7.33 (1H, d, J=7.9 Hz), 8.46 (1H, d, J=5.8 Hz).

(22B) Trans-4-[(2-cyanopyridin-4-yl)oxy]-N-methyl-N-(3-methyl-4-{[(3S)-3-methylpiperazin-1-yl]methyl}phenyl)cyclohexanecarboxamide Tert-butyl (2S)-4-{4-[({trans-4-[(2-cyanopyridin-4-yl)oxy]cyclohexyl}carbonyl)(methyl)amino]-2-methylbenzyl}-2-methylpiperazine-1-carboxylate (100 mg, 0.178 mmol) produced in (22A) was dissolved in dichloromethane (1 mL), and trifluoroacetic acid (0.5 mL) was added thereto at room temperature, and then, the resulting mixture was stirred at room temperature for 1 hour.

To the residue obtained by distilling off the solvent in the reaction solution under reduced pressure, ethyl acetate was added. Thereafter, the organic layer was washed with a 2 N aqueous solution of sodium hydroxide and a saturated aqueous solution of sodium chloride and then dried over anhydrous sodium sulfate and filtered. Then, the solvent was distilled off under reduced pressure, whereby a crude product was obtained. The obtained crude product was purified by NH silica gel column chromatography (ethyl acetate:methanol=100:0 to 90:10 (v/v)), whereby the target compound was obtained as a solid (75 mg, yield: 91%).

$^1$H NMR (CD$_3$OD, 400 MHz): δ1.03 (3H, d, J=6.3 Hz), 1.09-1.19 (2H, m), 1.65-1.86 (5H, m), 2.05-2.15 (3H, m), 2.26-2.34 (1H, m), 2.42 (3H, s), 2.73-2.85 (4H, m), 2.90-2.94 (1H, m), 3.22 (3H, s), 3.52 (2H, s), 4.44-4.52 (1H, m), 7.08 (1H, d, J=8.0 Hz), 7.13 (1H, s), 7.17 (1H, dd, J=6.1 Hz, 2.8 Hz), 7.39 (1H, d, J=8.0 Hz), 7.43 (1H, d, J=2.8 Hz), 8.42 (1H, d, J=6.1 Hz).

MS (FAB) m/z: 462 (M+H)$^+$.

(22C) Trans-4-[(2-cyanopyridin-4-yl)oxy]-N-methyl-N-(3-methyl-4-{[(3S)-3-methylpiperazin-1-yl]methyl}phenyl)cyclohexanecarboxamide hydrochloride Trans-4-[(2-cyanopyridin-4-yl)oxy]-N-methyl-N-(3-methyl-4-{[(3S)-3-methylpiperazin-1-yl]methyl}phenyl)cyclohexanecarboxamide (390 mg, 0.85 mmol) produced in (22B) was dissolved in dioxane (5 mL) and water (20 mL), and 1 N hydrochloric acid (850 μL, 0.85 mmol) was added thereto at room temperature, and then, the resulting mixture was frozen at −78° C. The frozen mixture was lyophilized using a lyophilizer, whereby the target compound was obtained as a white solid (414 mg, yield: 99%).

MS (ESI) m/z: 462 (M+H)$^+$.

Example 23

Trans-4-[4-fluoro-3-(hydroxymethyl)phenoxy]-N-methyl-N-(3-methyl-4-{[(3S)-3-methylpiperazin-1-yl]methyl}phenyl)cyclohexanecarboxamide

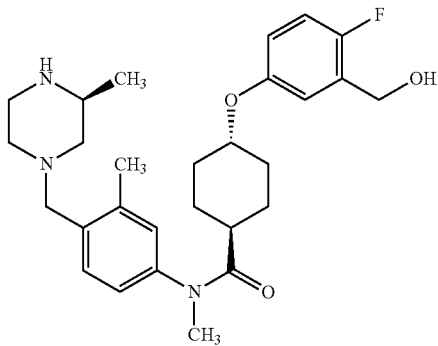 [SMILES: Cc1cc(N(C)C(=O)[C@H]2CC[C@H](Oc3ccc(F)c(CO)c3)CC2)ccc1CN1CCN[C@@H](C)C1]

(23A) Tert-butyl (2S)-4-{4-[({trans-4-[4-fluoro-3-(methoxycarbonyl)phenoxy]cyclohexyl}carbonyl)(methyl)amino]-2-methylbenzyl}-2-methylpiperazine-1-carboxylate Tert-butyl (2S)-4-(4-{[(cis-4-hydroxycyclohexyl)carbonyl](methyl)amino}-2-methylbenzyl)-2-methylpiperazine-1-carboxylate (1.60 g, 3.49 mmol) produced in (2A) was dissolved in toluene (50 mL), and methyl 2-fluoro-5-hydroxybenzoate (592 mg, 3.49 mmol) and cyanomethylenetributylphosphorane (1.68 mL, 6.28 mmol) were added thereto at room temperature, and then, the resulting mixture was stirred for 5 hours while heating to reflux.

The residue obtained by distilling off the solvent in the reaction solution under reduced pressure was purified by silica gel column chromatography (hexane:ethyl acetate=80:20 to 50:50 (v/v)), whereby the target compound was obtained as a brown oil (829 mg, yield: 39%).

$^1$H NMR (CDCl$_3$, 400 MHz): δ1.06-1.26 (2H, m), 1.23 (3H, d, J=6.7 Hz), 1.47 (9H, s), 1.49-1.84 (4H, m), 1.98-2.31 (5H, m), 2.39 (3H, s), 2.60 (1H, m), 2.73 (1H, m), 3.08 (1H, m), 3.23 (3H, s), 3.43 (2H, s), 3.78-3.86 (1H, m), 3.90 (3H, s), 4.13 (1H, m), 4.22 (1H, m), 6.92-7.06 (4H, m), 7.29-7.38 (2H, m).

(23B) Tert-butyl (2S)-4-{4-[({trans-4-[4-fluoro-3-(hydroxymethyl)phenoxy]cyclohexyl}carbonyl)(methyl)amino]-2-methylbenzyl}-2-methylpiperazine-1-carboxylate Tert-butyl (2S)-4-{4-[({trans-4-[4-fluoro-3-(methoxycarbonyl)phenoxy]cyclohexyl}carbonyl)(methyl)amino]-2-methylbenzyl}-2-methylpiperazine-1-carboxylate (414 mg, 0.678 mmol) produced in (23A) was dissolved in tetrahydrofuran (20 mL), and lithium aluminum hydride (77.2 mg, 2.03 mmol) was added thereto at 0° C., and then, the resulting mixture was stirred at 0° C. for 15 minutes.

To the reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 0:100 (v/v)), whereby the target compound was obtained as a light yellow oil (310 mg, yield: 78%).

$^1$H NMR (CDCl$_3$, 400 MHz): δ1.05-1.20 (2H, m), 1.23 (3H, d, J=6.7 Hz), 1.47 (9H, s), 1.60-1.82 (4H, m), 1.97-2.17 (3H, m), 2.17-2.27 (2H, m), 2.39 (3H, s), 2.59 (1H, d, J=11.0 Hz), 2.73 (1H, d, J=11.0 Hz), 3.08 (1H, m), 3.23 (3H, s), 3.43 (2H, s), 3.82 (1H, d, J=13.7 Hz), 4.08 (1H, m), 4.22 (1H, m), 4.70 (2H, d, J=5.9 Hz), 6.71 (1H, m), 6.86-6.99 (4H, m), 7.22 (1H, t, J=7.8 Hz), 7.31 (1H, d, J=8.2 Hz).

(23C) Trans-4-[4-fluoro-3-(hydroxymethyl)phenoxy]-N-methyl-N-(3-methyl-4-{[(3S)-3-methylpiperazin-1-yl]methyl}phenyl)cyclohexanecarboxamide Tert-butyl (2S)-4-{4-[({trans-4-[4-fluoro-3-(hydroxymethyl)phenoxy]cyclohexyl}carbonyl)(methyl)amino]-2-methylbenzyl}-2-methylpiperazine-1-carboxylate (310 mg, 0.532 mmol) produced in (23B) was dissolved in dichloromethane (4 mL), and trifluoroacetic acid (1 mL) was added thereto at room temperature, and then, the resulting mixture was stirred at room temperature for 1 hour.

The residue obtained by distilling off the solvent in the reaction solution under reduced pressure was purified by NH silica gel column chromatography (ethyl acetate:methanol=100:0 to 0:90 (v/v)), whereby the target compound was obtained as a colorless oil (252 mg, yield: 98%).

$^1$H NMR (CDCl$_3$, 400 MHz): δ1.04 (3H, d, J=6.7 Hz), 1.07-1.20 (2H, m), 1.51-1.82 (5H, m), 2.01-2.13 (3H, m), 2.25 (1H, m), 2.37 (3H, s), 2.69-2.79 (2H, m), 2.80-3.01 (3H, m), 3.23 (3H, s), 3.45 (2H, s), 4.09 (1H, m), 4.69 (2H, s), 6.71 (1H, m), 6.87-6.98 (4H, m), 7.33 (1H, d, J=8.2 Hz).

MS (ESI) m/z: 484 (M+H)$^+$.

Example 24

Trans-4-[5-(hydroxymethyl)-2-methylphenoxy]-N-methyl-N-(3-methyl-4-{[(3S)-3-methylpiperazin-1-yl]methyl}phenyl)cyclohexanecarboxamide

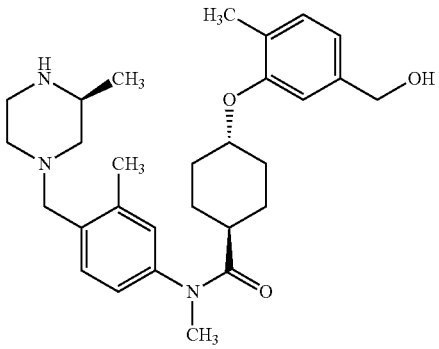 [SMILES: Cc1cc(N(C)C(=O)[C@H]2CC[C@H](Oc3cc(CO)ccc3C)CC2)ccc1CN1CCN[C@@H](C)C1]

(24A) 5-({[Tert-butyl(dimethyl)silyl]oxy}methyl)-2-methylphenol 5-(Hydroxymethyl)-2-methylphenol (300 mg, 2.17 mmol), which is a known compound, imidazole (295 mg, 4.34 mmol), and tert-butyl dimethyl silylchloride (490 mg, 3.25 mmol) were dissolved in N,N-dimethylformamide (5 mL), and the resulting mixture was stirred at 0° C. for 1 hour.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 95:5 (v/v)), whereby the target compound was obtained as a white solid (110 mg, yield: 20%).

$^1$H NMR (CDCl$_3$, 400 MHz): δ0.09 (6H, s), 0.94 (9H, s), 2.23 (3H, s), 4.66 (2H, s), 6.77 (1H, s), 6.78 (1H, d, J=7.8 Hz), 7.06 (1H, d, J=7.8 Hz).

(24B) Tert-butyl (2S)-4-{4-[({trans-4-[5-({[tert-butyl (dimethyl)silyl]oxy}methyl)-2-methylphenoxy] cyclohexyl}carbonyl)(methyl)amino]-2-methylbenzyl}-2-methylpiperazine-1-carboxylate 5-({[Tert-butyl(dimethyl)silyl]oxy}methyl)-2-methylphenol (110 mg, 0.44 mmol) produced in (24A) and tert-butyl (2S)-4-(4-{[(cis-4-hydroxycyclohexyl)carbonyl](methyl)amino}-2-methylbenzyl)-2-methylpiperazine-1-carboxylate (211 mg, 0.46 mmol) produced in (2A) were dissolved in toluene (5 mL), and the resulting mixture was stirred at 100° C. for 15 minutes. To the reaction solution, cyanomethylenetributylphosphorane (181 μL, 0.69 mmol) was added dropwise, and the resulting mixture was heated to reflux for 4 hours. After the temperature of the reaction solution was returned to room temperature, the solvent was distilled off under reduced pressure. The obtained residue was purified by silica gel column chromatography (hexane:ethyl acetate=100:0 to 80:20 (v/v)), whereby the target compound was obtained as a colorless oil (72 mg, yield: 22%).

MS (ESI) m/z: 695 (M+H)$^+$.

(24C) Trans-4-[5-(hydroxymethyl)-2-methylphenoxy]-N-methyl-N-(3-methyl-4-{[(3S)-3-methylpiperazin-1-yl]methyl}phenyl)cyclohexanecarboxamide Tert-butyl (2S)-4-{4-[({trans-4-[5-({[tert-butyl(dimethyl) silyl]oxy}methyl)-2-methylphenoxy]cyclohexyl}carbonyl) (methyl)amino]-2-methylbenzyl}-2-methylpiperazine-1-carboxylate (72 mg, 0.104 mmol) produced in (24B) was dissolved in dichloromethane (2 mL), and trifluoroacetic acid (2 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane: ethyl acetate:methanol=100:0:0 to 0:100:0 to 0:90:10 (v/v/v)), whereby the target compound was obtained as a colorless oil (30.1 mg, yield: 60%).

$^1$H NMR (CDCl$_3$, 400 MHz): δ1.05 (3H, d, J=6.3 Hz), 1.14-1.23 (2H, m), 1.65-1.80 (6H, m), 2.11 (3H, s), 2.19-2.31 (4H, m), 2.38 (3H, s), 2.76 (2H, d, J=11 Hz), 2.88-2.99 (3H, m), 3.23 (3H, s), 3.45 (2H, s), 4.11-4.19 (1H, m), 4.62 (2H, s), 6.82 (1H, d, J=7.5 Hz), 6.85 (1H, s), 6.94-6.96 (2H, m), 7.07 (1H, d, J=7.4 Hz), 7.33 (1H, d, J=7.9 Hz).

MS (ESI) m/z: 480 (M+H)$^+$.

Example 25

Trans-4-[4-chloro-3-(hydroxymethyl)phenoxy]-N-methyl-N-(3-methyl-4-{[(3S)-3-methylpiperazin-1-yl]methyl}phenyl)cyclohexanecarboxamide

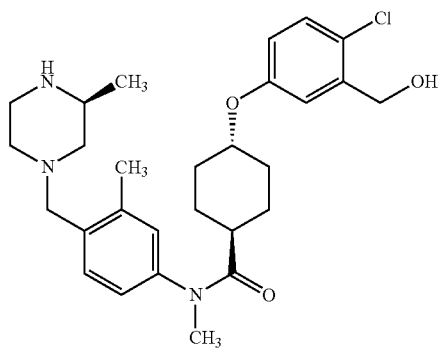 [SMILES: Cc1cc(N(C)C(=O)[C@H]2CC[C@H](Oc3ccc(Cl)c(CO)c3)CC2)ccc1CN1CCN[C@@H](C)C1]

$^1$H NMR (400 MHz, CDCl$_3$): δ1.05 (3H, d, J=6.3 Hz), 1.26 (2H, m), 1.54 (2H, m), 1.78 (3H, m), 1.96 (2H, m), 2.07 (1H, m), 2.20 (3H, m), 2.37 (3H, s), 2.76 (2H, m), 2.98 (4H, m), 3.19 (3H, s), 3.46 (3H, s), 6.91 (2H, m), 7.34 (1H, d, J=9.0 Hz), 7.52 (2H, d, J=9.0 Hz), 7.75 (2H, d, J=9.0 Hz).

MS (ESI) m/z: 500 (M+H)$^+$.

Example 26

Trans-4-[3-(2-hydroxy-2-methylpropyl)phenoxy]-N-methyl-N-(3-methyl-4-{[(3S)-3-methylpiperazin-1-yl]methyl}phenyl)cyclohexanecarboxamide

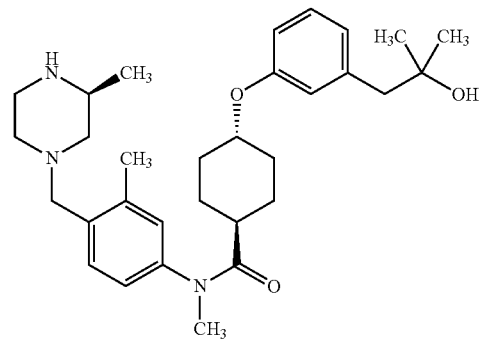 [SMILES: Cc1cc(N(C)C(=O)[C@H]2CC[C@H](Oc3cccc(CC(C)(C)O)c3)CC2)ccc1CN1CCN[C@@H](C)C1]

(26A) Trans-4-[3-(2-oxopropyl)phenoxy]cyclohexanecarboxylic acid 1-(3-Hydroxyphenyl)acetone (1.30 g, 8.66 mmol), which is a known compound, and ethyl cis-4-hydroxycyclohexanecarboxylate (2.24 g, 13.0 mmol), which is a known compound, were dissolved in tetrahydrofuran (50 mL), and di-tert-butyl azodicarboxylate (3.39 g, 14.7 mmol) and triphenylphosphine (3.86 g, 14.7 mmol) were added thereto at 0° C., and then, the resulting mixture was stirred overnight at room temperature.

After the solvent in the reaction solution was distilled off under reduced pressure, water was added thereto, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane: ethyl acetate=95:5 to 75:25 (v/v)), whereby a crude product (2.63 g) was obtained.

The obtained crude product (2.63 g) was dissolved in ethanol (50 mL), and a 2 N aqueous solution of sodium hydroxide (8.7 mL) was added thereto at room temperature, and the resulting mixture was stirred at 60° C. for 1 hour.

To the reaction solution, 2 N hydrochloric acid was added to make the solution acidic (pH=2), and extraction was performed with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=75:25 to 0:100 (v/v)), whereby the target compound was obtained as a white solid (0.38 g, yield: 16%).

$^1$H NMR (CDCl$_3$, 400 MHz): δ1.46-1.67 (4H, m), 2.11-2.21 (4H, m), 2.16 (3H, s), 2.42 (1H, m), 3.65 (2H, s), 4.21 (1H, m) 6.74 (1H, t, J=2.0 Hz), 6.77-6.82 (2H, m), 7.23 (1H, t, J=7.8 Hz).

(26B) Tert-butyl (2S)-2-methyl-4-{2-methyl-4-[methyl({trans-4-[3-(2-oxopropyl)phenoxy]cyclohexyl}carbonyl)amino]benzyl}piperazine-1-carboxylate Trans-4-[3-(2-oxopropyl)phenoxy]cyclohexanecarboxylic acid (380 mg, 1.38 mmol) produced in (26A) was dissolved in dichloromethane (8 mL), and dimethylformamide (2 μL, 0.03 mmol) and oxalyl chloride (240 μL, 2.75 mmol) were added thereto at room temperature, and then, the resulting mixture was stirred at room temperature for 2 hours. The solvent in the reaction solution was distilled off under reduced pressure, whereby an acid chloride was obtained as a crude product.

Tert-butyl (2S)-2-methyl-4-[2-methyl-4-(methylamino)benzyl]piperazine-1-carboxylate (459 mg, 1.38 mmol), which is a known compound, was dissolved in dichloromethane (8 mL), and triethylamine (383 μL, 2.75 mmol) and a dichloromethane solution (2 mL) of the previously prepared acid chloride were added thereto at 0° C., and then, the resulting mixture was stirred at 0° C. for 1.5 hours.

To the reaction solution, water was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=80:20 to 50:50 (v/v)), whereby the target compound was obtained as a colorless oil (567 mg, yield: 70%).

$^1$H NMR (CDCl$_3$, 400 MHz): δ1.08-1.22 (2H, m), 1.23 (3H, d, J=7.0 Hz), 1.47 (9H, s), 1.65-1.80 (4H, m), 2.03 (1H, m), 2.08-2.15 (2H, m), 2.13 (3H, s), 2.20-2.26 (2H, m), 2.39 (3H, s), 2.60 (1H, d, J=11.4 Hz), 2.74 (1H, d, J=11.0 Hz), 3.09 (1H, m), 3.23 (3H, s), 3.43 (2H, s), 3.62 (2H, s), 3.83 (1H, d, J=12.9 Hz), 4.17 (1H, m), 4.22 (1H, m), 6.67 (1H, m), 6.73-6.76 (2H, m), 6.93-6.96 (2H, m), 7.20 (1H, t, J=7.8 Hz), 7.31 (1H, d, J=7.8 Hz).

(26C) Tert-butyl (2S)-4-{4-[({trans-4-[3-(2-hydroxy-2-methylpropyl)phenoxy]cyclohexyl}carbonyl)(methyl)amino]-2-methylbenzyl}-2-methylpiperazine-1-carboxylate Tert-butyl (2S)-2-methyl-4-{2-methyl-4-[methyl({trans-4-[3-(2-oxopropyl)phenoxy]cyclohexyl}carbonyl)amino]benzyl}piperazine-1-carboxylate (110 mg, 0.19 mmol) produced in (26B) was dissolved in tetrahydrofuran (3 mL), and a solution of methyl magnesium bromide in tetrahydrofuran (1.10 M, 340 μL, 0.37 mmol) was added thereto at 0° C., and then, the resulting mixture was stirred at room temperature for 2 hours.

To the reaction solution, water was added, and the organic matter was extracted with ethyl acetate. The organic layer was dried over anhydrous sodium sulfate and filtered. Then, the solvent was distilled off under reduced pressure, whereby a crude product was obtained. This crude product was purified by silica gel column chromatography (hexane:ethyl acetate=67:33 to 0:100 (v/v)), whereby the target compound was obtained as a colorless oil (100 mg, yield: 86%).

$^1$H NMR (CDCl$_3$, 400 MHz): δ1.08-1.22 (2H, m), 1.21 (6H, s), 1.23 (3H, d, J=7.0 Hz), 1.47 (9H, s), 1.67-1.80 (4H, m), 2.03 (1H, m), 2.08-2.13 (2H, m), 2.20-2.25 (2H, m), 2.39 (3H, s), 2.60 (1H, d, J=11.4 Hz), 2.70 (2H, s), 2.74 (1H, d, J=11.0 Hz), 3.08 (1H, m), 3.23 (3H, s), 3.43 (2H, s), 3.82 (1H, d, J=12.9 Hz), 4.17 (1H, m), 4.22 (1H, m), 6.69 (1H, m), 6.72-6.77 (2H, m), 6.93-6.96 (2H, m), 7.18 (1H, t, J=7.8 Hz), 7.31 (1H, d, J=7.8 Hz).

(26D) Trans-4-[3-(2-hydroxy-2-methylpropyl)phenoxy]-N-methyl-N-(3-methyl-4-{[(3S)-3-methylpiperazin-1-yl]methyl}phenyl)cyclohexanecarboxamide Tert-butyl (2S)-4-{4-[({trans-4-[3-(2-hydroxy-2-methylpropyl)phenoxy]cyclohexyl}carbonyl)(methyl)amino]-2-methylbenzyl}-2-methylpiperazine-1-carboxylate (100 mg, 0.16 mmol) produced in (26C) was dissolved in dichloromethane (2 mL), and trifluoroacetic acid (190 μL) was added thereto at room temperature, and then, the resulting mixture was stirred overnight at room temperature.

To the reaction solution, a saturated aqueous solution of sodium hydrogen carbonate was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by NH silica gel column chromatography (dichloromethane:methanol=100:0 to 90:10 (v/v)), whereby the target compound was obtained as a colorless oil (78.2 mg, yield: 94%).

$^1$H NMR (CDCl$_3$, 400 MHz): δ1.04 (3H, d, J=7.0), 1.10-1.24 (2H, m), 1.21 (6H, s), 1.67-1.80 (5H, m), 2.03-2.13 (3H, m), 2.26 (1H, m), 2.37 (3H, s), 2.70 (2H, s), 2.73-2.78 (2H, m), 2.85-2.99 (3H, m), 3.23 (3H, s), 3.45 (2H, s), 4.17 (1H, m), 6.69 (1H, m), 6.72-6.77 (2H, m), 6.94-6.96 (2H, m), 7.18 (1H, t, J=7.8 Hz), 7.33 (1H, d, J=7.8 Hz).

MS (ESI) m/z: 508 (M+H)$^+$.

Example 27

Trans-4-{[3-(ethoxymethyl)phenyl]amino}-N-methyl-N-(3-methyl-4-{[(3S)-3-methylpiperazin-1-yl]methyl}phenyl)cyclohexanecarboxamide

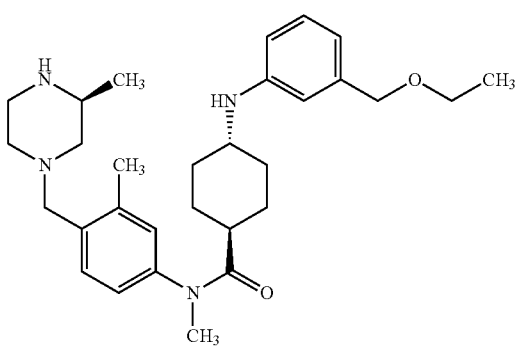 [SMILES: CCOCc1cccc(N[C@H]2CC[C@H](C(=O)N(C)c3ccc(CN4CCN[C@@H](C)C4)c(C)c3)CC2)c1]

(27A) 1-(Ethoxymethyl)-3-nitrobenzene

3-Nitrobenzyl alcohol (1.40 g, 9.14 mmol) was dissolved in dichloromethane (30 mL), and triethylamine (1.9 mL, 13.7 mmol), and methanesulfonyl chloride (806 μL, 10.1 mmol) was added thereto at 0° C., and then, the resulting mixture was stirred under a nitrogen atmosphere at 0° C. for 50 minutes.

To the reaction solution, a saturated aqueous solution of ammonium chloride was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained.

The obtained crude product was dissolved in ethanol (30 mL), and a solution of 20% sodium ethoxide in ethanol (3.8 mL, 9.60 mmol) was added thereto, and then, the resulting mixture was heated to reflux under a nitrogen atmosphere for 17 hours.

After the temperature of the reaction solution was returned to room temperature, a saturated aqueous solution of ammonium chloride was added thereto, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 75:25 (v/v)), whereby the target compound was obtained as a brown oil (1.80 g, yield: 100%).

$^1$H NMR (CDCl$_3$, 400 MHz): δ1.29 (3H, t, J=7.0 Hz), 3.60 (2H, q, J=7.0 Hz), 4.60 (2H, s), 7.52 (1H, t, J=7.8 Hz), 7.68 (1H, d, J=7.8 Hz), 8.15 (1H, d, J=8.2 Hz), 8.23 (1H, s).

(27B) 3-(Ethoxymethyl)aniline 1-(Ethoxymethyl)-3-nitrobenzene (1.80 g, 9.14 mmol) produced in (27A) was dissolved in methanol (70 mL), and an aqueous solution (25 mL) of ammonium chloride (1.53 g, 45.7 mmol) and iron powder (1.53 g, 27.42 mmol) were added thereto, and then, the resulting mixture was stirred under a nitrogen atmosphere at 90° C. for 3.5 hours.

After the temperature of the reaction solution was returned to room temperature, the solution was filtered through a Celite filter, and the solvent was distilled off under reduced pressure, and then, water was added thereto. Thereafter, the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=95:5 to 75:25 (v/v)), whereby the target compound was obtained as a yellow oil (1.40 g, yield: 92%).

$^1$H NMR (CDCl$_3$, 400 MHz): δ1.24 (3H, t, J=7.0 Hz), 3.53 (2H, q, J=7.0 Hz), 3.60-3.70 (2H, brs), 4.43 (2H, s), 6.51 (1H, dd, J=2.4, 7.8 Hz), 6.69-6.74 (2H, m), 7.12 (1H, t, J=7.6 Hz).

(27C) Ethyl trans-4-{[3-(ethoxymethyl)phenyl]amino}cyclohexanecarboxylate 3-(Ethoxymethyl)aniline (1.39 g, 8.31 mmol) produced in (27B), ethyl 4-cyclohexanonecarboxylate (1.41 g, 8.31 mmol), and acetic acid (4.8 mL, 83.1 mmol) were dissolved in tetrahydrofuran (40 mL), and sodium triacetoxy borohydride (3.52 g, 16.62 mmol) was added thereto, and then, the resulting mixture was stirred at room temperature for 5 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=95:5 to 80:20 (v/v)), whereby the target compound was obtained as a yellow oil (807 mg, yield: 32%).

$^1$H NMR (CDCl$_3$, 400 MHz): δ1.09-1.20 (2H, m), 1.24 (3H, t, J=7.0 Hz), 1.26 (3H, t, J=7.0 Hz), 1.51-1.65 (2H, m), 2.01-2.09 (2H, m), 2.16-2.24 (2H, m), 2.29 (1H, tt, J=3.6, 12.1 Hz), 3.27 (1H, tt, J=3.8, 11.2 Hz), 3.53 (2H, q, J=7.0 Hz), 4.13 (2H, q, J=7.0 Hz), 4.42 (2H, s), 6.50 (1H, dd, J=2.0, 8.0 Hz), 6.58 (1H, d, J=2.0 Hz), 6.64 (1H, d, J=7.4 Hz), 7.12 (1H, t, J=7.6 Hz).

(27D) Trans-4-{[3-(ethoxymethyl)phenyl]amino}cyclohexanecarboxylic acid

Ethyl trans-4-{[3-(ethoxymethyl)phenyl]amino}cyclohexanecarboxylate (800 mg, 2.62 mmol) produced in (27C) was dissolved in ethanol (15 mL), and a 5 N aqueous solution of sodium hydroxide (5 mL) was added thereto at room temperature, and then, the resulting mixture was stirred at room temperature for 45 minutes.

After 2 N hydrochloric acid was added to the reaction solution to neutralize the pH of the solution, water was added thereto, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=2:1 to 1:2 (v/v)), whereby the target compound was obtained as a light yellow oil (727 mg, yield: 100%).

$^1$H NMR (CD$_3$OD, 400 MHz): δ1.14-1.26 (2H, m), 1.20 (3H, t, J=7.0 Hz), 1.48-1.61 (2H, m), 1.99-2.08 (2H, m), 2.08-2.17 (2H, m), 2.27 (1H, tt, J=3.6, 12.1 Hz), 3.23 (1H, tt,

J=3.8, 11.2 Hz), 3.53 (2H, q, J=7.0 Hz), 4.40 (2H, s), 6.55-6.61 (2H, m), 6.63-6.66 (1H, m), 7.07 (1H, t, J=7.6 Hz).

(27E) Tert-butyl (2S)-4-(4-{[(trans-4-{[3-(ethoxymethyl)phenyl]amino}cyclohexyl)carbonyl](methyl)amino}-2-methylbenzyl)-2-methylpiperazine-1-carboxylate Trans-4-{[3-(ethoxymethyl)phenyl]amino}cyclohexanecarboxylic acid (400 mg, 1.44 mmol) produced in (27D) and tert-butyl (2S)-2-methyl-4-[2-methyl-4-(methylamino)benzyl]piperazine-1-carboxylate (481 mg, 1.44 mmol), which is a known compound, were dissolved in ethanol (5 mL), and 4-(4,6-dimethoxy-1,3,5-triazin-2-yl)-4-methylmorpholinium chloride hydrate (796 mg, about 2.9 mmol) was added thereto, and then, the resulting mixture was stirred under a nitrogen atmosphere at room temperature for 26 hours.

To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=90:10 to 50:50 (v/v)), whereby the target compound was obtained as a colorless solid (482 mg, yield: 56%).

$^1$H NMR (CDCl$_3$, 400 MHz): δ0.78-0.91 (2H, m), 1.22 (3H, d, J=6.7 Hz), 1.23 (3H, t, J=7.0 Hz), 1.46 (9H, s), 1.69-1.79 (4H, m), 1.98-2.13 (3H, m), 2.21 (1H, dd, J=3.3, 11.2 Hz), 2.38 (3H, s), 2.60 (1H, d, J=10.6 Hz), 2.73 (1H, d, J=11.7 Hz), 3.03-3.12 (1H, m), 3.19-3.29 (1H, m), 3.23 (3H, s), 3.43 (2H, s), 3.51 (2H, q, J=7.0 Hz), 3.70-3.75 (1H, m), 3.78-3.88 (2H, m), 4.17-4.26 (1H, brs), 4.40 (2H, s), 6.45 (1H, dd, J=1.6, 8.6 Hz), 6.52 (1H, s), 6.62 (1H, d, J=7.4 Hz), 6.92-6.98 (2H, m), 7.10 (1H, t, J=7.8 Hz), 7.30 (1H, d, J=7.8 Hz).

(27F) Trans-4-{[3-(ethoxymethyl)phenyl]amino}-N-methyl-N-(3-methyl-4-{[(3S)-3-methylpiperazin-1-yl]methyl}phenyl)cyclohexanecarboxamide Tert-butyl (2S)-4-(4-{[(trans-4-{[3-(ethoxymethyl)phenyl]amino}cyclohexyl)carbonyl](methyl)amino}-2-methylbenzyl)-2-methylpiperazine-1-carboxylate (170 mg, 0.287 mmol) produced in (27E) was dissolved in dichloromethane (1 mL), and trifluoroacetic acid (1 mL) was added thereto at room temperature, and then, the resulting mixture was stirred under a nitrogen atmosphere at room temperature for 30 minutes.

The residue obtained by distilling off the solvent in the reaction solution under reduced pressure was purified by NH silica gel column chromatography (ethyl acetate:methanol=100:0 to 90:10 (v/v)), whereby the target compound was obtained as a colorless oil (72.9 mg, yield: 52%).

$^1$H NMR (CDCl$_3$, 400 MHz): δ0.78-0.91 (2H, m), 1.04 (3H, d, J=6.3 Hz), 1.22 (3H, t, J=7.0 Hz), 1.68-1.80 (5H, m), 2.01-2.14 (3H, m), 2.17-2.28 (1H, m), 2.37 (3H, s), 2.70-2.79 (2H, m), 2.82-3.03 (3H, m), 3.23 (3H, s), 3.19-3.29 (1H, m), 3.45 (2H, s), 3.51 (2H, q, J=6.8 Hz), 4.40 (2H, s), 6.45 (1H, dd, J=2.0, 7.8 Hz), 6.52 (1H, s), 6.61 (1H, d, J=7.8 Hz), 6.92-6.98 (2H, m), 7.10 (1H, t, J=7.6 Hz), 7.32 (1H, d, J=7.8 Hz).

Example 28

Trans-4-{[3-(2-hydroxyethyl)phenyl]amino}-N-methyl-N-(3-methyl-4-{[(3S)-3-methylpiperazin-1-yl]methyl}phenyl)cyclohexanecarboxamide

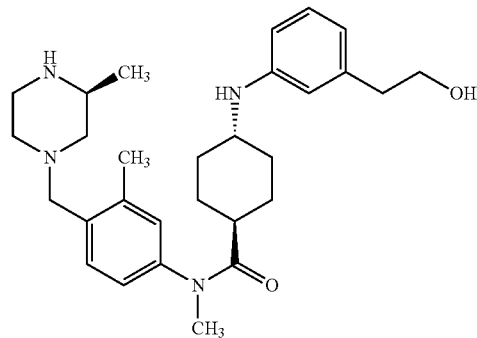 [SMILES: Cc1cc(N(C)C(=O)[C@H]2CC[C@H](Nc3cccc(CCO)c3)CC2)ccc1CN1CCN[C@@H](C)C1]

(28A) 2-(3-Aminophenyl)ethanol

3-Nitrophenethyl alcohol (5.80 g, 34.7 mmol) was dissolved in ethanol (80 mL), and 10% palladium on carbon (0.90 g) was added thereto, and then, the resulting mixture was stirred under a hydrogen atmosphere at room temperature for 1.5 hours.

The reaction solution was filtered through a Celite filter, and the solvent was distilled off under reduced pressure. The obtained residue was purified by silica gel column chromatography (hexane:ethyl acetate=80:20 to 40:60 (v/v)), whereby the target compound was obtained as a light yellow solid (4.65 g, yield: 98%).

$^1$H NMR (CDCl$_3$, 400 MHz): δ2.77 (2H, t, J=6.5 Hz), 3.45-3.78 (2H, brs), 3.82 (2H, t, J=6.5 Hz), 6.53-6.58 (2H, m), 6.62 (1H, d, J=7.4 Hz), 7.06-7.13 (1H, m).

(28B) Methyl trans-4-{[3-(2-hydroxyethyl)phenyl]amino}cyclohexanecarboxylate 2-(3-Aminophenyl)ethanol (4.45 g, 32.4 mmol) produced in (28A), ethyl 4-cyclohexanonecarboxylate (5.52 g, 32.4 mmol), and acetic acid (18.5 mL, 324 mmol) were dissolved in tetrahydrofuran (100 mL), and sodium triacetoxy borohydride (13.8 g, 64.9 mmol) was added thereto, and then, the resulting mixture was stirred at room temperature for 4 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=70:30 to 45:55 (v/v)), whereby the target compound was obtained as a colorless oil (1.93 g, yield: 19%).

$^1$H NMR (CDCl$_3$, 400 MHz): δ1.09-1.21 (2H, m), 1.26 (3H, t, J=7.2 Hz), 1.51-1.65 (2H, m), 2.01-2.10 (2H, m), 2.16-2.24 (2H, m), 2.29 (1H, tt, J=3.6, 12.1 Hz), 2.78 (2H, t, J=6.5 Hz), 3.25 (1H, tt, J=3.6, 11.2 Hz), 3.40-3.59 (1H, brs), 3.84 (2H, q, J=6.0 Hz), 4.14 (2H, q, J=7.2 Hz), 6.41-6.49 (2H, m), 6.55 (1H, d, J=7.4 Hz), 7.11 (1H, t, J=7.6 Hz).

(28C) Trans-4-{[3-(2-hydroxyethyl)phenyl]amino}cyclohexanecarboxylic acid

Methyl trans-4-{[3-(2-hydroxyethyl)phenyl]amino}cyclohexanecarboxylate (1.91 g, 6.25 mmol) produced in (28B) was dissolved in ethanol (10 mL) and tetrahydrofuran (10 mL), and a 5 N aqueous solution of sodium hydroxide (10 mL) was added thereto at room temperature, and then, the resulting mixture was stirred at 80° C. for 1 hour.

After 2 N hydrochloric acid was added to the reaction solution to neutralize the pH of the solution, water was added thereto, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=50: 50 to 0:100 (v/v)), whereby the target compound was obtained as a light yellow oil (1.48 g, yield: 90%).

$^1$H NMR (CDCl$_3$, 400 MHz): δ1.11-1.23 (2H, m), 1.55-1.67 (2H, m), 2.06-2.15 (2H, m), 2.17-2.27 (2H, m), 2.35 (1H, tt, J=3.5, 12.1 Hz), 2.78 (2H, t, J=6.5 Hz), 3.26 (1H, tt, J=3.9, 11.0 Hz), 3.84 (2H, t, J=6.5 Hz), 6.43-6.49 (2H, m), 6.55 (1H, d, J=7.8 Hz), 7.11 (1H, t, J=7.6 Hz).

(28D) Tert-butyl (2S)-4-(4-{[(trans-4-{[3-(2-hydroxyethyl)phenyl]amino}cyclohexyl)carbonyl](methyl)amino}-2-methylbenzyl)-2-methylpiperazine-1-carboxylate Trans-4-{[3-(2-hydroxyethyl)phenyl]amino}cyclohexanecarboxylic acid (1.47 g, 5.58 mmol) produced in (28C) and tert-butyl (2S)-2-methyl-4-[2-methyl-4-(methylamino)benzyl]piperazine-1-carboxylate (1.86 g, 5.58 mmol), which is a known compound, were dissolved in ethanol (20 mL), and 4-(4,6-dimethoxy-1,3,5-triazin-2-yl)-4-methylmorpholinium chloride hydrate (3.09 g, about 11 mmol) was added thereto, and then, the resulting mixture was stirred under a nitrogen atmosphere at room temperature for 17 hours.

To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=75:25 to 25:75 to 0:100 (v/v)), whereby the target compound was obtained as a colorless solid (2.09 g, yield: 65%).

$^1$H NMR (CDCl$_3$, 400 MHz): δ0.78-0.91 (2H, m), 1.22 (3H, d, J=6.7 Hz), 1.46 (9H, s), 1.61-1.80 (4H, m), 1.98-2.12 (3H, m), 2.16-2.26 (2H, m), 2.38 (3H, s), 2.60 (1H, d, J=11.0 Hz), 2.69-2.77 (1H, m), 2.76 (2H, t, J=6.5 Hz), 3.02-3.13 (1H, m), 3.17-3.28 (1H, m), 3.23 (3H, s), 3.43 (2H, m), 3.76-3.88 (1H, m), 3.82 (2H, t, J=6.3 Hz), 4.16-4.28 (1H, brs), 6.36-6.44 (2H, m), 6.52 (1H, d, J=7.8 Hz), 6.92-6.98 (2H, m), 7.08 (1H, t, J=7.6 Hz), 7.30 (1H, d, J=7.8 Hz).

(28E) Trans-4-{[3-(2-hydroxyethyl)phenyl]amino}-N-methyl-N-(3-methyl-4-{[(3S)-3-methylpiperazin-1-yl]methyl}phenyl)cyclohexanecarboxamide Tert-butyl (2S)-4-(4-{[(trans-4-{[3-(2-hydroxyethyl)phenyl]amino}cyclohexyl)carbonyl](methyl)amino}-2-methylbenzyl)-2-methylpiperazine-1-carboxylate (140 mg, 0.242 mmol) produced in (28D) was dissolved in dichloromethane (1 mL), and trifluoroacetic acid (1 mL) was added thereto at room temperature, and then, the resulting mixture was stirred under a nitrogen atmosphere at room temperature for 10 minutes.

The residue obtained by distilling off the solvent in the reaction solution under reduced pressure was purified by NH silica gel column chromatography (ethyl acetate:methanol=100:0 to 85:15 (v/v)), whereby the target compound was obtained as a colorless oil (109 mg, yield: 94%).

$^1$H NMR (CDCl$_3$, 400 MHz): δ0.79-0.91 (2H, m), 1.06 (3H, d, J=6.3 Hz), 1.62-1.84 (5H, m), 2.03-2.15 (3H, m), 2.17-2.28 (1H, m), 2.37 (3H, s), 2.71-2.80 (2H, m), 2.76 (2H, t, J=6.5 Hz), 2.86-3.04 (3H, m), 3.17-3.28 (1H, m), 3.23 (3H, s), 3.46 (2H, s), 3.82 (2H, t, J=6.5 Hz), 6.36-6.43 (2H, m), 6.52 (1H, d, J=7.0 Hz), 6.92-6.97 (2H, m), 7.08 (1H, t, J=7.6 Hz), 7.31 (1H, d, J=7.8 Hz).

Example 29

Trans-4-[4-fluoro-3-(2-hydroxyethyl)phenoxy]-N-methyl-N-(3-methyl-4-{[(3S)-3-methylpiperazin-1-yl]methyl}phenyl)cyclohexanecarboxamide

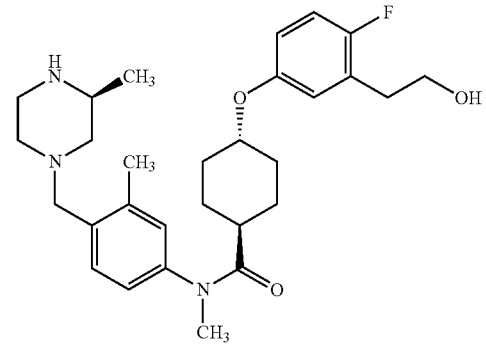 [SMILES: Cc1cc(N(C)C(=O)[C@H]2CC[C@H](Oc3ccc(F)c(CCO)c3)CC2)ccc1CN1CCN[C@@H](C)C1]

$^1$H NMR (CDCl$_3$, 400 MHz): δ1.04 (3H, d, J=6.7 Hz), 1.06-1.20 (2H, m), 1.46-1.82 (7H, m), 2.01-2.13 (3H, m), 2.25 (1H, m), 2.37 (3H, s), 2.70-2.79 (2H, m), 2.80-3.00 (3H, m), 3.23 (3H, s), 3.45 (2H, s), 3.84 (2H, t, J=6.5 Hz), 4.06 (1H, m), 6.62-6.72 (2H, m), 6.87-6.98 (3H, m), 7.33 (1H, m).
MS (ESI) m/z: 498 (M+H)$^+$.

Example 30

Trans-4-{3-[2-(isopropylamino)-2-oxoethyl]phenoxy}-N-methyl-N-(3-methyl-4-{[(3S)-3-methylpiperazin-1-yl]methyl}phenyl)cyclohexanecarboxamide

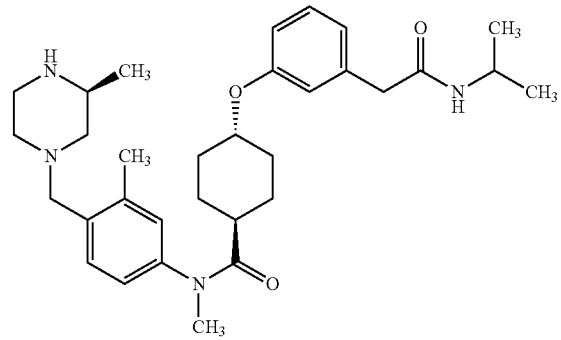 [SMILES: Cc1cc(N(C)C(=O)[C@H]2CC[C@H](Oc3cccc(CC(=O)NC(C)C)c3)CC2)ccc1CN1CCN[C@@H](C)C1]

(30A) [3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid Tert-butyl (2S)-4-{4-[({trans-4-[3-(2-methoxy-2-oxoethyl)phenoxy]cyclohexyl}carbonyl)(methyl)amino]-2-methylbenzyl}-2-methylpiperazine-1-carboxylate (211 mg, 0.348 mmol) produced in (6A) was dissolved in methanol (5 mL), and a 2 N aqueous solution of sodium hydroxide (870 μL, 1.74 mmol) was added thereto at room temperature, and then, the resulting mixture was stirred at 60° C. for 1 hour.

To the reaction solution, a saturated aqueous solution of ammonium chloride was added, and the organic matter was extracted with ethyl acetate. The organic layer was dried over anhydrous sodium sulfate and filtered. Then, the solvent was distilled off under reduced pressure, whereby the target compound was obtained as a colorless oil (201 mg, yield: 97%).

MS (ESI) m/z: 594 (M+H)$^+$.

(30B) Trans-4-{3-[2-(isopropylamino)-2-oxoethyl]phenoxy}-N-methyl-N-(3-methyl-4-{[(3S)-3-methylpiperazin-1-yl]methyl}phenyl)cyclohexanecarboxamide

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (118 mg, 0.199 mmol) produced in (30A), isopropylamine (85.5 μL, 0.995 mmol), and 4-(4,6-dimethoxy-1,3,5-triazin-2-yl)-4-methylmorpholinium chloride hydrate (113 mg, about 0.36 mmol) were dissolved in ethanol (3 mL), and the resulting mixture was stirred overnight at room temperature.

To the reaction solution, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby a crude product was obtained.

The obtained crude product was dissolved in dichloromethane (4 mL), and trifluoroacetic acid (1 mL) was added thereto at room temperature, and then, the resulting mixture was stirred at room temperature for 1 hour. The residue obtained by distilling off the solvent in the reaction solution under reduced pressure was purified by NH silica gel column chromatography (dichloromethane:methanol=100:0 to 90:10 (v/v)), whereby the target compound was obtained as a white solid (102 mg, yield: 96%).

$^1$H NMR (CDCl$_3$, 400 MHz): δ1.05 (6H, d, J=6.3 Hz), 1.06 (3H, d, J=6.3 Hz), 1.07-1.23 (2H, m), 1.63-1.85 (5H, m), 2.03-2.16 (4H, m), 2.26 (1H, m), 2.37 (3H, s), 2.71-2.81 (2H, m), 2.85-3.04 (3H, m), 3.23 (3H, s), 3.46 (2H, s), 3.47 (2H, s), 4.05 (1H, m), 4.18 (1H, m), 5.17 (1H, m), 6.71 (1H, s), 6.74-6.81 (2H, m), 6.93-6.98 (2H, m), 7.22 (1H, t, J=7.8 Hz), 7.33 (1H, d, J=8.2 Hz).

MS (ESI) m/z: 535 (M+H)$^+$.

(30C) Trans-4-{3-[2-(isopropylamino)-2-oxoethyl]phenoxy}-N-methyl-N-(3-methyl-4-{[(3S)-3-methylpiperazin-1-yl]methyl}phenyl)cyclohexanecarboxamide hydrochloride Trans-4-{3-[2-(isopropylamino)-2-oxoethyl]phenoxy}-N-methyl-N-(3-methyl-4-{[(3S)-3-methylpiperazin-1-yl]methyl}phenyl)cyclohexanecarboxamide (375 mg, 0.702 mmol) produced in (30B) was dissolved in dioxane (4 mL) and water (1 mL), and 1 N hydrochloric acid (351 μL, 0.710 mmol) was added thereto at room temperature, and then, the resulting mixture was frozen at −78° C. The frozen mixture was lyophilized using a lyophilizer, whereby the target compound was obtained as a white solid (383 mg, yield: 95%).

MS (ESI) m/z: 535 (M+H)$^+$.

Example 31

Trans-N-methyl-N-(3-methyl-4-{[(3S)-3-methylpiperazin-1-yl]methyl}phenyl)-4-{3-[2-oxo-2-(propylamino)ethyl]phenoxy}cyclohexanecarboxamide

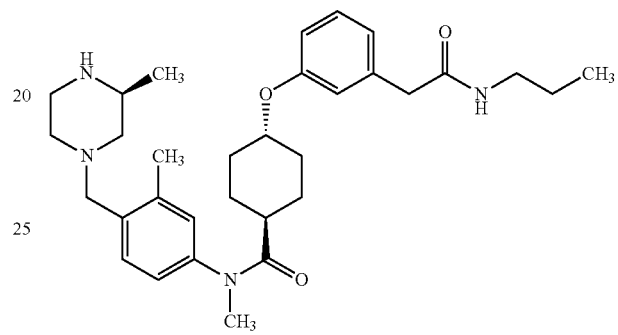

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (118 mg, 0.199 mmol) produced in (30A), propylamine (81.8 μl, 0.995 mmol), and 4-(4,6-dimethoxy-1,3,5-triazin-2-yl)-4-methylmorpholinium chloride hydrate (113 mg, about 0.36 mmol) were dissolved in ethanol (3 mL), and the resulting mixture was stirred overnight at room temperature.

To the reaction solution, a saturated aqueous solution of sodium hydrogen carbonate was added, and the organic matter was extracted with ethyl acetate. The organic layer was dried over anhydrous sodium sulfate and filtered. Then, the solvent was distilled off under reduced pressure, whereby a crude product was obtained.

The obtained crude product was dissolved in dichloromethane (4 mL), and trifluoroacetic acid (1 mL) was added thereto at room temperature, and then, the resulting mixture was stirred at room temperature for 1 hour. The residue obtained by distilling off the solvent in the reaction solution under reduced pressure was purified by NH silica gel column chromatography (dichloromethane:methanol=100:0 to 90:10 (v/v)), whereby the target compound was obtained as a white solid (95.6 mg, yield: 90%).

$^1$H NMR (CDCl$_3$, 400 MHz): δ0.83 (3H, t, J=7.4 Hz), 1.06 (3H, d, J=6.3 Hz), 1.09-1.23 (2H, m), 1.37-1.48 (2H, m), 1.63-1.87 (6H, m), 2.03-2.16 (3H, m), 2.26 (1H, m), 2.37 (3H, s), 2.71-2.80 (2H, m), 2.85-3.03 (3H, m), 3.15 (1H, m), 3.23 (3H, s), 3.46 (2H, s), 3.50 (2H, s), 4.17 (1H, m), 5.36 (1H, m), 6.72 (1H, s), 6.74-6.82 (2H, m), 6.92-6.99 (2H, m), 7.23 (1H, t, J=8.0 Hz), 7.33 (1H, d, J=7.8 Hz).

MS (ESI) m/z: 535 (M+H)$^+$.

Example 32

Trans-4-{3-[2-(diethylamino)-2-oxoethyl]phenoxy}-N-methyl-N-(3-methyl-4-{[(3S)-3-methylpiperazin-1-yl]methyl}phenyl)cyclohexanecarboxamide

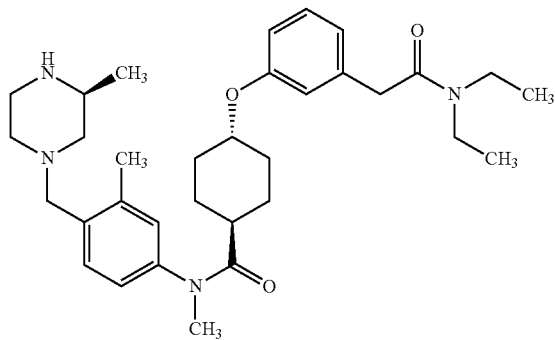 [SMILES: CCN(CC)C(=O)Cc1cccc(O[C@H]2CC[C@H](C(=O)N(C)c3ccc(CN4CCN[C@@H](C)C4)c(C)c3)CC2)c1]

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (300 mg, 0.51 mmol) produced in (30A), diethylamine hydrochloride (111 mg, 1.01 mmol), 4-(4,6-dimethoxy-1,3,5-triazin-2-yl)-4-methylmorpholinium chloride hydrate (282 mg, about 1.0 mmol), and N,N-diisopropylethylamine (266 µL, 1.53 mmol) were dissolved in N,N-dimethylformamide (3 mL), and the resulting mixture was stirred at room temperature for 6 hours. To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, and the obtained residue was roughly purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour. After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless solid (210 mg, yield: 75%).

$^1$H NMR (CDCl$_3$, 400 MHz): δ1.05 (3H, d, J=6.3 Hz), 1.08 (3H, t, J=7.2 Hz), 1.11 (3H, t, J=7.2 Hz), 1.13-1.16 (1H, m), 1.64-1.85 (7H, m), 2.07-2.10 (2H, m), 2.21-2.28 (1H, m), 2.37 (3H, s), 2.75 (2H, t, J=9.2 Hz), 2.84-3.00 (3H, m), 3.23 (3H, s), 3.27 (2H, q, J=7.2 Hz), 3.38 (2H, q, J=7.2 Hz), 3.45 (2H, s), 3.63 (2H, s), 4.12-4.19 (1H, m), 6.70-6.73 (2H, m), 6.79 (1H, d, J=7.4 Hz), 6.94-6.95 (2H, m), 7.17 (1H, t, J=7.9 Hz), 7.33 (1H, d, J=8.2 Hz).

MS (ESI) m/z: 549 (M+H)$^+$.

Example 33

Trans-4-{3-[2-(tert-butylamino)-2-oxoethyl]phenoxy}-N-methyl-N-(3-methyl-4-{[(3S)-3-methylpiperazin-1-yl]methyl}phenyl)cyclohexanecarboxamide

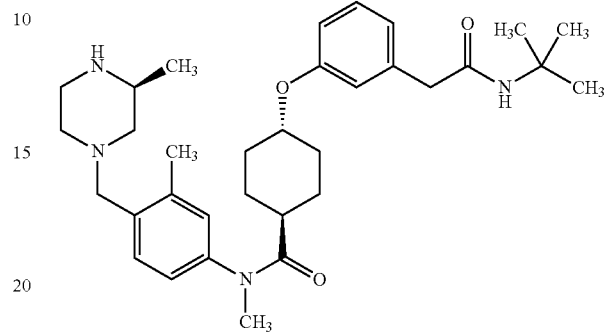

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (300 mg, 0.51 mmol) produced in (31A), tert-butylamine (64 µL, 0.61 mmol), 2-chloro-4,6-dimethoxy-1,3,5-triazine (107 mg, 0.61 mmol), and N-methylmorpholine (84 µL, 0.77 mmol) were dissolved in acetonitrile (3 mL), and the resulting mixture was stirred at room temperature for 6 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, and the obtained residue was roughly purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour. After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a white solid (152 mg, yield: 54%).

$^1$H NMR (CDCl$_3$, 400 MHz): δ1.05 (3H, d, J=6.3 Hz), 1.11-1.22 (2H, m), 1.27 (9H, s), 1.69-1.80 (7H, m), 2.07-2.11 (3H, m), 2.23-2.27 (1H, m), 2.38 (3H, s), 2.76 (2H, t, J=9.0 Hz), 2.85-2.99 (3H, m), 3.23 (3H, s), 3.42 (2H, s), 3.45 (2H, s), 4.15-4.21 (1H, m), 5.22 (1H, brs), 6.71 (1H, s), 6.74-6.79 (2H, m), 6.94-6.96 (2H, m), 7.21 (1H, t, J=8.0 Hz), 7.33 (1H, d, J=8.6 Hz).

MS (ESI) m/z: 549 (M+H)$^+$.

Example 34

Trans-4-(3-{2-[isopropyl(methyl)amino]-2-oxoethyl}phenoxy)-N-methyl-N-(3-methyl-4-{[(3S)-3-methylpiperazin-1-yl]methyl}phenyl)cyclohexanecarboxamide

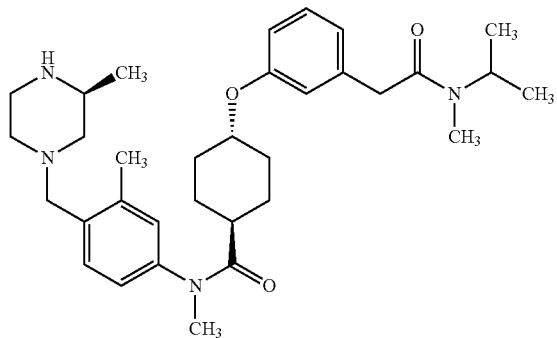 [SMILES: Cc1cc(N(C)C(=O)[C@H]2CC[C@H](Oc3cccc(CC(=O)N(C)C(C)C)c3)CC2)ccc1CN1CCN[C@@H](C)C1]

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (200 mg, 0.34 mmol) produced in (30A), N-isopropylmethylamine (75 mg, 1.02 mmol), and 4-(4,6-dimethoxy-1,3,5-triazin-2-yl)-4-methylmorpholinium chloride hydrate (282 mg, about 1.0 mmol) were dissolved in N,N-dimethylformamide (3 mL), and the resulting mixture was stirred at room temperature for 6 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, and the obtained residue was roughly purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour. After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless solid (50.0 mg, yield: 27%).

$^1$H NMR (CDCl$_3$, 400 MHz): δ1.03 (3H, d, J=6.5 Hz), 1.05 (3H, d, J=6.5 Hz), 1.07 (3H, d, J=7.0 Hz), 1.10-1.19 (2H, m), 1.64-1.78 (5H, m), 2.04-2.10 (3H, m), 2.21-2.29 (1H, m), 2.37 (3H, s), 2.73-2.78 (5H, m), 2.84-3.00 (3H, m), 3.23 (3H, s), 3.45 (2H, s), 3.64 (1H, s), 3.69 (1H, s), 4.03-4.10 (0.5H, m), 4.13-4.93 (1H, m), 4.87-4.93 (0.5H, m), 6.70-6.72 (2H, m), 6.78 (2H, d, J=7.4 Hz), 6.94-6.96 (2H, m), 7.17 (1H, t, J=7.7 Hz), 7.33 (1H, d, J=8.2 Hz).

MS (ESI) m/z: 549 (M+H)$^+$.

Example 35

Trans-4-(3-{2-[(2-ethoxyethyl)amino]-2-oxoethyl}phenoxy)-N-methyl-N-(3-methyl-4-{[(3S)-3-methylpiperazin-1-yl]methyl}phenyl)cyclohexanecarboxamide

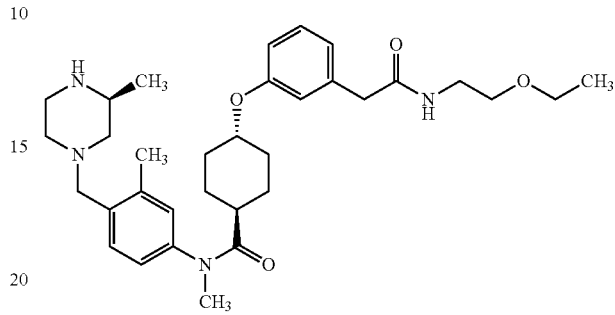

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (100 mg, 0.17 mmol) produced in (30A), 2-ethoxyethylamine (35 μL, 0.34 mmol), and 4-(4,6-dimethoxy-1,3,5-triazin-2-yl)-4-methylmorpholinium chloride hydrate (95 mg, about 0.34 mmol) were dissolved in N,N-dimethylformamide (3 mL), and the resulting mixture was stirred at room temperature for 6 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, and the obtained residue was roughly purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:80:20 (v/v/v)), whereby the target compound was obtained as a colorless oil (25.0 mg, yield: 26%).

$^1$H NMR (CDCl$_3$, 400 MHz): δ1.05 (3H, d, J=6.2 Hz), 1.10 (3H, t, J=7.1 Hz), 1.14-1.21 (2H, m), 1.65-1.79 (4H, m), 2.02-2.11 (4H, m), 2.23-2.29 (1H, m), 2.38 (3H, s), 2.76 (2H, t, J=9.0 Hz), 2.84-3.00 (3H, m), 3.23 (3H, s), 3.36-3.43 (6H, m), 3.45 (2H, s), 3.51 (2H, s), 4.13-4.21 (1H, m), 5.86 (2H, brs), 6.73-6.81 (3H, m), 6.94 (1H, d, J=7.0 Hz), 6.96 (1H, s), 7.21 (1H, t, J=7.9 Hz), 7.33 (1H, d, J=8.2 Hz).

MS (ESI) m/z: 565 (M+H)$^+$.

Example 36

Trans-N-methyl-N-(3-methyl-4-{[(3S)-3-methylpiperazin-1-yl]methyl}phenyl)-4-[3-(2-oxo-2-pyrrolidin-1-ylethyl)phenoxy]cyclohexanecarboxamide

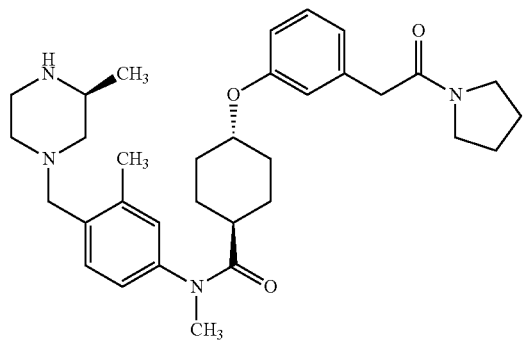 [SMILES: Cc1cc(N(C)C(=O)[C@H]2CC[C@H](Oc3cccc(CC(=O)N4CCCC4)c3)CC2)ccc1CN1CCN[C@@H](C)C1]

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (100 mg, 0.17 mmol) produced in (30A), pyrrolidine (28 µL, 0.34 mmol), and 4-(4,6-dimethoxy-1,3,5-triazin-2-yl)-4-methylmorpholinium chloride hydrate (95 mg, about 0.34 mmol) were dissolved in N,N-dimethylformamide (3 mL), and the resulting mixture was stirred at room temperature for 6 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, and the obtained residue was roughly purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:80:20 (v/v/v)), whereby the target compound was obtained as a colorless oil (31.0 mg, yield: 33%).

$^1$H NMR (CDCl$_3$, 400 MHz): δ1.05 (3H, d, J=6.6 Hz), 1.09-1.19 (2H, m), 1.64-2.00 (11H, m), 2.04-2.11 (3H, m), 2.11-2.28 (1H, m), 2.37 (3H, s), 2.76 (2H, t, J=9.5 Hz), 2.86-3.00 (3H, m), 3.23 (3H, s), 3.40 (2H, t, J=6.7 Hz), 3.45-3.49 (4H, m), 3.59 (2H, s), 4.13-4.19 (1H, m), 6.71 (1H, d, J=8.2 Hz), 6.76 (1H, s), 6.82 (1H, d, J=7.8 Hz), 6.94-6.95 (2H, m), 7.17 (1H, t, J=7.8 Hz), 7.33 (1H, d, J=8.2 Hz).

MS (ESI) m/z: 547 (M+H)$^+$.

Example 37

Trans-4-(3-{2-[(2,2-difluoroethyl)amino]-2-oxoethyl}phenoxy)-N-methyl-N-(3-methyl-4-{[(3S)-3-methylpiperazin-1-yl]methyl}phenyl)cyclohexanecarboxamide

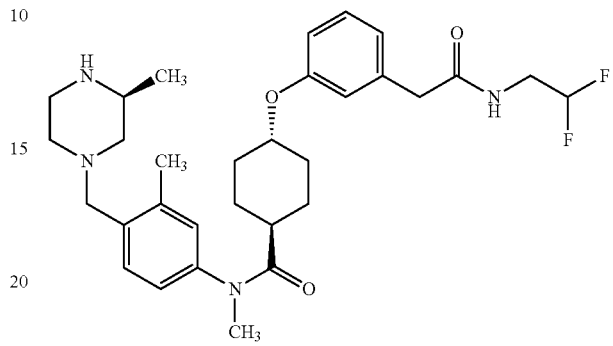

[3-({Trans-4-[(4-{[(3S)-4-(tert-butoxycarbonyl)-3-methylpiperazin-1-yl]methyl}-3-methylphenyl)(methyl)carbamoyl]cyclohexyl}oxy)phenyl]acetic acid (265 mg, 0.45 mmol) produced in (30A), 2,2-difluoroethylamine (73 mg, 0.90 mmol), 1H-benzotriazol-1-yloxytripyrrolidone phosphonium hexafluorophosphate (468 mg, 0.90 mmol), 1-hydroxybenzotriazole (122 mg, 0.90 mmol), and N,N-diisopropylethylamine (157 µL, 0.90 mmol) were dissolved in N,N-dimethylformamide (3 mL), and the resulting mixture was stirred at room temperature for 6 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was roughly purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour. After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless solid (110 mg, yield: 44%).

$^1$H NMR (CDCl$_3$, 400 MHz): δ1.05 (3H, d, J=6.7 Hz), 1.10-1.19 (2H, m), 1.65-1.86 (5H, m), 2.08-2.29 (5H, m), 2.38 (3H, s), 2.76 (2H, t, J=9.4 Hz), 2.86-2.99 (3H, m), 3.23 (3H, s), 3.45 (2H, s), 3.51-3.60 (4H, m), 4.09-4.19 (1H, m), 5.82 (1H, tt, J=56.3, 4.3 Hz), 6.70 (1H, brs), 6.5-6.76 (2H, m), 6.81 (1H, d, J=7.4 Hz), 6.94-6.96 (2H, m), 7.32 (1H, t, J=6.9 Hz), 7.34 (1H, d, J=7.9 Hz).

MS (ESI) m/z: 557 (M+H)$^+$.

Example 38

Trans-4-{3-[(butyrylamino)methyl]phenoxy}-N-methyl-N-(3-methyl-4-{[(3S)-3-methylpiperazin-1-yl]methyl}phenyl)cyclohexanecarboxamide

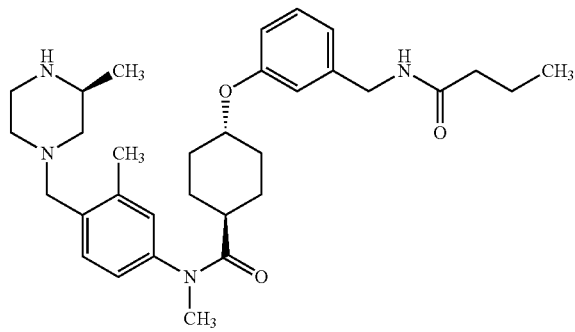 [SMILES: CCCC(=O)NCc1cccc(O[C@H]2CC[C@H](C(=O)N(C)c3ccc(CN4CCN[C@@H](C)C4)c(C)c3)CC2)c1]

(38A) Tert-butyl (2S)-4-{4-[({trans-4-[3-(bromomethyl)phenoxy]cyclohexyl}carbonyl)(methyl)amino]-2-methylbenzyl}-2-methylpiperazine-1-carboxylate Tert-butyl (2S)-4-{4-[({trans-4-[3-(hydroxymethyl)phenoxy]cyclohexyl}carbonyl)(methyl)amino]-2-methylbenzyl}-2-methylpiperazine-1-carboxylate (1.13 g, 2.0 mmol) produced in (5B) was dissolved in dichloromethane (10 mL), and triphenylphosphine (578 mg, 2.2 mmol) and carbon tetrabromide (728 mg, 2.2 mmol) were added thereto at room temperature, and then, the resulting mixture was stirred at room temperature for 3 hours.

The residue obtained by distilling off the solvent in the reaction solution under reduced pressure was purified by silica gel column chromatography (hexane:ethyl acetate=100:0 to 0:100 (v/v)), whereby the target compound was obtained as a light yellow solid (767 mg, yield: 61%).

$^1$H NMR (CDCl$_3$, 400 MHz): δ1.20-1.10 (2H, m), 1.23 (3H, d, J=4.1 Hz), 1.47 (9H, s), 1.83-1.68 (4H, m), 2.15-2.00 (3H, m), 2.28-2.19 (2H, m), 2.39 (3H, s), 2.60 (1H, d, J=11.3 Hz), 2.73 (1H, d, J=11.7 Hz), 3.14-3.02 (1H, m), 3.23 (3H, s), 3.43 (2H, s), 3.82 (1H, d, J=13.7 Hz), 4.27-4.13 (2H, m), 4.43 (2H, s), 6.78-6.74 (1H, m), 6.87-6.84 (1H, m), 6.98-6.91 (3H, m), 7.20 (1H, t, J=8.0 Hz), 7.31 (1H, d, J=7.8 Hz).

(38B) Trans-4-{3-[(butyrylamino)methyl]phenoxy}-N-methyl-N-(3-methyl-4-{[(3S)-3-methylpiperazin-1-yl]methyl}phenyl)cyclohexanecarboxamide Tert-butyl (2S)-4-{4-[({trans-4-[3-(bromomethyl)phenoxy]cyclohexyl}carbonyl)(methyl)amino]-2-methylbenzyl}-2-methylpiperazine-1-carboxylate (140 mg, 0.22 mmol) produced in (38A) and butyramide (60 μL, 0.66 mmol) were dissolved in N,N-dimethylformamide (3 mL), and the resulting mixture was cooled to 0° C. and stirred for 30 minutes. To the reaction solution, sodium hydride (63%, 13 mg, 0.33 mmol) was added, and the resulting mixture was stirred at room temperature for 4 hours.

To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, and the obtained residue was roughly purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless solid (62 mg, yield: 53%).

$^1$H NMR (CDCl$_3$, 400 MHz): δ0.96 (3H, t, J=7.4 Hz), 1.04 (3H, d, J=6.7 Hz), 1.10-1.20 (2H, m), 1.64-1.81 (7H, m), 2.06-2.10 (4H, m), 2.19 (2H, t, J=7.4 Hz), 2.23-2.28 (1H, m), 2.37 (3H, s), 2.75 (2H, t, J=9.4 Hz), 2.85-3.00 (3H, m), 3.23 (3H, s), 3.45 (2H, s), 4.11-4.18 (1H, m), 4.38 (2H, d, J=5.9 Hz), 5.75 (1H, brs), 6.73 (2H, m), 6.82 (1H, d, J=7.5 Hz), 6.93-6.96 (2H, m), 7.20 (1H, t, J=8.2 Hz), 7.33 (1H, d, J=8.2 Hz).

MS (ESI) m/z: 535 (M+H)$^+$.

Example 39

Trans-4-{3-[(isobutyrylamino)methyl]phenoxy}-N-methyl-N-(3-methyl-4-{[(3S)-3-methylpiperazin-1-yl]methyl}phenyl)cyclohexanecarboxamide

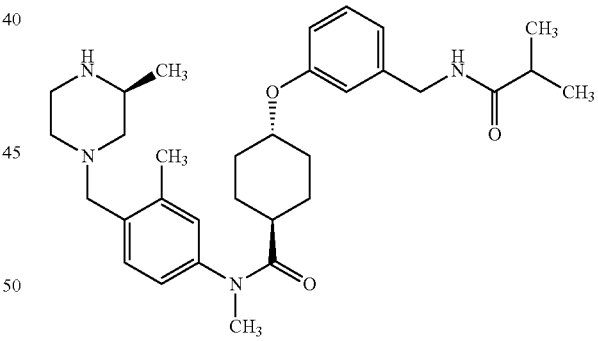

(39A) Benzyl cis-4-hydroxycyclohexanecarboxylate

Cis-4-hydroxycyclohexanecarboxylic acid (20.0 g, 0.14 mol), potassium carbonate (21.1 g, 0.15 mol), and benzyl bromide (16.1 mL, 0.13 mol) were dissolved in N,N-dimethylformamide (100 mL), and the resulting mixture was stirred at room temperature for 12 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a white solid (26.1 g, yield: 80%).

$^1$H NMR (CDCl$_3$, 400 MHz): δ1.62-1.74 (6H, m), 1.96-2.04 (2H, m), 2.42-2.47 (1H, m), 3.90-3.92 (1H, m), 5.13 (2H, s), 7.31-7.39 (5H, m).

(39B) Benzyl trans-4-[3-({[tert-butyl(dimethyl)silyl]oxy}methyl)phenoxy]cyclohexanecarboxylate Benzyl cis-4-hydroxycyclohexanecarboxylate (1.46 g, 6.23 mmol) produced in (39A) and 3-({[tert-butyl(dimethyl)silyl]oxy}methyl)phenol (1.49 g, 6.25 mmol), which is a known compound, were dissolved in toluene (50 mL), and the resulting mixture was stirred at 100° C. for 15 minutes. To the reaction solution, cyanomethylenetributylphosphorane (1.97 mL, 7.48 mmol) was added dropwise, and the resulting mixture was heated to reflux for 3 hours. The temperature of the reaction solution was returned to room temperature, and the solvent was distilled off under reduced pressure. The obtained residue was purified by silica gel column chromatography (hexane:ethyl acetate=100:0 to 90:10 (v/v)), whereby the target compound was obtained as a colorless oil (2.17 g, yield: 76%).

$^1$H NMR (CDCl$_3$, 400 MHz): δ0.10 (6H, s), 0.94 (9H, s), 1.43-1.54 (3H, m), 1.59-1.63 (1H, m), 2.07-2.13 (3H, m), 2.17-2.22 (1H, m), 2.38-2.45 (1H, m), 4.16-4.23 (1H, m), 4.71 (2H, s), 5.13 (2H, s), 6.77 (1H, dd, J=2.0 Hz, 7.8 Hz), 6.86 (1H, d, J=7.4 Hz), 6.90 (1H, s), 7.21 (1H, t, J=7.8 Hz), 7.32-7.38 (5H, m).

(39C) Benzyl trans-4-[3-(hydroxymethyl)phenoxy]cyclohexanecarboxylate

Benzyl trans-4-[3-({[tert-butyl(dimethyl)silyl]oxy}methyl)phenoxy]cyclohexanecarboxylate (2.17 g, 4.78 mmol) produced in (39B) was dissolved in tetrahydrofuran (10 mL), and a solution of tetrabutylammonium fluoride in tetrahydrofuran (1.0 M, 14.3 mL, 14.3 mmol) was added dropwise thereto, and then, the resulting mixture was stirred at room temperature for 2 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 80:20 (v/v)), whereby the target compound was obtained as a colorless oil (1.0 g, yield: 61%).

$^1$H NMR (CDCl$_3$, 400 MHz): δ1.43-1.53 (2H, m), 1.58-1.67 (2H, m), 2.09-2.21 (4H, m), 2.39-2.45 (1H, m), 4.20-4.25 (1H, m), 4.66 (2H, d, J=5.9 Hz), 5.13 (2H, s), 6.80-6.83 (1H, m), 6.91-6.93 (2H, m), 7.24-7.28 (1H, m), 7.33-7.40 (5H, m).

(39D) Benzyl trans-4-[3-(bromomethyl)phenoxy]cyclohexanecarboxylate

Benzyl trans-4-[3-(hydroxymethyl)phenoxy]cyclohexanecarboxylate (1.0 g, 2.94 mmol) produced in (39C) was dissolved in dichloromethane (20 mL), and carbon tetrabromide (1.46 g, 4.41 mmol) and triphenylphosphine (1.54 g, 5.88 mmol) were added thereto, and then the resulting mixture was stirred at room temperature for 5 hours. The reaction solvent was distilled off under reduced pressure, and the resulting residue was purified by silica gel column chromatography (hexane:ethyl acetate=100:0 to 95:5 (v/v)), whereby the target compound was obtained as a colorless oil (727 mg, yield: 61%).

$^1$H NMR (CDCl$_3$, 400 MHz): δ1.43-1.68 (4H, m), 2.09-2.20 (4H, m), 2.38-2.46 (1H, m), 4.19-4.25 (1H, m), 4.54 (2H, s), 5.13 (2H, s), 6.83 (1H, td, J=2.3 Hz, 9.0 Hz), 6.90-6.92 (1H, m), 6.95 (1H, d, J=8.6 Hz), 7.21-7.27 (1H, m), 7.33-7.40 (5H, m).

(39E) Trans-4-{3-[(isobutyrylamino)methyl]phenoxy}cyclohexanecarboxylic acid Benzyl trans-4-[3-(bromomethyl)phenoxy]cyclohexanecarboxylate (200 mg, 0.50 mmol) produced in (39D) and 2-methyl propanamide (52 mg, 0.60 mmol) were dissolved in N,N-dimethylformamide (3 mL), and sodium hydride (63%, 24 mg, 1.00 mmol) was added thereto, and then, the resulting mixture was stirred at room temperature for 2 hours.

To the reaction solution, water and ethyl acetate were added, and a liquid-liquid separation procedure was performed. To the obtained aqueous layer, 1 N hydrochloric acid was added, thereby adjusting the pH of the solution to 3. Then, ethyl acetate was added to the aqueous layer, and organic matter was extracted. The solvent was distilled off under reduced pressure, whereby the target compound was obtained as a colorless oil (146 mg, yield: 91%).

MS (ESI) m/z: 320 (M+H)$^+$.

(39F) Trans-4-{3-[(isobutyrylamino)methyl]phenoxy}-N-methyl-N-(3-methyl-4-{[(3S)-3-methylpiperazin-1-yl]methyl}phenyl)cyclohexanecarboxamide 4-{3-[(Isobutyrylamino)methyl]phenoxy}cyclohexanecarboxylic acid (146 mg, 0.46 mmol) produced in (39E), tert-butyl (2S)-2-methyl-4-[2-methyl-4-(methylamino)benzyl]piperazine-1-carboxylate (152 mg, 0.46 mmol), which is a known compound, and 4-(4,6-dimethoxy-1,3,5-triazin-2-yl)-4-methylmorpholinium chloride hydrate (191 mg, about 0.69 mmol) were dissolved in N,N-dimethylformamide (5 mL), and the resulting mixture was stirred at room temperature for 16 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, and the resulting residue was purified by silica gel column chromatography, whereby a crude product was obtained.

The obtained crude product was dissolved in dichloromethane (2 mL), and trifluoroacetic acid (2 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:

ethyl acetate:methanol=100:0:0 to 0:100:0 to 0:90:10 (v/v/v)), whereby the target compound was obtained as a colorless solid (18.0 mg, yield: 7%).

¹H NMR (CDCl₃, 400 MHz): δ1.06 (3H, d, J=6.7 Hz), 1.11-1.17 (1H, m), 1.18 (6H, d, J=6.7 Hz), 1.65-1.84 (5H, m), 2.08-2.15 (3H, m), 2.22-2.30 (1H, m), 2.32-2.43 (5H, m), 2.76 (2H, t, J=8.6 Hz), 2.89-2.95 (2H, m), 3.00-3.03 (1H, m), 3.23 (3H, s), 3.46 (2H, s), 4.11-4.19 (1H, m), 4.38 (2H, d, J=5.5 Hz), 5.76 (1H, brs), 6.74 (2H, m), 6.81 (1H, d, J=7.4 Hz), 6.94-6.96 (2H, m), 7.20 (1H, t, J=7.7 Hz), 7.33 (1H, d, J=8.2 Hz).

MS (ESI) m/z: 535 (M+H)⁺.

Example 40

Trans-N-methyl-N-(3-methyl-4-{[(3S)-3-methylpiperazin-1-yl]methyl}phenyl)-4-{3-[(2-oxopyrrolidin-1-yl)methyl]phenoxy}cyclohexanecarboxamide

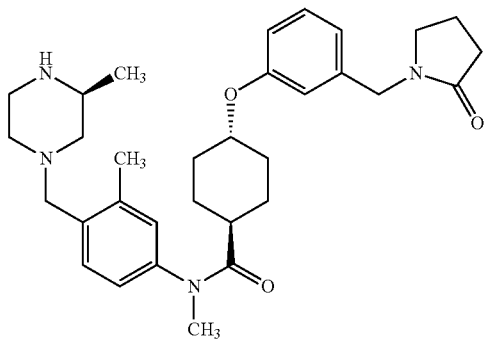 [SMILES: Cc1cc(N(C)C(=O)[C@H]2CC[C@H](Oc3cccc(CN4CCCC4=O)c3)CC2)ccc1CN1CCN[C@@H](C)C1]

(40A) 1-[3-(Benzyloxy)benzyl]pyrrolidin-2-one 1-(Benzyloxy)-3-(bromomethyl)benzene (380 mg, 1.37 mmol), which is a known compound, and 2-pyrrolidone (210 μL, 2.74 mmol) were dissolved in N,N-dimethylformamide (5 mL), and sodium hydride (63%, 105 mg, 2.74 mmol) was added thereto at 0° C., and then, the resulting mixture was stirred at room temperature for 1 hour.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 50:50 (v/v)), whereby the target compound was obtained as a colorless oil (318 mg, yield: 82%).

¹H NMR (CDCl₃, 400 MHz): δ1.93-2.00 (2H, m), 2.43 (2H, t, J=8.2 Hz), 3.23 (2H, t, J=7.1 Hz), 4.42 (2H, s), 5.06 (2H, s), 6.83-6.84 (2H, m), 6.86-6.91 (1H, m), 7.23 (1H, d, J=8.2 Hz), 7.31-7.44 (5H, m).

MS (ESI) m/z: 282 (M+H)⁺.

(40B) 1-(3-Hydroxybenzyl)pyrrolidin-2-one

To a solution (10 mL) of 1-[3-(benzyloxy)benzyl]pyrrolidin-2-one (318 mg, 1.13 mmol) produced in (40A) in ethanol, palladium on carbon (10% wet, 300 mg) was added under a nitrogen atmosphere, and the resulting mixture was stirred under a hydrogen atmosphere at room temperature for 3 hours. The reaction solution was filtered through a Celite filter, and the solvent was distilled off under reduced pressure, whereby the target compound was obtained as a colorless oil (230 mg, yield: 100%).

¹H NMR (CDCl₃, 400 MHz): δ1.96-2.04 (2H, m), 2.47 (2H, t, J=8.0 Hz), 3.31 (2H, t, J=7.4 Hz), 4.40 (2H, s), 6.75 (1H, d, J=7.4 Hz), 6.80 (1H, dd, J=2.4 Hz, 7.8 Hz), 6.83 (1H, s), 7.18 (1H, t, J=7.8 Hz), 7.52 (1H, brs).

(40C) Tert-butyl (2S)-2-methyl-4-(2-methyl-4-{methyl[(trans-4-{3-[(2-oxopyrrolidin-1-yl)methyl]phenoxy}cyclohexyl)carbonyl]amino}benzyl)piperazine-1-carboxylate 1-(3-Hydroxybenzyl)pyrrolidin-2-one (230 mg, 1.20 mmol) produced in (40B) and tert-butyl (2S)-4-(4-{[(cis-4-hydroxycyclohexyl)carbonyl](methyl)amino}-2-methylbenzyl)-2-methylpiperazine-1-carboxylate (552 mg, 1.20 mmol) produced in (2A) were dissolved in toluene (5 mL), and the resulting mixture was stirred at 100° C. for minutes. To the reaction solution, cyanomethylenetributylphosphorane (472 mg, 1.80 mmol) was added dropwise, and the resulting mixture was heated to reflux for 6 hours.

After the temperature of the reaction solution was returned to room temperature, the solvent was distilled off under reduced pressure. The obtained residue was purified by silica gel column chromatography (hexane:ethyl acetate=100:0 to 0:100 (v/v)), whereby the target compound was obtained as a colorless oil (179 mg, yield: 24%).

MS (ESI) m/z: 633 (M+H)⁺.

(40D) Trans-N-methyl-N-(3-methyl-4-{[(3S)-3-methylpiperazin-1-yl]methyl}phenyl)-4-{3-[(2-oxopyrrolidin-1-yl)methyl]phenoxy}cyclohexanecarboxamide Tert-butyl (2S)-2-methyl-4-(2-methyl-4-{methyl[(trans-4-{3-[(2-oxopyrrolidin-1-yl)methyl]phenoxy}cyclohexyl)carbonyl]amino}benzyl)piperazine-1-carboxylate (170 mg, 0.27 mmol) produced in (40C) was dissolved in dichloromethane (2 mL), and trifluoroacetic acid (2 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless oil (110 mg, yield: 77%).

¹H NMR (CDCl₃, 400 MHz): δ1.04 (3H, d, J=6.3 Hz), 1.10-1.20 (2H, m), 1.65-1.78 (6H, m), 1.95-2.02 (2H, m), 2.06-2.11 (3H, m), 2.22-2.29 (1H, m), 2.38 (3H, s), 2.43 (2H, t, J=8.0 Hz), 2.76 (2H, t, J=9.4 Hz), 2.85-2.99 (3H, m), 3.23-3.27 (5H, m), 3.45 (2H, s), 4.11-4.20 (1H, m), 4.38 (2H, s), 6.69 (1H, s), 6.74-6.79 (2H, m), 6.94-6.96 (2H, m), 7.20 (1H, t, J=7.8 Hz), 7.33 (1H, d, J=8.6 Hz).

MS (ESI) m/z: 533 (M+H)⁺.

Example 41

Trans-N-methyl-N-(3-methyl-4-{[(3S)-3-methylpiperazin-1-yl]methyl}phenyl)-4-[3-(2-oxopropyl)phenoxy]-cyclohexanecarboxamide

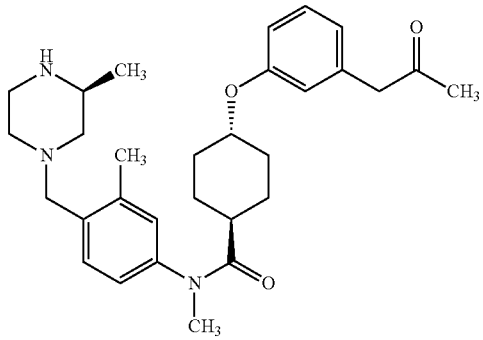 [SMILES: CC(=O)Cc1cccc(O[C@H]2CC[C@H](C(=O)N(C)c3ccc(CN4CCN[C@@H](C)C4)c(C)c3)CC2)c1]

Tert-butyl (2S)-2-methyl-4-{2-methyl-4-[methyl({trans-4-[3-(2-oxopropyl)phenoxy]cyclohexyl}carbonyl)amino]benzyl}piperazine-1-carboxylate (100 mg, 0.17 mmol) produced in (26B) was dissolved in dichloromethane (2 mL), and trifluoroacetic acid (195 µL) was added thereto at room temperature, and then, the resulting mixture was stirred overnight at room temperature.

To the reaction solution, a saturated aqueous solution of sodium hydrogen carbonate was added, and the organic matter was extracted with dichloromethane. The organic layer was dried over anhydrous sodium sulfate and filtered. Then, the solvent was distilled off under reduced pressure, whereby a crude product was obtained. This crude product was purified by NH silica gel column chromatography (dichloromethane:methanol=100:0 to 90:10 (v/v)), whereby the target compound was obtained as a colorless oil (32.2 mg, yield: 39%).

$^1$H NMR (CDCl$_3$, 400 MHz): δ1.05 (3H, d, J=6.7 Hz), 1.10-1.20 (2H, m), 1.65-1.80 (5H, m), 2.06-2.13 (3H, m), 2.13 (3H, s), 2.26 (1H, m), 2.37 (3H, s), 2.73-2.78 (2H, m), 2.87-2.31 (3H, m), 3.23 (3H, s), 3.45 (2H, s), 3.62 (2H, s), 4.17 (1H, m), 6.67 (1H, m), 6.73-6.76 (2H, m), 6.94-6.96 (2H, m), 7.20 (1H, t, J=7.8 Hz), 7.34 (1H, d, J=7.8 Hz).

MS (ESI) m/z: 492 (M+H)$^+$.

Example 42

Trans-N-methyl-N-(3-methyl-4-{[(3S)-3-methylpiperazin-1-yl]methyl}phenyl)-4-[3-(methylsulfonyl)phenoxy]-cyclohexanecarboxamide

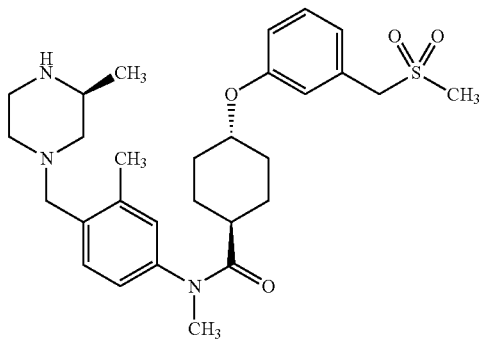 [SMILES: Cc1cc(N(C)C(=O)[C@H]2CC[C@H](Oc3cccc(CS(C)(=O)=O)c3)CC2)ccc1CN1CCN[C@@H](C)C1]

(42A) Trans-N-methyl-N-(3-methyl-4-{[(3S)-3-methylpiperazin-1-yl]methyl}phenyl)-4-[3-(methylsulfonyl)phenoxy]-cyclohexanecarboxamide Tert-butyl (2S)-4-{4-[({trans-4-[3-(bromomethyl)phenoxy]cyclohexyl}carbonyl)(methyl)amino]-2-methylbenzyl}-2-methylpiperazine-1-carboxylate (126 mg, 0.2 mmol) produced in (38A) was dissolved in dimethylformamide (2 mL), and sodium methanesulfinate (24 mg, 0.24 mmol) was added thereto at room temperature, and then, the resulting mixture was stirred at room temperature for 2 hours.

To the reaction solution, water was added, and the organic matter was extracted with ethyl acetate. The organic layer was dried over anhydrous sodium sulfate and filtered. Then, the solvent was distilled off under reduced pressure, whereby a crude product was obtained.

The obtained crude product was dissolved in dichloromethane (1 mL), and trifluoroacetic acid (1 mL) was added thereto at room temperature, and then, the resulting mixture was stirred at room temperature for 2 hours.

The solvent in the reaction solution was distilled off under reduced pressure, and to the obtained residue, a 1 N aqueous solution of sodium hydroxide was added, and the organic matter was extracted with dichloromethane. The organic layer was dried over anhydrous sodium sulfate and filtered. Then, the solvent was distilled off under reduced pressure, whereby a crude product was obtained. The obtained crude product was purified by NH silica gel column chromatography (ethyl acetate:methanol=100:0 to 80:20 (v/v)), whereby the target compound was obtained as a colorless oil (70 mg, yield: 66%).

$^1$H NMR (CDCl$_3$, 400 MHz): δ1.04 (3H, d, J=6.3 Hz), 1.23-1.09 (2H, m), 1.84-1.65 (5H, m), 2.16-2.06 (3H, m), 2.33-2.20 (1H, m), 2.37 (3H, s), 2.79-2.71 (5H, m), 3.03-2.81 (3H, m), 3.23 (3H, s), 3.45 (2H, s), 4.24-4.14 (3H, m), 6.89-6.84 (2H, m), 6.97-6.91 (3H, m), 7.35-7.24 (2H, m).

MS (ESI) m/z: 528 (M+H)$^+$.

(42B) Trans-N-methyl-N-(3-methyl-4-{[(3S)-3-methylpiperazin-1-yl]methyl}phenyl)-4-[3-(methylsulfonyl)phenoxy]-cyclohexanecarboxamide hydrochloride Trans-N-methyl-N-(3-methyl-4-{[(3S)-3-methylpiperazin-1-yl]methyl}phenyl)-4-[3-(methylsulfonyl)phenoxy]-cyclohexanecarboxamide (390 mg, 0.62 mmol) produced in (42A) was dissolved in dioxane (1 mL) and water (1 mL), and 1 N hydrochloric acid (620 µL, 0.62 mmol) was added thereto at room temperature, and then, the resulting mixture was frozen at −78° C. The frozen mixture was lyophilized using a lyophilizer, whereby the target compound was obtained as a white solid (340 mg, yield: 97%).

MS (ESI) m/z: 528 (M+H)$^+$

Example 43

3-({Trans-4-[methyl(3-methyl-4-{[(3S)-3-methylpiperazin-1-yl]methyl}phenyl)carbamoyl]cyclohexyl}oxy)benzylmethylcarbamate

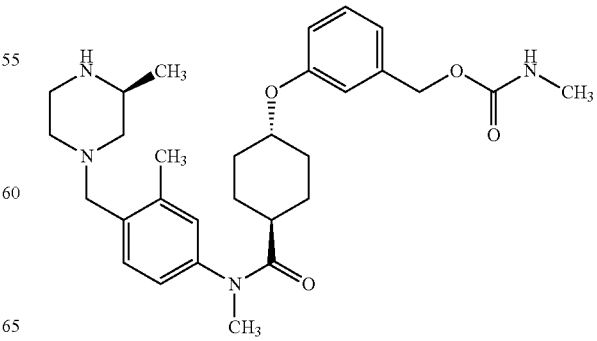

(43A) Tert-butyl (2S)-2-methyl-4-[2-methyl-4-(methyl{[trans-4-(3-{[(methylcarbamoyl)oxy]methyl}phenoxy)cyclohexyl]carbonyl}amino)benzyl]piperazine-1-carboxylate Triphosgene (41 mg, 0.138 mmol) was dissolved in dichloromethane (3 mL), and a solution of tert-butyl (2S)-4-{4-[({trans-4-[3-(hydroxymethyl)phenoxy]cyclohexyl}carbonyl)(methyl)amino]-2-methylbenzyl}-2-methylpiperazine-1-carboxylate (130 mg, 0.230 mmol) produced in (5B) and pyridine (28 µL, 0.345 mmol) in dichloromethane (2 mL) was added thereto at 0° C., and then, the resulting mixture was stirred under nitrogen atmosphere at 0° C. for 15 minutes. The resulting solution was added dropwise at 0° C. to a solution obtained by dissolving a solution of methylamine in tetrahydrofuran (2 M, 173 µL, 0.345 mmol) and triethylamine (96 µL, 0.690 mmol) in dichloromethane (2 mL), and the resulting mixture was stirred under a nitrogen atmosphere at room temperature for 16 hours.

To the reaction solution, a saturated aqueous solution of ammonium chloride was added, and extraction was performed with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=90:10 to 30:70 (v/v)), whereby the target compound was obtained as a colorless solid (39.6 mg, yield: 28%).

$^1$H NMR (CDCl$_3$, 400 MHz): δ1.07-1.21 (2H, m), 1.23 (3H, d, J=6.7 Hz), 1.47 (9H, s), 1.64-1.82 (4H, m), 1.98-2.15 (3H, m), 2.18-2.29 (2H, m), 2.39 (3H, s), 2.60 (1H, d, J=11.3 Hz), 2.73 (1H, d, J=12.1 Hz), 2.81 (3H, d, J=4.7 Hz), 3.03-3.13 (1H, m), 3.24 (3H, s), 3.43 (2H, s), 3.79-3.86 (1H, m), 4.13-4.26 (2H, m), 4.65-4.74 (1H, brs), 5.04 (2H, s), 6.78 (1H, d, J=7.8 Hz), 6.82 (1H, s), 6.89 (1H, d, J=7.4 Hz), 6.93-6.98 (2H, m), 7.22 (1H, t, J=8.0 Hz), 7.32 (1H, d, J=7.8 Hz).

(43B) 3-({Trans-4-[methyl(3-methyl-4-{[(3S)-3-methylpiperazin-1-yl]methyl}phenyl)carbamoyl]cyclohexyl}oxy)benzylmethylcarbamate Tert-butyl (2S)-2-methyl-4-[2-methyl-4-(methyl{[trans-4-(3-{[(methylcarbamoyl)oxy]methyl}phenoxy)cyclohexyl]carbonyl}amino)benzyl]piperazine-1-carboxylate (37.0 mg, 0.0594 mmol) produced in (43A) was dissolved in dichloromethane (1 mL), and trifluoroacetic acid (1 mL) was added thereto at room temperature, and then, the resulting mixture was stirred under a nitrogen atmosphere at room temperature for 10 minutes.

The residue obtained by distilling off the solvent in the reaction solution under reduced pressure was purified by NH silica gel column chromatography (hexane:ethyl acetate:methanol=1:2:0 to 0:1:0 to 0:15:1 (v/v/v)), whereby the target compound was obtained as a colorless oil (28.8 mg, yield: 94%).

$^1$H NMR (CDCl$_3$, 400 MHz): δ1.04 (3H, d, J=6.3 Hz), 1.09-1.22 (2H, m), 1.67-1.83 (5H, m), 2.03-2.16 (3H, m), 2.21-2.31 (1H, m), 2.37 (3H, s), 2.71-2.80 (2H, m), 2.81 (3H, d, J=4.7 Hz), 2.85-3.02 (3H, m), 3.23 (3H, s), 3.45 (2H, s), 4.12-4.24 (1H, m), 4.63-4.76 (1H, brs), 5.04 (2H, s), 6.78 (1H, d, J=7.8 Hz), 6.82 (1H, s), 6.89 (1H, d, J=7.0 Hz), 6.92-6.98 (2H, m), 7.22 (1H, t, J=7.8 Hz), 7.33 (1H, d, J=7.4 Hz).

MS (ESI) m/z: 523 (M+H)$^+$.

Example 44

2-[3-({Trans-4-[methyl(3-methyl-4-{[(3S)-3-methylpiperazin-1-yl]methyl}phenyl)carbamoyl]cyclohexyl}oxy)phenyl]ethylcarbamate

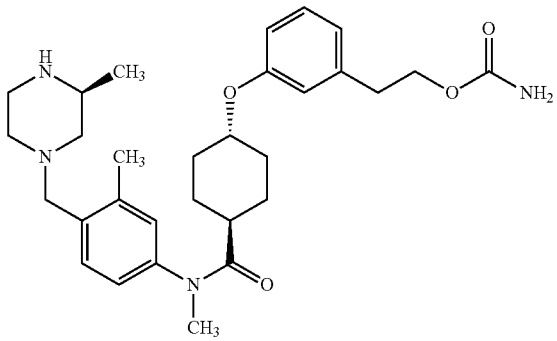 [SMILES: Cc1cc(N(C)C(=O)[C@H]2CC[C@H](Oc3cccc(CCOC(N)=O)c3)CC2)ccc1CN1CCN[C@@H](C)C1]

(44A) Tert-butyl (2S)-4-(4-{[(trans-4-{3-[2-(carbamoyloxy)ethyl]phenoxy}cyclohexyl)carbonyl](methyl)amino}-2-methylbenzyl)-2-methylpiperazine-1-carboxylate Triphosgene (80 mg, 0.269 mmol) was dissolved in dichloromethane (4 mL), and a solution of tert-butyl (2S)-4-{4-[({trans-4-[3-(2-hydroxyethyl)phenoxy]cyclohexyl}carbonyl)(methyl)amino]-2-methylbenzyl}-2-methylpiperazine-1-carboxylate (260 mg, 0.448 mmol) produced in (7A) and pyridine (54 µL, 0.672 mmol) in dichloromethane (3 mL) was added thereto at 0° C., and then, the resulting mixture was stirred under a nitrogen atmosphere at 0° C. for 20 minutes. The resulting solution was added dropwise at 0° C. to a solution of tetrahydrofuran (2 mL) containing a 28% aqueous solution of ammonia (200 µL) and triethylamine (186 µL, 1.34 mmol), and then, the resulting mixture was stirred under a nitrogen atmosphere at 0° C. for 2 hours.

To the reaction solution, a saturated aqueous solution of ammonium chloride was added, and the extraction was performed with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=80:20 to 40:60 (v/v)), whereby the target compound was obtained as a colorless oil (250 mg, yield: 90%).

$^1$H NMR (CDCl$_3$, 400 MHz): δ1.06-1.20 (2H, m), 1.22 (3H, d, J=6.7 Hz), 1.46 (9H, s), 1.63-1.82 (4H, m), 1.97-2.15 (3H, m), 2.17-2.29 (2H, m), 2.38 (3H, s), 2.59 (1H, d, J=11.3 Hz), 2.73 (1H, d, J=11.0 Hz), 2.87 (2H, t, J=6.7 Hz), 3.08 (1H, t, J=12.5 Hz), 3.23 (3H, s), 3.42 (2H, s), 3.82 (1H, d, J=11.0 Hz), 4.07-4.28 (4H, m), 4.60-4.77 (2H, brs), 6.66-6.73 (2H, m), 6.76 (1H, d, J=7.0 Hz), 6.91-6.99 (2H, m), 7.12-7.21 (1H, m), 7.31 (1H, d, J=7.8 Hz).

(44B) 2-[3-({Trans-4-[methyl(3-methyl-4-{[(3S)-3-methylpiperazin-1-yl]methyl}phenyl)carbamoyl]cyclohexyl}oxy)phenyl]ethylcarbamate Tert-butyl (2S)-4-(4-{[(trans-4-{3-[2-(carbamoyloxy)ethyl]phenoxy}cyclohexyl)carbonyl](methyl) amino}-2- methylbenzyl)-2-methylpiperazine-1-carboxylate (250 mg, 0.402 mmol) produced in (44A) was dissolved in dichloromethane (1 mL), and trifluoroacetic acid (1 mL) was added thereto at room temperature, and then, the resulting mixture was stirred under a nitrogen atmosphere at room temperature for 5 minutes.

The solvent in the reaction solution was distilled off under reduced pressure, whereby a crude product was obtained. The obtained crude product was purified by NH silica gel column chromatography (ethyl acetate:methanol=100:0 to 90:10 (v/v)), whereby the target compound was obtained as a colorless oil (101 mg, yield: 48%).

$^1$H NMR (CDCl$_3$, 400 MHz): δ1.05 (3H, d, J=6.3 Hz), 1.08-1.21 (2H, m), 1.64-1.81 (5H, m), 2.06-2.15 (3H, m), 2.21-2.30 (1H, m), 2.37 (3H, s), 2.71-2.80 (2H, m), 2.87 (2H, t, J=6.9 Hz), 2.84-3.01 (3H, m), 3.23 (3H, s), 3.45 (2H, s), 4.11-4.21 (1H, m), 4.25 (2H, t, J=6.9 Hz), 4.55-4.75 (2H, brs), 6.67-6.74 (2H, m), 6.77 (1H, d, J=7.4 Hz), 6.92-6.97 (2H, m), 7.17 (1H, t, J=8.2 Hz), 7.33 (1H, d, J=7.8 Hz).

MS (ESI) m/z: 523 (M+H)$^+$.

Example 45

2-[3-({Trans-4-[methyl(3-methyl-4-{[(3S)-3-methylpiperazin-1-yl]methyl}phenyl)carbamoyl]cyclohexyl}oxy)phenyl]ethylmethylcarbamate

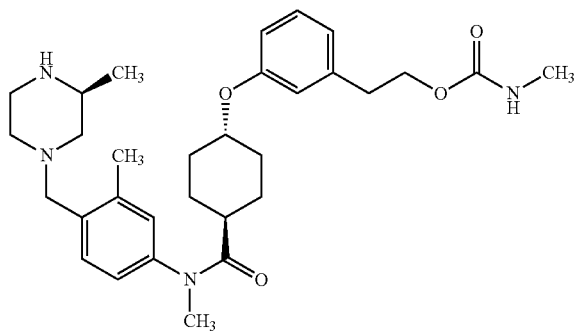 [SMILES: CNC(=O)OCCc1cccc(O[C@H]2CC[C@H](C(=O)N(C)c3ccc(CN4CCN[C@@H](C)C4)c(C)c3)CC2)c1]

(45A) Tert-butyl (2S)-2-methyl-4-[2-methyl-4-(methyl{[trans-4-(3-{2-[(methylcarbamoyl)oxy]ethyl}phenoxy)cyclohexyl]carbonyl}amino)benzyl]piperazine-1-carboxylate Triphosgene (75 mg, 0.251 mmol) was dissolved in dichloromethane (4 mL), and a solution of tert-butyl (2S)-4-{4-[({trans-4-[3-(2-hydroxyethyl)phenoxy]cyclohexyl}carbonyl)(methyl)amino]-2-methylbenzyl}-2-methylpiperazine-1-carboxylate (243 mg, 0.419 mmol) produced in (7A) and pyridine (51 μL, 0.629 mmol) in dichloromethane (3 mL) was added thereto at 0° C., and then, the resulting mixture was stirred under a nitrogen atmosphere at 0° C. for 25 minutes. The resulting solution was added dropwise at 0° C. to a solution of tetrahydrofuran (2 mL) containing an aqueous solution of methylamine (about 40%, 200 μL) and triethylamine (174 μL, 1.26 mmol), and then, the resulting mixture was stirred under a nitrogen atmosphere at 0° C. for 1.5 hours.

To the reaction solution, a saturated aqueous solution of ammonium chloride was added, and the extraction was performed with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=90:10 to 40:60 (v/v)), whereby the target compound was obtained as a colorless oil (256 mg, yield: 96%).

$^1$H NMR (CDCl$_3$, 400 MHz): δ1.08-1.20 (2H, m), 1.23 (3H, d, J=7.0 Hz), 1.47 (9H, s), 1.63-1.82 (4H, m), 1.98-2.15 (3H, m), 2.19-2.26 (2H, m), 2.39 (3H, s), 2.60 (1H, d, J=11.0 Hz), 2.73 (1H, d, J=11.0 Hz), 2.78 (3H, d, J=4.7 Hz), 2.85 (2H, t, J=7.0 Hz), 3.04-3.13 (1H, m), 3.23 (3H, s), 3.43 (2H, s), 3.82 (1H, d, J=13.3 Hz), 4.11-4.30 (2H, m), 4.25 (2H, t, J=6.9 Hz), 4.53-4.61 (1H, brs), 6.66-6.72 (2H, m), 6.77 (1H, d, J=7.4 Hz), 6.92-6.98 (2H, m), 7.16 (1H, t, J=8.0 Hz), 7.31 (1H, d, J=7.8 Hz).

(45B) 2-[3-({Trans-4-[methyl(3-methyl-4-{[(3S)-3-methylpiperazin-1-yl]methyl}phenyl)carbamoyl]cyclohexyl}oxy)phenyl]ethylmethylcarbamate Tert-butyl (2S)-2-methyl-4-[2-methyl-4-(methyl{[trans-4-(3-{2-[(methylcarbamoyl)oxy]ethyl}phenoxy)cyclohexyl]carbonyl}amino)benzyl]piperazine-1-carboxylate (250 mg, 0.393 mmol) produced in (45A) was dissolved in dichloromethane (1 mL), and trifluoroacetic acid (1 mL) was added thereto at room temperature, and then, the resulting mixture was stirred under a nitrogen atmosphere at room temperature for 15 minutes.

The solvent in the reaction solution was distilled off under reduced pressure, whereby a crude product was obtained. The obtained crude product was purified by NH silica gel column chromatography (hexane:ethyl acetate:methanol=50:50:0 to 0:100:0 to 0:90:10 (v/v/v)), whereby the target compound was obtained as a colorless oil (158 mg, yield: 75%).

$^1$H NMR (CDCl$_3$, 400 MHz): δ1.04 (3H, d, J=6.3 Hz), 1.08-1.21 (2H, m), 1.64-1.82 (5H, m), 2.02-2.14 (3H, m), 2.20-2.30 (1H, m), 2.37 (3H, s), 2.70-2.82 (5H, m), 2.82-2.92 (4H, m), 2.92-3.01 (1H, m), 3.23 (3H, s), 3.45 (2H, s), 4.11-4.20 (1H, m), 4.24 (2H, t, J=7.0 Hz), 4.52-4.62 (1H, brs), 6.66-6.72 (2H, m), 6.76 (1H, d, J=7.4 Hz), 6.92-6.97 (2H, m), 7.16 (1H, t, J=8.0 Hz), 7.33 (1H, d, J=8.2 Hz).

MS (ESI) m/z: 537 (M+H)$^+$.

Example 46

2-[3-({Trans-4-[methyl(3-methyl-4-{[(3S)-3-methylpiperazin-1-yl]methyl}phenyl)carbamoyl]cyclohexyl}amino)phenyl]ethyl dimethylcarbamate

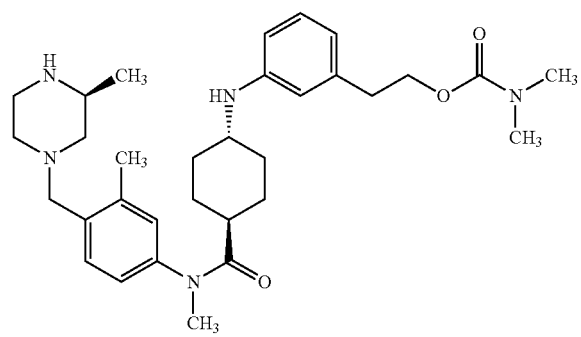 [SMILES: Cc1cc(N(C)C(=O)[C@H]2CC[C@H](Nc3cccc(CCOC(=O)N(C)C)c3)CC2)ccc1CN1CCN[C@@H](C)C1]

(46A) Tert-butyl (2S)-4-{4-[({trans-4-[(3-{2-[(dimethylcarbamoyl)oxy]ethyl}phenyl)amino]cyclohexyl}carbonyl)(methyl)amino]-2-methylbenzyl}-2-methylpiperazine-1-carboxylate Tert-butyl (2S)-4-(4-{[(trans-4-{[3-(2-hydroxyethyl)phenyl]amino}cyclohexyl)carbonyl](methyl)amino}-2-methylbenzyl)-2-methylpiperazine-1-carboxylate (260 mg, 0.449 mmol) produced in (28D), disuccinimidyl carbonate (115 mg, 0.449 mmol), and dimethylaminopyridine (16 mg, 0.135 mmol) were dissolved in acetonitrile (5.0 mL), and the resulting mixture was stirred under a nitrogen atmosphere at room temperature for 3 hours. Then, to the reaction solution, a solution of dimethylamine in tetrahydrofuran (2 M, 270 μL, 0.539 mmol) was added, and the resulting mixture was stirred at room temperature for 30 minutes.

To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=60:40 to 30:70 (v/v)), whereby the target compound was obtained as a colorless solid (126 mg, yield: 43%).

$^1$H NMR (CDCl$_3$, 400 MHz): δ0.77-0.91 (2H, m), 1.23 (3H, d, J=6.7 Hz), 1.46 (9H, s), 1.68-1.80 (4H, m), 1.97-2.12 (3H, m), 2.22 (2H, dd, J=11.0, 3.9 Hz), 2.38 (3H, s), 2.60 (1H, d, J=11.4 Hz), 2.73 (1H, d, J=10.6 Hz), 2.83 (2H, t, J=7.0 Hz), 2.87 (3H, s), 2.90 (3H, s), 3.01-3.03 (1H, m), 3.17-3.27 (1H, m), 3.23 (3H, s), 3.43 (2H, s), 3.82 (1H, d, J=13.3 Hz), 4.17-4.27 (1H, m), 4.22 (2H, t, J=7.0 Hz), 6.36-6.43 (2H, m), 6.53 (1H, d, J=7.4 Hz), 6.92-6.98 (2H, m), 7.02-7.09 (1H, m), 7.31 (1H, d, J=7.8 Hz).

(46B) 2-[3-({Trans-4-[methyl(3-methyl-4-{[(3S)-3-methylpiperazin-1-yl]methyl}phenyl)carbamoyl]cyclohexyl}amino)phenyl]ethyl dimethylcarbamate Tert-butyl (2S)-4-{4-[({trans-4-[(3-{2-[(dimethylcarbamoyl)oxy]ethyl}phenyl)amino]cyclohexyl}carbonyl)(methyl)amino]-2-methylbenzyl}-2-methylpiperazine-1-carboxylate (323 mg, 0.497 mmol) produced in (46A) was dissolved in dichloromethane (1 mL), and trifluoroacetic acid (1 mL) was added thereto at room temperature, and then, the resulting mixture was stirred under a nitrogen atmosphere at room temperature for 7 minutes.

The residue obtained by distilling off the solvent in the reaction solution under reduced pressure was purified by NH silica gel column chromatography (ethyl acetate:methanol=100:0 to 85:15 (v/v)), whereby the target compound was obtained as a colorless solid (204 mg, yield: 75%).

$^1$H NMR (CDCl$_3$, 400 MHz): δ0.78-0.91 (2H, m), 1.03 (3H, d, J=6.7 Hz), 1.67-1.80 (5H, m), 2.02-2.12 (3H, m), 2.17-2.28 (1H, m), 2.37 (3H, s), 2.72-2.92 (12H, m), 2.92-3.00 (1H, m), 3.17-3.26 (1H, m), 3.23 (3H, s), 3.44 (2H, s), 4.23 (2H, t, J=7.0 Hz), 6.37-6.43 (2H, m), 6.52 (1H, d, J=7.0 Hz), 6.92-6.97 (2H, m), 7.03-7.09 (1H, m), 7.32 (1H, d, J=7.4H).

MS (ESI) m/z: 550 (M+H)$^+$.

Example 47

2-[3-({Trans-4-[methyl(3-methyl-4-{[(3S)-3-methylpiperazin-1-yl]methyl}phenyl)carbamoyl]cyclohexyl}amino)phenyl]ethyl methylcarbamate

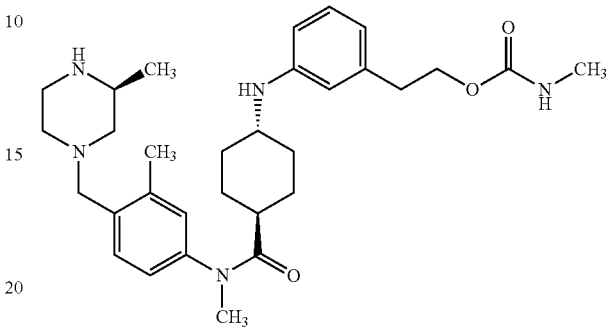

(47A) Tert-butyl (2S)-2-methyl-4-{2-methyl-4-[methyl({trans-4-[(3-{2-[(methylcarbamoyl)oxy]ethyl}phenyl)amino]cyclohexyl}carbonyl)amino]benzyl}piperazine-1-carboxylate Tert-butyl (2S)-4-(4-{[(trans-4-{[3-(2-hydroxyethyl)phenyl]amino}cyclohexyl)carbonyl](methyl)amino}-2-methylbenzyl)-2-methylpiperazine-1-carboxylate (200 mg, 0.346 mmol) produced in (28D), disuccinimidyl carbonate (89 mg, 0.346 mmol), and dimethylaminopyridine (13 mg, 0.104 mmol) were dissolved in acetonitrile (3.0 mL), and then, the resulting mixture was stirred under a nitrogen atmosphere at room temperature for 17 hours.

The residue obtained by distilling off the solvent in the reaction solution under reduced pressure was roughly purified by silica gel column chromatography (hexane:ethyl acetate=70:30 to 30:70 (v/v)). The obtained crude product was dissolved in acetonitrile (3.0 mL), and a solution of methylamine in tetrahydrofuran (2 M, 208 μL, 0.415 mmol) was added thereto, and then, the resulting mixture was stirred at room temperature for 1 hour.

To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=70:30 to 30:70 (v/v)), whereby the target compound was obtained as a colorless solid (70.1 mg, yield: 32%).

$^1$H NMR (CDCl$_3$, 400 MHz): δ0.75-0.90 (2H, m), 1.22 (3H, d, J=7.0 Hz), 1.46 (9H, s), 1.68-1.80 (4H, m), 1.98-2.12 (3H, m), 2.17-2.26 (2H, m), 2.38 (3H, s), 2.60 (1H, d, J=11.0 Hz), 2.70-2.85 (3H, m), 2.78 (3H, d, J=4.7 Hz), 3.01-3.13 (1H, m), 3.17-3.25 (1H, m), 3.23 (3H, s), 3.43 (2H, s), 3.81 (1H, d, J=13.3 Hz), 4.16-4.28 (1H, m), 4.24 (2H, t, J=7.0 Hz), 4.55-4.64 (1H, brs), 6.36-6.43 (2H, m), 6.51 (1H, d, J=7.4 Hz), 6.92-6.98 (2H, m), 7.06 (1H, t, J=7.8 Hz), 7.30 (1H, d, J=7.8 Hz).

(47B) 2-[3-({Trans-4-[methyl(3-methyl-4-{[(3S)-3-methylpiperazin-1-yl]methyl}phenyl)carbamoyl]cyclohexyl}amino)phenyl]ethyl methylcarbamate Tert-butyl (2S)-2-methyl-4-{2-methyl-4-[methyl({trans-4-[(3-{2-[(methylcarbamoyl)oxy]ethyl}phenyl)amino]cyclohexyl}carbonyl)amino]benzyl}piperazine-1-carboxylate (65.1 mg, 0.102 mmol) produced in (47A) was dissolved in dichloromethane (1 mL), and trifluoroacetic acid (1 mL) was added thereto at room temperature, and then, the resulting mixture was stirred under a nitrogen atmosphere at room temperature for 10 minutes.

The residue obtained by distilling off the solvent in the reaction solution under reduced pressure was purified by NH silica gel column chromatography (ethyl acetate:methanol=100:0 to 85:15 (v/v)), whereby the target compound was obtained as a colorless solid (50.9 mg, yield: 93%).

$^1$H NMR (CDCl$_3$, 400 MHz): 0.79-0.91 (2H, m), 1.05 (3H, d, J=6.3 Hz), 1.69-1.81 (5H, m), 2.03-2.13 (3H, m), 2.18-2.29 (1H, m), 2.38 (3H, s), 2.71-3.01 (10H, m), 3.17-3.27 (1H, m), 3.23 (3H, s), 3.45 (2H, s), 4.24 (2H, t, J=7.0 Hz), 4.55-4.65 (1H, brs), 6.36-6.43 (2H, m), 6.52 (1H, d, J=7.4 Hz), 6.93-6.97 (2H, m), 7.06 (1H, t, J=7.6 Hz), 7.33 (1H, d, J=8.6 Hz).

MS (ESI) m/z: 536 (M+H)$^+$.

Example 48

Methyl [3-({trans-4-[methyl(3-methyl-4-{[(3S)-3-methylpiperazin-1-yl]methyl}phenyl)carbamoyl]cyclohexyl}oxy)benzyl]carbamate

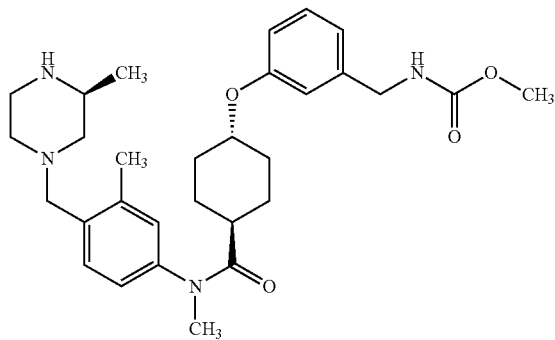 [SMILES: COC(=O)NCc1cccc(O[C@H]2CC[C@H](C(=O)N(C)c3ccc(CN4CCN[C@@H](C)C4)c(C)c3)CC2)c1]

(48A) Methyl trans-4-(3-cyanophenoxy)cyclohexanecarboxylate

3-Cyanophenol (3.00 g, 25.2 mmol) and methyl cis-4-hydroxycyclohexanecarboxylate (2.66 g, 16.8 mmol) were dissolved in toluene (80 mL), and cyanomethylenetributylphosphorane (6.6 mL, 25.2 mmol) was added thereto, and then, the resulting mixture was heated to reflux under a nitrogen atmosphere for 2.5 hours.

After the temperature of the reaction solution was returned to room temperature, the solvent in the reaction solution was distilled off under reduced pressure. The obtained residue was purified by NH silica gel column chromatography (hexane:ethyl acetate=95:5 to 90:10 (v/v)), whereby the target compound was obtained as a brown oil (2.19 g, yield: 50%).

$^1$H NMR (CDCl$_3$, 400 MHz): δ1.44-1.68 (4H, m), 2.06-2.21 (4H, m), 2.38 (1H, tt, J=3.7, 11.2 Hz), 3.70 (3H, s), 4.22 (1H, tt, J=3.9, 9.8 Hz), 7.08-7.15 (2H, m), 7.22 (1H, d, J=7.4 Hz), 7.36 (1H, t, J=7.8 Hz).

(48B) Trans-4-(3-cyanophenoxy)cyclohexanecarboxylic acid

Methyl trans-4-(3-cyanophenoxy)cyclohexanecarboxylate (1.10 g, 4.24 mmol) produced in (48A) was dissolved in methanol (5 mL) and tetrahydrofuran (5 mL), and a 5 N aqueous solution of sodium hydroxide (5 mL) was added thereto, and then, the resulting mixture was stirred at room temperature for 1 hour.

To the reaction solution, water was added, and the organic matter was extracted with ethyl acetate. To the aqueous layer, 5 N hydrochloric acid was added to neutralize the pH of the aqueous layer, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=10:1 to 1:1 (v/v)), whereby the target compound was obtained as a light red solid (770 mg, yield: 74%).

$^1$H NMR (CD$_3$OD, 400 MHz): δ1.42-1.54 (2H, m), 1.57-1.69 (2H, m), 2.03-2.10 (2H, m), 2.12-2.20 (2H, m), 2.35 (1H, tt, J=3.8, 11.4 Hz), 4.32-4.40 (1H, m), 7.21-7.27 (3H, m), 7.42 (1H, t, J=8.2 Hz).

(48C) Tert-butyl (2S)-4-{4-[{[trans-4-(3-cyanophenoxy)cyclohexyl]carbonyl}(methyl)amino]-2-methylbenzyl}-2-methylpiperazine-1-carboxylate Trans-4-(3-cyanophenoxy)cyclohexanecarboxylic acid (762 mg, 3.11 mmol) produced in (48B) and tert-butyl (2S)-2-methyl-4-[2-methyl-4-(methylamino)benzyl]piperazine-1-carboxylate (1.04 g, 3.11 mmol), which is a known compound, were dissolved in ethanol (20 mL), and 4-(4,6-dimethoxy-1,3,5-triazin-2-yl)-4-methylmorpholinium chloride hydrate (1.72 g, about 6.2 mmol) was added thereto, and then, the resulting mixture was stirred under a nitrogen atmosphere at room temperature for 21 hours.

To the reaction solution, water was added, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=95:5 to 70:30 to 30:70 (v/v)), whereby the target compound was obtained as a colorless solid (1.24 g, yield: 71%).

$^1$H NMR (CDCl$_3$, 400 MHz): δ1.11-1.25 (2H, m), 1.23 (3H, d, J=6.7 Hz), 1.46 (9H, s), 1.68-1.84 (4H, m), 1.99-2.14 (3H, m), 2.19-2.30 (2H, m), 2.39 (3H, s), 2.60 (1H, d, J=11.4 Hz), 2.73 (1H, d, J=11.0 Hz), 3.02-3.13 (1H, m), 3.24 (3H, s), 3.43 (2H, s), 3.82 (1H, d, J=12.5 Hz), 4.15-4.26 (2H, m), 6.93-6.98 (2H, m), 7.03-7.09 (2H, m), 7.19 (1H, d, J=7.4 Hz), 7.30-7.35 (2H, m).

(48D) Tert-butyl (2S)-4-{4-[({trans-4-[3-(aminomethyl)phenoxy]cyclohexyl}carbonyl)(methyl)amino]-2-methylbenzyl}-2-methylpiperazine-1-carboxylate Tert-butyl (2S)-4-{4-[{[trans-4-(3-cyanophenoxy)cyclohexyl]carbonyl}(methyl)amino]-2-methylbenzyl}-2-methylpiperazine-1-carboxylate (4.00 g, 7.13 mmol) produced in (48C) and cobalt chloride dihydrate (3.39 g, 14.3 mmol) were dissolved in methanol (100 mL), and sodium borohydride (1.89 g, 49.9 mmol) was added thereto little by little at −10° C., and then, the resulting mixture was stirred at −10° C. for 45 minutes.

To the reaction solution, water was added, and the resulting mixture was filtered through a Celite filter. Thereafter, the solvent was distilled off under reduced pressure, and then, water was added thereto, and extraction was performed with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate=70:30 to 100:0 (v/v)), whereby the target compound was obtained as a colorless solid (1.67 g, yield: 43%).

$^1$H NMR (CDCl$_3$, 400 MHz): δ1.09-1.20 (2H, m), 1.23 (3H, d, J=6.7 Hz), 1.47 (9H, s), 1.64-1.82 (4H, m), 1.98-2.07 (1H, m), 2.07-2.15 (2H, m), 2.19-2.28 (2H, m), 2.39 (3H, s), 2.60 (1H, d, J=11.3 Hz), 2.73 (1H, d, J=11.3 Hz), 3.02-3.13 (1H, m), 3.23 (3H, s), 3.43 (2H, s), 3.77-3.85 (1H, m), 3.81 (2H, s), 4.14-4.27 (2H, m), 6.72 (1H, dd, J=2.0, 7.8 Hz), 6.80 (1H, s), 6.85 (1H, d, J=7.8 Hz), 6.93-6.99 (2H, m), 7.20 (1H, t, J=7.8 Hz), 7.31 (1H, d, J=7.8 Hz).

(48E) Tert-butyl (2S)-4-{4-[{[trans-4-(3-{[methoxycarbonyl)amino]methyl}phenoxy)cyclohexyl]carbonyl}(methyl)amino]-2-methylbenzyl}-2-methylpiperazine-1-carboxylate Tert-butyl (2S)-4-{4-[({trans-4-[3-(aminomethyl)phenoxy]cyclohexyl}carbonyl)(methyl)amino]-2-methylbenzyl}-2-methylpiperazine-1-carboxylate (110 mg, 0.195 mmol) produced in (48D) was dissolved in dichloromethane (2 mL), and triethylamine (54 μL, 0.390 mmol) and methyl chloroformate (18 μL, 0.234 mmol) were added thereto at 0° C., and then, the resulting mixture was stirred at room temperature for 15 minutes.

To the reaction solution, a saturated aqueous solution of ammonium chloride was added, and the extraction was performed with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=90:10 to 40:60 (v/v)), whereby the target compound was obtained as a colorless solid (99.5 mg, yield: 82%).

$^1$H NMR (CDCl$_3$, 400 MHz): δ1.08-1.21 (2H, m), 1.23 (3H, d, J=6.7 Hz), 1.46 (9H, s), 1.61-1.82 (4H, m), 1.99-2.14 (3H, m), 2.19-2.29 (2H, m), 2.39 (3H, s), 2.60 (1H, d, J=11.0 Hz), 2.73 (1H, d, J=11.3 Hz), 3.02-3.13 (1H, m), 3.23 (3H, s), 3.43 (2H, s), 3.70 (3H, s), 3.82 (1H, d, J=13.3 Hz), 4.12-4.26 (2H, m), 4.31 (2H, d, J=5.5 Hz), 4.92-5.01 (1H, brs), 6.71-6.78 (2H, m), 6.83 (1H, d, J=7.4 Hz), 6.93-6.98 (2H, m), 7.20 (1H, t, J=7.8 Hz), 7.32 (1H, d, J=7.8 Hz).

(48F) Methyl [3-({trans-4-[methyl(3-methyl-4-{[(3S)-3-methylpiperazin-1-yl]methyl}phenyl)carbamoyl]cyclohexyl}oxy)benzyl]carbamate Tert-butyl (2S)-4-{4-[{[trans-4-(3-{[(methoxycarbonyl)amino]methyl}phenoxy)cyclohexyl]carbonyl}(methyl)amino]-2-methylbenzyl}-2-methylpiperazine-1-carboxylate (93.0 mg, 0.149 mmol) produced in (48E) was dissolved in dichloromethane (1 mL), and trifluoroacetic acid (1 mL) was added thereto at room temperature, and then, the resulting mixture was stirred under a nitrogen atmosphere at room temperature for 15 minutes.

The residue obtained by distilling off the solvent in the reaction solution under reduced pressure was purified by NH silica gel column chromatography (hexane:ethyl acetate=50:50 to 0:100 (v/v)), whereby the target compound was obtained as a colorless solid (60.4 mg, yield: 78%).

$^1$H NMR (CDCl$_3$, 400 MHz): δ1.03 (3H, d, J=6.7 Hz), 1.08-1.21 (2H, m), 1.64-1.82 (5H, m), 2.02-2.13 (3H, m), 2.20-2.30 (1H, m), 2.37 (3H, s), 2.75 (2H, t, J=9.2 Hz), 2.82-3.00 (3H, m), 3.23 (3H, s), 3.45 (2H, s), 3.70 (3H, s), 4.11-4.21 (1H, m), 4.31 (2H, d, J=6.3 Hz), 4.90-5.00 (1H, brs), 6.71-6.77 (2H, m), 6.82 (1H, d, J=7.4 Hz), 6.92-6.98 (2H, m), 7.20 (1H, t, J=8.0 Hz), 7.33 (1H, d, J=8.2 Hz).

Example 49

Methyl [3-({trans-4-[methyl(3-methyl-4-{[(3S)-3-methylpiperazin-1-yl]methyl}phenyl)carbamoyl]cyclohexyl}amino)benzyl]carbamate

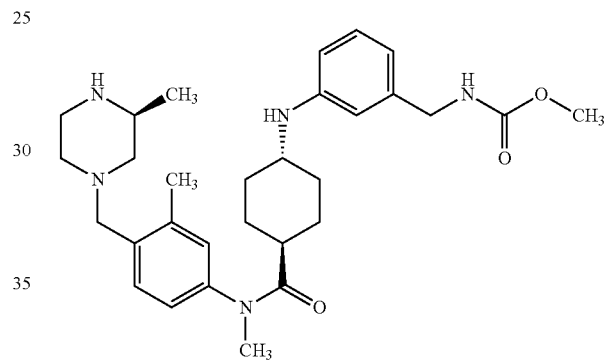

(49A) Ethyl trans-4-[(3-{[(tert-butoxycarbonyl)amino]methyl}phenyl)amino]cyclohexanecarboxylate Tert-butyl (3-aminobenzyl)carbamate (1.70 g, 7.65 mmol), which is a known compound, and ethyl 4-oxocyclohexanecarboxylate (1.69 g, 9.94 mmol) were dissolved in tetrahydrofuran (100 mL), and sodium triacetoxy borohydride (2.55 g, 11.5 mmol) was added thereto little by little. After acetic acid (3 mL) was added dropwise thereto, the resulting mixture was stirred at room temperature for 16 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 60:40 (v/v)), whereby the target compound was obtained as a colorless oil (860 mg, yield: 30%).

$^1$H NMR (CDCl$_3$, 400 MHz): δ1.08-1.18 (2H, m), 1.26 (3H, t, J=7.1 Hz), 1.46 (9H, s), 1.53-1.63 (2H, m), 2.05 (2H, dd, J=3.1 Hz, 14.9 Hz), 2.18 (2H, dd, J=3.5 Hz, 13.3 Hz), 2.28 (1H, tt, J=3.5 Hz, 12.1 Hz), 3.20-3.28 (1H, m), 4.13 (2H, q, J=7.2 Hz), 4.21 (2H, d, J=5.4 Hz), 4.85 (1H, brs), 6.46-6.49 (2H, m), 6.57 (1H, d, J=7.4 Hz), 7.10 (1H, t, J=7.8 Hz).

(49B) Ethyl trans-4-[(3-{[(methoxycarbonyl)amino]methyl}phenyl)amino]cyclohexanecarboxylate Ethyl trans-4-[(3-{[(tert-butoxycarbonyl)amino]methyl}phenyl)amino]cyclohexanecarboxylate (860 mg, 2.28 mmol) obtained in (49A) was dissolved in dichloromethane (30 mL), and trifluoroacetic acid (8 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 1 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained.

The obtained crude product was dissolved in dichloromethane (5 mL), and methyl chloroformate (112 μL, 1.44 mmol) and pyridine (50 μL) were added thereto at 0° C. The temperature of the reaction solution was returned to room temperature, and the solution was stirred for 1 hour.

To the reaction solution, water was added, and the organic matter was extracted with dichloromethane. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 80:20 (v/v)), whereby the target compound was obtained as a colorless oil (240 mg, yield: 99%).

$^1$H NMR (CDCl$_3$, 400 MHz): δ1.09-1.19 (2H, m), 1.26 (3H, t, J=7.0 Hz), 1.53-1.64 (2H, m), 2.05 (2H, dd, J=3.2 Hz, 11.7 Hz), 2.19 (2H, dd, J=3.1 Hz, 13.7 Hz), 2.28 (1H, tt, J=3.5 Hz, 12.1 Hz), 3.21-3.28 (1H, m), 3.52 (1H, s), 3.70 (3H, s), 4.13 (2H, q, J=7.0 Hz), 4.27 (2H, d, J=5.9 Hz), 4.95 (1H, brs), 6.48-6.50 (2H, m), 6.59 (1H, d, J=7.4 Hz), 7.10 (1H, t, J=8.0 Hz).

(49C) Trans-4-[(3-{[(methoxycarbonyl)amino]methyl}phenyl)amino]cyclohexanecarboxylic acid To a solution (3 mL) of ethyl trans-4-[(3-{[methoxycarbonyl)amino]methyl}phenyl)amino]cyclohexanecarboxylate (240 mg, 0.72 mmol) obtained in (49B) in tetrahydrofuran, a 1 N aqueous solution of sodium hydroxide (2.2 mL, 2.20 mmol) and methanol (3 mL) were added, and the resulting mixture was stirred at room temperature for 1 hour.

To the reaction solution, a 1 N aqueous solution of hydrochloric acid (5 mL, 5.00 mmol) was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby the target compound was obtained as a colorless solid (180 mg, yield: 82%).

$^1$H NMR (CDCl$_3$, 400 MHz): δ1.11-1.21 (2H, m), 1.55-1.66 (2H, m), 2.08-2.13 (2H, m), 2.20 (2H, dd, J=3.1 Hz, 13.7 Hz), 2.28 (1H, tt, J=3.5 Hz, 12.1 Hz), 3.22-3.30 (1H, m), 3.70 (3H, s), 4.28 (2H, d, J=5.9 Hz), 4.93 (1H, brs), 6.49-6.51 (2H, m), 6.59 (1H, d, J=7.4 Hz), 7.12 (1H, t, J=8.2 Hz).

(49D) Tert-butyl (2S)-4-{4-[({trans-4-[(3-{[methoxycarbonyl)amino]methyl}phenyl)amino]cyclohexyl}carbonyl)(methyl)amino]-2-methylbenzyl}-2-methylpiperazine-1-carboxylate Trans-4-[(3-{[methoxycarbonyl)amino]methyl}phenyl)amino]cyclohexanecarboxylic acid (150 mg, 0.49 mmol) obtained in (49C), tert-butyl (2S)-2-methyl-4-[2-methyl-4-(methylamino)benzyl]piperazine-1-carboxylate (163 mg, 0.49 mmol), which is a known compound, and 4-(4,6-dimethoxy-1,3,5-triazin-2-yl)-4-methylmorpholinium chloride hydrate (271 mg, about 0.98 mmol) were dissolved in N,N-dimethylformamide (5 mL), and the resulting mixture was stirred at room temperature for 16 hours.

To the reaction solution, water was added, and the organic matter was extracted with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=100:0 to 0:100 (v/v)), whereby the target compound was obtained as a colorless oil (162 mg, yield: 53%).

MS (ESI) m/z: 622 (M+H)$^+$.

(49E) Methyl [3-({trans-4-[methyl(3-methyl-4-{[(3S)-3-methylpiperazin-1-yl]methyl}phenyl)carbamoyl]cyclohexyl}amino)benzyl]carbamate Tert-butyl (2S)-4-{4-[({trans-4-[(3-{[methoxycarbonyl)amino]methyl}phenyl)amino]cyclohexyl}carbonyl)(methyl)amino]-2-methylbenzyl}-2-methylpiperazine-1-carboxylate (162 mg, 0.26 mmol) obtained in (49D) was dissolved in dichloromethane (2 mL), and trifluoroacetic acid (2 mL) was added thereto at room temperature, and then, the resulting mixture was stirred under a nitrogen atmosphere at room temperature for 1 hour.

After toluene (10 mL) was added to the reaction solution, the solvent was distilled off under reduced pressure. To the obtained residue, a 2 N aqueous solution of sodium hydroxide was added, and the organic matter was extracted with dichloromethane. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by NH silica gel column chromatography (hexane:ethyl acetate:methanol=100:0:0 to 0:100:0 to 0:90:10 (v/v/v)), whereby the target compound was obtained as a colorless oil (72 mg, yield: 53%).

$^1$H NMR (CDCl$_3$, 400 MHz): δ0.80-0.90 (2H, m), 1.05 (3H, d, J=6.3 Hz), 1.70-1.78 (5H, m), 2.07-2.10 (3H, m), 2.19-2.23 (2H, m), 2.37 (3H, s), 2.75 (2H, t, J=9.2 Hz), 2.65-2.99 (3H, m), 3.19-3.23 (1H, m), 3.23 (3H, s), 3.45 (2H, s), 3.68 (3H, s), 4.24 (2H, d, J=5.5 Hz), 5.07 (1H, brs), 6.43-6.44 (2H, m), 6.54 (1H, d, J=7.4 Hz), 6.94-6.96 (2H, m), 7.09 (1H, t, J=8.0 Hz), 7.32 (1H, d, J=7.8 Hz).

MS (ESI) m/z: 522 (M+H)$^+$.

Example 50

Trans-N-methyl-N-(3-methyl-4-{[(3S)-3-methylpiperazin-1-yl]methyl}phenyl)-4-{3-[(2-oxo-1,3-oxazolidin-3-yl)methyl]phenoxy}cyclohexanecarboxamide

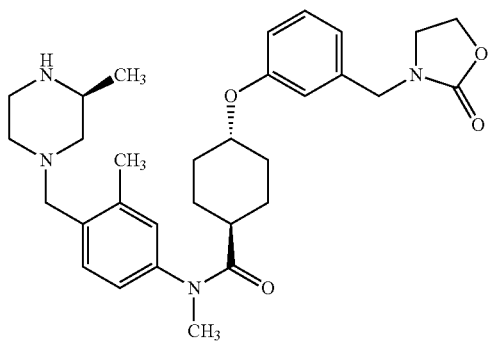 [SMILES: Cc1cc(N(C)C(=O)[C@H]2CC[C@H](Oc3cccc(CN4CCOC4=O)c3)CC2)ccc1CN1CCN[C@@H](C)C1]

(50A) Tert-butyl (2S)-4-{4-[({trans-4-[3-({[(2-chloroethoxy)carbonyl]amino}methyl)phenoxy]cyclohexyl}carbonyl)(methyl)amino]-2-methylbenzyl}-2-methylpiperazine-1-carboxylate Tert-butyl (2S)-4-{4-[({trans-4-[3-(aminomethyl)phenoxy]cyclohexyl}carbonyl)(methyl)amino]-2-methylbenzyl}-2-methylpiperazine-1-carboxylate (180 mg, 0.319 mmol) produced in (48D) was dissolved in dichloromethane (2 mL), and triethylamine (88 μL, 0.638 mmol) and 2-chloroethyl chloroformate (40 μL, 0.382 mmol) were added thereto at 0° C., and then, the resulting mixture was stirred at room temperature for 50 minutes.

To the reaction solution, a saturated aqueous solution of ammonium chloride was added, and extraction was performed with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=90:10 to 50:50 (v/v)), whereby the target compound was obtained as a colorless solid (206 mg, yield: 96%).

$^1$H NMR (CDCl$_3$, 400 MHz): δ1.07-1.19 (2H, m), 1.23 (3H, d, J=6.7 Hz), 1.47 (9H, s), 1.67-1.82 (4H, m), 1.99-2.14 (3H, m), 2.19-2.29 (2H, m), 2.39 (3H, s), 2.60 (1H, d, J=11.0 Hz), 2.73 (1H, d, J=11.0 Hz), 3.02-3.13 (1H, s), 3.24 (3H, s), 3.43 (2H, s), 3.65-3.71 (2H, m), 3.78-3.86 (1H, m), 4.12-4.26 (2H, m), 4.28-4.38 (4H, m), 5.04-5.12 (1H, brs), 6.72-6.77 (2H, m), 6.83 (1H, d, J=7.4 Hz), 6.92-6.98 (2H, m), 7.18-7.24 (1H, m), 7.32 (1H, d, J=7.8 Hz).

(50B) Tert-butyl (2S)-2-methyl-4-(2-methyl-4-{methyl[(trans-4-{3-[(2-oxo-1,3-oxazolidin-3-yl)methyl]phenoxy}cyclohexyl)carbonyl]amino}benzyl)piperazine-1-carboxylate Tert-butyl (2S)-4-{4-[({trans-4-[3-({[(2-chloroethoxy)carbonyl]amino}methyl)phenoxy]cyclohexyl}carbonyl)(methyl)amino]-2-methylbenzyl}-2-methylpiperazine-1-carboxylate (202 mg, 0.301 mmol) produced in (50A) was dissolved in tetrahydrofuran (5 mL), and sodium hydride (63%, 12 mg, 0.316 mmol) was added thereto, and then, the resulting mixture was heated to reflux under a nitrogen atmosphere for 3 hours.

After the temperature of the reaction solution was returned to room temperature, a saturated aqueous solution of ammonium chloride was added thereto, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate=70:30 to 30:70 (v/v)), whereby the target compound was obtained as a colorless solid (168 mg, yield: 88%).

$^1$H NMR (CDCl$_3$, 400 MHz): δ1.07-1.31 (2H, m), 1.23 (3H, d, J=6.7 Hz), 1.47 (9H, s), 1.61-1.83 (4H, m), 1.99-2.14 (3H, m), 2.19-2.29 (2H, m), 2.39 (3H, s), 2.60 (1H, d, J=11.0 Hz), 2.73 (1H, d, J=10.6 Hz), 3.02-3.12 (1H, m), 3.23 (3H, s), 3.38-3.45 (4H, m), 3.82 (1H, d, J=13.3 Hz), 4.13-4.25 (2H, m), 4.26-4.33 (2H, m), 4.36 (2H, s), 6.73-6.81 (2H, m), 6.83 (1H, d, J=7.8 Hz), 6.93-6.98 (2H, m), 7.23 (1H, t, J=7.8 Hz), 7.32 (1H, d, J=7.8 Hz).

(50C) Trans-N-methyl-N-(3-methyl-4-{[(3S)-3-methylpiperazin-1-yl]methyl}phenyl)-4-{3-[(2-oxo-1,3-oxazolidin-3-yl)methyl]phenoxy}cyclohexanecarboxamide Tert-butyl (2S)-2-methyl-4-(2-methyl-4-{methyl[(trans-4-{3-[(2-oxo-1,3-oxazolidin-3-yl)methyl]phenoxy}cyclohexyl)carbonyl]amino}benzyl)piperazine-1-carboxylate (162 mg, 0.255 mmol) produced in (50B) was dissolved in dichloromethane (1 mL), and trifluoroacetic acid (1 mL) was added thereto at room temperature, and then, the resulting mixture was stirred under a nitrogen atmosphere at room temperature for 15 minutes.

The residue obtained by distilling off the solvent in the reaction solution under reduced pressure was purified by NH silica gel column chromatography (ethyl acetate:methanol=100:0 to 90:10 (v/v)), whereby the target compound was obtained as a colorless solid (76.4 mg, yield: 56%).

$^1$H NMR (CDCl$_3$, 400 MHz): δ1.04 (3H, d, J=6.3 Hz), 1.09-1.22 (2H, m), 1.67-1.83 (5H, m), 2.03-2.14 (3H, m), 2.20-2.32 (1H, m), 2.38 (3H, s), 2.71-2.79 (2H, m), 2.83-3.01 (3H, m), 3.23 (3H, s), 3.38-3.44 (2H, m), 3.45 (2H, s), 4.11-4.21 (1H, m), 4.27-4.33 (2H, m), 4.36 (2H, s), 6.74 (1H, s), 6.78 (1H, dd, J=2.2, 8.4 Hz), 6.83 (1H, d, J=7.4 Hz), 6.93-6.97 (2H, m), 7.23 (1H, t, J=7.8 Hz), 7.33 (1H, d, J=8.2 Hz).

MS (ESI) m/z: 535 (M+H)$^+$.

Example 51

Trans-4-(3-{[(dimethylcarbamoyl)(methyl)amino]methyl}phenoxy)-N-methyl-N-(3-methyl-4-{[(3S)-3-methylpiperazin-1-yl]methyl}phenyl)cyclohexanecarboxamide

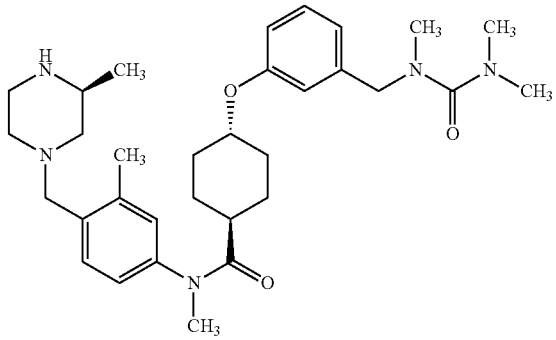 [SMILES: Cc1cc(N(C)C(=O)[C@H]2CC[C@H](Oc3cccc(CN(C)C(=O)N(C)C)c3)CC2)ccc1CN1CCN[C@@H](C)C1]

(51A) Tert-butyl (2S)-4-[{[trans-4-(3-{[(dimethylcarbamoyl)amino]methyl}phenoxy)cyclohexyl]carbonyl}(methyl)amino]-2-methylbenzyl}-2-methylpiperazine-1-carboxylate Triphosgene (110 mg, 0.372 mmol) was dissolved in dichloromethane (4 mL), and a solution of tert-butyl (2S)-4-{4-[({trans-4-[3-(aminomethyl)phenoxy]cyclohexyl}carbonyl)(methyl)amino]-2-methylbenzyl}-2-methylpiperazine-1-carboxylate (350 mg, 0.620 mmol) produced in (48D) and pyridine (75 μL, 0.930 mmol) in dichloromethane (4 mL) was added thereto at 0° C., and then, the resulting mixture was stirred under a nitrogen atmosphere at 0° C. for 30 minutes. The resulting solution was added dropwise at 0° C. to a solution of dichloromethane (2 mL) containing a solution of dimethylamine in tetrahydrofuran (2 M, 620 μL, 1.24 mmol) and triethylamine (258 μL, 1.86 mmol), and then, the resulting mixture was stirred under a nitrogen atmosphere at 0° C. for 45 minutes.

To the reaction solution, a saturated aqueous solution of ammonium chloride was added, and extraction was performed with ethyl acetate. The organic layer was washed with a saturated aqueous solution of sodium chloride and then dried over anhydrous magnesium sulfate and filtered. Then, the solvent was distilled off under reduced pressure, whereby a crude product was obtained. The obtained crude product was purified by silica gel column chromatography (hexane:ethyl acetate:methanol=40:60:0 to 0:100:0 to 0:80:20 (v/v/v)), whereby the target compound was obtained as a light yellow solid (283 mg, yield: 72%).

$^1$H NMR (CDCl$_3$, 400 MHz): δ1.07-1.20 (2H, m), 1.23 (3H, d, J=7.0 Hz), 1.47 (9H, s), 1.64-1.82 (4H, m), 1.98-2.15 (3H, m), 2.18-2.30 (2H, m), 2.39 (3H, s), 2.60 (1H, d, J=11.4 Hz), 2.73 (1H, d, J=10.2 Hz), 2.92 (6H, s), 3.03-3.14 (1H, m), 3.23 (3H, s), 3.43 (2H, s), 3.82 (1H, d, J=12.1 Hz), 4.12-4.27 (2H, m), 4.37 (2H, d, J=5.5 Hz), 4.56-4.63 (1H, m), 6.73 (1H, dd, J=1.8, 8.0 Hz), 6.78 (1H, s), 6.86 (1H, d, J=7.4 Hz), 6.92-6.98 (2H, m), 7.20 (1H, t, J=7.8 Hz), 7.32 (1H, d, J=7.8 Hz).

(51B) Tert-butyl (2S)-4-{4-[{[trans-4-(3-{[(dimethylcarbamoyl)(methyl)amino]methyl}phenoxy)cyclohexyl]carbonyl}(methyl)amino]-2-methylbenzyl}-2-methylpiperazine-1-carboxylate Tert-butyl (2S)-4-{4-[{[trans-4-(3-{[(dimethylcarbamoyl)amino]methyl}phenoxy)cyclohexyl]carbonyl}(methyl)amino]-2-methylbenzyl}-2-methylpiperazine-1-carboxylate (177 mg, 0.278 mmol) produced in (51A) was dissolved in tetrahydrofuran (3 mL), and sodium hydride (63%, 12 mg, 0.306 mmol) was added thereto, and then, the resulting mixture was stirred at room temperature for 15 minutes. Thereafter, methyl iodide (19 μL, 0.306 mmol) was added thereto, and the resulting mixture was stirred under a nitrogen atmosphere at room temperature for 45 minutes and then heated to reflux under a nitrogen atmosphere for 7 hours.

After the temperature of the reaction solution was returned to room temperature, a saturated aqueous solution of ammonium chloride was added thereto, and the organic matter was extracted with ethyl acetate. The organic layer was washed with water and a saturated aqueous solution of sodium chloride and then dried over anhydrous magnesium sulfate and filtered. Then, the solvent was distilled off under reduced pressure, whereby a crude product was obtained. This crude product was purified by silica gel column chromatography (hexane:ethyl acetate:methanol=50:50:0 to 0:100:0 to 0:85:15 (v/v/v)), whereby the target compound was obtained as a colorless solid (125 mg, yield: 69%).

$^1$H NMR (CDCl$_3$, 400 MHz): δ1.08-1.20 (2H, m), 1.23 (3H, d, J=6.7 Hz), 1.46 (9H, s), 1.67-1.82 (4H, m), 1.99-2.06 (1H, m), 2.07-2.15 (2H, m), 2.18-2.27 (2H, m), 2.39 (3H, s), 2.60 (1H, d, J=11.0 Hz), 2.69-2.76 (1H, m), 2.71 (3H, s), 2.83 (6H, s), 3.04-3.13 (1H, m), 3.23 (3H, s), 3.43 (2H, s), 3.82 (1H, d, J=12.5 Hz), 4.12-4.26 (2H, m), 4.30 (2H, s), 6.71-6.76 (2H, m), 6.81 (1H, d, =7.4 Hz), 6.92-6.98 (2H, m), 7.20 (1H, t, J=8.2 Hz), 7.31 (1H, d, J=7.4 Hz).

(51C) Trans-4-(3-{[(dimethylcarbamoyl)(methyl)amino]methyl}phenoxy)-N-methyl-N-(3-methyl-4-{[(3S)-3-methylpiperazin-1-yl]methyl}phenyl)cyclohexanecarboxamide Tert-butyl (2S)-4-{4-[{[trans-4-(3-{[(dimethylcarbamoyl)(methyl)amino]methyl}phenoxy)cyclohexyl]carbonyl}(methyl)amino]-2-methylbenzyl}-2-methylpiperazine-1-carboxylate (120 mg, 0.185 mmol) produced in (51B) was dissolved in dichloromethane (1 mL), and trifluoroacetic acid (1 mL) was added thereto at room temperature, and then, the resulting mixture was stirred under a nitrogen atmosphere at room temperature for 15 minutes.

The residue obtained by distilling off the solvent in the reaction solution under reduced pressure was purified by NH silica gel column chromatography (ethyl acetate:methanol=100:0 to 75:25 (v/v)), whereby the target compound was obtained as a colorless solid (57.1 mg, yield: 56%).

$^1$H NMR (CDCl$_3$, 400 MHz): δ1.04 (3H, d, J=6.3 Hz), 1.09-1.21 (2H, m), 1.69-1.81 (5H, m), 2.02-2.14 (3H, m), 2.20-2.30 (1H, m), 2.37 (3H, s), 2.68-2.79 (2H, m), 2.71 (3H, s), 2.80-3.03 (3H, m), 2.83 (6H, s), 3.23 (3H, s), 3.45 (2H, s), 4.10-4.21 (1H, m), 4.30 (2H, s), 6.70-6.75 (2H, m), 6.81 (1H, d, J=7.8 Hz), 6.92-6.97 (2H, m), 7.19 (1H, t, J=8.2 Hz), 7.33 (1H, d, J=7.8 Hz).

MS (ESI) m/z: 550 (M+H)$^+$.

Example 52

Trans-4-(3-{[(dimethylcarbamoyl)amino]methyl}phenoxy)-N-methyl-N-(3-methyl-4-{[(3S)-3-methylpiperazin-1-yl]methyl}phenyl)cyclohexanecarboxamide

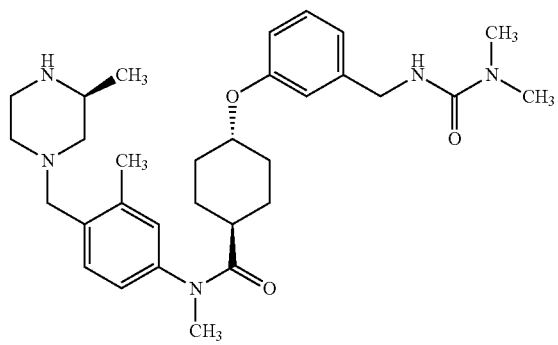 [SMILES: Cc1cc(N(C)C(=O)[C@H]2CC[C@H](Oc3cccc(CNC(=O)N(C)C)c3)CC2)ccc1CN1CCN[C@@H](C)C1]

The same reaction as in (51C) was performed using tert-butyl (2S)-4-{4-[{[trans-4-(3-{[(dimethylcarbamoyl)amino]methyl}phenoxy)cyclohexyl]carbonyl}(methyl)amino]-2-methylbenzyl}-2-methylpiperazine-1-carboxylate (100 mg, 0.157 mmol) produced in (51A), whereby the target compound was obtained as a colorless solid (75.8 mg, yield: 90%).

¹H NMR (CDCl₃, 400 MHz): δ1.04 (3H, d, J=6.3 Hz), 1.08-1.22 (2H, m), 1.63-1.82 (5H, m), 2.02-2.15 (3H, m), 2.20-2.31 (1H, m), 2.37 (3H, s), 2.70-2.80 (2H, m), 2.82-3.00 (3H, m), 2.92 (6H, s), 3.23 (3H, s), 3.45 (2H, s), 4.12-4.22 (1H, m), 4.37 (2H, d, J=5.5 Hz), 4.55-4.63 (1H, m), 6.70-6.80 (2H, m), 6.86 (1H, d, J=7.4 Hz), 6.92-6.97 (2H, m), 7.19 (1H, t, J=8.0 Hz), 7.33 (1H, d, J=7.8 Hz).

MS (ESI) m/z: 536 (M+H)⁺.

Example 53

Trans-4-{3-[(2-methoxyethoxy)methyl]phenoxy}-N-methyl-N-(3-methyl-4-{[(3S)-3-methylpiperazin-1-yl]methyl}phenyl)cyclohexanecarboxamide

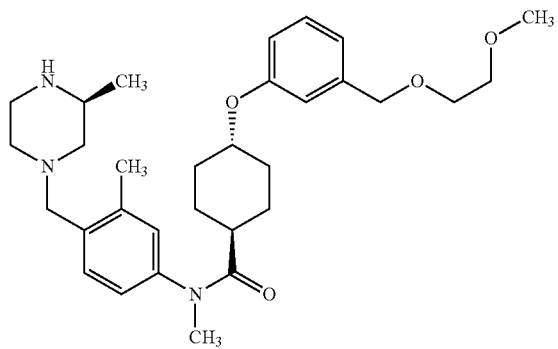 [SMILES: COCCOCc1cccc(O[C@H]2CC[C@H](C(=O)N(C)c3ccc(CN4CCN[C@@H](C)C4)c(C)c3)CC2)c1]

(53A) Trans-4-{3-[(2-methoxyethoxy)methyl]phenoxy}-N-methyl-N-(3-methyl-4-{[(3S)-3-methylpiperazin-1-yl]methyl}phenyl)cyclohexanecarboxamide ¹H NMR (CDCl₃, 400 MHz): δ1.04 (3H, d, J=6.3 Hz), 1.14-1.16 (1H, m), 1.68-1.76 (5H, m), 2.07-2.10 (4H, m), 2.24-2.27 (1H, m), 2.37 (3H, s), 2.75 (2H, t, J=9.5 Hz), 2.89-2.96 (3H, m), 3.23 (3H, s), 3.39 (3H, s), 3.45 (2H, s), 3.56-3.60 (4H, m), 4.17-4.19 (1H, m), 4.51 (2H, s), 6.73-6.75 (1H, m), 6.84 (1H, s), 6.87-6.88 (1H, m), 6.94-6.95 (2H, m), 7.20 (1H, t, J=7.8 Hz), 7.33 (1H, d, J=7.8 Hz).

MS (ESI) m/z: 524 (M+H)⁺.

(53B) Trans-4-{3-[(2-methoxyethoxy)methyl]phenoxy}-N-methyl-N-(3-methyl-4-{[(3S)-3-methylpiperazin-1-yl]methyl}phenyl)cyclohexanecarboxamide hydrochloride Trans-4-{3-[(2-methoxyethoxy)methyl]phenoxy}-N-methyl-N-(3-methyl-4-{[(3S)-3-methylpiperazin-1-yl]methyl}phenyl)cyclohexanecarboxamide (329 mg, 0.63 mmol) produced in (53A) was dissolved in dioxane (2 mL), and 2 N hydrochloric acid (315 μL, 0.63 mmol) was added thereto at room temperature, and then, the resulting mixture was frozen at −78° C. The frozen mixture was lyophilized using a lyophilizer, whereby the target compound was obtained as a white solid (352 mg, yield: 100%).

MS (ESI) m/z: 524 (M+H)⁺.

Example 54

Trans-4-{3-[(2-hydroxyethoxy)methyl]phenoxy}-N-methyl-N-(3-methyl-4-{[(3S)-3-methylpiperazin-1-yl]methyl}phenyl)cyclohexanecarboxamide ¹H NMR (CDCl₃, 400 MHz): δ1.03 (3H, d, J=6.3 Hz). 1.15 (2H, dd, J=11.9, 5.9 Hz), 1.70-1.75 (6H, m), 2.09-2.12 (2H, m), 2.24-2.26 (1H, m), 2.37 (3H, s), 2.75 (2H, t, J=11.0 Hz), 2.89-2.96 (3H, m), 3.23 (3H, s), 3.45 (2H, s), 3.58 (2H, dd, J=6.3, 2.9 Hz), 3.75 (2H, t, J=3.9 Hz), 4.17-4.19 (1H, m), 4.50 (2H, s), 6.76 (1H, d, J=8.3 Hz), 6.82 (1H, s), 6.87 (1H, d, J=7.3 Hz), 6.94-6.95 (2H, m), 7.22 (1H, t, J=7.6 Hz), 7.33 (1H, d, J=7.3 Hz).

Example 55

Trans-4-(3-{[(1R)-2-hydroxy-1-methylethoxy]methyl}phenoxy)-N-methyl-N-(3-methyl-4-{[(3S)-3-methylpiperazin-1-yl]methyl}phenyl)cyclohexanecarboxamide ¹H NMR (CDCl₃, 400 MHz): δ1.04 (3H, d, J=5.9 Hz), 1.15-1.16 (4H, m), 1.64-1.83 (6H, m), 2.09-2.12 (2H, m), 2.24-2.27 (1H, m), 2.36 (3H, d, J=7.3 Hz), 2.74-2.76 (2H, m), 2.89-2.96 (4H, m), 3.23 (3H, s), 3.44 (3H, s), 3.49 (1H, dd, J=11.7, 6.8 Hz), 3.60 (1H, dd, J=11.2, 3.4 Hz), 3.65-3.66 (1H, m), 4.17-4.19 (1H, m), 4.42 (1H, d, J=11.7 Hz), 4.59 (1H, d, J=11.7 Hz), 6.76 (1H, d, J=8.8 Hz), 6.83 (1H, s), 6.88 (1H, d, J=7.8 Hz), 6.94-6.95 (2H, m), 7.21 (1H, t, J=7.8 Hz), 7.33 (1H, d, J=7.8 Hz).

MS (ESI) m/z: 524 (M+H)⁺.

Example 56

Trans-4-[3-({[(2R)-2-hydroxypropyl]oxy}methyl)phenoxy]-N-methyl-N-(3-methyl-4-{[(3S)-3-methylpiperazin-1-yl]methyl}phenyl)cyclohexanecarboxamide

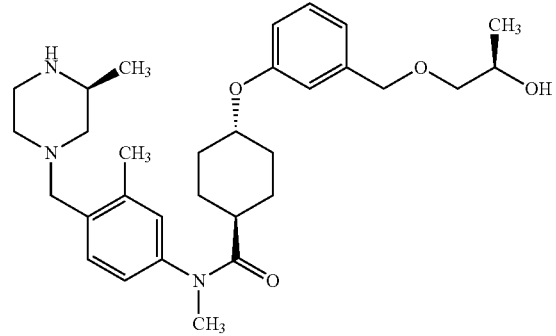 [SMILES: Cc1cc(N(C)C(=O)[C@H]2CC[C@H](Oc3cccc(COC[C@@H](C)O)c3)CC2)ccc1CN1CCN[C@@H](C)C1]

(56A) Trans-4-[3-({[(2R)-2-hydroxypropyl]oxy}methyl)phenoxy]-N-methyl-N-(3-methyl-4-{[(3S)-3-methylpiperazin-1-yl]methyl}phenyl)cyclohexanecarboxamide ¹H NMR (CDCl₃, 400 MHz) δ: 1.04 (3H, d, J=6.3 Hz), 1.13-1.15 (3H, m), 1.73 (6H, m), 2.08-2.11 (3H, m), 2.24-2.27 (1H, m), 2.37 (3H, s), 2.74-2.77 (2H, m), 2.89-2.95 (3H, m), 3.24-3.28 (4H, m), 3.44-3.46 (3H, m), 3.98 (1H, t, J=4.7 Hz), 4.18 (1H, t, J=13.9 Hz), 4.49 (2H, s), 6.77 (1H, d, J=8.2

Hz), 6.81 (1H, s), 6.87 (1H, d, J=7.8 Hz), 6.95 (2H, d, J=6.6 Hz), 7.22 (1H, t, J=7.8 Hz), 7.33 (1H, d, J=8.2 Hz).
MS (ESI) m/z: 524 (M+H)$^+$.

(56B) Trans-4-[3-({[(2R)-2-hydroxypropyl]oxy}methyl)phenoxy]-N-methyl-N-(3-methyl-4-{[(3S)-3-methylpiperazin-1-yl]methyl}phenyl)cyclohexanecarboxamide hydrochloride Trans-4-[3-({[(2R)-2-hydroxypropyl]oxy}methyl)phenoxy]-N-methyl-N-(3-methyl-4-{[(3S)-3-methylpiperazin-1-yl]methyl}phenyl)cyclohexanecarboxamide (236 mg, 0.45 mmol) produced in (56A) was dissolved in dioxane (2 mL), and 2 N hydrochloric acid (225 μL, 0.45 mmol) was added thereto at room temperature, and then, the resulting mixture was frozen at −78° C. The frozen mixture was lyophilized using a lyophilizer, whereby the target compound was obtained as a white solid (251 mg, yield: 100%).
MS (ESI) m/z: 524 (M+H)$^+$.

Example 57

Trans-4-{3-[(2-hydroxy-2-methylpropoxy)methyl]phenoxy}-N-methyl-N-(3-methyl-4-{[(3S)-3-methylpiperazin-1-yl]methyl}phenyl)cyclohexanecarboxamide

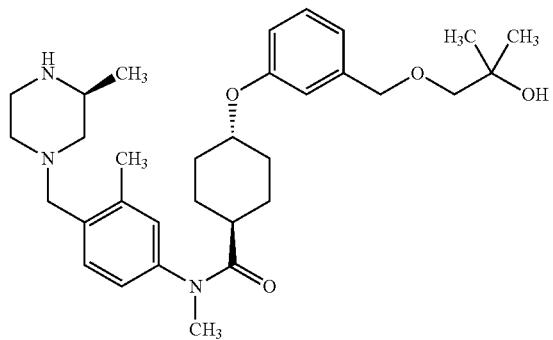 [SMILES: Cc1cc(N(C)C(=O)[C@H]2CC[C@H](Oc3cccc(COCC(C)(C)O)c3)CC2)ccc1CN1CCN[C@@H](C)C1]

(57A) Tert-butyl trans-4-{3-[(2-ethoxy-2-oxoethoxy)methyl]phenoxy}cyclohexanecarboxylate To a solution of [3-(benzyloxy)phenyl]methanol (2.27 g, 10.6 mmol) in dichloromethane (100 mL), triethylamine (2.2 mL, 15.9 mmol) and methanesulfonyl chloride (0.93 mL, 11.7 mmol) were added, and the resulting mixture was stirred at 0° C. for 1 hour.
To the reaction solution, 1 N hydrochloric acid was added, and extraction was performed with ethyl acetate. The obtained organic layer was washed with water and a saturated aqueous solution of sodium chloride and then dried over anhydrous sodium sulfate. Then, the solvent was distilled off under reduced pressure, whereby a crude product was obtained.
The obtained crude product was dissolved in N,N-dimethylformamide (70 mL), and sodium hydride (63%, 812 mg, 21.2 mmol) was added thereto at room temperature, and then, the resulting mixture was stirred at room temperature for minutes. Thereafter, ethyl glycolate (1.7 g, 15.9 mmol) was added to the reaction solution, and the resulting mixture was stirred at 50° C. for 2 hours.

To the reaction solution, a saturated aqueous solution of ammonium chloride was added, and extraction was performed with ethyl acetate. The obtained organic layer was washed with water and a saturated aqueous solution of sodium chloride and then dried over anhydrous sodium sulfate. Then, the solvent was distilled off under reduced pressure, and the obtained residue was roughly purified by silica gel column chromatography, whereby a crude product was obtained.
To a solution of the obtained crude product in methanol (30 mL), palladium on carbon (10%, 100 mg) was added, and the resulting mixture was stirred under a hydrogen atmosphere at room temperature for 1 hour.
The reaction solution was filtered through a Celite filter, and the obtained mother liquor was concentrated under reduced pressure, whereby a crude product was obtained.
To a solution (40 mL) of the obtained crude product in toluene, tert-butyl cis-4-hydroxycyclohexanecarboxylate (722 mg, 3.6 mmol) and cyanomethylenetributylphosphorane (1.0 g, 4.3 mmol) were added, and the resulting mixture was stirred at 100° C. for 90 minutes.
The solvent was distilled off under reduced pressure, and the obtained residue was purified by silica gel column chromatography (hexane:ethyl acetate=95:5 to 85:15 (v/v)), whereby the target compound was obtained as a colorless oil (856 mg, yield: 60%).
$^1$H NMR (CDCl$_3$, 400 MHz): δ1.29 (3H, t, J=7.2 Hz), 1.45-1.60 (13H, m), 2.03-2.06 (2H, m), 2.16-2.20 (2H, m), 2.21-2.27 (1H, m), 4.09 (2H, s), 4.18-4.27 (3H, m), 4.60 (2H, s), 6.83-6.84 (1H, m), 6.91-6.93 (2H, m), 7.24 (1H, d, J=8.2 Hz).

(57B) Trans-4-{3-[(2-ethoxy-2-oxoethoxy)methyl]phenoxy}cyclohexanecarboxylic acid To a solution of tert-butyl trans-4-{3-[(2-ethoxy-2-oxoethoxy)methyl]phenoxy}cyclohexanecarboxylate (856 mg, 2.18 mmol) produced in (57A) in dichloromethane (20 mL), trifluoroacetic acid (10 mL) was added at room temperature, and the resulting mixture was stirred at room temperature for 1 hour.
The solvent was distilled off under reduced pressure, and the obtained residue was purified by silica gel column chromatography (hexane:ethyl acetate=50:50 to 0:100 (v/v)), whereby the target compound was obtained as a colorless oil (601 mg, yield: 82%).
$^1$H NMR (CDCl$_3$, 400 MHz): δ1.29 (3H, t, J=7.0 Hz), 1.46-1.68 (4H, m), 2.11-2.22 (4H, m), 2.45 (1H, tt, J=10.9, 3.6 Hz), 4.10 (2H, s), 4.20-4.28 (4H, m), 4.61 (2H, s), 6.84 (1H, dd, J=8.2, 2.3 Hz), 6.93 (2H, m), 7.24-7.27 (1H, m).

(57C) Tert-butyl (2S)-4-(4-{[(trans-4-{3-[(2-ethoxy-2-oxoethoxy)methyl]phenoxy}cyclohexyl)carbonyl](methyl)amino}-2-methylbenzyl)-2-methylpiperazine-1-carboxylate To a solution of trans-4-{3-[(2-ethoxy-2-oxoethoxy)methyl]phenoxy}cyclohexanecarboxylic acid (601 mg, 1.79 mmol) produced in (57B) and tert-butyl (2S)-2-methyl-4-[2-methyl-4-(methylamino)benzyl]piperazine-1-carboxylate (595 mg, 1.79 mmol), which is a known compound, in N,N-dimethylformamide (20 mL), 4-(4,6-dimethoxy-1,3,5-triazin-2-yl)-4-methylmorpholinium chloride hydrate (1.1 g, about 3.6 mmol) was added at room temperature, and the resulting mixture was stirred at room temperature for 17 hours.

To the reaction solution, water was added, and extraction was performed with ethyl acetate. The obtained organic layer was washed with water and a saturated aqueous solution of sodium chloride and then dried over anhydrous sodium sulfate. Then, the solvent was distilled off under reduced pressure, and the obtained residue was purified by silica gel column chromatography (hexane:ethyl acetate=80:20 to 50:50 (v/v)), whereby the target compound was obtained as a colorless oil (529 mg, yield: 45%).

$^1$H NMR (CDCl$_3$, 400 MHz): δ1.15-1.17 (2H, m), 1.23 (3H, d, J=4.1 Hz), 1.27-1.29 (4H, m), 1.47 (9H, s), 1.71-1.74 (5H, m), 2.03-2.04 (1H, m), 2.10-2.12 (2H, m), 2.22-2.23 (2H, m), 2.39 (3H, s), 2.60 (1H, d, J=10.9 Hz), 2.74 (1H, d, J=11.3 Hz), 3.07-3.10 (1H, m), 3.23 (3H, s), 3.43 (2H, s), 3.96 (2H, s), 4.22-4.24 (3H, m), 4.58 (2H, s), 6.78 (1H, d, J=8.2 Hz), 6.86 (1H, s), 6.90-6.95 (3H, m), 7.22 (1H, t, J=7.8 Hz), 7.32 (1H, d, J=7.8 Hz).

(57D) Tert-butyl (2S)-4-(4-{[(trans-4-{3-[(2-hydroxy-2-methylpropoxy)methyl]phenoxy}cyclohexyl)carbonyl](methyl)amino}-2-methylbenzyl)-2-methylpiperazine-1-carboxylate To a solution of tert-butyl (2S)-4-(4-{[(trans-4-{3-[(2-ethoxy-2-oxoethoxy)methyl]phenoxy}cyclohexyl)carbonyl](methyl)amino}-2-methylbenzyl)-2-methylpiperazine-1-carboxylate (1.19 g, 1.83 mmol) produced in (57C) in tetrahydrofuran (20 mL), a solution of methyl magnesium bromide in tetrahydrofuran (1.0 M, 7.3 mL, 7.3 mmol) was added at 0° C., and the resulting mixture was stirred at 0° C. for 2 hours.

To the reaction solution, a saturated aqueous solution of ammonium chloride was added, and extraction was performed with ethyl acetate. The obtained organic layer was washed with water and a saturated aqueous solution of sodium chloride and then dried over anhydrous sodium sulfate. Then, the solvent was distilled off under reduced pressure, and the obtained residue was roughly purified by silica gel column chromatography, whereby a crude product was obtained.

To a solution of the obtained crude product in dichloromethane (1 mL), trifluoroacetic acid (10 mL) was added at room temperature, and the resulting mixture was stirred at room temperature for 30 minutes.

The solvent was distilled off under reduced pressure, and the obtained residue was purified by NH silica gel column chromatography (ethyl acetate:methanol=100:0 to 90:10 (v/v)), whereby the target compound was obtained as a colorless oil (329 mg, yield: 89%).

$^1$H NMR (CDCl$_3$, 400 MHz): δ1.04 (3H, d, J=6.3 Hz), 1.09-1.23 (2H, m), 1.21 (6H, s), 1.63-1.84 (5H, m), 2.01-2.17 (3H, m), 2.23-2.26 (1H, m), 2.37 (3H, s), 2.70-2.79 (2H, m), 2.81-3.00 (3H, m), 3.23 (3H, s), 3.29 (2H, s), 3.45 (2H, s), 4.19 (1H, m), 4.51 (2H, s), 6.76 (1H, m), 6.81 (1H, s), 6.87 (1H, d, J=7.8 Hz), 6.91-6.97 (2H, m), 7.22 (1H, t, J=7.8 Hz), 7.33 (1H, d, J=8.2 Hz).

MS (ESI) m/z: 538 (M+H)$^+$.

(57E) Trans-4-{3-[(2-hydroxy-2-methylpropoxy)methyl]phenoxy}-N-methyl-N-(3-methyl-4-{[(3S)-3-methylpiperazin-1-yl]methyl}phenyl)cyclohexanecarboxamide hydrochloride Trans-4-{3-[(2-hydroxy-2-methylpropoxy)methyl]phenoxy}-N-methyl-N-(3-methyl-4-{[(3S)-3-methylpiperazin-1-yl]methyl}phenyl)cyclohexanecarboxamide (329 mg, 0.61 mmol) produced in (57D) was dissolved in dioxane (2 mL), and 2 N hydrochloric acid (306 µL, 0.61 mmol) was added thereto at room temperature, and then, the resulting mixture was frozen at −78° C. The frozen mixture was lyophilized using a lyophilizer, whereby the target compound was obtained as a white solid (350 mg, yield: 100%).

MS (ESI) m/z: 538 (M+H)$^+$.

Example 58

Trans-4-({3-[(2-hydroxy-2-methylpropoxy)methyl]phenyl}amino)-N-methyl-N-(3-methyl-4-{[(3S)-3-methylpiperazin-1-yl]methyl}phenyl)cyclohexanecarboxamide

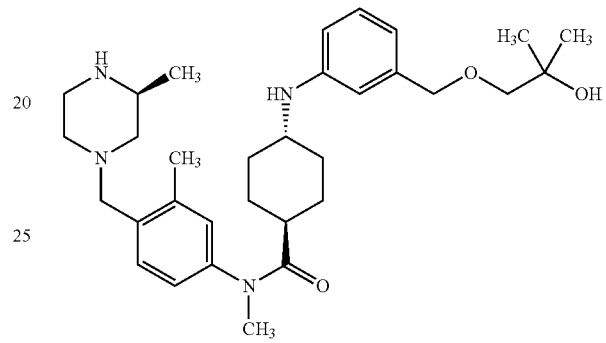

(58A) Ethyl [(3-aminobenzyl)oxy]acetate

To a solution of 3-nitrobenzyl alcohol (3.0 g, 19.6 mmol) in dichloromethane (100 mL), triethylamine (3.4 mL, 23.5 mmol) and methanesulfonyl chloride (1.9 mL, 23.5 mmol) were added, and the resulting mixture was stirred at 0° C. for 1 hour.

To the reaction solution, 1 N hydrochloric acid was added, and extraction was performed with ethyl acetate. The obtained organic layer was washed with water and a saturated aqueous solution of sodium chloride and then dried over anhydrous sodium sulfate. Then, the solvent was distilled off under reduced pressure, whereby a crude product was obtained.

To a solution of the obtained crude product in N,N-dimethylformamide (100 mL), sodium hydride (1.5 g, 21.2 mmol) was added at room temperature, and the resulting mixture was stirred at room temperature for 10 minutes. Thereafter, ethyl glycolate (3.1 g, 29.4 mmol) was added thereto at room temperature, and the resulting mixture was stirred for 3 hours.

To the reaction solution, a saturated aqueous solution of ammonium chloride was added, and extraction was performed with ethyl acetate. The obtained organic layer was washed with water and a saturated aqueous solution of sodium chloride and then dried over anhydrous sodium sulfate. Then, the solvent was distilled off under reduced pressure, whereby a crude product was obtained.

To a solution of the obtained crude product in methanol (100 mL) and water (10 mL), iron powder (3.3 g, 58.8 mmol) and ammonium chloride (5.2 g, 98.0 mmol) were added at room temperature, and the resulting mixture was stirred at 80° C. for 5 hours.

The reaction solution was filtered through a Celite filter, and the solvent in the obtained mother liquor was distilled off under reduced pressure, and the obtained residue was purified by silica gel column chromatography (hexane:ethyl acetate=80:20 to 50:50 (v/v)), whereby the target compound was obtained as a colorless oil (1.8 g, yield: 44%).

$^1$H NMR (CDCl$_3$, 400 MHz): δ1.31 (4H, dd, J=7.8, 6.6 Hz), 4.18 (2H, s), 4.23-4.28 (3H, m), 4.73 (2H, s), 7.55 (1H, t, J=7.8 Hz), 7.74 (1H, d, J=7.8 Hz), 8.17 (1H, dt, J=8.2, 1.2 Hz), 8.26 (1H, s).

(58B) Tert-butyl (2S)-4-{4-[{[trans-4-({3-[(2-ethoxy-2-oxoethoxy)methyl]phenyl}amino)cyclohexyl]carbonyl}(methyl)amino]-2-methylbenzyl}-2-methylpiperazine-1-carboxylate To a solution of ethyl [(3-aminobenzyl)oxy]acetate (2.61 g, 12.6 mmol) produced in (58A) in tetrahydrofuran (80 mL), tert-butyl 4-oxocyclohexanecarboxylate (3.2 g, 13.9 mmol), sodium triacetoxy borohydride (4.0 g, 18.9 mmol), and acetic acid (2.0 g, 33.3 mmol) were added at room temperature, and the resulting mixture was stirred at room temperature for 2 hours.

To the reaction solution, water was added, and extraction was performed twice with ethyl acetate. The obtained organic layer was washed with water and a saturated aqueous solution of sodium chloride and then dried over anhydrous sodium sulfate. Then, the solvent was distilled off under reduced pressure, and the obtained residue was roughly purified by silica gel column chromatography, whereby a crude product was obtained.

To a solution of the obtained crude product in methanol (20 mL), palladium on carbon (10%, 92 mg) was added at room temperature, and the resulting mixture was stirred under a hydrogen atmosphere at room temperature for 1 hour.

The reaction solution was filtered through a Celite filter, and the solvent in the obtained mother liquor was distilled off under reduced pressure, and the obtained residue was roughly purified by silica gel column chromatography, whereby a crude product was obtained.

To a solution of the obtained crude product and tert-butyl (2S)-2-methyl-4-[2-methyl-4-(methylamino)benzyl]piperazine-1-carboxylate (634 mg, 1.90 mmol), which is a known compound, in N,N-dimethylformamide (20 mL), 4-(4,6-dimethoxy-1,3,5-triazin-2-yl)-4-methylmorpholinium chloride hydrate (1.1 g, 3.80 mmol) was added at room temperature, and the resulting mixture was stirred at room temperature for 15 hours.

To the reaction solution, water was added, and extraction was performed with ethyl acetate. The obtained organic layer was washed with water and a saturated aqueous solution of sodium chloride and then dried over anhydrous sodium sulfate. Then, the solvent was distilled off under reduced pressure, and the obtained residue was purified by silica gel column chromatography (hexane:ethyl acetate=80:20 to 50:50 (v/v)), whereby the target compound was obtained as a colorless oil (523 mg, yield: 42%).

$^1$H NMR (CDCl$_3$, 400 MHz): δ0.84-0.86 (2H, m), 1.24-1.28 (7H, m), 1.46 (9H, s), 1.72-1.74 (3H, m), 2.02-2.07 (3H, m), 2.20-2.23 (2H, m), 2.38 (3H, s), 2.60 (1H, d, J=11.3 Hz), 2.73 (1H, d, J=11.3 Hz), 3.06-3.09 (1H, m), 3.22-3.25 (4H, m), 3.43 (2H, s), 3.80-3.83 (1H, m), 4.05 (2H, s), 4.21-4.23 (3H, m), 4.53 (2H, s), 6.48 (1H, d, J=7.8 Hz), 6.54 (1H, s), 6.63 (1H, d, J=7.4 Hz), 6.94-6.96 (2H, m), 7.11 (1H, t, J=7.8 Hz), 7.31 (1H, d, J=7.8 Hz).

(58C) Trans-4-({3-[(2-hydroxy-2-methylpropoxy)methyl]phenyl}amino)-N-methyl-N-(3-methyl-4-{[(3S)-3-methylpiperazin-1-yl]methyl}phenyl)cyclohexanecarboxamide To a solution of tert-butyl (2S)-4-{4-[{[trans-4-({3-[(2-ethoxy-2-oxoethoxy)methyl]phenyl} amino)cyclohexyl]carbonyl}(methyl)amino]-2-methylbenzyl}-2-methylpiperazine-1-carboxylate (523 mg, 0.81 mmol) produced in (58B) in tetrahydrofuran (10 mL), a solution of methyl magnesium bromide in tetrahydrofuran (0.98 M, 2.5 mL, 2.42 mmol) was added at 0° C., and the resulting mixture was stirred at room temperature for 2 hours.

To the reaction solution, a saturated aqueous solution of ammonium chloride was added, and extraction was performed with ethyl acetate. The obtained organic layer was washed with water and a saturated aqueous solution of sodium chloride and then dried over anhydrous sodium sulfate. Then, the solvent was distilled off under reduced pressure, and the obtained residue was roughly purified by silica gel column chromatography, whereby a crude product was obtained.

To a solution of the obtained crude product in dichloromethane (1 mL), trifluoroacetic acid (10 mL) was added at room temperature, and the resulting mixture was stirred at room temperature for 30 minutes.

The solvent was distilled off under reduced pressure, and the obtained residue was purified by NH silica gel column chromatography (ethyl acetate:methanol=100:0 to 90:10 (v/v)), whereby the target compound was obtained as a colorless oil (259 mg, yield: 100%).

$^1$H NMR (CDCl$_3$, 400 MHz): δ0.83-0.90 (2H, m), 1.03 (3H, d, J=6.3 Hz), 1.22 (6H, s), 1.66-1.80 (5H, m), 2.04-2.13 (3H, m), 2.17-2.30 (1H, m), 2.37 (3H, s), 2.71-2.78 (2H, m), 2.81-3.00 (3H, m), 3.22-3.24 (4H, m), 3.28 (2H, s), 3.44 (2H, s), 4.47 (2H, s), 6.43-6.53 (2H, m), 6.61 (1H, d, J=7.4 Hz), 6.91-6.98 (2H, m), 7.11 (1H, t, J=7.8 Hz), 7.32 (1H, d, J=8.2 Hz).

MS (ESI) m/z: 537 (M+H)$^+$.

(58D) Trans-4-({3-[(2-hydroxy-2-methylpropoxy)methyl]phenyl}amino)-N-methyl-N-(3-methyl-4-{[(3S)-3-methylpiperazin-1-yl]methyl}phenyl)cyclohexanecarboxamide hydrochloride Trans-4-({3-[(2-hydroxy-2-methylpropoxy)methyl]phenyl}amino)-N-methyl-N-(3-methyl-4-{[(3S)-3-methylpiperazin-1-yl]methyl}phenyl)cyclohexanecarboxamide (259 mg, 0.48 mmol) produced in (58C) was dissolved in dioxane (2 mL), and 2 N hydrochloric acid (241 μL, 0.48 mmol) was added thereto at room temperature, and then, the resulting mixture was frozen at −78° C. The frozen mixture was lyophilized using a lyophilizer, whereby the target compound was obtained as a white solid (275 mg, yield: 100%).

MS (ESI) m/z: 537 (M+H)$^+$.

Example 59

Trans-4-(3-{[2-(isopropylamino)-2-oxoethoxy]methyl}phenoxy)-N-methyl-N-(3-methyl-4-{[(3S)-3-methylpiperazin-1-yl]methyl}phenyl)cyclohexanecarboxamide $^1$H NMR (CDCl$_3$, 400 MHz) δ: 1.04 (3H, d, J=6.3 Hz), 1.15-1.17 (8H, m), 1.65-1.77 (5H, m), 2.06-2.10 (3H, m), 2.25-2.28 (1H, m), 2.37 (3H, s), 2.75 (2H, t, J=9.0 Hz), 2.87-2.99 (3H, m), 3.23 (3H, s), 3.45 (2H, s), 3.92 (2H, s), 4.09-4.12 (1H, m), 4.17-4.20 (1H, m), 4.49 (2H, s), 6.36 (1H, brs), 6.79-6.80 (2H, m), 6.86 (1H, d, J=7.4 Hz), 6.94-6.95 (2H, m), 7.22-7.26 (1H, m), 7.33 (1H, d, J=7.8 Hz).

MS (ESI) m/z: 565 (M+H)$^+$.

Example 60

Trans-4-[3-fluoro-5-(hydroxymethyl)phenoxy]-N-methyl-N-(3-methyl-4-{[(3S)-3-methylpiperazin-1-yl]methyl}phenyl)cyclohexanecarboxamide $^1$H NMR (CDCl$_3$, 400 MHz): δ1.04 (3H, d, J=6.3 Hz), 1.08-1.22 (2H, m), 1.49-1.83 (5H, m), 2.02-2.14 (3H, m), 2.26 (1H, m), 2.37 (3H, s), 2.70-2.79 (2H, m), 2.83-3.01 (3H, m), 3.23 (3H, s), 3.45 (2H, s), 4.15 (1H, m), 4.62 (2H, s), 6.46 (1H, m), 6.60-6.67 (2H, m), 6.91-6.98 (2H, m), 7.33 (1H, d, J=8.2 Hz).

Example 61

Trans-4-{[4-chloro-3-(hydroxymethyl)phenyl]amino}-N-methyl(3-methyl-4-{[(3S)-3-methylpiperazin-1-yl]methyl}phenyl)cyclohexanecarboxamide $^1$H NMR (CDCl$_3$, 400 MHz): δ0.83-0.86 (2H, m), 1.05 (3H, d, J=6.3 Hz), 1.73-1.76 (5H, m), 2.05-2.08 (3H, m), 2.21-2.23 (1H, m), 2.34 (3H, s), 2.75 (2H, t, J=9.6 Hz), 2.88-3.00 (3H, m), 3.22-3.24 (4H, m), 3.45 (2H, s), 4.66 (2H, s), 6.39 (1H, dd, J=8.6, 3.1 Hz), 6.63 (1H, d, J=2.7 Hz), 6.93-6.95 (2H, m), 7.08 (1H, d, J=8.6 Hz), 7.32 (1H, d, J=7.8 Hz).
MS (ESI) m/z: 499 (M+H)+.

Example 62

Tert-butyl [3-({trans-4-[methyl(3-methyl-4-{[(3S)-3-methylpiperazin-1-yl]methyl}phenyl)carbamoyl]cyclohexyl}oxy)phenyl]acetate $^1$H NMR (CDCl$_3$, 400 MHz): δ1.04 (3H, d, J=6.3 Hz), 1.08-1.22 (2H, m), 1.43 (9H, s), 1.63-1.85 (5H, m), 2.02-2.16 (3H, m), 2.26 (1H, m), 2.37 (3H, s), 2.71-2.80 (2H, m), 2.82-3.03 (3H, m), 3.23 (3H, s), 3.45 (2H, s), 3.46 (2H, s), 4.17 (1H, m), 6.69-6.78 (2H, m), 6.81 (1H, d, J=7.8 Hz), 6.92-6.98 (2H, m), 7.17 (1H, t, J=7.8 Hz), 7.33 (1H, d, J=8.2 Hz).

Test Example 1

Bioactivity Test (Measurement of Intestinal Contractile Activity)

(1) Animal Used

A male NZW rabbit (body weight: 2.5 to 3.0 kg, KITAYAMA LABES CO., LTD., NAGANO) was used.

(2) Reagent

Carbachol (carbamylcholine chloride, Sigma-Aldrich Japan K.K.) was purchased and used. Each test compound was dissolved in dimethyl sulfoxide (DMSO, Sigma-Aldrich Japan K.K.), and then suspended in physiological saline. Carbachol was dissolved in physiological saline.

(3) Experimental Method and Results

Pentobarbital sodium (Kyoritsu Seiyaku Corporation, Osaka) was administered to the rabbit through the auricular vein, and the rabbit was euthanized by exsanguination under anesthesia. Thereafter, the duodenum was excised from the rabbit and rapidly rinsed with Krebs solution (NaCl 120.0 mM, KCl 4.7 mM, CaCl$_2$ 2.4 mM, KH$_2$PO$_4$ 1.0 mM, MgSO$_4$ 1.2 mM, NaHCO$_3$ 24.5 mM, and glucose 5.6 mM, pH 7.4). Then, a longitudinal muscle strip (length: 10 mm, width: 3 mm) was prepared from the duodenal smooth muscle layer obtained by stripping off the mucosal layer from the duodenum. The prepared strip was mounted in an organ bath and contained in 20 mL of Krebs solution gassed with 95% O$_2$ and 5% CO$_2$ at 31° C. so as to suppress excessive locomotion, and a tension of 1 g was applied thereto. The strip was left to stand for 1 hour or more while replacing the Krebs solution every 15 minutes until the strip was equilibrated. Before starting the experiment, stimulation with carbachol at 10 μM was repeatedly applied until a reproducible contraction was obtained. The contractile activity was measured with an FD pickup (TB-611T, Nihon Kohden Corporation, Tokyo) and recorded on a pen recorder (RECTI HORIZ-8K, Sanei, Tokyo). Each test compound was added to the Krebs solution at 0.01 nM to 10 μM, and the strip was contracted by cumulative dosing. The contractile activity at each concentration was determined when the contractile activity at the time of stimulation with carbachol at 10 μM was taken as 100%, and the EC50 value of each test compound was determined. The EC50 values are shown below.

TABLE 1

| Example No. | EC50 value (nM) |
| --- | --- |
| 1 | 28.0 |
| 4 (hydrochloride) | 2.5 |
| 5 (hydrochloride) | 7.3 |
| 16 (hydrochloride) | 2.4 |
| 22 (hydrochloride) | 4.8 |
| 30 (hydrochloride) | 3.0 |
| 33 | 1.5 |
| 34 | 2.1 |
| 42 (hydrochloride) | 4.8 |
| 53 (hydrochloride) | 6.8 |
| 56 (hydrochloride) | 1.2 |
| 57 (hydrochloride) | 11.3 |
| 58 (hydrochloride) | 0.9 |

Formulation Example 1

Powder

A powder can be obtained by mixing the compound of the invention (5 g), lactose (895 g), and cornstarch (100 g) using a blender.

Formulation Example 2

Granule

After the compound of the invention (5 g), lactose (865 g), and low-substituted hydroxypropyl cellulose (100 g) are mixed, an aqueous solution of 10% hydroxypropyl cellulose (300 g) is added thereto and the resulting mixture is kneaded. The resulting kneaded material is granulated using an extrusion granulator, followed by drying, whereby a granule is obtained.

Formulation Example 3

Tablet

After the compound of the invention (5 g), lactose (90 g), cornstarch (34 g), crystalline cellulose (20 g), and magnesium stearate (1 g) are mixed using a blender, the resulting mixture is tableted by a tableting machine, whereby a tablet is obtained.

The invention claimed is:
1. A compound represented by formula (I) or a pharmacologically acceptable salt thereof:

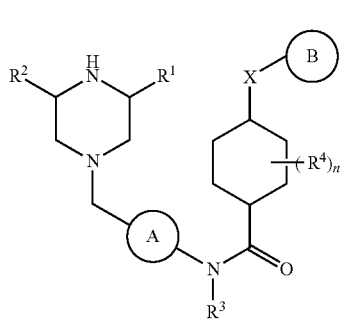

wherein A represents a phenylene group (the phenylene group may be optionally substituted with 1 to 3 groups selected from a C1-C3 alkyl group, a C1-C3 alkoxy group, and a halogen atom); B represents a phenyl group optionally substituted with 1 to 5 groups selected from substituent group α, or a pyridyl group optionally substituted with 1 to 5 groups selected from substituent group α; $R^1$ represents a hydrogen atom or a C1-C3 alkyl group; $R^2$ represents a hydrogen atom or a C1-C3 alkyl group; $R^3$ represents a C1-C6 alkyl group, a C3-C10 cycloalkyl group, a C1-C3 alkoxy C1-C3 alkyl group, or a C1-C3 hydroxyalkyl group; $R^4$ represents a hydrogen atom, a C1-C6 alkyl group, or a halogen atom; n represents an integer of 1 to 4; X represents methylene, —O—, —NH—, —N(C1-C3 alkyl)-, —C(=O)—, —S—, —S(O)—, —S(O₂)— or a single bond;
and substituent group α consists of a halogen atom, a C1-C6 alkyl group {the alkyl group may be optionally substituted with 1 to 3 groups selected from a C1-C6 aliphatic acyl group, a carboxyl group, a C1-C6 alkoxycarbonyl group, an aminocarbonyl group (the aminocarbonyl group may be optionally substituted with 1 or 2 groups selected from a C1-C6 alkyl group, a C1-C6 haloalkyl group, and a C1-C6 alkoxy C1-C6 alkyl group), a carbamido group optionally substituted with one or three C1-C6 alkyl groups, a C1-C6 aliphatic acylamino group which may be optionally substituted with a C1-C6 alkoxy group, a C1-C6 aliphatic acyl C1-C6 alkylamino group, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C3-C10 cycloalkyl group (the cycloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group may be optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group may be optionally substituted with 1 to 3 groups selected from a hydroxy group, a C1-C6 alkoxy group, a C1-C6 hydroxyalkyl group, an aminocarbonyl group which may be optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a $C_6$-$C_{10}$ aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a cyano group, a nitro group, a C1-C6 alkylsulfonyl group, a C1-C6 dialkylaminosulfonyl group, and a C6-C10 aryl group.

2. The compound or pharmacologically acceptable salt thereof according to claim 1, wherein A is a phenylene group which may be optionally substituted with one to three C1-C3 alkyl groups.

3. The compound or pharmacologically acceptable salt thereof according to claim 1, wherein B is a phenyl group which may be optionally substituted with 1 to 5 groups selected from substituent group α.

4. The compound or pharmacologically acceptable salt thereof according to claim 1, wherein B is a pyridyl group which may be optionally substituted with 1 to 5 groups selected from substituent group α.

5. The compound or pharmacologically acceptable salt thereof according to claim 1, wherein $R^1$ is a C1-C3 alkyl group.

6. The compound or pharmacologically acceptable salt thereof according to claim 1, wherein $R^2$ is a hydrogen atom.

7. The compound or pharmacologically acceptable salt thereof according to claim 1, wherein $R^3$ is a C1-C3 alkyl group.

8. The compound or pharmacologically acceptable salt thereof according to claim 1, wherein $R^4$ is a hydrogen atom.

9. The compound or pharmacologically acceptable salt thereof according to claim 1, wherein X is —O— or —NH—.

10. A compound represented by formula (IA) or a pharmacologically acceptable salt thereof:

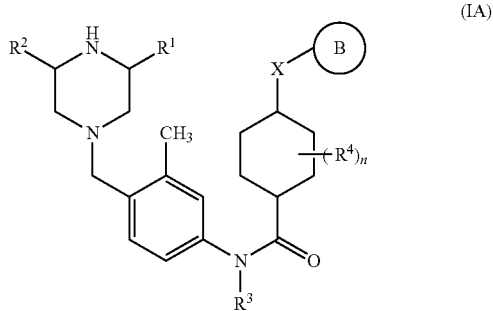

wherein B represents a phenyl group which may be optionally substituted with 1 to 5 groups selected from substituent group α, or a pyridyl group which may be optionally substituted with 1 to 5 groups selected from substituent group α; R¹ represents a hydrogen atom or a C1-C3 alkyl group; R² represents a hydrogen atom or a C1-C3 alkyl group; R³ represents a C1-C6 alkyl group, a C3-C10 cycloalkyl group, a C1-C3 alkoxy C1-C3 alkyl group, or a C1-C3 hydroxyalkyl group; R⁴ represents a hydrogen atom, a C1-C6 alkyl group, or a halogen atom; n represents an integer of 1 to 4; X represents methylene, —O—, —NH—, —N(C1-C3 alkyl)-, —C(=O)—, —S—, —S(O)—, —S(O₂)— or a single bond;

and substituent group α consists of a halogen atom, a C1-C6 alkyl group {the alkyl group being optionally substituted with 1 to 3 groups selected from a C1-C6 aliphatic acyl group, a carboxyl group, a C1-C6 alkoxycarbonyl group, an aminocarbonyl group (the aminocarbonyl group being optionally substituted with 1 or 2 groups selected from a C1-C6 alkyl group, a C1-C6 haloalkyl group, and a C1-C6 alkoxy C1-C6 alkyl group), a carbamido group optionally substituted with one or three C1-C6 alkyl groups, a C1-C6 aliphatic acylamino group optionally substituted with a C1-C6 alkoxy group, a C1-C6 aliphatic acyl C1-C6 alkylamino group, an C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C3-C10 cycloalkyl group (the cycloalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group being optionally substituted with 1 to 3 groups selected from a hydroxy group, a C1-C6 alkoxy group, a C1-C6 hydroxyalkyl group, an aminocarbonyl group optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a C6-C10 aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a cyano group, a nitro group, a C1-C6 alkylsulfonyl group, a C1-C6 dialkylaminosulfonyl group, and a C6-C10 aryl group.

11. A compound represented by formula (IB) or a pharmacologically acceptable salt thereof:

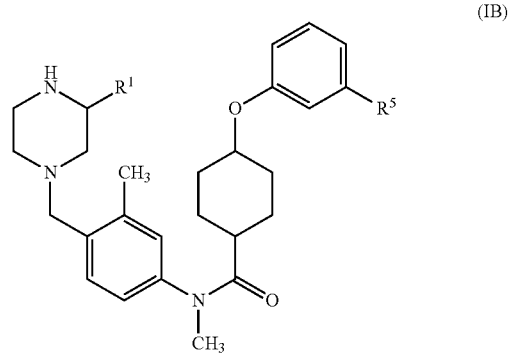

(IB)

wherein R¹ represents a hydrogen atom or a C1-C3 alkyl group; R⁵ represents a group selected from substituent group α;

and substituent group α consists of a halogen atom, a C1-C6 alkyl group {the alkyl group being optionally substituted with 1 to 3 groups selected from a C1-C6 aliphatic acyl group, a carboxyl group, a C1-C6 alkoxycarbonyl group, an aminocarbonyl group (the aminocarbonyl group being optionally substituted with 1 or 2 groups selected from a C1-C6 alkyl group, a C1-C6 haloalkyl group, and a C1-C6 alkoxy C1-C6 alkyl group), a carbamido group optionally substituted with one or three C1-C6 alkyl groups, a C1-C6 aliphatic acylamino group optionally substituted with a C1-C6 alkoxy group, a C1-C6 aliphatic acyl C1-C6 alkylamino group, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C3-C10 cycloalkyl group (the cycloalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group being optionally substituted with 1 to 3 groups selected from a hydroxy group, a C1-C6 alkoxy group, a C1-C6 hydroxyalkyl group, an aminocarbonyl group optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a C6-C10 aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a cyano group, a nitro group, a C1-C6 alkylsulfonyl group, a C1-C6 dialkylaminosulfonyl group, and a C6-C10 aryl group.

12. The compound or pharmacologically acceptable salt thereof according to claim 10, wherein $R^1$ is a methyl group.

13. The compound or pharmacologically acceptable salt thereof according to claim 11, wherein $R^5$ is a C1-C6 alkyl group {the alkyl group being optionally substituted with 1 to 3 groups selected from a C1-C6 aliphatic acyl group, a carboxyl group, a C1-C6 alkoxycarbonyl group, an aminocarbonyl group (the aminocarbonyl group being optionally substituted with 1 or 2 groups selected from a C1-C6 alkyl group, a C1-C6 haloalkyl group, and a C1-C6 alkoxy C1-C6 alkyl group), a carbamido group optionally substituted with one or three C1-C6 alkyl groups, a C1-C6 aliphatic acylamino group optionally substituted with a C1-C6 alkoxy group, a C1-C6 aliphatic acyl C1-C6 alkylamino group, a C1-C6 alkylsulfonyl group, a 4- to 10-membered heterocyclic group containing 1 to 4 heteroatoms which may be the same or different and are selected from nitrogen, oxygen, and sulfur, and a 4- to 10-membered heterocyclic carbonyl group containing 1 to 4 heteroatoms which may be the same or different and are selected from nitrogen, oxygen, and sulfur}, a C1-C6 hydroxyalkyl group (the hydroxyalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), or a C1-C6 alkoxy C1-C6 alkyl group (the alkoxyalkyl group being optionally substituted with 1 to 3 groups selected from a hydroxy group, a C1-C6 alkoxy group, a C1-C6 hydroxyalkyl group, an aminocarbonyl group optionally substituted with C1-C6 alkyl, a carboxyl group, a C1-C6 alkoxycarbonyl group, and a 4- to 10-membered heterocyclic group containing 1 to 4 heteroatoms which may be the same or different and are selected from nitrogen, oxygen, and sulfur).

14. A compound represented by formula (I) or a pharmacologically acceptable salt thereof:

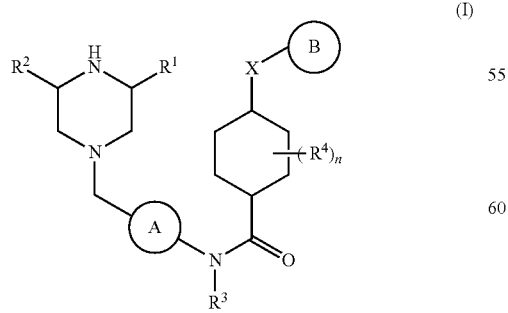

wherein A represents a phenylene group (the phenylene group being optionally substituted with 1 to 3 groups selected from a C1-C3 alkyl group, a C1-C3 alkoxy group, and a halogen atom); B represents a phenyl group which may be optionally substituted with 1 to 5 groups selected from substituent group α, or a pyridyl group which may be optionally substituted with 1 to 5 groups selected from substituent group α; $R^1$ represents a hydrogen atom or a C1-C3 alkyl group; $R^2$ represents a hydrogen atom or a C1-C3 alkyl group; $R^3$ represents a C1-C6 alkyl group, a C3-C10 cycloalkyl group, a C1-C3 alkoxy C1-C3 alkyl group, or a C1-C3 hydroxyalkyl group; $R^4$ represents a hydrogen atom, a C1-C6 alkyl group, or a halogen atom; n represents an integer of 1 to 4; X represents methylene, —O—, —NH—, —N(C1-C3 alkyl)-, —C(=O)—, —S—, —S(O)—, —S(O$_2$)— or a single bond; and substituent group α consists of a halogen atom, a C1-C6 alkyl group (the alkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C3-C10 cycloalkyl group (the cycloalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 haloalkyl group (the haloalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 hydroxyalkyl group (the hydroxyalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur), a C1-C6 alkoxy C1-C6 alkyl group (the alkoxyalkyl group being optionally substituted with 1 to 3 groups selected from a carboxyl group, a C1-C6 alkoxycarbonyl group, and a 4- to 10-membered heterocyclic group containing 1 to 4 heteroatoms which may be the same or different and are selected from nitrogen, oxygen, and sulfur) a 4- to 10-membered heterocyclic group containing 1 to 4 heteroatoms which may be the same or different and are selected from nitrogen, oxygen, and sulfur, a C1-C6 aminoalkyl group, a C1-C6 alkoxy group, a C1-C6 haloalkoxy group, a C1-C6 hydroxyalkoxy group, a C6-C10 aryloxy group, a C1-C6 alkylthio group, a carboxyl group, a C1-C6 alkoxycarbonyl group, a hydroxy group, a C1-C6 aliphatic acyl group, an amino group, a C1-C6 alkylamino group, a C3-C10 cycloalkylamino group, a C1-C6 dialkylamino group, a C1-C6 alkoxyamino group, a C1-C6 aliphatic acylamino group, a C1-C6 dialkylamino group, a C1-C6 alkylsulfonyl group, a C1-C6 dialkylaminosulfonyl group, and a C6-C10 aryl group.

15. The compound of claim 1, wherein the pharmacologically acceptable salt is selected from the group consisting of hydrofluoride, hydrochloride, hydrobromide, hydroiodide, nitrate, perchlorate, sulfate, phosphate, methanesulfonate, trifluoromethanesulfonate, ethanesulfonate, benzenesulfonate, p-toluenesulfonate, acetate, malate, fumarate, succinate, citrate, adsorbate, tartlet, oxalate, maleate, glycine salt, lysine salt, arginine salt, omithine sale, glutamic acid salt, and aspartic acid salt.

16. A medicament comprising the compound or pharmacologically acceptable salt thereof according to claim 1 as an active ingredient.

17. A method for treating irritable bowel syndrome with constipation, diabetic gastroparesis, or constipation, comprising administering an effective amount of the medicament according to claim 16 to a subject in need thereof.

18. The method of claim 17, wherein the subject is a human.

* * * * *

UNITED STATES PATENT AND TRADEMARK OFFICE
CERTIFICATE OF CORRECTION

PATENT NO. : 9,051,255 B2  Page 1 of 2
APPLICATION NO. : 14/142479
DATED : June 9, 2015
INVENTOR(S) : Toda et al.

It is certified that error appears in the above-identified patent and that said Letters Patent is hereby corrected as shown below:

| COLUMN | LINE(S) | ERROR |
|---|---|---|
| In the specification | | |
| 7 | 42 | "with 1 to groups" should read --with 1 to 3 groups-- |
| 24 | 49 | "preferably conversion" should read --preferably converted-- |
| 88 | 21 | "for minutes." should read --for 15 minutes.-- |
| 109 | 64-65 | "for minutes." should read --for 30 minutes.-- |
| In the claims | | |
| 118 Claim 1, | 19 line 70 | "$C_6$-$C_{10}$" should read --C6-C10-- |
| 119 Claim 10, | 26 line 28 | "group, an a" should read --group, a-- |
| 122 Claim 14, | 47 line 49 | "sulfur) a" should read --sulfur), a-- |
| 122 Claim 14, | 59 line 61 | "a C1-C6 dialkylamino group," should read --a cyano group, a nitro group,-- |
| 123 Claim 15 | 1 | "adsorbate," should read --ascorbate,-- |

Signed and Sealed this
Fifth Day of April, 2016

Michelle K. Lee
*Director of the United States Patent and Trademark Office*

CERTIFICATE OF CORRECTION (continued)
U.S. Pat. No. 9,051,255 B2

| COLUMN | LINE(S) | ERROR |
|---|---|---|
| 123 Claim 15 | 1 | "tartlet," should read --tartrate,-- |
| 123 Claim 15 | 2 | "omithine sale," should read --ornithine salt-- |